(12) United States Patent
Nakaya et al.

(10) Patent No.: US 9,738,634 B2
(45) Date of Patent: Aug. 22, 2017

(54) HETEROCYCLIC AMIDE COMPOUND AND HERBICIDE

(71) Applicant: SYNGENTA PARTICIPATIONS AG, Basel (CH)

(72) Inventors: Yoshihiko Nakaya, Funebashi (JP); Yoshihide Masuzawa, Funebashi (JP); Takamasa Furuhashi, Funebashi (JP); Yuuki Miyakado, Funebashi (JP); Hiroyasu Hotta, Funebashi (JP); Masamitsu Inaba, Funebashi (JP)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/021,409

(22) PCT Filed: Sep. 11, 2014

(86) PCT No.: PCT/JP2014/074142
§ 371 (c)(1),
(2) Date: Mar. 11, 2016

(87) PCT Pub. No.: WO2015/037680
PCT Pub. Date: Mar. 19, 2015

(65) Prior Publication Data
US 2016/0221998 A1 Aug. 4, 2016

(30) Foreign Application Priority Data

Sep. 11, 2013 (JP) ................................. 2013-188211
Sep. 11, 2013 (JP) ................................. 2013-188213

(51) Int. Cl.
| | | |
|---|---|---|
| *C07D 413/12* | (2006.01) | |
| *A01N 43/88* | (2006.01) | |
| *C07D 413/14* | (2006.01) | |
| *A01N 43/86* | (2006.01) | |
| *C07D 417/12* | (2006.01) | |

(Continued)

(52) U.S. Cl.
CPC ........... *C07D 413/12* (2013.01); *A01N 43/86* (2013.01); *A01N 43/88* (2013.01); *A01N 53/00* (2013.01); *C07D 413/14* (2013.01); *C07D 417/12* (2013.01); *C07D 417/14* (2013.01)

(58) Field of Classification Search
CPC ............................. C07D 413/12; A01N 43/88
See application file for complete search history.

(56) References Cited

U.S. PATENT DOCUMENTS 4,289,524 A 9/1981 Belkind

FOREIGN PATENT DOCUMENTS

| | | |
|---|---|---|
| CN | 103159744 A | 6/2013 |
| EP | 0022653 A1 | 1/1981 |
| EP | 0122761 A2 | 10/1984 |
| JP | 61212575 A2 | 9/1986 |
| JP | 8311026 A | 11/1996 |
| JP | 200197958 A | 4/2001 |
| JP | 2007182456 A2 | 7/2007 |
| WO | 9518113 A1 | 7/1995 |
| WO | 9522523 A1 | 8/1995 |
| WO | 9700865 A1 | 1/1997 |
| WO | 2008096398 A1 | 8/2008 |
| WO | 2010119906 A1 | 10/2010 |

OTHER PUBLICATIONS

E Rajanarendar et al., "Microwave-assisted Synthesis of New Isoxazolyl triazinethiones and Isoxazolyl oxadiazinethiones in dry media" J Heterocyclic Chem, vol. 42, Issue 711 (2005) p. 711.

(Continued)

*Primary Examiner* — Kahsay Habte
(74) *Attorney, Agent, or Firm* — James Cueva

(57) ABSTRACT

Provided are: a heterocyclic amide compound represented by formula (1); and a herbicide containing the heterocyclic amide compound. In the formula, G represents a group represented by formula (G-1) or (G-2); each of W and $W^1$ independently represents an oxygen atom or the like; each of $Z^1$ and $Z^{a1}$ represents a phenyl group or the like; $Z^2$ represents an aromatic heterocycle; each of $R^1$ and $R^2$ independently represents a $C_1$-$C_6$ alkyl group or the like; $R_3$ represents a hydrogen atom, a $C_1$-$C_6$ alkyl group or the like; and each of $R^4$, $R^{a4}$, $R^5$, $R^{a5}$, $R^6$, $R^{a6}$ and $R^7$ independently represents a hydrogen atom or the like.

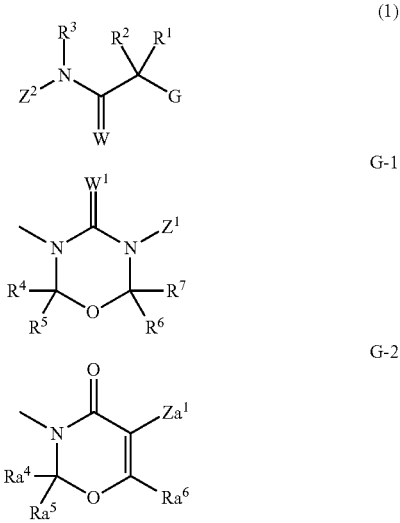

14 Claims, No Drawings

(51) Int. Cl.
*C07D 417/14* (2006.01)
*A01N 53/00* (2006.01)

(56) References Cited

OTHER PUBLICATIONS

Atanas P Venkov et al., "Intraqmolecular Cyclization Reactions of N-Alkylaryl- and N, N-Dialkylarylureas with Aldehydes," Synthetic Communications, Taylor and Francis, vol. 26 Issue 17, pp. 3217-3224 (1996).
Ryuichi Shiba et al., "The Formation Pathway of 3,5-Bis(methoxymethyl)perhydro-1,3,5-oxadiazin-4-one." The Chemical Society of Japan, vol. 62, No. 6, pp. 1930-1933, (1989).
A A Ersenbraun et al., "Synthesis of 3,5-disubstituted tetrahydro-4H-1,3,5-oxadiazin-4-ones" Development Department, Nitrogen Division, Allied Chemical Corporation, vol. 29, p. 2777-2778, Sep. 1964.

HETEROCYCLIC AMIDE COMPOUND AND HERBICIDE

RELATED APPLICATION INFORMATION

This application is a 371 of International Application No. PCT/JP2014/074142, filed Sep. 11, 2014, which claims priority to Japanese Application No. P2013-188211, filed Sep. 11, 2013, and Japanese Application No. P2013-188213, filed Sep. 11, 2013 the contents of which are incorporated herein by reference herein.

TECHNOLOGICAL FIELD

The present invention relates to a novel heterocyclic amide compound and salts thereof, and to pesticides, in particular herbicides, containing the heterocyclic amide compound and salts thereof as the active component. Further, pesticide in the present invention means insecticide, acaricide, nematicide, herbicide, fungicide and the like in the agricultural and horticultural field.

PRIOR ART

For example, in patent references 1 to 10 and non-patent references 1 to 4, some types of heterocyclic amide compound are disclosed, but there has been no disclosure whatever relating to the heterocyclic amide compounds of the present invention.

PREVIOUS LITERATURE REFERENCES

Patent References

[Patent Reference 1] International Laid-open Specification 2010/119906
[Patent Reference 2] International Laid-open Specification 95/18113
[Patent Reference 3] International Laid-open Specification 95/22523
[Patent Reference 4] European Laid-open Patent Application 122761 specification
[Patent Reference 5] US Laid-open Patent Application 4289524 specification
[Patent Reference 6] European Laid-Open Patent Application 22653 specification
[Patent Reference 7] Japanese Laid-Open Application 61-212575 publication
[Patent Reference 8] Japanese Laid-Open Application 4-89485 publication
[Patent Reference 9] Japanese Laid-Open Application 8-311026 publication
[Patent Reference 10] Japanese Laid-Open Application 2007-182456 publication

Non-Patent References

[Non-patent Reference 1] Journal of Heterocyclic Chemistry, 2005, Vol. 42, p. 711
[Non-patent Reference 2] Synthetic Communications, 1996, Vol. 26, p. 3217
[Non-patent Reference 3] Bulletin of the Chemical Society of Japan, 1989, Vol. 62, p. 1930
[Non-patent Reference 4] Journal of Organic Chemistry, 1964, Vol. 29, p. 2777

OUTLINE OF INVENTION

Problem to be Solved by Invention

The purpose of the present invention is to provide a chemical substance useful as an active component of a herbicide, which reliably exhibits efficacy against various weeds at lower dosages, and is very safe, with which problems such as soil contamination and effects on subsequent crops have been decreased.

Means of Solving Problem

The present inventors, as a result of repeated and diligent research with the aim of solving the aforesaid problems, discovered that the novel heterocyclic amide compounds of the present invention represented by the following formula (1) are very useful compounds which have excellent herbicidal activity as herbicides, and high safety towards target crops, and have practically no harmful effects on non-target organisms such as mammals, fish and beneficial insects, and thus achieved the present invention.

That is to say, the present invention relates to [1] to [14] below.

[1] A heterocyclic amide compound represented by the formula (1):

[Chem. 1]

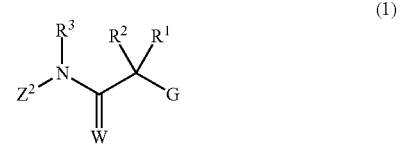

(1)

[in the formula, W represents an oxygen atom or sulfur atom, $R^1$ and $R^2$ either each independently represent hydrogen atom, $C_1$-$C_6$ alkyl or ($C_1$-$C_6$) alkyl optionally substituted with $R^8$, or else by $R^1$ and $R^2$ together forming a $C_2$-$C_6$ alkylene chain, $R^1$ and $R^2$ together with the linking carbon atom may form a 3-7 membered ring, $R^3$ represents hydrogen atom, $C_1$-$C_6$ alkyl or ($C_1$-$C_6$) alkyl optionally substituted with $R^9$, $R^8$ represents halogen atom or —$OR^{10}$, $R^9$ represents halogen atom or —$OR^{11}$, $R^{10}$ and $R^{11}$ each independently represent hydrogen atom or $C_1$-$C_6$ alkyl, G represents a ring represented by G-1 or G-2, (a) if G represents a ring represented by G-1,

[Chem. 2]

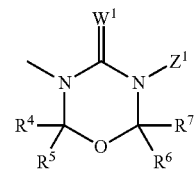

G-1

$W^1$ represents oxygen atom or sulfur atom, $Z^1$ represents $C_1$-$C_6$ alkyl, ($C_1$-$C_6$) alkyl optionally substituted with $R^{12}$, $C_3$-$C_6$ cycloalkyl, ($C_3$-$C_6$) cycloalkyl optionally substituted with $R^{12}$, $C_2$-$C_6$ alkenyl, ($C_2$-$C_6$) alkenyl optionally substituted with $R^{12}$, $C_2$-$C_6$ alkynyl, ($C_2$-$C_6$) alkynyl optionally substituted with $R^{12}$, phenyl, phenyl substituted with $(R^{13})_{p1}$ or Q-1 to Q-3, and
$Z^2$ represents an aromatic heterocyclic ring represented by any of T-1 to T-24,
[Chem. 3]
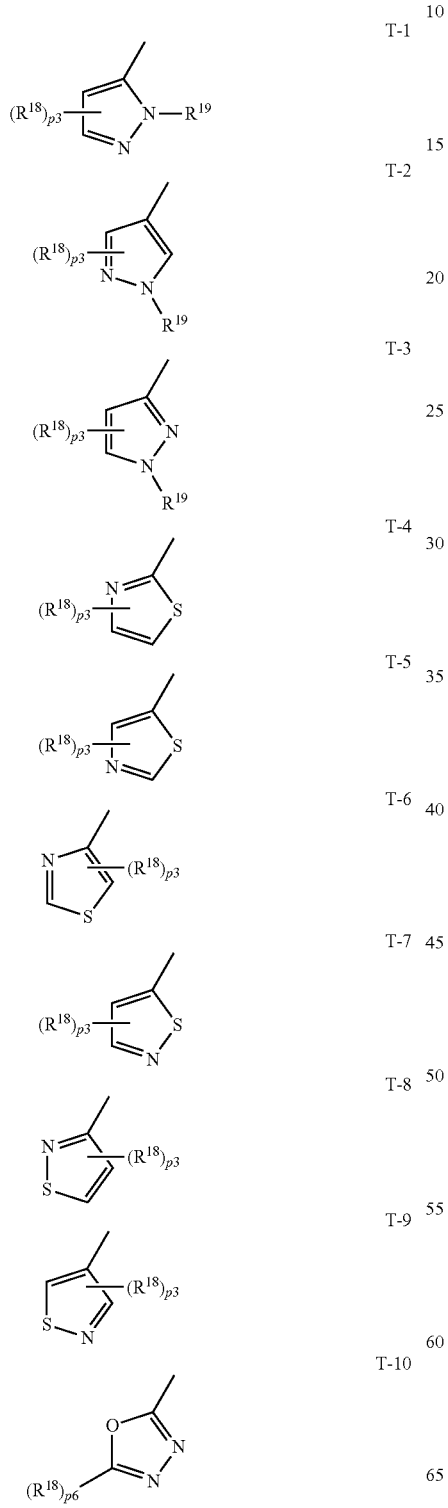
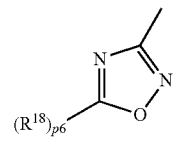
T-11
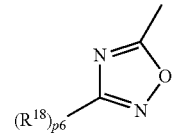
T-12
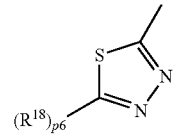
T-13
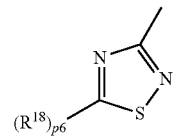
T-14
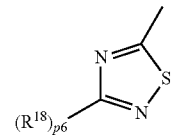
T-15
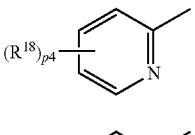
T-16
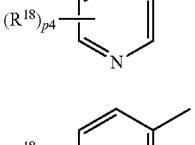
T-17
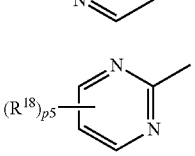
T-18
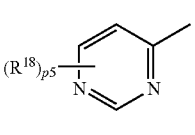
T-19
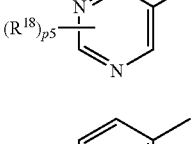
T-20
T-21
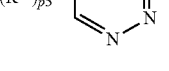
T-22

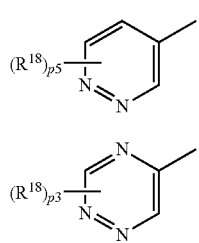

T-23

T-24

$R^4$, $R^5$, $R^6$ and $R^7$ each independently represent hydrogen atom or $C_1$-$C_6$ alkyl, Q-1 to Q-3 represent the aromatic heterocyclic rings respectively represented by the following structural formulae,

[Chem. 4]

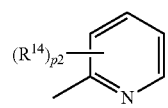

Q-1

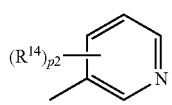

Q-2

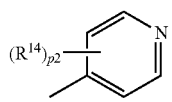

Q-3

$R^{12}$ represents halogen atom, phenyl or —$OR^5$, $R^{13}$ represents halogen atom, $C_1$-$C_6$ alkyl, $C_1$-$C_6$ haloalkyl or —$OR^{16}$, and when p1 represents a whole number 2 or more, each $R^{13}$ may be the same or different, furthermore, if 2 $R^{13}$ are adjacent, the 2 adjacent $R^{13}$, by forming —$CH_2CH_2CH_2$—, —$CH_2CH_2O$—, —$CH_2OCH_2$—, —$OCH_2O$—, —$CH_2CH_2S$—, —$CH_2SCH_2$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$CH_2CH_2CH_2S$—, —$OCH_2CH_2S$— or —CH=CH—CH=CH—, may form a 5-membered ring or 6-membered ring together with the carbon atom to which the 2 $R^{13}$ are each bound, and in that case the hydrogen atoms bound to each carbon atom forming the ring may optionally be substituted with halogen atom(s), $C_1$-$C_6$ alkyl group(s) or $C_1$-$C_6$ haloalkyl group(s), $R^{14}$ represents halogen atom, $C_1$-$C_6$ alkyl, $C_1$-$C_6$ haloalkyl or —$OR^{17}$, and when p2 represents a whole number 2 or more, each $R^{14}$ may be the same or different, furthermore, if 2 $R^{14}$ are adjacent, the 2 adjacent $R^{14}$, by forming —$CH_2CH_2CH_2$—, —$CH_2CH_2O$—, —$CH_2OCH_2$—, —$OCH_2O$—, —$CH_2CH_2S$—, —$CH_2SCH_2$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$CH_2CH_2CH_2S$—, —$OCH_2CH_2S$— or —CH=CH—CH=CH—, may form a 5-membered ring or 6-membered ring together with the carbon atom to which the 2 $R^{14}$ are each bound, and, in that case, the hydrogen atoms bound to each carbon atom forming the ring may optionally be substituted with halogen atom(s), $C_1$-$C_6$ alkyl group(s) or $C_1$-$C_6$ haloalkyl group(s), $R^{15}$ represents hydrogen atom or $C_1$-$C_6$ alkyl, $R^{16}$ represents hydrogen atom, $C_1$-$C_6$ alkyl, $C_1$-$C_6$ haloalkyl or phenyl, $R^{17}$ represents $C_1$-$C_6$ alkyl, $C_1$-$C_6$ haloalkyl or phenyl, $R^{18}$ represents halogen atom, $C_1$-$C_6$ alkyl, $C_1$-$C_6$ haloalkyl, $C_3$-$C_6$ cycloalkyl, cyano, —C(O)$OR^{20}$, phenyl, —$OR^{23}$, nitro, —N($R^{24}$)$R^{25}$, —S(O)$_qR^{26}$ or V-1 to V-8, and when p3, p4 or p5 represents a whole number 2 or more, each $R^{18}$ may be the same or different, furthermore, if 2 $R^{18}$ are adjacent, the 2 adjacent $R^{18}$, by forming —$CH_2CH_2CH_2$—, —$CH_2CH_2O$—, —$CH_2OCH_2$—, —$OCH_2O$—, —$CH_2CH_2S$—, —$CH_2SCH_2$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$CH_2CH_2CH_2S$—, —$OCH_2CH_2S$— or —CH=CH—CH=CH—, may form a 5-membered ring or 6-membered ring together with the carbon atom to which the 2 $R^{18}$ are each bound, and in that case the hydrogen atoms bound to each carbon atom forming the ring may optionally be substituted with halogen atom(s), $C_1$-$C_6$ alkyl group(s) or $C_1$-$C_6$ haloalkyl group(s), V-1 to V-8 represent the aromatic heterocyclic rings respectively represented by the following structural formulae,

[Chem. 5]

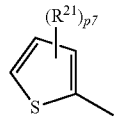

V-1

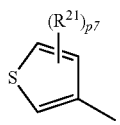

V-2

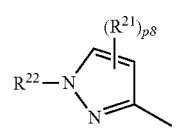

V-3

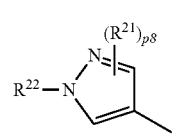

V-4

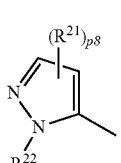

V-5

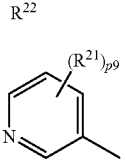

V-6

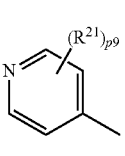

V-7

-continued

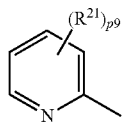
V-8

R[19] and R[20] each independently represent $C_1$-$C_6$ alkyl or $C_1$-$C_6$ haloalkyl, R[21] represents halogen atom, $C_1$-$C_6$ alkyl or $C_1$-$C_6$ haloalkyl, and when p7, p8 or p9 represents a whole number 2 or more, each R[21] may be the same or different, furthermore, if 2 R[21] are adjacent, the 2 adjacent R[21], by forming —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —CH$_2$CH$_2$CH$_2$S—, —OCH$_2$CH$_2$S— or —CH=CH—CH=CH—, may form a 5-membered ring or 6-membered ring together with the carbon atom to which the 2 R[21] are each bound, and in that case the hydrogen atoms bound to each carbon atom forming the ring may optionally be substituted with halogen atom(s), $C_1$-$C_6$ alkyl group(s) or $C_1$-$C_6$ haloalkyl group(s), R[22] represents $C_1$-$C_6$ alkyl or $C_1$-$C_6$ haloalkyl, R[23] represents hydrogen atom, $C_1$-$C_6$ alkyl, $C_1$-$C_6$ haloalkyl or phenyl, R[24] and R[25] each independently represent hydrogen atom or $C_1$-$C_6$ alkyl, or else R[24], by forming a $C_2$-$C_6$ alkylene chain together with R[25], can form a 3-7 membered ring together with the linking nitrogen atom, and in this case this alkylene chain can contain 1 oxygen atom, sulfur atom or nitrogen atom, and may optionally be substituted with halogen atom(s), $C_1$-$C_6$ alkyl group(s), $C_1$-$C_6$ haloalkyl group(s), $C_1$-$C_6$ alkoxy group(s), formyl group(s), $C_1$-$C_6$ alkylcarbonyl group(s), $C_1$-$C_6$ alkoxycarbonyl group(s) or oxo group(s), R[26] represents $C_1$-$C_6$ alkyl or $C_1$-$C_6$ haloalkyl,
p1 represents a whole number 1, 2, 3, 4 or 5,
p2 represents a whole number 0, 1, 2, 3 or 4,
p3 represents a whole number 0, 1 or 2,
p4 represents a whole number 0, 1, 2, 3 or 4,
p5 represents a whole number 0, 1, 2 or 3,
p6 represents a whole number 0 or 1,
p7 represents a whole number 0, 1, 2 or 3,
p8 represents a whole number 0, 1 or 2,
p9 represents a whole number 0, 1, 2, 3 or 4, and
q represents a whole number 0, 1 or 2, or (b) if G represents a ring represented by G-2,

[Chem. 6]

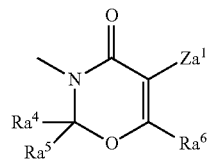
G-2

Za[1] represents phenyl, phenyl substituted with (Ra[13])$_{pa1}$ or Qa-1 to Qa-8,
Z[2] represents an aromatic heterocyclic ring represented by any of Ta-1 to Ta-13

[Chem. 7]

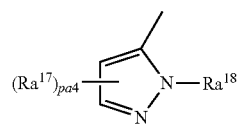
Ta-1

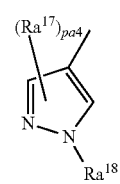
Ta-2

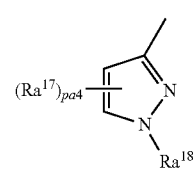
Ta-3

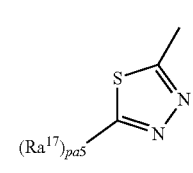
Ta-4

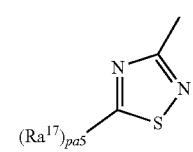
Ta-5

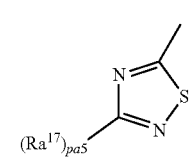
Ta-6

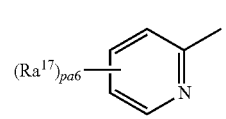
Ta-7

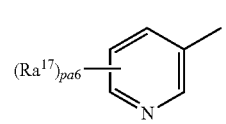
Ta-8

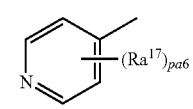
Ta-9

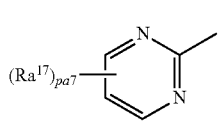
Ta-10

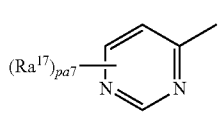
Ta-11

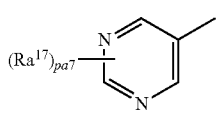
Ta-12

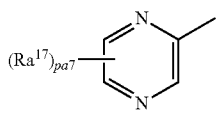
Ta-13

Ra$^4$ and Ra$^5$ each independently represent hydrogen atom or C$_1$-C$_6$ alkyl, Ra$^6$ represents hydrogen atom, C$_1$-C$_6$ alkyl or (C$_1$-C$_6$) alkyl optionally substituted with Ra$^9$, Qa-1 to Qa-8 represent the aromatic heterocyclic rings respectively represented by the following structural formulae,

[Chem. 8]

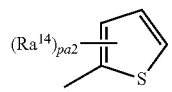
Qa-1

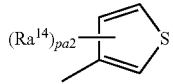
Qa-2

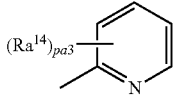
Qa-3

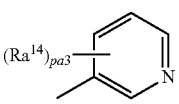
Qa-4

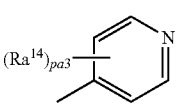
Qa-5

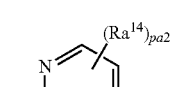
Qa-6

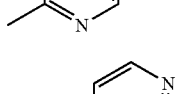
Qa-7

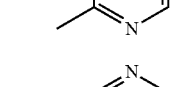
Qa-8

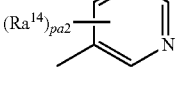

Ra$^9$ represents halogen atom or —ORa$^{12}$,

Ra$^{12}$ represents hydrogen atom or C$_1$-C$_6$ alkyl,

Ra$^{13}$ represents halogen atom, C$_1$-C$_6$ alkyl, C$_1$-C$_6$ haloalkyl or —ORa$^{15}$, and when pa1 represents a whole number 2 or more, each Ra$^{13}$ may be the same or different, furthermore, if 2 Ra$^{13}$ are adjacent, the 2 adjacent Ra$^{13}$, by forming —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —CH$_2$CH$_2$CH$_2$S—, —OCH$_2$CH$_2$S— or —CH═CH—CH═CH—, may form a 5-membered ring or 6-membered ring together with the carbon atom to which the 2 R$^{13}$ are each bound, and in that case the hydrogen atoms bound to each carbon atom forming the ring may optionally be substituted with halogen atom(s), C$_1$-C$_6$ alkyl group(s) or C$_1$-C$_6$ haloalkyl group(s), Ra$^{14}$ represents halogen atom, C$_1$-C$_6$ alkyl, C$_1$-C$_6$ haloalkyl or —ORa$^{16}$, and when pa2 or pa3 represents a whole number 2 or more, each Ra$^{14}$ may be the same or different, furthermore, if 2 Ra$^{14}$ are adjacent, the 2 adjacent Ra$^{14}$, by forming —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —CH$_2$CH$_2$CH$_2$S—, —OCH$_2$CH$_2$S— or —CH═CH—CH═CH—, may form a 5-membered ring or 6-membered ring together with the carbon atom to which the 2 R$^{14}$ are each bound, and in that case the hydrogen atoms bound to each carbon atom forming the ring may optionally be substituted with halogen atom(s), C$_1$-C$_6$ alkyl group(s) or C$_1$-C$_6$ haloalkyl group(s), Ra$^{15}$ represents hydrogen atom, C$_1$-C$_6$ alkyl, C$_1$-C$_6$ haloalkyl or phenyl, Ra$^{16}$ represents C$_1$-C$_6$ alkyl, C$_1$-C$_6$ haloalkyl or phenyl, Ra$^{17}$ represents halogen atom, C$_1$-C$_6$ alkyl, C$_1$-C$_6$ haloalkyl, C$_3$-C$_6$ cycloalkyl, cyano, —C(O)ORa$^{19}$, phenyl, —ORa$^{21}$, nitro, —N(Ra$^{22}$)Ra$^{23}$, —S(O)$_{qa}$Ra$^{24}$ or Va-1 to Va-3, and when pa4, pa6 or pa7 represents a whole number 2 or more, each Ra$^{17}$ may be the same or different, furthermore, if 2 Ra$^{17}$ are adjacent, the 2 adjacent Ra$^{17}$, by forming —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —CH$_2$CH$_2$CH$_2$S—, —OCH$_2$CH$_2$S— or —CH═CH—CH═CH—, may form a 5-membered ring or 6-membered ring together with the carbon atom to which the 2 Ra$^{17}$ are each bound, and in that case the hydrogen atoms bound to each carbon atom forming the ring may optionally be substituted with halogen atom(s), C$_1$-C$_6$ alkyl group(s) or C$_1$-C$_6$ haloalkyl group(s), Va-1 to Va-3 represent the aromatic heterocyclic rings respectively represented by the following structural formulae,

[Chem. 9]

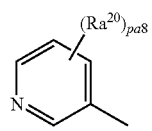
Va-1

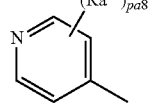
Va-2

-continued

Va-3

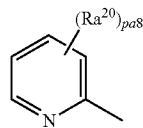

Ra$^{18}$ and Ra$^{19}$ each independently represent C$_1$-C$_6$ alkyl or C$_1$-C$_6$ haloalkyl, Ra$^{20}$ represents halogen atom, C$_1$-C$_6$ alkyl or C$_1$-C$_6$ haloalkyl, and when pa8 represents a whole number 2 or more, each Ra$^{20}$ may be the same or different, furthermore, if 2 Ra$^{20}$ are adjacent, the 2 adjacent Ra$^{20}$, by forming —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —CH$_2$CH$_2$CH$_2$S—, —OCH$_2$CH$_2$S— or —CH=CH—CH=CH—, may form a 5-membered ring or 6-membered ring together with the carbon atom to which the 2 Ra$^{20}$ are each bound, and in that case the hydrogen atoms bound to each carbon atom forming the ring may optionally be substituted with halogen atom(s), C$_1$-C$_6$ alkyl group(s) or C$_1$-C$_6$ haloalkyl group(s), Ra$^{21}$ represents C$_1$-C$_6$ alkyl, C$_1$-C$_6$ haloalkyl or phenyl, Ra$^{22}$ and Ra$^{23}$ each independently represent hydrogen atom or C$_1$-C$_6$ alkyl, or else Ra$^{22}$, by forming a C$_2$-C$_6$ alkylene chain together with Ra$^{23}$, can form a 3-7 membered ring together with the linking nitrogen atom, and in this case this alkylene chain can contain 1 oxygen atom, sulfur atom or nitrogen atom, and may optionally be substituted with halogen atom(s), C$_1$-C$_6$ alkyl group(s), C$_1$-C$_6$ haloalkyl group(s), C$_1$-C$_6$ alkoxy group(s), formyl group(s), C$_1$-C$_6$ alkylcarbonyl group(s) or C$_1$-C$_6$ alkoxycarbonyl group(s), Ra$^{24}$ represents C$_1$-C$_6$ alkyl or C$_1$-C$_6$ haloalkyl, pa1 represents a whole number 1, 2, 3, 4 or 5,
pa2 represents a whole number 0, 1, 2 or 3,
pa3 represents a whole number 0, 1, 2, 3 or 4,
pa4 represents a whole number 0, 1 or 2,
pa5 represents a whole number 0 or 1,
pa6 represents a whole number 0, 1, 2, 3 or 4,
pa7 represents a whole number 0, 1, 2 or 3,
pa8 represents a whole number 0, 1, 2, 3 or 4, and
qa represents a whole number 0, 1 or 2.] or a salt thereof.

The heterocyclic amide compound or salt thereof stated in the aforesaid [1], characterized in that G represents a ring represented by G-1.

[3]
The heterocyclic amide compound or salt thereof stated in the aforesaid [2], characterized in that R$^4$, R$^5$, R$^6$ and R$^7$ represent hydrogen atoms, R$^8$, R$^9$, R$^{12}$ and R$^{14}$ each independently represent halogen atom, R$^{16}$ represents hydrogen atom, C$_1$-C$_6$ alkyl or C$_1$-C$_6$ haloalkyl, R$^{18}$ represents halogen atom, C$_1$-C$_6$ alkyl, C$_1$-C$_6$ haloalkyl, C$_3$-C$_6$ cycloalkyl, cyano, —C(O)OR$^{20}$, phenyl, —OR$^{23}$, nitro, —S(O)$_q$R$^{26}$, V-2, V-5 or V-6, and when p3, p4 or p5 represents a whole number 2 or more, each R$^{18}$ may be the same or different, furthermore, if 2 R$^{18}$ are adjacent, the 2 adjacent R$^{18}$, by forming —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —CH$_2$CH$_2$CH$_2$S—, —OCH$_2$CH$_2$S— or —CH=CH—CH=CH—, may form a 5-membered ring or 6-membered ring together with the carbon atom to which the 2 R$^{18}$ are each bound, and in that case the hydrogen atoms bound to each carbon atom forming the ring may optionally be substituted with halogen atom(s), C$_1$-C$_6$ alkyl group(s) or C$_1$-C$_6$ haloalkyl group(s), and R$^{21}$ represents halogen atom.

[4]
The heterocyclic amide compound or salt thereof stated in the aforesaid [3], characterized in that W represents oxygen atom, R$^1$ and R$^2$ each independently represent hydrogen atom or C$_1$-C$_6$ alkyl, or else by R$^1$ forming a C$_2$ alkylene chain together with R$^2$, R$^1$ and R$^2$ may form a 3-membered ring together with the linking carbon atom, R$^3$ represents hydrogen atom or C$_1$-C$_6$ alkyl, R$^{13}$ represents halogen atom, C$_1$-C$_6$ alkyl, C$_1$-C$_6$ haloalkyl or —OR$^{16}$, R$^{16}$ represents C$_1$-C$_6$ alkyl or C$_1$-C$_6$ haloalkyl, R$^{18}$ represents halogen atom, C$_1$-C$_6$ alkyl, C$_1$-C$_6$ haloalkyl, C$_3$-C$_6$ cycloalkyl, cyano, —C(O)OR$^{20}$, phenyl, —OR$^{23}$, nitro, —S(O)$_q$R$^{26}$, V-2, V-5 or V-6, and if 2 R$^{18}$ are adjacent, the 2 adjacent R$^{18}$, by forming —CH=CH—CH=CH—, may form a 6-membered ring together with the carbon atom to which the 2 R$^{18}$ are each bound, R$^{20}$ and R$^{22}$ each independently represent C$_1$-C$_6$ alkyl, R$^{23}$ represents C$_1$-C$_6$ alkyl, C$_1$-C$_6$ haloalkyl or phenyl, and R$^{26}$ represents C$_1$-C$_6$ alkyl.

[5]
The heterocyclic amide compound or salt thereof stated in the aforesaid [4], characterized in that Z$^1$ represents C$_3$-C$_6$ cycloalkyl, (C$_3$-C$_6$) cycloalkyl optionally substituted with R$^{12}$, phenyl, phenyl substituted with (R$^{13}$)$_{p1}$ or Q-1 to Q-3, Z$^2$ represents T-1, T-2, T-3, T-4, T-5, T-6, T-7, T-8, T-9, T-10, T-13, T-14, T-15, T-16, T-17, T-18, T-19, T-20, T-21, T-22, T-23 or T-24, R$^{13}$ represents halogen atom, C$_1$-C$_6$ alkyl or —OR$^{16}$, and R$^{16}$ represents C$_1$-C$_6$ alkyl.

[6]
The heterocyclic amide compound or salt thereof stated in the aforesaid [5], characterized in that Z$^2$ represents T-1, T-2, T-3, T-4, T-7, T-10, T-13, T-14, T-15, T-16, T-17, T-18, T-19, T-20, T-21, T-22, T-23 or T-24.

[7]
The heterocyclic amide compound or salt thereof stated in the aforesaid [6], characterized in that Z$^1$ represents phenyl, phenyl substituted with (R$^{13}$)$_{p1}$ or Q-2, and Z$^2$ represents T-1, T-3, T-4, T-7, T-10, T-13, T-14, T-15, T-16, T-17, T-18, T-19, T-20, T-22 or T-24.

[8]
The heterocyclic amide compound or salt thereof stated in the aforesaid [1], characterized in that G represents a ring represented by G-2.

[9]
The heterocyclic amide compound or salt thereof stated in the aforesaid [8], characterized in that R$^1$ and R$^2$ each independently represent C$_1$-C$_6$ alkyl or (C$_1$-C$_6$) alkyl optionally substituted with R$^8$, or else by R$^1$ and R$^2$ together forming a C$_2$-C$_6$ alkylene chain, R$^1$ and R$^2$ together with the linking carbon atom may form a 3-7 membered ring, R$^3$ represents hydrogen atom, R$^8$ represents halogen atom, Ra$^4$ and Ra$^5$ represent hydrogen atoms, $Ra^6$ represents $C_1$-$C_6$ alkyl or ($C_1$-$C_6$) alkyl optionally substituted with $Ra^9$, $Ra^9$ represents halogen atom, $Ra^{13}$ represents halogen atom, $C_1$-$C_6$ alkyl or $C_1$-$C_6$ haloalkyl, and when pa1 represents a whole number 2 or more, each $Ra^{13}$ may be the same or different, furthermore, if 2 $Ra^{13}$ are adjacent, the 2 adjacent $Ra^{13}$, by forming —$CH_2CH_2CH_2$—, —$CH_2CH_2O$—, —$CH_2OCH_2$—, —$OCH_2O$—, —$CH_2CH_2S$—, —$CH_2SCH_2$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$CH_2CH_2CH_2S$—, —$OCH_2CH_2S$— or —CH=CH—CH=CH—, may form a 5-membered ring or 6-membered ring together with the carbon atom to which the 2 $Ra^{13}$ are each bound, and in that case the hydrogen atoms bound to each carbon atom forming the ring may optionally be substituted with halogen atom(s), $C_1$-$C_6$ alkyl group(s) or $C_1$-$C_6$ haloalkyl group(s), $Ra^{14}$ represents halogen atom, $C_1$-$C_6$ alkyl or $C_1$-$C_6$ haloalkyl, and when pa2 or pa3 represents a whole number 2 or more, each $Ra^{14}$ may be the same or different, furthermore, if 2 $Ra^{14}$ are adjacent, the 2 adjacent $Ra^{14}$, by forming —$CH_2CH_2CH_2$—, —$CH_2CH_2O$—, —$CH_2OCH_2$—, —$OCH_2O$—, —$CH_2CH_2S$—, —$CH_2SCH_2$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$CH_2CH_2CH_2S$—, —$OCH_2CH_2S$— or —CH=CH—CH=CH—, may form a 5-membered ring or 6-membered ring together with the carbon atom to which the 2 $Ra^{14}$ are each bound, and in that case the hydrogen atoms bound to each carbon atom forming the ring may optionally be substituted with halogen atom(s), $C_1$-$C_6$ alkyl group(s) or $C_1$-$C_6$ haloalkyl group(s), $Ra^{17}$ represents halogen atom, $C_1$-$C_6$ alkyl, $C_1$-$C_6$ haloalkyl, $C_3$-$C_6$ cycloalkyl, cyano, —C(O)O$Ra^{19}$, phenyl, —O$Ra^{21}$, nitro, —S(O)$_{qa}Ra^{24}$ or Va-1 to Va-3, and when pa4, pa6 or pa7 represents a whole number 2 or more, each $Ra^{17}$ may be the same or different, furthermore, if 2 $Ra^{17}$ are adjacent, the 2 adjacent $Ra^{17}$, by forming —$CH_2CH_2CH_2$—, —$CH_2CH_2O$—, —$CH_2OCH_2$—, —$OCH_2O$—, —$CH_2CH_2S$—, —$CH_2SCH_2$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$CH_2CH_2CH_2S$—, —$OCH_2CH_2S$— or —CH=CH—CH=CH—, may form a 5-membered ring or 6-membered ring together with the carbon atom to which the 2 $Ra^{17}$ are each bound, and in that case the hydrogen atoms bound to each carbon atom forming the ring may optionally be substituted with halogen atom(s), $C_1$-$C_6$ alkyl group(s) or $C_1$-$C_6$ haloalkyl group(s), and $Ra^{20}$ represents halogen atom.

[10]

The heterocyclic amide compound or salt thereof stated in the aforesaid [9], characterized in that W represents oxygen atom, $R^1$, $R^2$ and $Ra^6$ each independently represent $C_1$-$C_6$ alkyl, $Ra^{13}$ represents halogen atom, $Ra^{14}$ represents halogen atom, and if 2 $Ra^{14}$ are adjacent, the 2 adjacent $Ra^{14}$, by forming —CH=CH—CH=CH—, may form a 6-membered ring together with the carbon atom to which the 2 $Ra^{14}$ are each bound, $Ra^{17}$ represents halogen atom, $C_1$-$C_6$ alkyl, $C_1$-$C_6$ haloalkyl, cyano, —C(O)O$Ra^{19}$, phenyl, —O$Ra^{21}$, —S(O)$_{qa}Ra^2$ or Va-1, and if 2 $Ra^{17}$ are adjacent, the 2 adjacent $Ra^{17}$, by forming —CH=CH—CH=CH—, may form a 6-membered ring together with the carbon atom to which the 2 $Ra^{17}$ are each bound, and $Ra^{18}$, $Ra^{19}$ and $Ra^{24}$ each independently represent $C_1$-$C_6$ alkyl.

[11]

The heterocyclic amide compound or salt thereof stated in the aforesaid [10], characterized in that $Za^1$ represents phenyl, phenyl substituted with $(Ra^{13})_{pa1}$, Qa-1, Qa-2, Qa-3, Qa-4, Qa-5 or Qa-8, and $Z^2$ represents Ta-2, Ta-4, Ta-5, Ta-6, Ta-7, Ta-8, Ta-9, Ta-11 or Ta-13.

[12]

The heterocyclic amide compound or salt thereof stated in the aforesaid [11], characterized in that $Za^1$ represents phenyl, Qa-1, Qa-2, Qa-4, Qa-5 or Qa-8, and $Z^2$ represents Ta-2, Ta-4, Ta-6, Ta-7, Ta-8, Ta-9, Ta-11 or Ta-13.

[13]

A pesticide characterized in that 1 or 2 or more selected from the heterocyclic amide compounds or salt thereof stated in the aforesaid [1] to [12] are contained as active component(s).

[14]

A herbicide characterized in that 1 or 2 or more selected from the heterocyclic amide compounds or salt thereof stated in the aforesaid [1] to [12] are contained as active component(s).

Effect of the Invention

The compounds of the present invention have excellent herbicidal activity against various weeds, high safety towards target crops, have practically no harmful effects on non-target organisms such as mammals, fish and beneficial insects, are low-residue and place little burden on the environment.

Consequently, the present invention can provide herbicides useful in agricultural and horticultural fields such as paddy fields, farmland and orchards.

EMBODIMENTS OF THE INVENTION

Depending on the nature of the substituents, E-form and Z-form geometric isomers may be present in the compounds included in the present invention, but the present invention includes these E-forms, Z-forms or mixtures containing E-forms and Z-forms in any proportions. Further, optically active forms due to the presence of 1 or 2 or more asymmetric carbon atoms are present in the compounds included in the present invention, but the present invention includes all optically active forms or racemic forms.

Among the compounds included in the present invention, those which can be made into acid addition salts by usual methods can for example be made into salts of hydrogen halide acids such as as hydrofluoric acid, hydrochloric acid, hydrobromic acid and hydriodic acid, salts of inorganic acids such as nitric acid, sulfuric acid, phosphoric acid, chloric acid and perchloric acid, salts of sulfonic acids such as methanesulfonic acid, ethanesulfonic acid, trifluoromethanesulfonic acid, benzenesulfonic acid and p-toluenesulfonic acid, salts of carboxylic acids such as formic acid, acetic acid, propionic acid, trifluoroacetic acid, fumaric acid, tartaric acid, oxalic acid, maleic acid, malic acid, succinic acid, benzoic acid, mandelic acid, ascorbic acid, lactic acid, gluconic acid and citric acid, or salts of amino acids such as glutamic acid and aspartic acid.

Alternatively, among the compounds included in the present invention, those which can be made into metal salts by usual methods can for example be made into salts of alkali metals such as lithium, sodium and potassium, salts of alkaline earth metals such as calcium, barium and magnesium or salts of aluminum.

Next, concrete examples of various substituent groups indicated in the present specification are shown below. Herein, respectively, n-means normal, i-iso, s-secondary and tert-tertiary, and Ph means phenyl.

As halogen atoms in the present specification, fluorine atom, chlorine atom, bromine atom and iodine atom are mentioned. Also, in the present specification the term "halo" also indicates these halogen atoms.

The term $C_a$-$C_b$ alkyl in the present specification indicates a linear or branched hydrocarbon group made up of a to b carbon atoms, and for example the methyl group, ethyl group, n-propyl group, i-propyl group, n-butyl group, i-butyl group, s-butyl group, tert-butyl group, n-pentyl group, 1,1-dimethylpropyl group, n-hexyl group and the like are mentioned as concrete examples, and are selected within the range of the respective specified number of carbon atoms.

The term $C_a$-$C_b$ cycloalkyl in the present specification indicates a cyclic hydrocarbon group made up of a to b carbon atoms, and can form a single 3-membered to 6-membered ring or a condensed ring structure. Further, each ring may be optionally substituted with alkyl group(s) within the range of the specified number of carbon atoms. For example, cyclopropyl group, 1-methylcyclopropyl group, 2-methylcyclopropyl group, 2,2-dimethylcyclopropyl group, cyclobutyl group, cyclopentyl group, cyclohexyl group and the like are mentioned as concrete examples, and are selected within the range of the respective specified number of carbon atoms.

The term $C_a$-$C_b$ alkenyl in the present specification indicates an unsaturated hydrocarbon group which is linear or branched and made up of a to b carbon atoms, and has 1 or 2 or more double bonds in the molecule, and for example the vinyl group, 1-propenyl group, 2-propenyl group, 1-methylethenyl group, 2-butenyl group, 2-methyl-2-propenyl group, 3-methyl-2-butenyl group, 1,1-dimethyl-2-propenyl group and the like are mentioned as concrete examples, and are selected within the range of the respective specified number of carbon atoms.

The term $C_a$-$C_b$ alkynyl in the present specification indicates an unsaturated hydrocarbon group which is linear or branched and made up of a to b carbon atoms, and has 1 or 2 or more triple bonds in the molecule, and for example the ethynyl group, 1-propynyl group, 2-propynyl group, 1-butynyl group, 2-butynyl group, 3-butynyl group, 1,1-dimethyl-2-propynyl group and the like are mentioned as concrete examples, and are selected within the range of the respective specified number of carbon atoms.

The term $C_a$-$C_b$ haloalkyl in the present specification indicates a linear or branched hydrocarbon group made up of a to b carbon atoms wherein hydrogen atom(s) bound to carbon atoms are optionally substituted with halogen atom(s). In that case, if these are substituted with 2 or more halogen atoms, these halogen atoms may be the same or different. For example, the fluoromethyl group, chloromethyl group, bromomethyl group, iodomethyl group, difluoromethyl group, dichloromethyl group, trifluoromethyl group, chlorodifluoromethyl group, trichloromethyl group, bromodifluoromethyl group, 2-fluoroethyl group, 2-chloroethyl group, 2-bromoethyl group, 2,2-difluoroethyl group, 2,2,2-trifluoroethyl group, 2-chloro-2,2-difluoroethyl group, 2,2,2-trichloroethyl group, 1,1,2,2-tetrafluoroethyl group, 2-chloro-1,1,2-trifluoroethyl group, pentafluoroethyl group, 3,3,3-trifluoropropyl group, 2,2,3,3,3-pentafluoropropyl group, 1,1,2,3,3,3-hexafluoropropyl group, heptafluoropropyl group, 2,2,2-trifluoro-1-(trifluoromethyl)ethyl group, 1,2,2,2-tetrafluoro-1-(trifluoro-methyl)ethyl group, 2,2,3,3,4,4,4-heptafluorobutyl group, nonafluorobutyl group and the like are mentioned as concrete examples, and are selected within the range of the respective specified number of carbon atoms.

The term $C_a$-$C_b$ alkoxy in the present specification represents an alkyl-O— group, with the aforesaid meaning that it is made up of a to b carbon atoms, and for example the methoxy group, ethoxy group, n-propyloxy group, i-propyloxy group, n-butyloxy group, s-butyloxy group, i-butyloxy group, tert-butyloxy group, n-pentyloxy group, n-hexyloxy group and the like are mentioned as concrete examples, and are selected within the range of the respective specified number of carbon atoms.

The term $C_a$-$C_b$ alkylcarbonyl in the present specification represents an alkyl-C(O)— group, with the aforesaid meaning that it is made up of a to b carbon atoms, and for example $CH_3C(O)$— group, $CH_3CH_2C(O)$— group, $CH_3CH_2CH_2C(O)$— group, $(CH_3)_2CHC(O)$— group, $CH_3(CH_2)_3C(O)$— group, $(CH_3)_2CHCH_2C(O)$— group, $CH_3CH_2CH(CH_3)C(O)$— group, $(CH_3)_3CC(O)$— group, $CH_3(CH_2)_4C(O)$— group, $CH_3(CH_2)_5C(O)$— group and the like are mentioned as concrete examples, and are selected within the range of the respective specified number of carbon atoms.

The term $C_a$-$C_b$ alkoxycarbonyl in the present specification represents an alkyl-O—C(O)— group, with the aforesaid meaning that it is made up of a to b carbon atoms, and for example $CH_3OC(O)$— group, $CH_3CH_2OC(O)$— group, $CH_3CH_2CH_2OC(O)$— group, $(CH_3)_2CHOC(O)$— group, $CH_3(CH_2)_3OC(O)$— group, $(CH_3)_2CHCH_2OC(O)$— group, $(CH_3)_3COC(O)$— group and the like are mentioned as concrete examples, and are selected within the range of the respective specified number of carbon atoms.

Terms such as $(C_a$-$C_b)$ alkyl optionally substituted with $R^8$ in the present specification represent an alkyl group with the aforesaid meaning that it is made up of a to b carbon atoms, wherein hydrogen atom(s) bound to carbon atoms are optionally substituted with any $R^8$, and is selected within the range of the respective specified number of carbon atoms. In that case, if 2 or more substituents Re are present on the respective $(C_a$-$C_b)$ alkyl groups, the respective $R^8$ may be the same or different.

Terms such as $(C_a$-$C_b)$ cycloalkyl optionally substituted with $R^{12}$ in the present specification represent a cycloalkyl group with the aforesaid meaning that it is made up of a to b carbon atoms, wherein hydrogen atom(s) bound to carbon atoms are optionally substituted with any $R^{12}$, and is selected within the range of the respective specified number of carbon atoms. In that case, if 2 or more substituents $R^{12}$ are present on the respective $(C_a$-$C_b)$ cycloalkyl groups, the respective $R^{12}$ may be the same or different, furthermore the substituted positions may be in a cyclic structure part or a side-chain part, or they may be in both of these.

Terms such as $(C_a$-$C_b)$ alkenyl optionally substituted with $R^{12}$ in the present specification represent an alkenyl group with the aforesaid meaning that it is made up of a to b carbon atoms, wherein hydrogen atom(s) bound to carbon atoms are optionally substituted with any $R^{12}$, and is selected within the range of the respective specified number of carbon atoms. In that case, if 2 or more substituents $R^{12}$ are present on the respective $(C_a$-$C_b)$ alkenyl groups, the respective $R^{12}$ may be the same or different.

Terms such as $(C_a$-$C_b)$ alkynyl optionally substituted with $R^{12}$ in the present specification represent an alkynyl group with the aforesaid meaning that it is made up of a to b carbon atoms, wherein hydrogen atom(s) bound to carbon atoms are optionally substituted with any $R^{12}$, and is selected within the range of the respective specified number of carbon atoms. In that case, if 2 or more substituents $R^{12}$ are present on the respective ($C_a$-$C_b$) alkynyl groups, the respective $R^{12}$ may be the same or different.

As concrete examples of the term "by $R^1$ and $R^2$ together forming a $C_2$-$C_6$ alkylene chain, $R^1$ and $R^2$ together with the linking carbon atom may form a 3-7 membered ring" in the present specification, for example cyclopropane, cyclobutane, cyclopentane, cyclohexane and the like are mentioned, and are selected within the range of the respective specified number of carbon atoms.

As Concrete Examples of the Terms

"$R^{24}$, by forming a $C_2$-$C_6$ alkylene chain together with $R^{25}$, can form a 3-7 membered ring together with the linking nitrogen atom, and in this case this alkylene chain may contain 1 oxygen atom, sulfur atom or nitrogen atom," and "$Ra^{22}$, by forming a $C_2$-$C_6$ alkylene chain together with $Ra^{23}$, can form a 3-7 membered ring together with the linking nitrogen atom, and in this case this alkylene chain may contain 1 oxygen atom, sulfur atom or nitrogen atom," in the present specification, for example aziridine, azetidine, azetidin-2-one, pyrrolidine, pyrrolidin-2-one, oxazolidine, oxazolidin-2-one, thiazolidine, thiazolidin-2-one, imidazolidine, imidazolidin-2-one, piperidine, piperidin-2-one, morpholine, tetrahydro-1,3-oxazin-2-one, thiomorpholine, tetrahydro-1,3-thiazin-2-one, piperazine, tetrahydropyrimidin-2-one, homopiperidine, homopiperidin-2-one and the like are mentioned, and are selected within the range of the respective specified number of carbon atoms.

Next, production methods for the compounds of the present invention are explained below.

Production Method A

The heterocyclic amide compounds represented by the formula (1) can for example be produced by reacting a compound represented by the formula (2) and a compound represented by the formula (3a).

[Chem. 10]

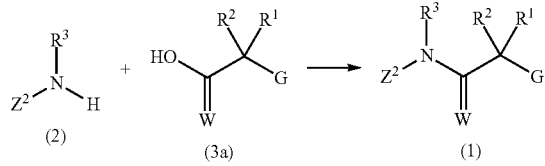

The compounds of the present invention represented by the formula (1) [in the formula, G, W, $Z^2$, $R^1$, $R^2$ and $R^3$ have the same meanings as aforesaid] can be produced by reacting compounds represented by the formula (2) [in the formula, $Z^2$ and $R^3$ have the same meanings as aforesaid] or salts thereof and compounds represented by the formula (3a) [in the formula, G, W, $R^1$ and $R^2$ have the same meanings as aforesaid] or salts thereof with or without a solvent, using a base if necessary, and a condensing agent if necessary, after addition of additives if necessary.

In this reaction, in the range from 0.1 to 100 equivalents of the compound represented by the formula (3a) per equivalent of compound represented by the formula (2) can be used.

If a solvent is used, the solvent used should be inactive in the reaction, and for example polar solvents such as N,N-dimethylformamide, N,N-dimethylacetamide, acetonitrile, dimethyl sulfoxide and 1,3-dimethyl-2-imidazolinone, ethers such as diethyl ether, tetrahydrofuran, 1,4-dioxane, 1,2-dimethoxyethane and diphenyl ether, aromatic hydrocarbons such as benzene, toluene and xylene, halogenated hydrocarbons such as methylene chloride, chloroform, carbon tetrachloride and 1,2-dichloroethane, and aliphatic hydrocarbons such as n-pentane and n-hexane are mentioned. These solvents can be used singly, or mixtures of 2 or more thereof can be used.

If a base is used, as the base used, an organic base such as triethylamine, pyridine, 4-(dimethylamino)pyridine, or an inorganic base such as potassium carbonate or sodium carbonate can be used, and in the range from 0.1 to 50 equivalents per equivalent of compound represented by the formula (2) can be used.

If a condensing agent is used, as the condensing agent used, 1H-benzotriazol-1-yloxy-tris(dimethylamino)phosphonium hexafluorophosphate, N,N'-dicyclohexylcarbodiimide, 1-(3-dimethylaminopropyl)-3-ethylcarbodiimide hydrochloride, 2-chloro-1-methyl-pyridinium iodide and the like are mentioned, and in the range from 0.1 to 50 equivalents per equivalent of compound represented by the formula (2) can be used.

If an additive is used, as the additive used, 3H-[1,2,3] triazolo[4,5-b]pyridin-3-ol, 1-hydroxybenzotriazole and the like are mentioned, and in the range from 0.1 to 50 equivalents per equivalent of compound represented by the formula (2) can be used.

The reaction temperature can be set at any temperature from −78° C. to the reflux temperature of the reaction mixture, and the reaction time varies depending on the concentrations of the reaction substrates and the reaction temperature, but can usually be set in the range from 5 minutes to 100 hours.

Some compounds represented by the formula (2) are known compounds, and some can be obtained as commercial products.

Some compounds represented by the formula (3a) are known compounds, and can be produced by publicly known methods. For example, they can easily be produced by the methods described in International Laid-open Specification 95/18113 and the like.

Production Method B

The heterocyclic amide compounds represented by the formula (1) can for example be produced by reacting a compound represented by the formula (2) and a compound represented by the formula (3b).

[Chem. 11]

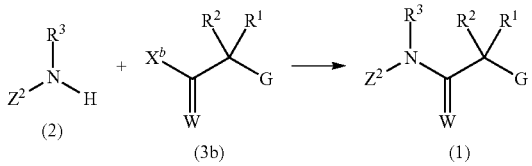

The compounds of the present invention represented by the formula (1) can be produced by reacting a compound represented by the formula (2) or salts thereof and a compound represented by the formula (3b) [in the formula, $X^b$ represents a leaving group such as a halogen atom, and G, W, $R^1$ and $R^2$ have the same meanings as aforesaid] or salts thereof with or without a solvent, using a base if necessary.

In this reaction, in the range from 0.1 to 100 equivalents of compound represented by the formula (3b) per equivalent of compound represented by the formula (2) can be used.

If a solvent is used, the solvent used should be inactive in the reaction, and for example polar solvents such as N,N-dimethylformamide, N,N-dimethylacetamide, acetonitrile, dimethyl sulfoxide and 1,3-dimethyl-2-imidazolinone, ethers such as diethyl ether, tetrahydrofuran, 1,4-dioxane, 1,2-dimethoxyethane and diphenyl ether, aromatic hydrocarbons such as benzene, toluene and xylene, halogenated hydrocarbons such as methylene chloride, chloroform, carbon tetrachloride and 1,2-dichloroethane, and aliphatic hydrocarbons such as n-pentane and n-hexane are mentioned. These solvents can be used singly, or mixtures of 2 or more thereof can be used.

If a base is used, as the base used, organic bases such as triethylamine, pyridine, 4-(dimethylamino)pyridine, 1,8-diazabicyclo[5,4,0]-7-undecene, or inorganic bases such as potassium carbonate, sodium carbonate and sodium hydride can be used, and in the range from 0.1 to 50 equivalents per equivalent of compound represented by the formula (2) can be used.

The reaction temperature can be set at any temperature from −78° C. to the reflux temperature of the reaction mixture, and the reaction time varies depending on the concentrations of the reaction substrates and the reaction temperature, but can usually be set in the range from 5 minutes to 100 hours.

Production Method C

Heterocyclic amide compounds represented by the formula (A-2) can for example be produced by reacting a compound represented by the formula (A-1) and a sulfiding agent.

[Chem. 12]

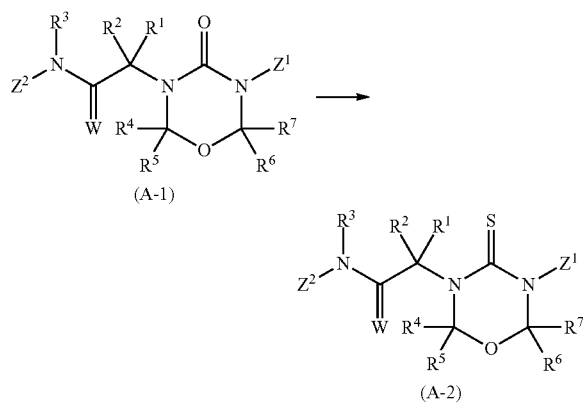

(A-1)

(A-2)

Compounds of the present invention represented by the formula (A-2) [in the formula, W, $Z^1$, $Z^2$, $R^1$, $R^2$, $R^3$, $R^4$, $R^5$, $R^6$ and $R^7$ have the same meanings as aforesaid] can be produced by reacting a compound represented by the formula (A-1) [in the formula, W, $Z^1$, $Z^2$, $R^1$, $R^2$, $R^3$, $R^4$, $R^5$, $R^6$ and $R^7$ have the same meanings as aforesaid] or salts thereof and a sulfiding agent, with or without a solvent, with addition of additive(s) if necessary.

In this reaction, in the range from 0.1 to 100 equivalents of sulfiding agent per equivalent of compound represented by the formula (A-1) can be used.

As the sulfiding agent used, for example 2,4-bis(4-methoxyphenyl)-1,3-dithia-2,4-diphosphetan-2,4-disulfide (Lawesson's reagent) and the like are mentioned.

If a solvent is used, the solvent used should be inactive in the reaction, and for example polar solvents such as N,N-dimethylformamide, N,N-dimethylacetamide, acetonitrile, dimethyl sulfoxide and 1,3-dimethyl-2-imidazolinone, ethers such as diethyl ether, tetrahydrofuran, 1,4-dioxane, 1,2-dimethoxyethane and diphenyl ether, aromatic hydrocarbons such as benzene, toluene and xylene, and aliphatic hydrocarbons such as n-pentane and n-hexane are mentioned. These solvents can be used singly, or mixtures of 2 or more thereof can be used.

If an additive is used, as the additive used, ethers such as 1,4,7,10,13,16-hexaoxacyclo-octadecane, quaternary ammonium salts such as tetra-n-butylammonium bromide and the like can be used, and in the range from 0.1 to 50 equivalents per equivalent of compound represented by the formula (A-1) can be used.

The reaction temperature can be set at any temperature from −78° C. to the reflux temperature of the reaction mixture, and the reaction time varies depending on the concentrations of the reaction substrates and the reaction temperature, but can usually be set in the range from 5 minutes to 100 hours.

In production method A to production method C, the compounds of the present invention can be obtained by normal workup of the reaction mixture after the end of the reaction, such as by concentrating directly, or concentrating after dissolving in an organic solvent and washing with water, or pouring into ice-water and concentrating after extraction with an organic solvent. Further, if purification is needed, they can be isolated and purified by any purification methods such as recrystallization, column chromatography, thin layer chromatography and liquid chromatography fractionation.

Some compounds represented by the formula (A-3) can be synthesized according to reaction scheme 1.

Reaction scheme 1

[Chem.13]

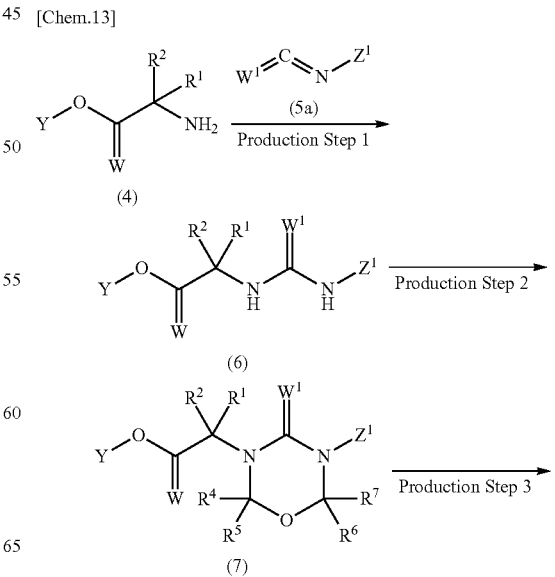

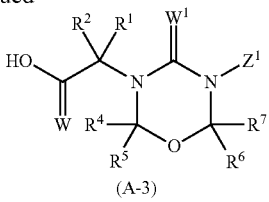

(A-3)

(Production Step 1)

Compounds represented by the formula (6) [in the formula, Y, W, $W^1$, $Z^1$, $R^1$ and $R^2$ have the same meanings as aforesaid] can be produced by reacting a compound represented by the formula (4) [in the formula, Y represents $C_1$-$C_6$ alkyl such as methyl or ethyl or benzyl group, and W, $R^1$ and $R^2$ have the same meanings as aforesaid] or salts thereof and a compound represented by the formula (5a) [in the formula, $W^1$ and $Z^1$ have the same meanings as aforesaid] or salts thereof, with or without a solvent, using a base if necessary.

In this reaction, in the range from 0.1 to 100 equivalents of compound represented by the formula (5a) can be used per equivalent of compound represented by the formula (4).

If a solvent is used, the solvent used should be inactive in the reaction, and for example polar solvents such as N,N-dimethylformamide, N,N-dimethylacetamide, acetonitrile, dimethyl sulfoxide and 1,3-dimethyl-2-imidazolinone, ethers such as diethyl ether, tetrahydrofuran, 1,4-dioxane, 1,2-dimethoxyethane and diphenyl ether, aromatic hydrocarbons such as benzene, toluene and xylene, halogenated hydrocarbons such as methylene chloride, chloroform, carbon tetrachloride and 1,2-dichloroethane, and aliphatic hydrocarbons such as n-pentane and n-hexane are mentioned. These solvents can be used singly, or mixtures of 2 or more thereof can be used.

If a base is used, as the base used, organic bases such as triethylamine, pyridine, 4-(dimethylamino)pyridine and diisopropylethylamine, or inorganic bases such as potassium carbonate and sodium carbonate can be used, and in the range from 0.1 to 50 equivalents per equivalent of compound represented by the formula (4) can be used.

The reaction temperature can be set at any temperature from −78° C. to the reflux temperature of the reaction mixture, and the reaction time varies depending on the concentrations of the reaction substrates and the reaction temperature, but can usually be set in the range from 5 minutes to 100 hours.

Compounds represented by the formula (6) can be obtained by normal workup of the reaction mixture after the end of the reaction, by concentrating directly, or concentrating after dissolving in an organic solvent and washing with water, or pouring into ice-water and concentrating after extraction with an organic solvent. Further, if purification is needed, they can be isolated and purified by any purification methods such as recrystallization, column chromatography, thin layer chromatography and liquid chromatography fractionation.

Further, the compounds represented by the formula (6) produced by this method can be used as such in the next step reaction without isolation and purification.

Some compounds represented by the formula (4) and the formula (5a) are known compounds, and some can be obtained as commercial products.

(Production Step 2)

Compounds represented by the formula (7) [in the formula, Y, W, $W^1$, $Z^1$, $R^1$, $R^2$, $R^4$, $R^5$, $R^6$ and $R^7$ have the same meanings as aforesaid] can be produced by reacting a compound represented by the formula (6) or salts thereof and formaldehyde, with or without a solvent, using an acid if necessary.

In this reaction, in the range from 0.1 to 100 equivalents of formaldehyde per equivalent of compound represented by the formula (6) can be used.

As the formaldehyde used, for example formalin, paraformaldehyde and the like are mentioned.

If a solvent is used, the solvent used should be inactive in the reaction, and for example polar solvents such as N,N-dimethylformamide, N,N-dimethylacetamide, acetonitrile, dimethyl sulfoxide and 1,3-dimethyl-2-imidazolinone, aromatic hydrocarbons such as benzene, toluene and xylene, halogenated hydrocarbons such as methylene chloride, chloroform, carbon tetrachloride and 1,2-dichloroethane, and aliphatic hydrocarbons such as n-pentane and n-hexane are mentioned. These solvents can be used singly, or mixtures of 2 or more thereof can be used.

If an acid is used, as the acid used, hydrochloric acid, sulfuric acid, formic acid, acetic acid, trifluoroacetic acid, methanesulfonic acid and the like can be used, and in the range from 0.1 to 100 equivalents per equivalent of compound represented by the formula (6) can be used.

The reaction temperature can be set at any temperature from −78° C. to the reflux temperature of the reaction mixture, and the reaction time varies depending on the concentrations of the reaction substrates and the reaction temperature, but can usually be set in the range from 5 minutes to 100 hours.

The compounds represented by the formula (7) can be obtained by normal workup of the reaction mixture after the end of the reaction, by concentrating directly, or concentrating after dissolving in an organic solvent and washing with water, or pouring into ice-water and concentrating after extraction with an organic solvent. Further, if purification is needed, they can be isolated and purified by any purification methods such as recrystallization, column chromatography, thin layer chromatography and liquid chromatography fractionation.

Further, the compounds represented by the formula (7) produced by this method can be used as such in the next step reaction without isolation and purification.

(Production Step 3)

Compounds represented by the formula (A-3) [in the formula, W, $W^1$, $Z^1$, $R^1$, $R^2$, $R^4$, $R^5$, $R^6$ and $R^7$ have the same meanings as aforesaid] can be produced by reacting a compound represented by the formula (7) or salts thereof and a base, with or without a solvent.

As the base used, organic bases such as triethylamine, pyridine and 4-(dimethylamino)pyridine, or inorganic bases such as potassium carbonate, sodium carbonate, potassium hydroxide or sodium hydroxide can be used, and in the range from 0.1 to 100 equivalents per equivalent of compound represented by the formula (7) can be used.

If a solvent is used, the solvent used should be inactive in the reaction, and for example polar solvents such as N,N-dimethylformamide, N,N-dimethylacetamide, acetonitrile, dimethyl sulfoxide, 1,3-dimethyl-2-imidazolinone and water, ethers such as diethyl ether, tetrahydrofuran, 1,4-dioxane, 1,2-dimethoxyethane and diphenyl ether, alcohols such as methanol and ethanol, aromatic hydrocarbons such as benzene, toluene and xylene, and aliphatic hydrocarbons such as n-pentane and n-hexane are mentioned. These solvents can be used singly, or mixtures of 2 or more thereof can be used.

The reaction temperature can be set at any temperature from −78° C. to the reflux temperature of the reaction mixture, and the reaction time varies depending on the concentrations of the reaction substrates and the reaction temperature, but can usually be set in the range from 5 minutes to 100 hours.

The production intermediates which are the starting materials for production method A can be obtained by normal workup of the reaction mixture after the end of the reaction, by concentrating directly, or concentrating after dissolving in an organic solvent and washing with water, or pouring into ice-water and concentrating after extraction with an organic solvent. Further, if purification is needed, they can be isolated and purified by any purification methods such as recrystallization, column chromatography, thin layer chromatography and liquid chromatography fractionation.

Further, the production intermediates produced by this method can be used as such in the next step reaction without isolation and purification.

Some compounds represented by the formula (6) can be synthesized according to reaction scheme 2 shown below.

Reaction scheme 2

[Chem.14]

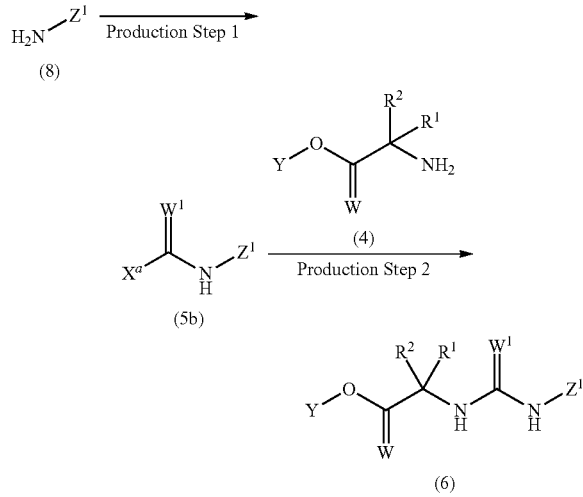

(Production Step 1)

Compounds represented by the formula (5b) [in the formula, $X^a$ represents a leaving group such as chlorine atom, 1-imidazolyl, 4-nitrophenoxy or trichloromethoxy, and $W^1$ and $Z^1$ have the same meanings as aforesaid] can be produced by reacting a compound represented by the formula (8) [in the formula, $Z^1$ has the same meanings as aforesaid] or salts thereof and a carbonylating agent, with or without a solvent, using a base if necessary.

In this reaction, in the range from 0.1 to 100 equivalents of carbonylating agent per equivalent of compound represented by the formula (8) can be used.

As the carbonylating agent used, for example, triphosgene, 1,1'-carbonyldiimidazole, (4-nitrophenyl) chloroformate and the like are mentioned.

If a solvent is used, the solvent used should be inactive in the reaction, and for example polar solvents such as N,N-dimethylformamide, N,N-dimethylacetamide, acetonitrile, dimethyl sulfoxide and 1,3-dimethyl-2-imidazolinone, ethers such as diethyl ether, tetrahydrofuran, 1,4-dioxane, 1,2-dimethoxyethane and diphenyl ether, aromatic hydrocarbons such as benzene, toluene and xylene, halogenated hydrocarbons such as methylene chloride, chloroform, carbon tetrachloride and 1,2-dichloroethane, and aliphatic hydrocarbons such as n-pentane and n-hexane are mentioned. These solvents can be used singly, or mixtures of 2 or more thereof can be used.

If a base is used, as the base used, organic bases such as triethylamine, pyridine, 4-(dimethylamino)pyridine and diisopropylethylamine, or inorganic bases such as potassium carbonate and sodium carbonate can be used, and in the range from 0.1 to 50 equivalents per equivalent of compound represented by the formula (8) can be used.

The reaction temperature can be set at any temperature from −78° C. to the reflux temperature of the reaction mixture, and the reaction time varies depending on the concentrations of the reaction substrates and the reaction temperature, but can usually be set in the range from 5 minutes to 100 hours.

The compounds represented by the formula (5b) can be obtained by normal workup of the reaction mixture after the end of the reaction, by concentrating directly, or concentrating after dissolving in an organic solvent and washing with water, or pouring into ice-water and concentrating after extraction with an organic solvent. Further, if purification is needed, they can be isolated and purified by any purification methods such as recrystallization, column chromatography, thin layer chromatography and liquid chromatography fractionation.

Further, the compounds represented by the formula (5b) produced by this method can be used as such in the next step reaction without isolation and purification.

Some compounds represented by the formula (8) are known compounds, and some can be obtained as commercial products.

(Production Step 2)

Compounds represented by the formula (6) can be produced by reacting a compound represented by the formula (5b) or salts thereof and a compound represented by the formula (4) or salts thereof, with or without a solvent, using a base if necessary.

In this reaction, in the range from 0.1 to 100 equivalents of compound represented by the formula (4) per equivalent of compound represented by the formula (5b) can be used.

If a solvent is used, the solvent used should be inactive in the reaction, and for example polar solvents such as N,N-dimethylformamide, N,N-dimethylacetamide, acetonitrile, dimethyl sulfoxide and 1,3-dimethyl-2-imidazolinone, ethers such as diethyl ether, tetrahydrofuran, 1,4-dioxane, 1,2-dimethoxyethane and diphenyl ether, aromatic hydrocarbons such as benzene, toluene and xylene, halogenated hydrocarbons such as methylene chloride, chloroform, carbon tetrachloride and 1,2-dichloroethane, and aliphatic hydrocarbons such as n-pentane and n-hexane are mentioned. These solvents can be used singly, or mixtures of 2 or more thereof can be used.

If a base is used, as the base used, organic bases such as triethylamine, pyridine, 4-(dimethylamino)pyridine and diisopropylethylamine, or inorganic bases such as potassium carbonate and sodium carbonate can be used, and in the range from 0.1 to 50 equivalents per equivalent of compound represented by the formula (5b) can be used.

The reaction temperature can be set at any temperature from −78° C. to the reflux temperature of the reaction mixture, and the reaction time varies depending on the concentrations of the reaction substrates and the reaction temperature, but can usually be set in the range from 5 minutes to 100 hours.

The compounds represented by the formula (6) can be obtained by normal workup of the reaction mixture after the end of the reaction, by concentrating directly, or concentrating after dissolving in an organic solvent and washing with water, or pouring into ice-water and concentrating after extraction with an organic solvent. Further, if purification is needed, they can be isolated and purified by any purification methods such as recrystallization, column chromatography, thin layer chromatography and liquid chromatography fractionation.

Further, the compounds represented by the formula (6) produced by this method can be used as such in the next step reaction without isolation and purification.

Some compounds represented by the formula (B-3) can be synthesized according to reaction scheme 3 shown below.

Reaction scheme 3

[Chem.15]

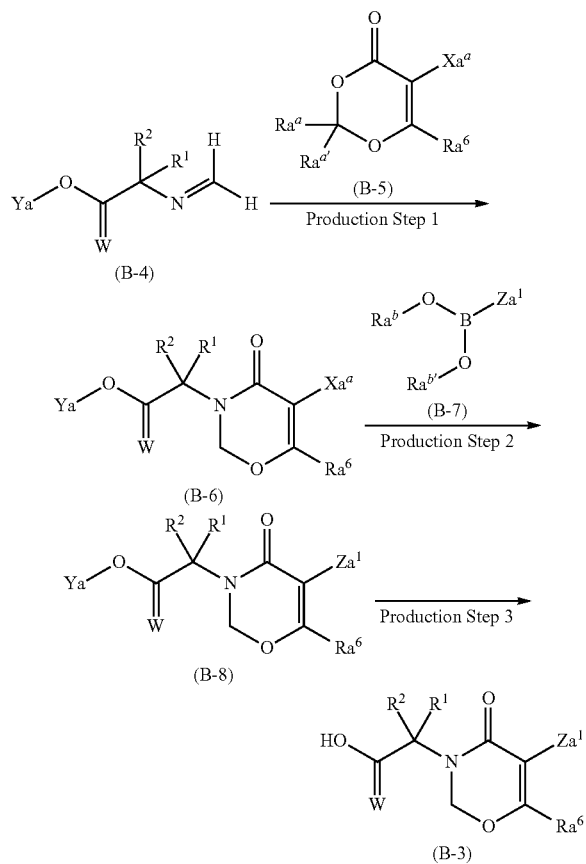

(Production Step 1)

Compounds represented by the formula (B-6) [in the formula, $Xa^a$, Ya, W, $R^1$, $R^2$ and $Ra^6$ have the same meanings as aforesaid] can be produced by reacting a compound represented by the formula (B-4) [in the formula, Ya represents $C_1$-$C_6$ alkyl such as methyl or ethyl or $C_1$-$C_6$ alkyl substituted with phenyl or p-nitrophenyl or the like, and W, $R^1$ and $R^2$ have the same meanings as aforesaid] or salts thereof and a compound represented by the formula (B-5) [in the formula, $Xa^a$ represents a halogen atom such as bromine atom or iodine atom, $Ra^a$ and $Ra^{a\prime}$ represent $C_1$-$C_6$ alkyl such as methyl, and $Ra^6$ has the same meanings as aforesaid] or salts thereof, with or without a solvent, using an acid if necessary.

In this reaction, in the range from 0.1 to 100 equivalents of compound represented by the formula (B-5) per equivalent of compound represented by the formula (B-4) can be used.

If a solvent is used, the solvent used should be inactive in the reaction, and for example polar solvents such as N,N-dimethylformamide, N,N-dimethylacetamide, acetonitrile, dimethyl sulfoxide and 1,3-dimethyl-2-imidazolinone, ethers such as diethyl ether, tetrahydrofuran, 1,4-dioxane, 1,2-dimethoxyethane and diphenyl ether, aromatic hydrocarbons such as benzene, toluene and xylene, halogenated hydrocarbons such as methylene chloride, chloroform, carbon tetrachloride and 1,2-dichloroethane, and aliphatic hydrocarbons such as n-pentane and n-hexane are mentioned. These solvents can be used singly, or mixtures of 2 or more thereof can be used.

If an acid is used, as the acid used, hydrochloric acid, sulfuric acid, formic acid, acetic acid, trifluoroacetic acid, methanesulfonic acid and the like can be used, and in the range from 0.1 to 100 equivalents per equivalent of compound represented by the formula (B-4) can be used.

The reaction temperature can be set at any temperature from −78° C. to the reflux temperature of the reaction mixture, and the reaction time varies depending on the concentrations of the reaction substrates and the reaction temperature, but can usually be set in the range from 5 minutes to 100 hours.

The compounds represented by the formula (B-4) can be obtained by normal workup of the reaction mixture after the end of the reaction, by concentrating directly, or concentrating after dissolving in an organic solvent and washing with water, or pouring into ice-water and concentrating after extraction with an organic solvent. Further, if purification is needed, they can be isolated and purified by any purification methods such as recrystallization, column chromatography, thin layer chromatography and liquid chromatography fractionation.

Further, the compounds represented by the formula (B-6) produced by this method can be used as such in the next step reaction without isolation and purification.

Some compounds represented by the formula (B-4) are known compounds, and can be produced by publicly known methods. For example, they can easily be produced by the methods described in International Laid-open Specification 95/18113 and the like.

Some compounds represented by the formula (B-5) are known compounds, and can be produced by publicly known methods. For example, they can easily be produced by the methods described in Japanese Laid-Open Specification 4-89485 and the like.

(Production Step 2)

Compounds represented by the formula (B-8) [in the formula, Ya, $Za^1$, W, $R^1$, $R^2$ and $Ra^6$ have the same meanings as aforesaid] can be produced by reacting a compound represented by the formula (B-6) or salts thereof and a compound represented by the formula (B-7) [in the formula, $Ra^b$ and $Ra^{b\prime}$ represent hydrogen atom or $C_1$-$C_6$ alkyl such as methyl, and $Za^1$ has the same meanings as aforesaid] or salts thereof, with or without a solvent, using a base if necessary, and a catalyst if necessary, after addition of additives if necessary.

In this reaction, in the range from 0.1 to 100 equivalents of compound represented by the formula (B-7) per equivalent of compound represented by the formula (B-6) can be used.

If a solvent is used, the solvent used should be inactive in the reaction, and for example polar solvents such as N,N- dimethylformamide, N,N-dimethylacetamide, acetonitrile, dimethyl sulfoxide and 1,3-dimethyl-2-imidazolinone and water, ethers such as diethyl ether, tetrahydrofuran, 1,4-dioxane, 1,2-dimethoxyethane and diphenyl ether, alcohols such as methanol and ethanol, aromatic hydrocarbons such as benzene, toluene and xylene, halogenated hydrocarbons such as methylene chloride, chloroform, carbon tetrachloride and 1,2-dichloroethane, and aliphatic hydrocarbons such as n-pentane and n-hexane are mentioned. These solvents can be used singly, or mixtures of 2 or more thereof can be used.

If a base is used, as the base used, organic bases such as triethylamine, pyridine, 4-(dimethylamino)pyridine and diisopropylethylamine, or inorganic bases such as potassium carbonate and sodium carbonate can be used, and in the range from 0.1 to 50 equivalents per equivalent of compound represented by the formula (B-6) can be used.

If a catalyst is used, as the catalyst used, complex catalysts such as dichlorobis(triphenyl-phosphine)palladium, tetrakis(triphenyl-phosphine)palladium and [1,3-bis(2,6-diisopropyl-phenyl)imidazol-2-ylidene] (3-chloropyridyl)palladium (2) dichloride are mentioned, and in the range from 0.001 to 0.5 equivalents per equivalent of compound represented by the formula (B-6) can be used.

If an additive is used, as the additive used, ethers such as 1,4,7,10,13,16-hexaoxa-cyclooctadecane, quaternary ammonium salts such as tetra-n-butylammonium bromide and the like can be used, and in the range from 0.1 to 50 equivalents per equivalent of compound represented by the formula (B-6) can be used.

The reaction temperature can be set at any temperature from −78° C. to the reflux temperature of the reaction mixture, and the reaction time varies depending on the concentrations of the reaction substrates and the reaction temperature, but can usually be set in the range from 5 minutes to 100 hours.

The compounds represented by the formula (B-8) can be obtained by normal workup of the reaction mixture after the end of the reaction, by concentrating directly, or concentrating after dissolving in an organic solvent and washing with water, or pouring into ice-water and concentrating after extraction with an organic solvent. Further, if purification is needed, they can be isolated and purified by any purification methods such as recrystallization, column chromatography, thin layer chromatography and liquid chromatography fractionation.

Further, the compounds represented by the formula (B-8) produced by this method can be used as such in the next step reaction without isolation and purification.

Some compounds represented by the formula (B-7) are known compounds, and some can be obtained as commercial products.

(Production Step 3)

The compounds represented by the formula (B-3) [in the formula, W, $Za^1$, $R^1$, $R^2$ and $Ra^6$ have the same meanings as aforesaid] can be produced by reacting a compound represented by the formula (B-8) or salts thereof and a base, with or without a solvent.

As the base used, organic bases such as triethylamine, pyridine and 4-(dimethylamino)pyridine, or inorganic bases such as potassium carbonate, sodium carbonate, potassium hydroxide and sodium hydroxide can be used, and in the range from 0.1 to 100 equivalents per equivalent of compound represented by the formula (B-8) can be used.

If a solvent is used, the solvent used should be inactive in the reaction, and for example polar solvents such as N,N-dimethylformamide, N,N-dimethylacetamide, acetonitrile, dimethyl sulfoxide and 1,3-dimethyl-2-imidazolinone and water, ethers such as diethyl ether, tetrahydrofuran, 1,4-dioxane, 1,2-dimethoxyethane and diphenyl ether, alcohols such as methanol and ethanol, aromatic hydrocarbons such as benzene, toluene and xylene, and aliphatic hydrocarbons such as n-pentane and n-hexane are mentioned. These solvents can be used singly, or mixtures of 2 or more thereof can be used.

The reaction temperature can be set at any temperature from −78° C. to the reflux temperature of the reaction mixture, and the reaction time varies depending on the concentrations of the reaction substrates and the reaction temperature, but can usually be set in the range from 5 minutes to 100 hours.

The production intermediates which are the starting materials for production method A can be obtained by normal workup of the reaction mixture after the end of the reaction, by concentrating directly, or concentrating after dissolving in an organic solvent and washing with water, or pouring into ice-water and concentrating after extraction with an organic solvent. Further, if purification is needed, they can be isolated and purified by any purification methods such as recrystallization, column chromatography, thin layer chromatography and liquid chromatography fractionation.

Further, the production intermediates produced by this method can be used as such in the next step reaction without isolation and purification.

Some compounds represented by the formula (B-8) can be synthesized according to reaction scheme 4, shown below.

Reaction scheme 4

[Chem. 16]

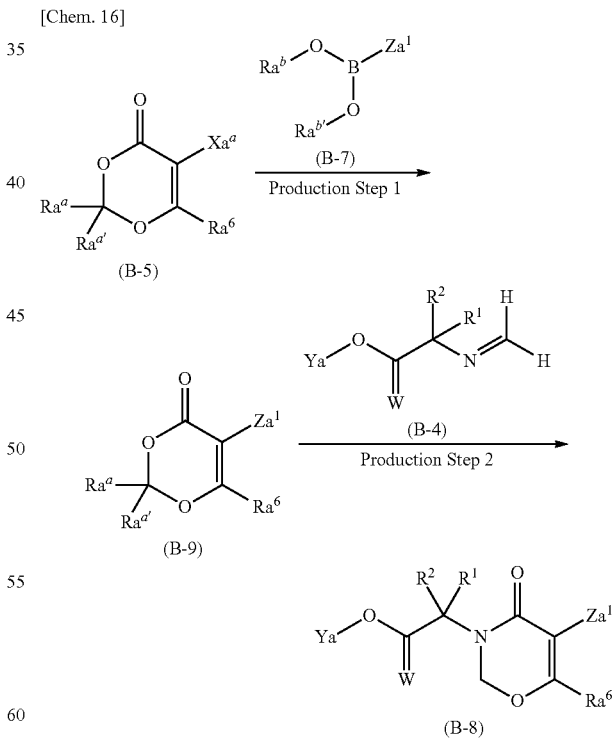

(Production Step 1)

Compounds represented by the formula (B-9) [in the formula, $Za^1$, $Ra^a$, $Ra^{a'}$ and $Ra^6$ have the same meanings as aforesaid] can be produced by reacting a compound represented by the formula (B-5) or salts thereof and a compound represented by the formula (B-7) or salts thereof, with or without a solvent, using a base if necessary, and a catalyst if necessary, after addition of additives if necessary.

In this reaction, in the range from 0.1 to 100 equivalents of compound represented by the formula (B-7) per equivalent of compound represented by the formula (B-5) can be used.

If a solvent is used, the solvent used should be inactive in the reaction, and for example polar solvents such as N,N-dimethylformamide, N,N-dimethylacetamide, acetonitrile, dimethyl sulfoxide and 1,3-dimethyl-2-imidazolinone and water, ethers such as diethyl ether, tetrahydrofuran, 1,4-dioxane, 1,2-dimethoxyethane and diphenyl ether, alcohols such as methanol and ethanol, aromatic hydrocarbons such as benzene, toluene and xylene, halogenated hydrocarbons such as methylene chloride, chloroform, carbon tetrachloride and 1,2-dichloroethane, and aliphatic hydrocarbons such as n-pentane and n-hexane are mentioned. These solvents can be used singly, or mixtures of 2 or more thereof can be used.

If a base is used, as the base used, organic bases such as triethylamine, pyridine, 4-(dimethylamino)pyridine and diisopropylethylamine, or inorganic bases such as potassium carbonate and sodium carbonate can be used, and in the range from 0.1 to 50 equivalents per equivalent of compound represented by the formula (B-5) can be used.

If a catalyst is used, as the catalyst used, complex catalysts such as dichlorobis(triphenylphosphine)palladium, tetrakis(triphenylphosphine)-palladium and [1,3-bis(2,6-diisopropylphenyl)-imidazol-2-ylidene](3-chloropyridyl)palladium (2) dichloride are mentioned, in the range from 0.001 to 0.5 equivalents per equivalent of compound represented by the formula (B-5) can be used.

If an additive is used, as the additive used, ethers such as 1,4,7,10,13,16-hexaoxa-cyclooctadecane, quaternary ammonium salts such as tetra-n-butylammonium bromide and the like can be used, in the range from 0.1 to 50 equivalents per equivalent of compound represented by the formula (B-5) can be used.

The reaction temperature can be set at any temperature from −78° C. to the reflux temperature of the reaction mixture, and the reaction time varies depending on the concentrations of the reaction substrates and the reaction temperature, but can usually be set in the range from 5 minutes to 100 hours.

The compounds represented by the formula (B-9) can be obtained by normal workup of the reaction mixture after the end of the reaction, by concentrating directly, or concentrating after dissolving in an organic solvent and washing with water, or pouring into ice-water and concentrating after extraction with an organic solvent. Further, if purification is needed, they can be isolated and purified by any purification methods such as recrystallization, column chromatography, thin layer chromatography and liquid chromatography fractionation.

Further, the compounds represented by the formula (B-9) produced by this method can be used as such in the next step reaction without isolation and purification.

(Production Step 2)

Compounds represented by the formula (B-8) can be produced by reacting a compound represented by the formula (B-4) or salts thereof with a compound represented by the formula (B-9) or salts thereof, with or without a solvent, using an acid if necessary.

In this reaction, in the range from 0.1 to 100 equivalents of compound represented by the formula (B-9) per equivalent of compound represented by the formula (B-4) can be used.

If a solvent is used, the solvent used should be inactive in the reaction, and for example polar solvents such as N,N-dimethylformamide, N,N-dimethylacetamide, acetonitrile, dimethyl sulfoxide and 1,3-dimethyl-2-imidazolinone, ethers such as diethyl ether, tetrahydrofuran, 1,4-dioxane, 1,2-dimethoxyethane and diphenyl ether, aromatic hydrocarbons such as benzene, toluene and xylene, halogenated hydrocarbons such as methylene chloride, chloroform, carbon tetrachloride and 1,2-dichloroethane, and aliphatic hydrocarbons such as n-pentane and n-hexane are mentioned. These solvents can be used singly, or mixtures of 2 or more thereof can be used.

If an acid is used, as the acid used, hydrochloric acid, sulfuric acid, formic acid, acetic acid, trifluoroacetic acid, methanesulfonic acid and the like can be used, and in the range from 0.1 to 100 equivalents per equivalent of compound represented by the formula (B-4) can be used.

The reaction temperature can be set at any temperature from −78° C. to the reflux temperature of the reaction mixture, and the reaction time varies depending on the concentrations of the reaction substrates and the reaction temperature, but can usually be set in the range from 5 minutes to 100 hours.

The compounds represented by the formula (B-8) can be obtained by normal workup of the reaction mixture after the end of the reaction, by concentrating directly, or concentrating after dissolving in an organic solvent and washing with water, or pouring into ice-water and concentrating after extraction with an organic solvent. Further, if purification is needed, they can be isolated and purified by any purification methods such as recrystallization, column chromatography, thin layer chromatography and liquid chromatography fractionation.

Further, the compounds represented by the formula (B-8) produced by this method can be used as such in the next step reaction without isolation and purification.

Some compounds represented by the formula (B-9) can be synthesized according to reaction scheme 5, shown below.

Reaction scheme 5

[Chem.17]

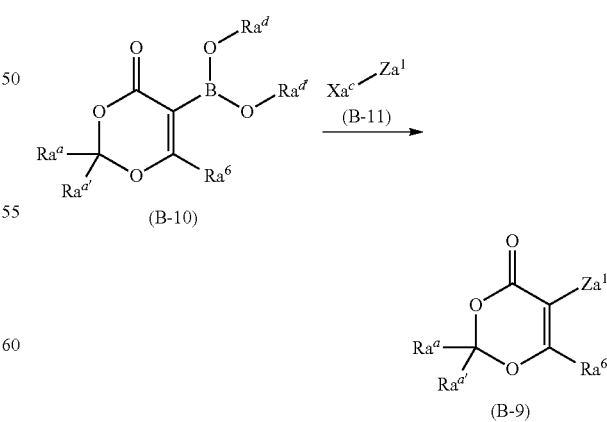

Compounds represented by the formula (B-9) can be produced by reacting a compound represented by the formula (B-10) [in the formula, $Ra^d$ and $Ra^{d'}$ represent hydrogen atom or $C_1$-$C_6$ alkyl such as methyl, and $Ra^a$, $Ra^{a'}$ and $Ra^6$ have the same meanings as aforesaid] or salts thereof and a compound represented by the formula (B-11) [in the formula, $Xa^c$ represents a halogen atom such as a bromine atom or iodine atom, and $Za^1$ has the same meanings as aforesaid] or salts thereof, with or without a solvent, using a base if necessary, and a solvent if necessary, after addition of additives if necessary.

In this reaction, in the range from 0.1 to 100 equivalents of compound represented by the formula (B-11) per equivalent of compound represented by the formula (B-10) can be used.

If a solvent is used, the solvent used should be inactive in the reaction, and for example polar solvents such as N,N-dimethylformamide, N,N-dimethylacetamide, acetonitrile, dimethyl sulfoxide and 1,3-dimethyl-2-imidazolinone and water, ethers such as diethyl ether, tetrahydrofuran, 1,4-dioxane, 1,2-dimethoxyethane and diphenyl ether, alcohols such as methanol and ethanol, aromatic hydrocarbons such as benzene, toluene and xylene, halogenated hydrocarbons such as methylene chloride, chloroform, carbon tetrachloride and 1,2-dichloroethane, and aliphatic hydrocarbons such as n-pentane and n-hexane are mentioned. These solvents can be used singly, or mixtures of 2 or more thereof can be used.

If a base is used, as the base used, organic bases such as triethylamine, pyridine, 4-(dimethylamino)pyridine and diisopropylethylamine, or inorganic bases such as potassium carbonate and sodium carbonate can be used, and in the range from 0.1 to 50 equivalents per equivalent of compound represented by the formula (B-10) can be used.

If a catalyst is used, as the catalyst used, complex catalysts such as dichlorobis(triphenylphosphine)palladium, tetrakis(triphenylphosphine)palladium and [1,3-bis(2,6-diisopropylphenyl)imidazol-2-ylidene] (3-chloropyridyl)palladium(2) dichloride are mentioned, and in the range from 0.001 to 0.5 equivalents per equivalent of compound represented by the formula (B-10) can be used.

If an additive is used, as the additive used, ethers such as 1,4,7,10,13,16-hexaoxa-cyclooctadecane, quaternary ammonium salts such as tetra-n-butylammonium bromide and the like can be used, and in the range from 0.1 to 50 equivalents per equivalent of compound represented by the formula (B-10) can be used.

The reaction temperature can be set at any temperature from −78° C. to the reflux temperature of the reaction mixture, and the reaction time varies depending on the concentrations of the reaction substrates and the reaction temperature, but can usually be set in the range from 5 minutes to 100 hours.

The compounds represented by the formula (B-9) can be obtained by normal workup of the reaction mixture after the end of the reaction, by concentrating directly, or concentrating after dissolving in an organic solvent and washing with water, or pouring into ice-water and concentrating after extraction with an organic solvent. Further, if purification is needed, they can be isolated and purified by any purification methods such as recrystallization, column chromatography, thin layer chromatography and liquid chromatography fractionation.

Further, the compounds represented by the formula (B-9) produced by this method can be used as such in the next step reaction without isolation and purification.

Some compounds represented by the formula (B-10) are known compounds, and can be produced by publicly known methods. For example, they can easily be produced by the methods described in Organic Letters, 2006, Vol. 8, p. 305.

Some compounds represented by the formula (B-11) are known compounds, and some can be obtained as commercial products.

Some compounds represented by the formula (3b) can be synthesized according to reaction scheme 6, shown below.

Reaction Scheme 6

[Chem.18]

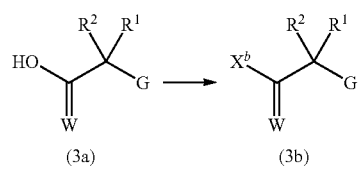

(3a)        (3b)

Compounds represented by the formula (3b) can be produced by reacting a compound represented by the formula (3a) or salts thereof and a halogenating agent, with or without a solvent, using a base if necessary.

As the halogenating agent used, for example thionyl chloride, oxalyl chloride, phosphoryl chloride and the like are mentioned. As regards equivalents of halogenating agent, in the range from 0.1 to 100 equivalents per equivalent of compound represented by the formula (3a) can be used.

If a solvent is used, the solvent used should be inactive in the reaction, and for example polar solvents such as N,N-dimethylformamide, N,N-dimethylacetamide, acetonitrile, dimethyl sulfoxide and 1,3-dimethyl-2-imidazolinone, ethers such as diethyl ether, tetrahydrofuran, 1,4-dioxane, 1,2-dimethoxyethane and diphenyl ether, aromatic hydrocarbons such as benzene, toluene and xylene, halogenated hydrocarbons such as methylene chloride, chloroform, carbon tetrachloride and 1,2-dichloroethane, and aliphatic hydrocarbons such as n-pentane and n-hexane are mentioned. These solvents can be used singly, or mixtures of 2 or more thereof can be used.

If a base is used, as the base used, organic bases such as triethylamine, pyridine and 4-(dimethylamino)pyridine, or inorganic bases such as potassium carbonate and sodium carbonate can be used, and in the range from 0.1 to 50 equivalents per equivalent of compound represented by the formula (3a) can be used. These bases can be used singly, or mixtures of 2 or more thereof can be used.

The reaction temperature can be set at any temperature from −78° C. to the reflux temperature of the reaction mixture, and the reaction time varies depending on the concentrations of the reaction substrates and the reaction temperature, but can usually be set in the range from 5 minutes to 100 hours.

The production intermediates which are the starting materials for production method B can be obtained by normal workup after the end of the reaction.

Further, the production intermediates produced by this method can be used as such in the next step reaction without isolation and purification.

As active compounds included in the present invention, the compounds shown in table No. 1 to table No. 2 are mentioned. However, the compounds of table No. 1 to table No. 2 are for illustration, and the present invention is not limited only to these. Also, in the tables, the term Me represents a methyl group, and similarly below, Et represents ethyl group, Pr propyl group, OMe methoxy group, OEt ethoxy group, OPh phenoxy group, SMe methylthio group, Ph phenyl group, CO$_2$Me methoxycarbonyl group, n-normal, i-iso and c-cyclo respectively.
In the tables, the structures of the aromatic heterocyclic rings represented by J-1 to J-119 and Ja-1 to Ja-85 respectively are shown below.
[Chem. 19]
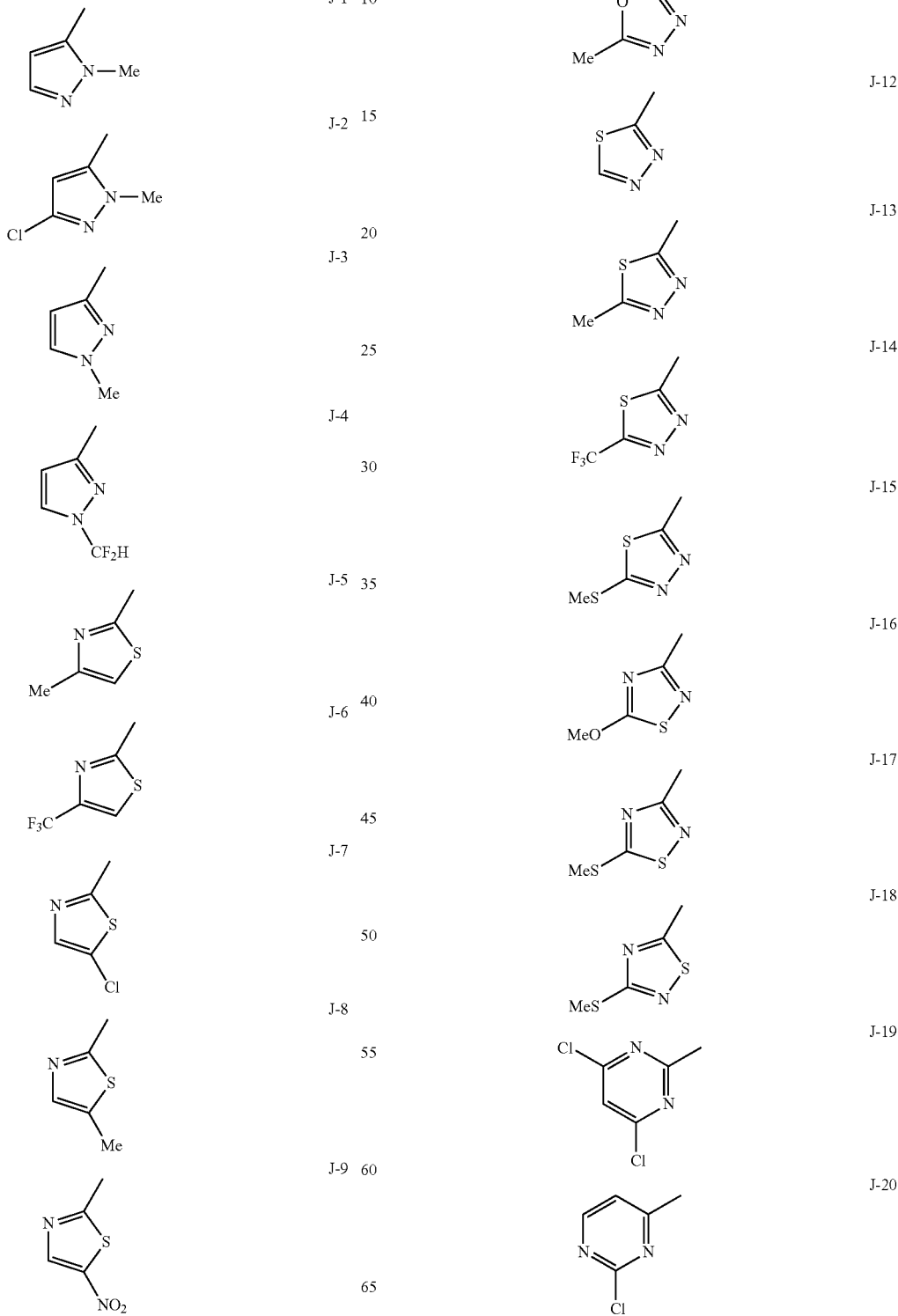

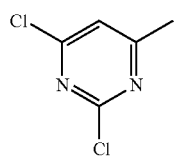 J-21
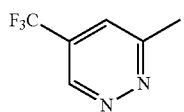 J-22
[Chem. 20]
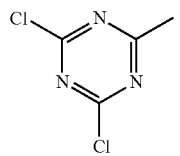 J-23
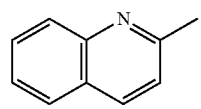 J-24
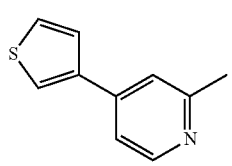 J-25
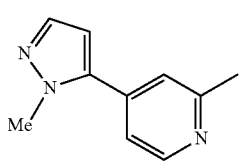 J-26
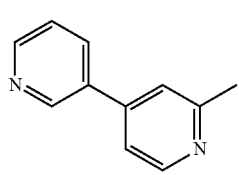 J-27
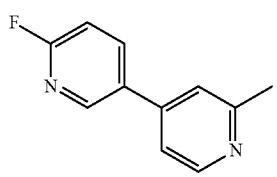 J-28
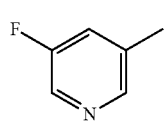 J-29
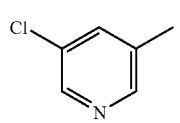 J-30
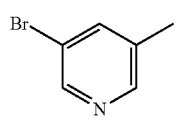 J-31
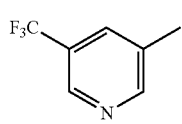 J-32
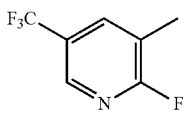 J-33
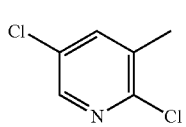 J-34
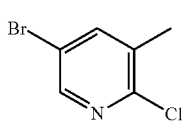 J-35
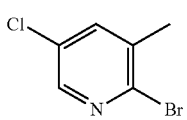 J-36
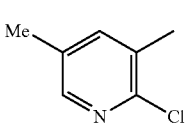 J-37
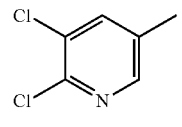 J-38
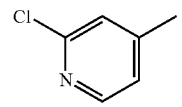 J-39
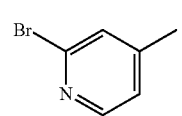 J-40
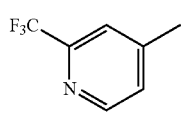 J-41
J-42
J-43

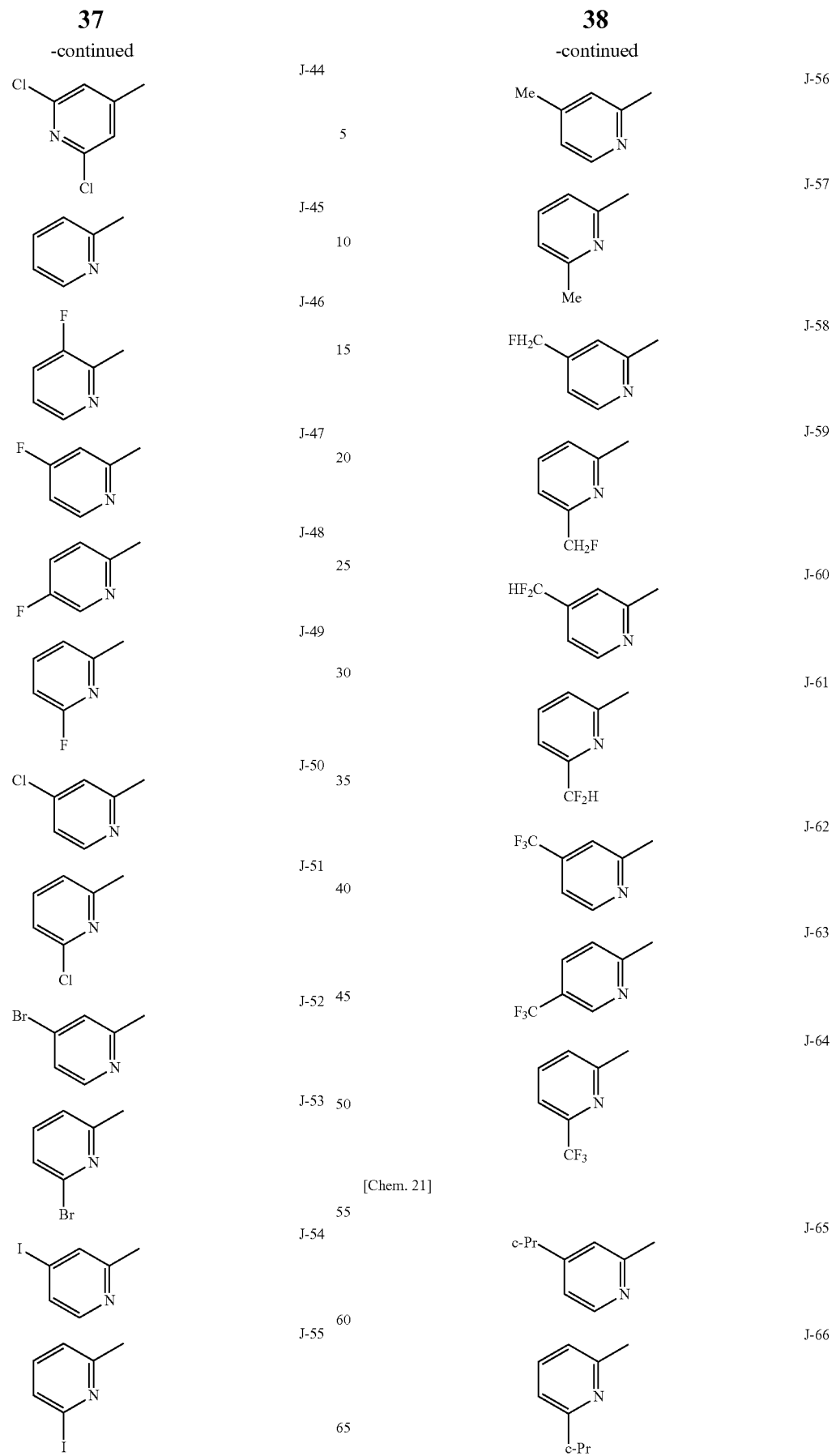

-continued
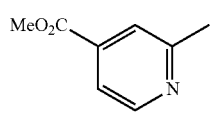 J-67
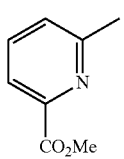 J-68
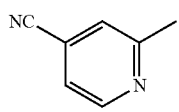 J-69
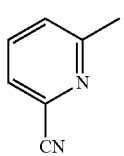 J-70
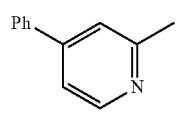 J-71
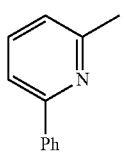 J-72
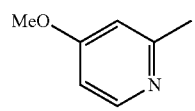 J-73
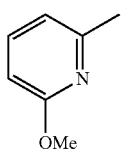 J-74
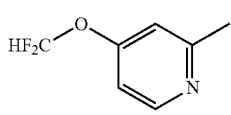 J-75
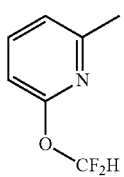 J-76
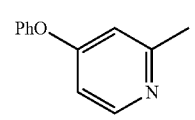 J-77
-continued
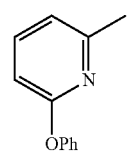 J-78
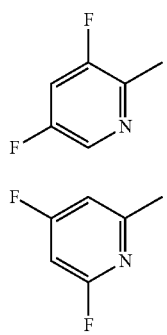 J-79
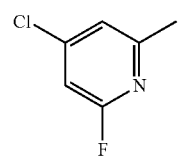 J-80
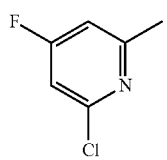 J-81
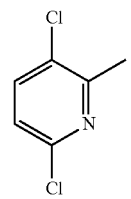 J-82
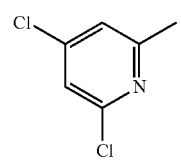 J-83
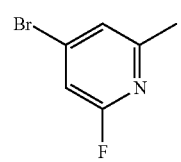 J-84
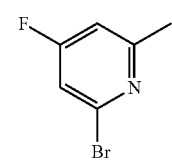 J-85
J-86

-continued
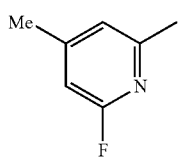 J-87
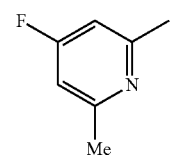 J-88
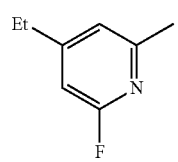 J-89
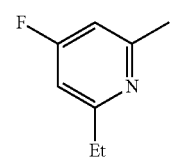 J-90
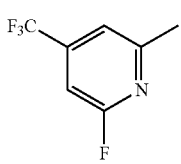 J-91
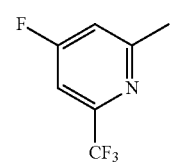 J-92
[Chem. 22]
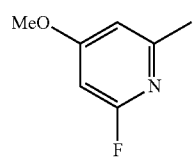 J-93
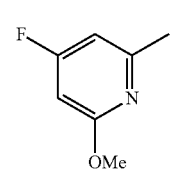 J-94
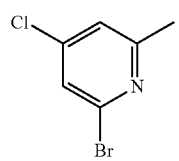 J-95
-continued
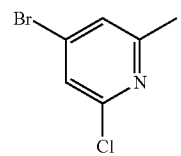 J-96
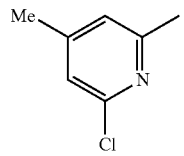 J-97
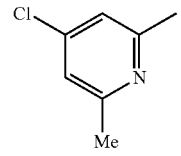 J-98
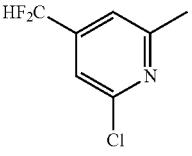 J-99
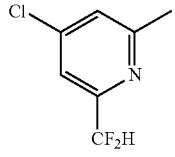 J-100
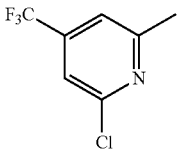 J-101
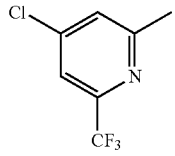 J-102
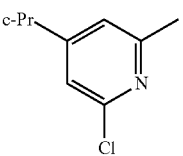 J-103
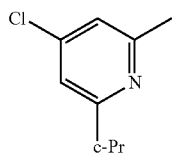 J-104
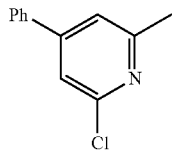 J-105

-continued
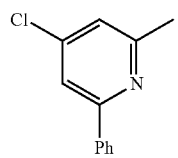 J-106
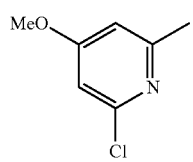 J-107
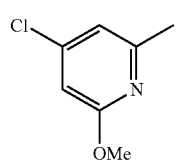 J-108
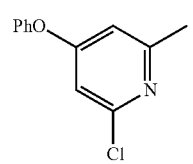 J-109
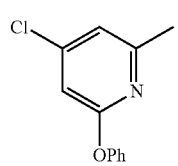 J-110
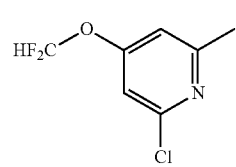 J-111
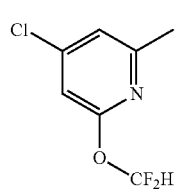 J-112
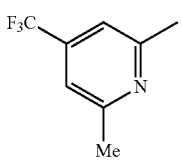 J-113
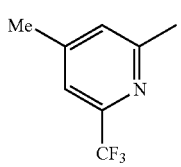 J-114
-continued
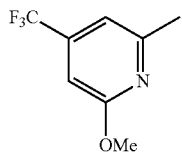 J-115
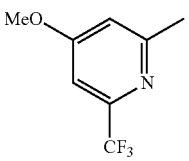 J-116
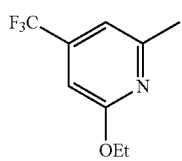 J-117
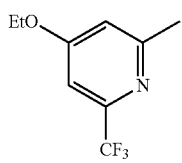 J-118
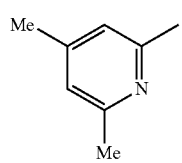 J-119
[Chem. 23]
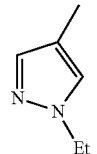 Ja-1
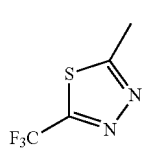 Ja-2
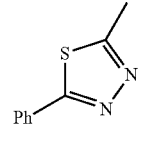 Ja-3
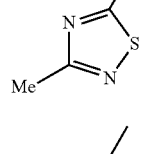 Ja-4
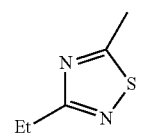 Ja-5

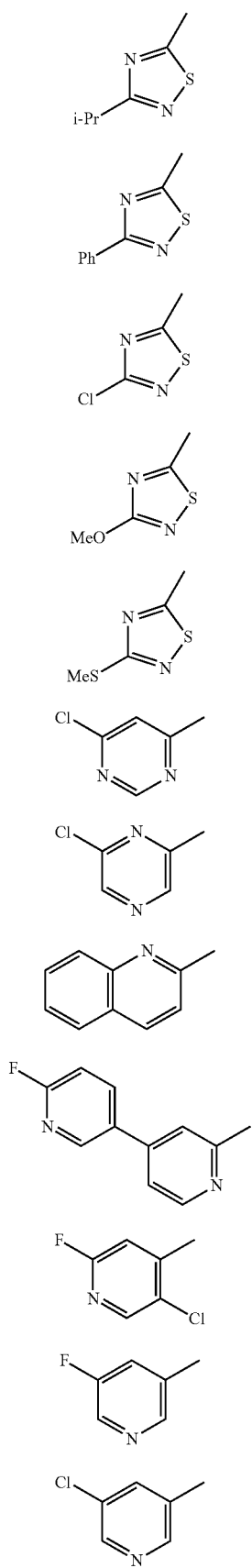
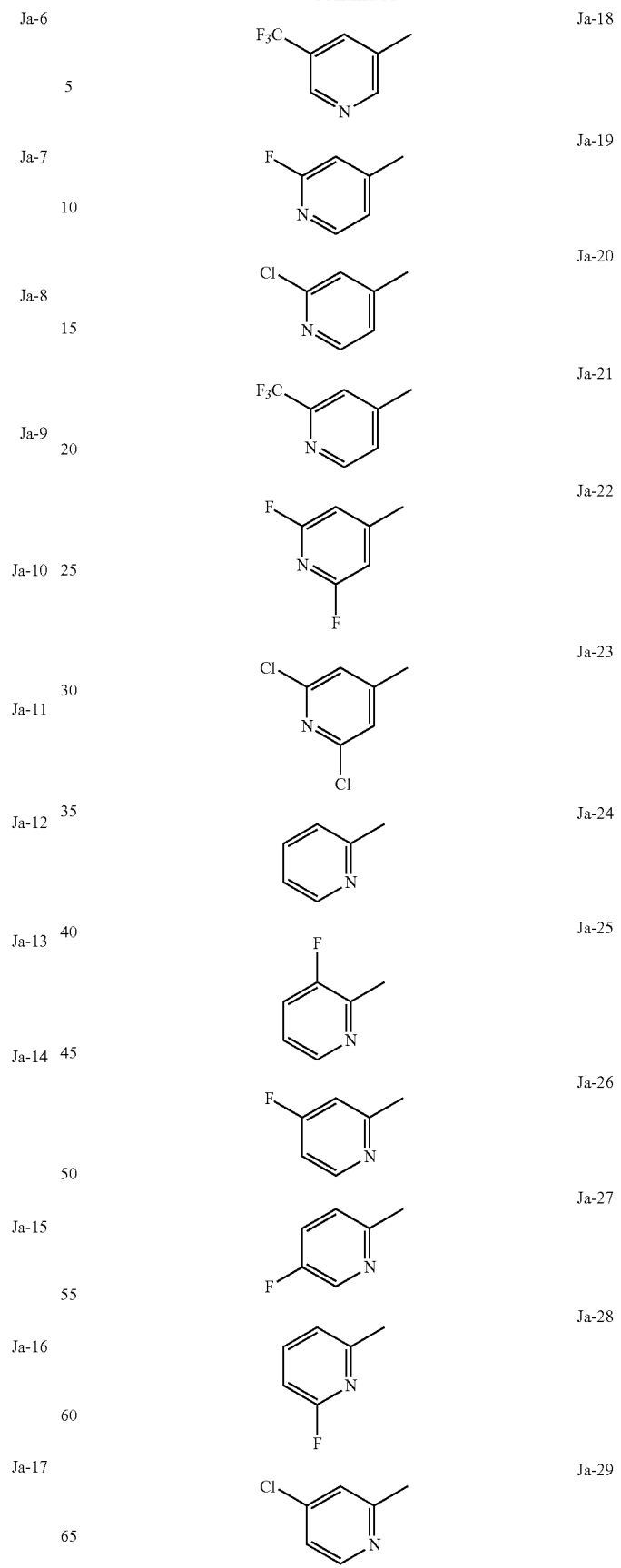

-continued
| | | |
|---|---|---|
| 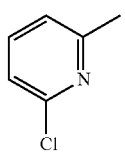 | Ja-30 | |
| 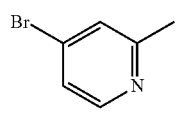 | Ja-31 | |
| 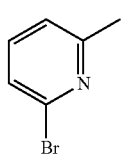 | Ja-32 | |
| 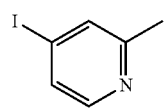 | Ja-33 | |
| 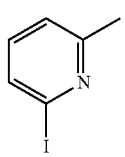 | Ja-34 | |
| 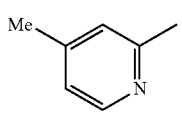 | Ja-35 | |
| 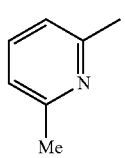 | Ja-36 | |
| 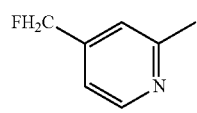 | Ja-37 | |
| 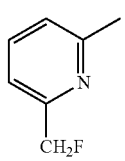 | Ja-38 | |
| 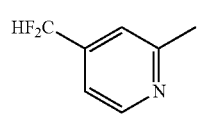 | Ja-39 | |
| 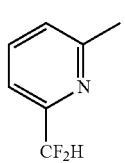 | Ja-40 | |
[Chem. 24]
-continued
| | | |
|---|---|---|
| 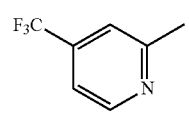 | Ja-41 | |
| 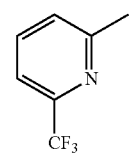 | Ja-42 | |
| 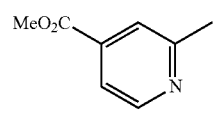 | Ja-43 | |
| 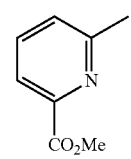 | Ja-44 | |
| 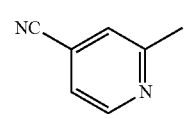 | Ja-45 | |
| 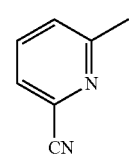 | Ja-46 | |
| 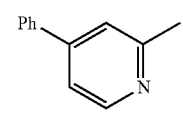 | Ja-47 | |
| 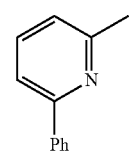 | Ja-48 | |
| 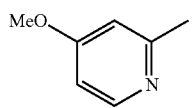 | Ja-49 | |
| 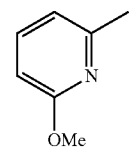 | Ja-50 | |
| 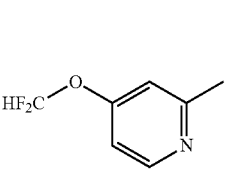 | Ja-51 | |

-continued

| Structure | Label |
|---|---|
| 2-methyl-6-(difluoromethoxy)pyridine | Ja-52 |
| 4-fluoro-2-methyl-6-fluoropyridine | Ja-53 |
| 4-chloro-2-methyl-6-chloropyridine | Ja-54 |
| 4-bromo-2-methyl-6-fluoropyridine | Ja-55 |
| 4-fluoro-2-methyl-6-bromopyridine | Ja-56 |
| 4-methyl-2-methyl-6-fluoropyridine | Ja-57 |
| 4-fluoro-2-methyl-6-methylpyridine | Ja-58 |
| 4-ethyl-2-methyl-6-fluoropyridine | Ja-59 |
| 4-fluoro-2-methyl-6-ethylpyridine | Ja-60 |

[Chem. 25]

-continued

| Structure | Label |
|---|---|
| 4-(trifluoromethyl)-2-methyl-6-fluoropyridine | Ja-61 |
| 4-fluoro-2-methyl-6-(trifluoromethyl)pyridine | Ja-62 |
| 4-methoxy-2-methyl-6-fluoropyridine | Ja-63 |
| 4-fluoro-2-methyl-6-methoxypyridine | Ja-64 |
| 4-chloro-2-methyl-6-bromopyridine | Ja-65 |
| 4-bromo-2-methyl-6-chloropyridine | Ja-66 |
| 4-methyl-2-methyl-6-chloropyridine | Ja-67 |
| 4-chloro-2-methyl-6-methylpyridine | Ja-68 |
| 4-(difluoromethyl)-2-methyl-6-chloropyridine | Ja-69 |
| 4-chloro-2-methyl-6-(difluoromethyl)pyridine | Ja-70 |

TABLE NO. 1
[Chem. 26]
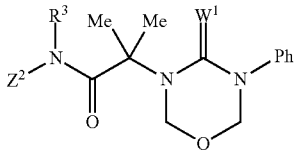
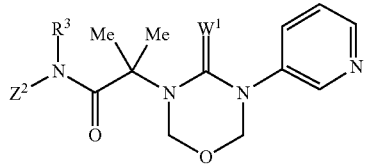
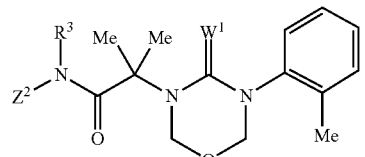
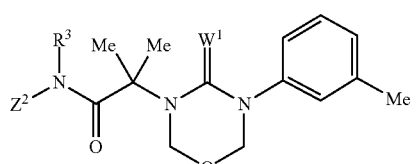
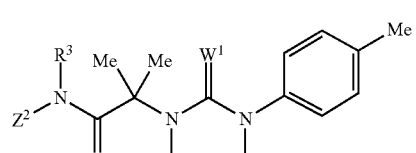

TABLE NO. 1-continued
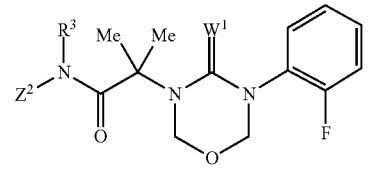
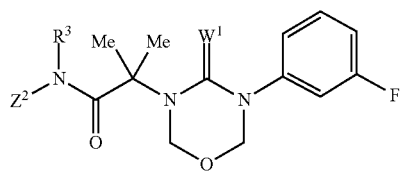
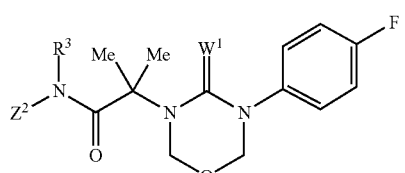
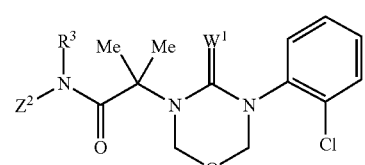
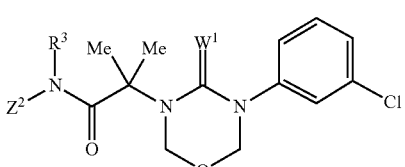
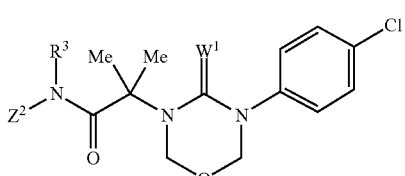
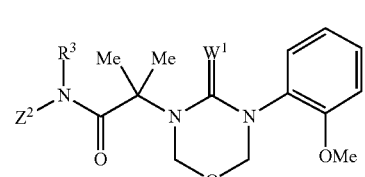
[Chem. 27]
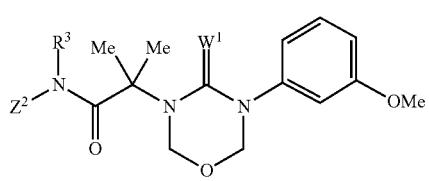
TABLE NO. 1-continued
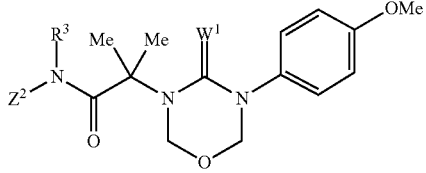
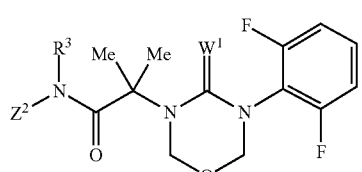
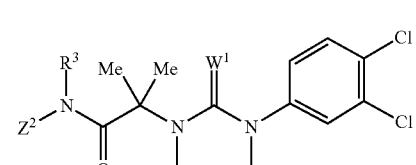
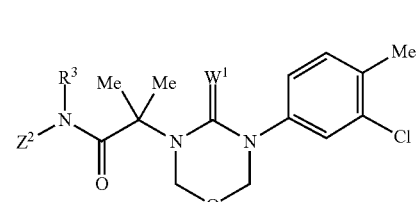
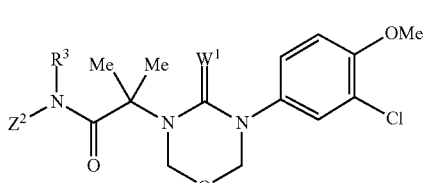
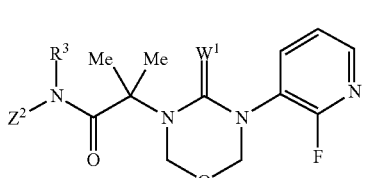
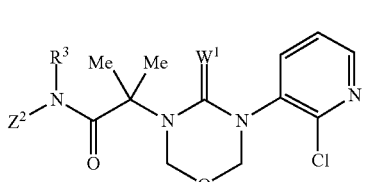
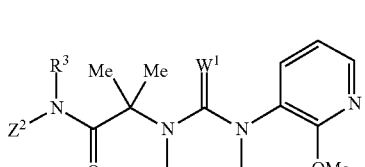

TABLE NO. 1-continued
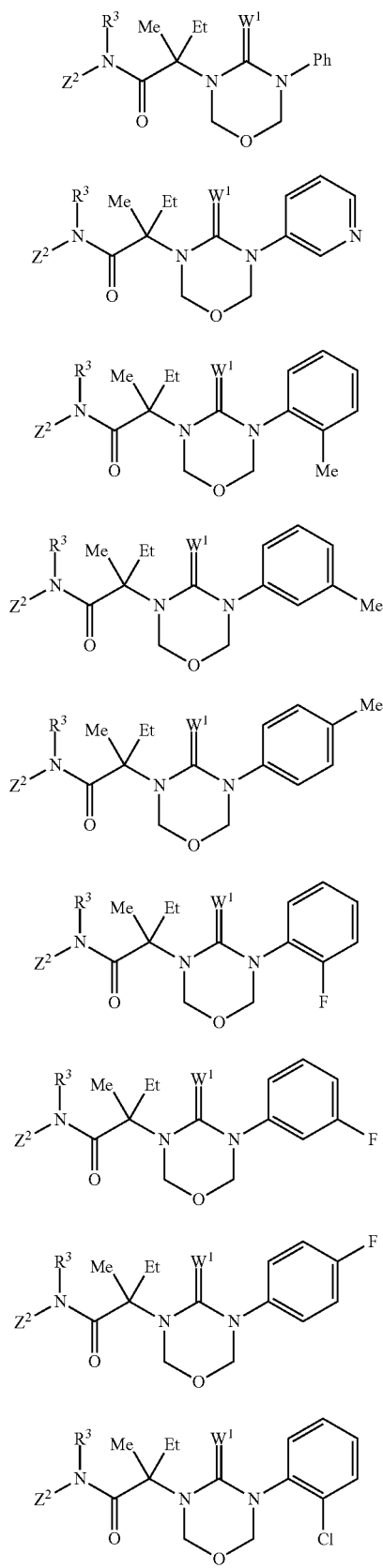
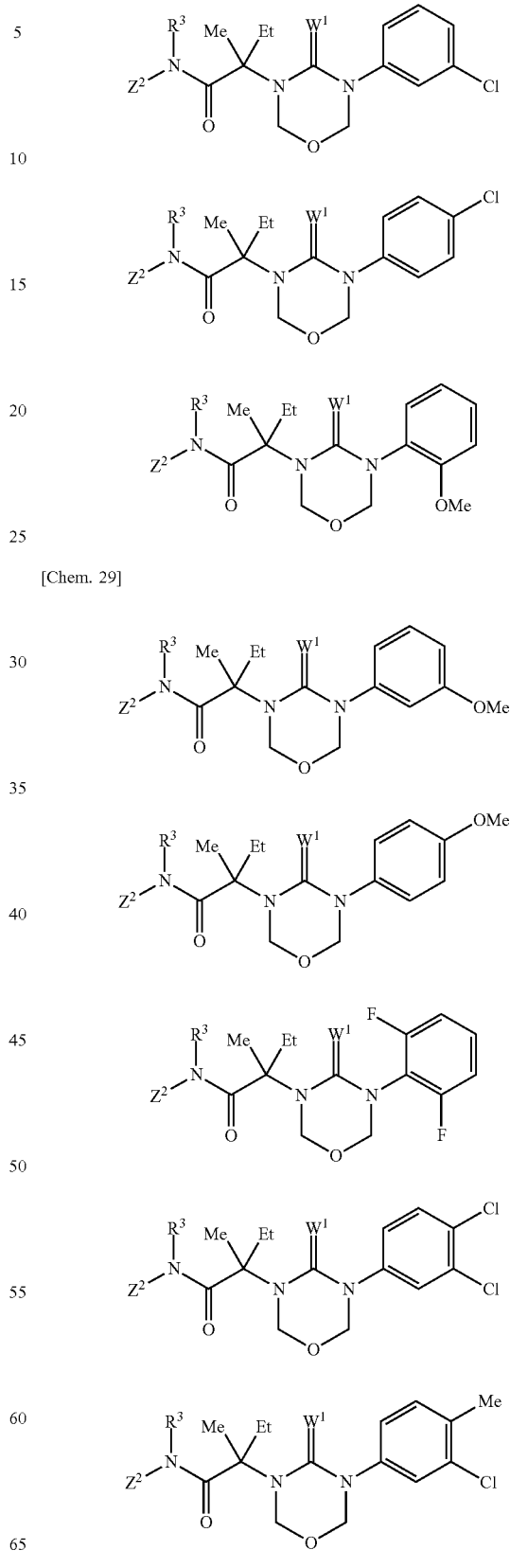

TABLE NO. 1-continued
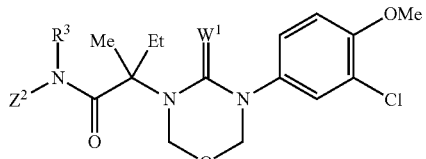
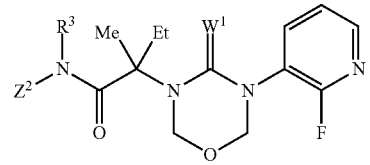
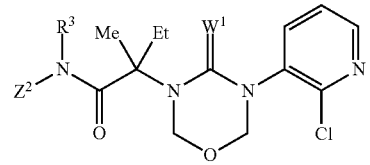
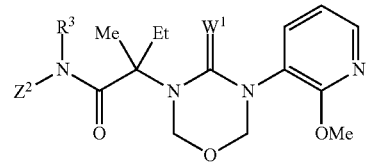
[Chem. 30]
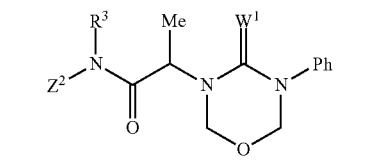
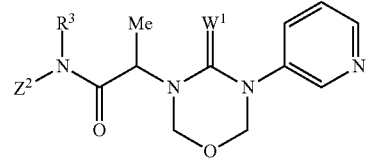
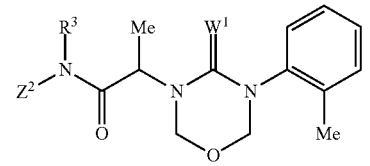
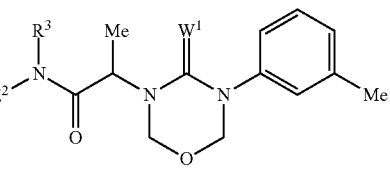
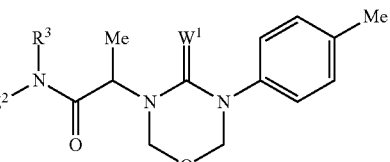
TABLE NO. 1-continued
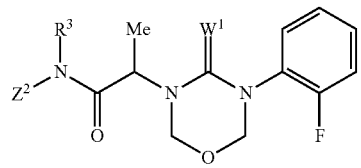
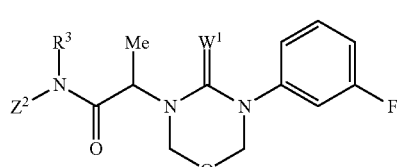
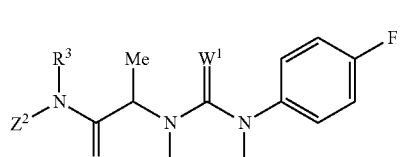
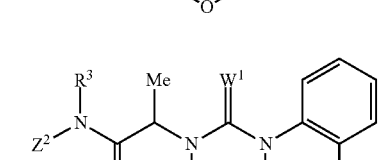
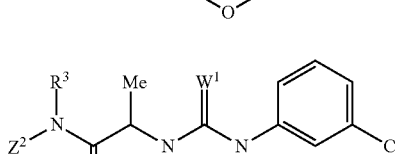
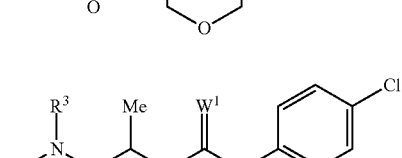
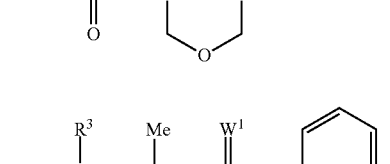
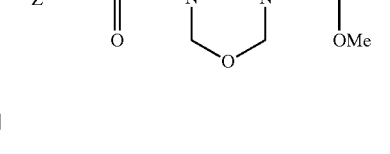
[Chem. 31]
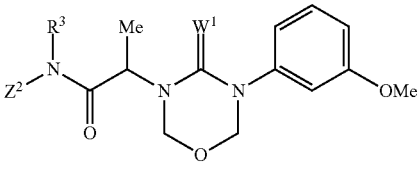

TABLE NO. 1-continued
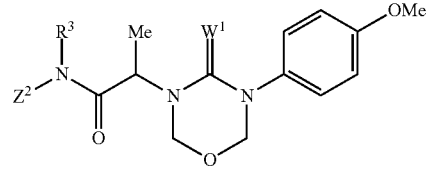
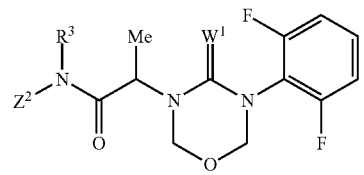
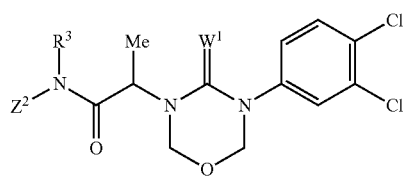
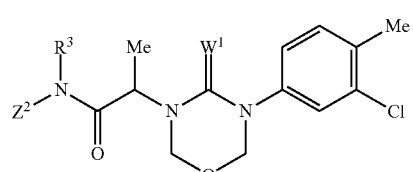
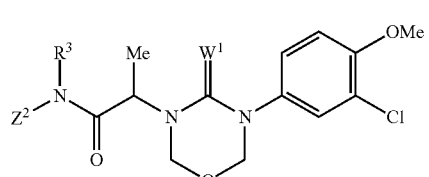
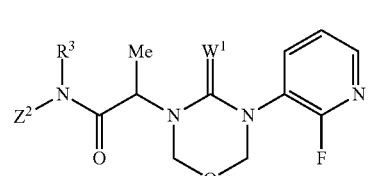
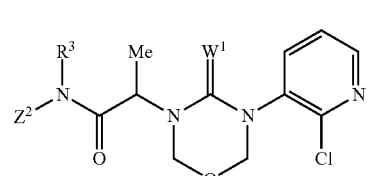
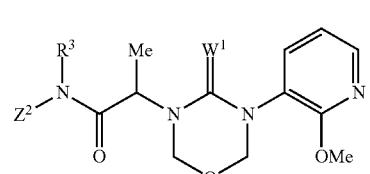
TABLE NO. 1-continued
[Chem. 32]
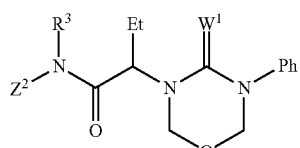
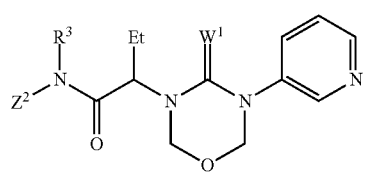
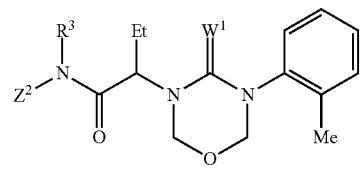
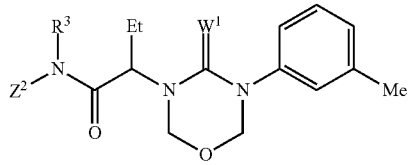
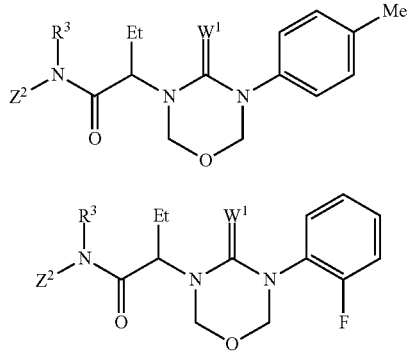
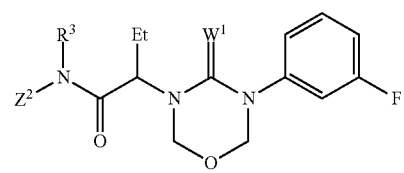
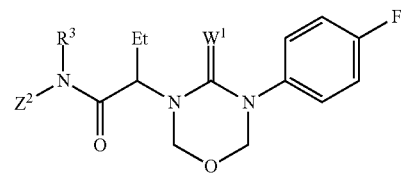
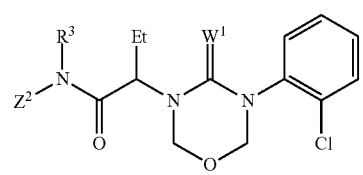

TABLE NO. 1-continued
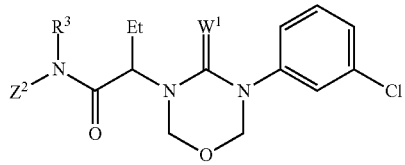
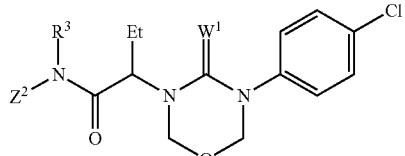
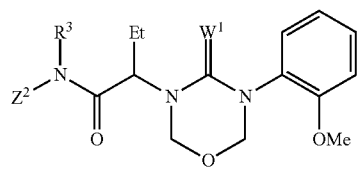
[Chem. 33]
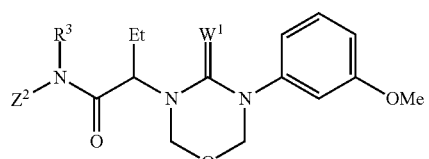
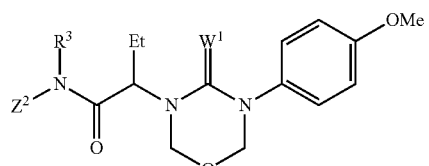
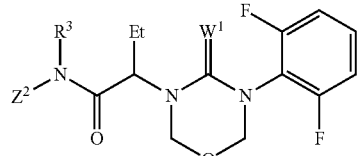
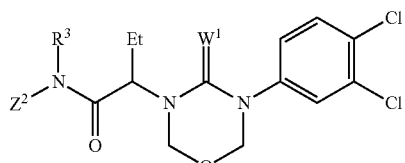
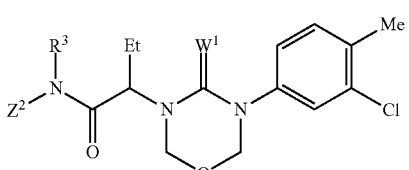
TABLE NO. 1-continued
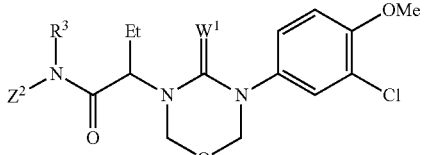
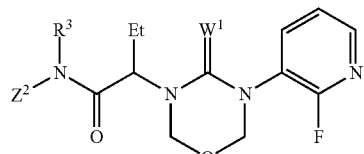
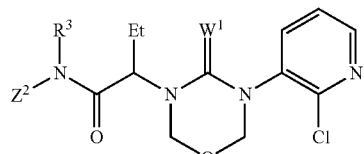
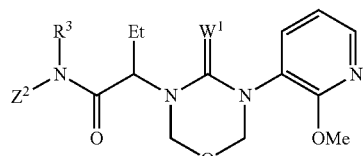
[Chem. 34]
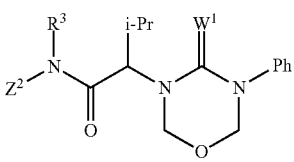
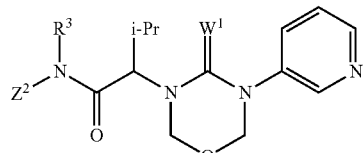
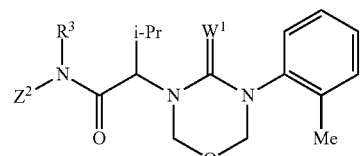
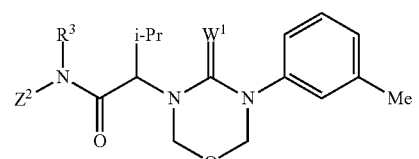
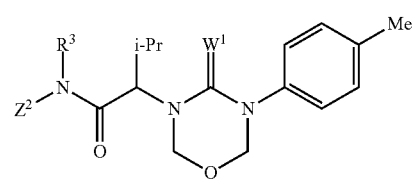

TABLE NO. 1-continued
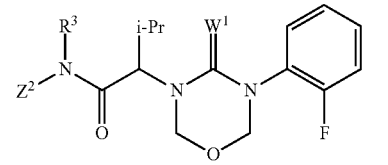
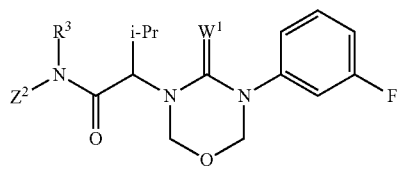
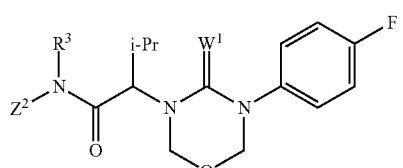
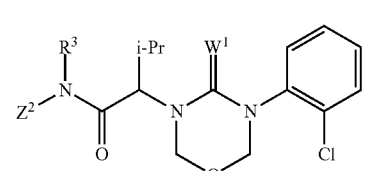
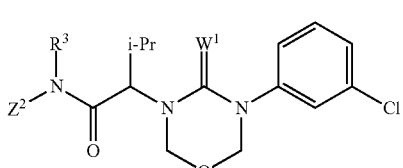
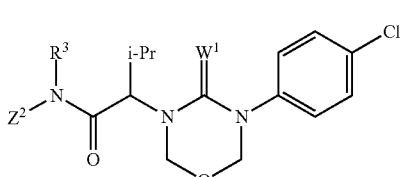
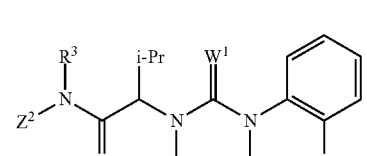
[Chem. 35]
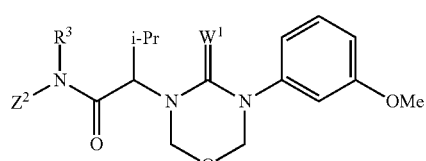
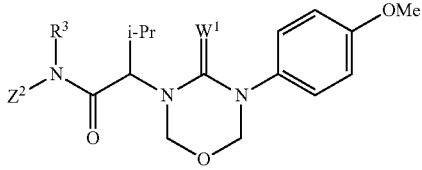
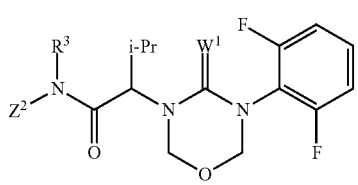
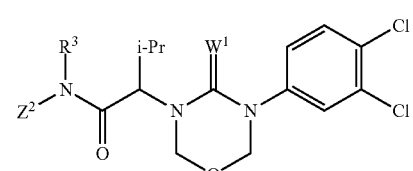
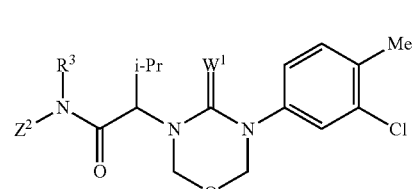
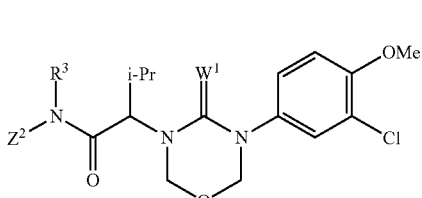
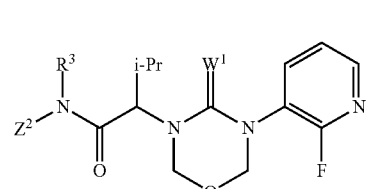
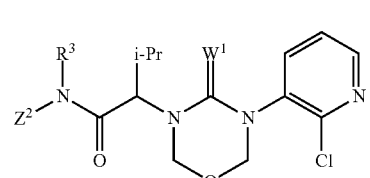
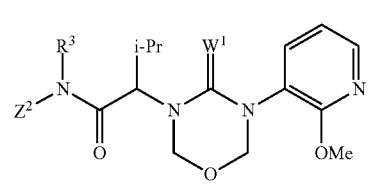

TABLE NO. 1-continued
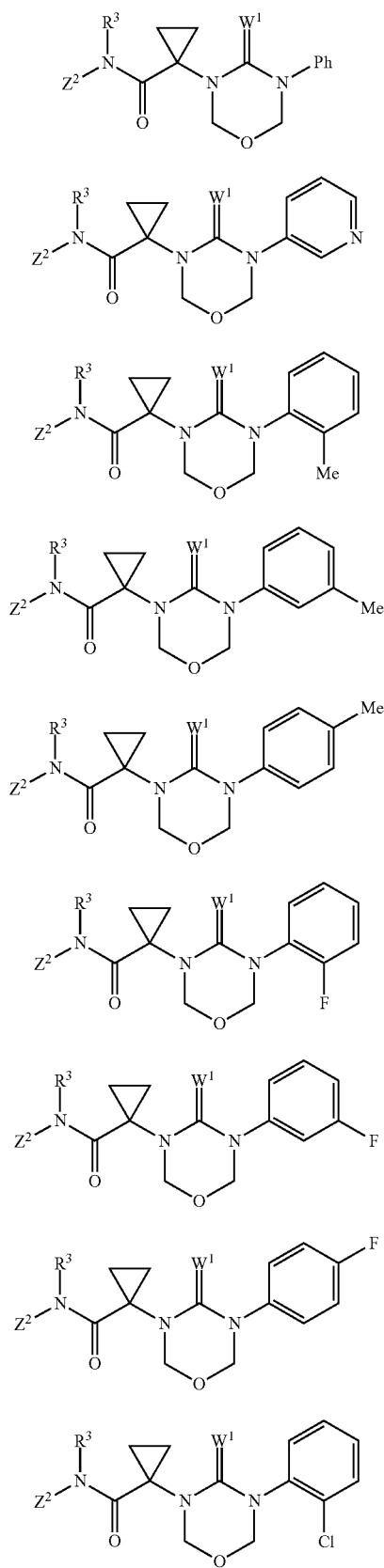
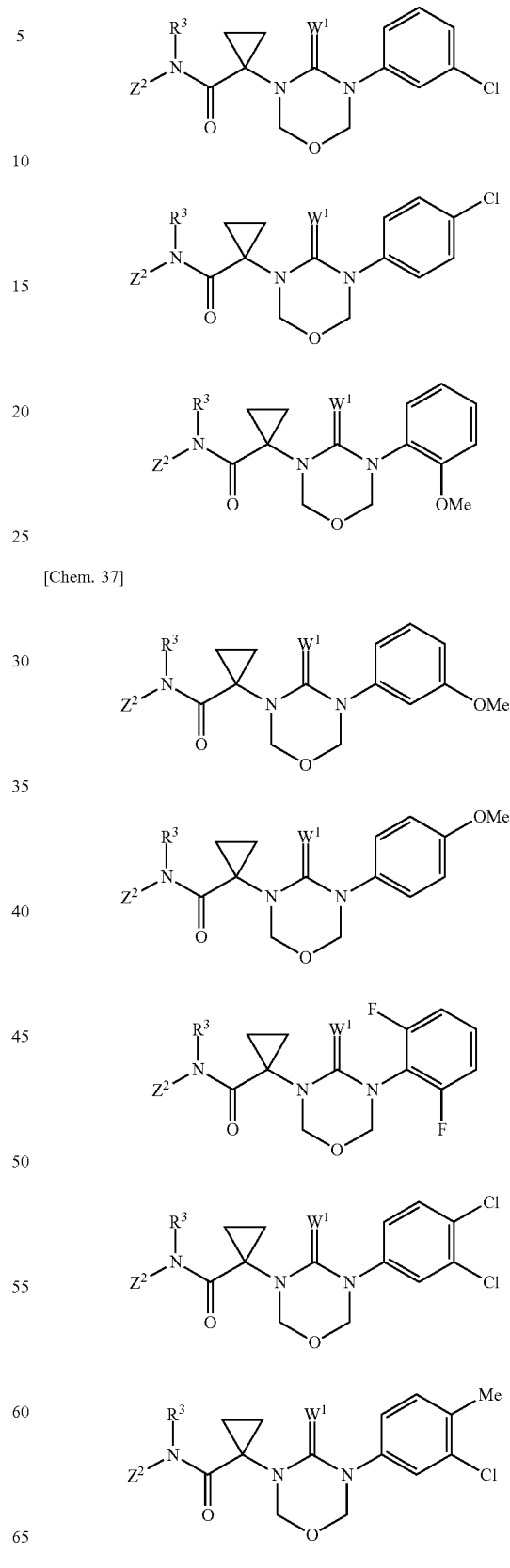

TABLE NO. 1-continued

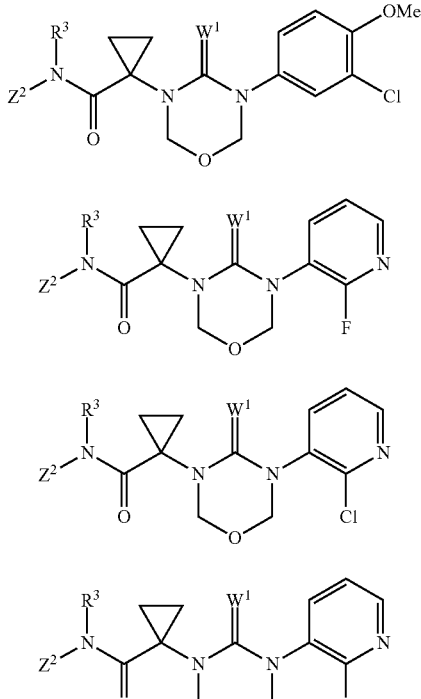

TABLE 1

| W¹ | Z² | R³ |
|---|---|---|
| O | J-1 | H |
| O | J-2 | H |
| O | J-3 | H |
| O | J-4 | H |
| O | J-5 | H |
| O | J-6 | H |
| O | J-7 | H |
| O | J-8 | H |
| O | J-9 | H |
| O | J-10 | H |
| O | J-11 | H |
| O | J-12 | H |
| O | J-13 | H |
| O | J-14 | H |
| O | J-15 | H |
| O | J-16 | H |
| O | J-17 | H |
| O | J-18 | H |
| O | J-19 | H |
| O | J-20 | H |
| O | J-21 | H |
| O | J-22 | H |
| O | J-23 | H |
| O | J-24 | H |
| O | J-25 | H |
| O | J-26 | H |
| O | J-27 | H |
| O | J-28 | H |
| O | J-29 | H |
| O | J-30 | H |
| O | J-31 | H |
| O | J-32 | H |
| O | J-33 | H |
| O | J-34 | H |
| O | J-35 | H |
| O | J-36 | H |
| O | J-37 | H |
| O | J-38 | H |

TABLE 1-continued

| W¹ | Z² | R³ |
|---|---|---|
| O | J-39 | H |
| O | J-40 | H |
| O | J-41 | H |
| O | J-42 | H |
| O | J-43 | H |
| O | J-44 | H |
| O | J-45 | H |
| O | J-46 | H |
| O | J-47 | H |
| O | J-48 | H |
| O | J-49 | H |
| O | J-50 | H |
| O | J-51 | H |
| O | J-52 | H |
| O | J-53 | H |
| O | J-54 | H |
| O | J-55 | H |
| O | J-56 | H |
| O | J-57 | H |
| O | J-58 | H |
| O | J-59 | H |
| O | J-60 | H |
| O | J-61 | H |
| O | J-62 | H |
| O | J-63 | H |
| O | J-64 | H |
| O | J-65 | H |
| O | J-66 | H |
| O | J-67 | H |
| O | J-68 | H |
| O | J-69 | H |
| O | J-70 | H |
| O | J-71 | H |
| O | J-72 | H |
| O | J-73 | H |
| O | J-74 | H |
| O | J-75 | H |
| O | J-76 | H |
| O | J-77 | H |
| O | J-78 | H |
| O | J-79 | H |
| O | J-80 | H |
| O | J-81 | H |
| O | J-82 | H |
| O | J-83 | H |
| O | J-84 | H |
| O | J-85 | H |
| O | J-86 | H |
| O | J-87 | H |
| O | J-88 | H |
| O | J-89 | H |
| O | J-90 | H |
| O | J-91 | H |
| O | J-92 | H |
| O | J-93 | H |
| O | J-94 | H |
| O | J-95 | H |
| O | J-96 | H |
| O | J-97 | H |
| O | J-98 | H |
| O | J-99 | H |
| O | J-100 | H |
| O | J-101 | H |
| O | J-102 | H |
| O | J-103 | H |
| O | J-104 | H |
| O | J-105 | H |
| O | J-106 | H |
| O | J-107 | H |
| O | J-108 | H |
| O | J-109 | H |
| O | J-110 | H |
| O | J-111 | H |
| O | J-112 | H |
| O | J-113 | H |
| O | J-114 | H |
| O | J-115 | H |
| O | J-116 | H |

TABLE 1-continued

| W¹ | Z² | R³ |
|---|---|---|
| O | J-117 | H |
| O | J-118 | H |
| O | J-119 | H |

TABLE 2

| W¹ | Z² | R³ |
|---|---|---|
| O | J-1 | Me |
| O | J-2 | Me |
| O | J-3 | Me |
| O | J-4 | Me |
| O | J-5 | Me |
| O | J-6 | Me |
| O | J-7 | Me |
| O | J-8 | Me |
| O | J-9 | Me |
| O | J-10 | Me |
| O | J-11 | Me |
| O | J-12 | Me |
| O | J-13 | Me |
| O | J-14 | Me |
| O | J-15 | Me |
| O | J-16 | Me |
| O | J-17 | Me |
| O | J-18 | Me |
| O | J-19 | Me |
| O | J-20 | Me |
| O | J-21 | Me |
| O | J-22 | Me |
| O | J-23 | Me |
| O | J-24 | Me |
| O | J-25 | Me |
| O | J-26 | Me |
| O | J-27 | Me |
| O | J-28 | Me |
| O | J-29 | Me |
| O | J-30 | Me |
| O | J-31 | Me |
| O | J-32 | Me |
| O | J-33 | Me |
| O | J-34 | Me |
| O | J-35 | Me |
| O | J-36 | Me |
| O | J-37 | Me |
| O | J-38 | Me |
| O | J-39 | Me |
| O | J-40 | Me |
| O | J-41 | Me |
| O | J-42 | Me |
| O | J-43 | Me |
| O | J-44 | Me |
| O | J-45 | Me |
| O | J-46 | Me |
| O | J-47 | Me |
| O | J-48 | Me |
| O | J-49 | Me |
| O | J-50 | Me |
| O | J-51 | Me |
| O | J-52 | Me |
| O | J-53 | Me |
| O | J-54 | Me |
| O | J-55 | Me |
| O | J-56 | Me |
| O | J-57 | Me |
| O | J-58 | Me |
| O | J-59 | Me |
| O | J-60 | Me |
| O | J-61 | Me |
| O | J-62 | Me |
| O | J-63 | Me |
| O | J-64 | Me |
| O | J-65 | Me |
| O | J-66 | Me |
| O | J-67 | Me |

TABLE 2-continued

| W¹ | Z² | R³ |
|---|---|---|
| O | J-68 | Me |
| O | J-69 | Me |
| O | J-70 | Me |
| O | J-71 | Me |
| O | J-72 | Me |
| O | J-73 | Me |
| O | J-74 | Me |
| O | J-75 | Me |
| O | J-76 | Me |
| O | J-77 | Me |
| O | J-78 | Me |
| O | J-79 | Me |
| O | J-80 | Me |
| O | J-81 | Me |
| O | J-82 | Me |
| O | J-83 | Me |
| O | J-84 | Me |
| O | J-85 | Me |
| O | J-86 | Me |
| O | J-87 | Me |
| O | J-88 | Me |
| O | J-89 | Me |
| O | J-90 | Me |
| O | J-91 | Me |
| O | J-92 | Me |
| O | J-93 | Me |
| O | J-94 | Me |
| O | J-95 | Me |
| O | J-96 | Me |
| O | J-97 | Me |
| O | J-98 | Me |
| O | J-99 | Me |
| O | J-100 | Me |
| O | J-101 | Me |
| O | J-102 | Me |
| O | J-103 | Me |
| O | J-104 | Me |
| O | J-105 | Me |
| O | J-106 | Me |
| O | J-107 | Me |
| O | J-108 | Me |
| O | J-109 | Me |
| O | J-110 | Me |
| O | J-111 | Me |
| O | J-112 | Me |
| O | J-113 | Me |
| O | J-114 | Me |
| O | J-115 | Me |
| O | J-116 | Me |
| O | J-117 | Me |
| O | J-118 | Me |
| O | J-119 | Me |

TABLE 3

| W¹ | Z² | R³ |
|---|---|---|
| O | J-1 | Et |
| O | J-2 | Et |
| O | J-3 | Et |
| O | J-4 | Et |
| O | J-5 | Et |
| O | J-6 | Et |
| O | J-7 | Et |
| O | J-8 | Et |
| O | J-9 | Et |
| O | J-10 | Et |
| O | J-11 | Et |
| O | J-12 | Et |
| O | J-13 | Et |
| O | J-14 | Et |
| O | J-15 | Et |
| O | J-16 | Et |
| O | J-17 | Et |
| O | J-18 | Et |

TABLE 3-continued

| W¹ | Z² | R³ |
|---|---|---|
| O | J-19 | Et |
| O | J-20 | Et |
| O | J-21 | Et |
| O | J-22 | Et |
| O | J-23 | Et |
| O | J-24 | Et |
| O | J-25 | Et |
| O | J-26 | Et |
| O | J-27 | Et |
| O | J-28 | Et |
| O | J-29 | Et |
| O | J-30 | Et |
| O | J-31 | Et |
| O | J-32 | Et |
| O | J-33 | Et |
| O | J-34 | Et |
| O | J-35 | Et |
| O | J-36 | Et |
| O | J-37 | Et |
| O | J-38 | Et |
| O | J-39 | Et |
| O | J-40 | Et |
| O | J-41 | Et |
| O | J-42 | Et |
| O | J-43 | Et |
| O | J-44 | Et |
| O | J-45 | Et |
| O | J-46 | Et |
| O | J-47 | Et |
| O | J-48 | Et |
| O | J-49 | Et |
| O | J-50 | Et |
| O | J-51 | Et |
| O | J-52 | Et |
| O | J-53 | Et |
| O | J-54 | Et |
| O | J-55 | Et |
| O | J-56 | Et |
| O | J-57 | Et |
| O | J-58 | Et |
| O | J-59 | Et |
| O | J-60 | Et |
| O | J-61 | Et |
| O | J-62 | Et |
| O | J-63 | Et |
| O | J-64 | Et |
| O | J-65 | Et |
| O | J-66 | Et |
| O | J-67 | Et |
| O | J-68 | Et |
| O | J-69 | Et |
| O | J-70 | Et |
| O | J-71 | Et |
| O | J-72 | Et |
| O | J-73 | Et |
| O | J-74 | Et |
| O | J-75 | Et |
| O | J-76 | Et |
| O | J-77 | Et |
| O | J-78 | Et |
| O | J-79 | Et |
| O | J-80 | Et |
| O | J-81 | Et |
| O | J-82 | Et |
| O | J-83 | Et |
| O | J-84 | Et |
| O | J-85 | Et |
| O | J-86 | Et |
| O | J-87 | Et |
| O | J-88 | Et |
| O | J-89 | Et |
| O | J-90 | Et |
| O | J-91 | Et |
| O | J-92 | Et |
| O | J-93 | Et |
| O | J-94 | Et |
| O | J-95 | Et |
| O | J-96 | Et |
| O | J-97 | Et |
| O | J-98 | Et |
| O | J-99 | Et |
| O | J-100 | Et |
| O | J-101 | Et |
| O | J-102 | Et |
| O | J-103 | Et |
| O | J-104 | Et |
| O | J-105 | Et |
| O | J-106 | Et |
| O | J-107 | Et |
| O | J-108 | Et |
| O | J-109 | Et |
| O | J-110 | Et |
| O | J-111 | Et |
| O | J-112 | Et |
| O | J-113 | Et |
| O | J-114 | Et |
| O | J-115 | Et |
| O | J-116 | Et |
| O | J-117 | Et |
| O | J-118 | Et |
| O | J-119 | Et |

TABLE 4

| W¹ | Z² | R³ |
|---|---|---|
| O | J-1 | n-Pr |
| O | J-2 | n-Pr |
| O | J-3 | n-Pr |
| O | J-4 | n-Pr |
| O | J-5 | n-Pr |
| O | J-6 | n-Pr |
| O | J-7 | n-Pr |
| O | J-8 | n-Pr |
| O | J-9 | n-Pr |
| O | J-10 | n-Pr |
| O | J-11 | n-Pr |
| O | J-12 | n-Pr |
| O | J-13 | n-Pr |
| O | J-14 | n-Pr |
| O | J-15 | n-Pr |
| O | J-16 | n-Pr |
| O | J-17 | n-Pr |
| O | J-18 | n-Pr |
| O | J-19 | n-Pr |
| O | J-20 | n-Pr |
| O | J-21 | n-Pr |
| O | J-22 | n-Pr |
| O | J-23 | n-Pr |
| O | J-24 | n-Pr |
| O | J-25 | n-Pr |
| O | J-26 | n-Pr |
| O | J-27 | n-Pr |
| O | J-28 | n-Pr |
| O | J-29 | n-Pr |
| O | J-30 | n-Pr |
| O | J-31 | n-Pr |
| O | J-32 | n-Pr |
| O | J-33 | n-Pr |
| O | J-34 | n-Pr |
| O | J-35 | n-Pr |
| O | J-36 | n-Pr |
| O | J-37 | n-Pr |
| O | J-38 | n-Pr |
| O | J-39 | n-Pr |
| O | J-40 | n-Pr |
| O | J-41 | n-Pr |
| O | J-42 | n-Pr |
| O | J-43 | n-Pr |
| O | J-44 | n-Pr |
| O | J-45 | n-Pr |
| O | J-46 | n-Pr |
| O | J-47 | n-Pr |

TABLE 4-continued

| W¹ | Z² | R³ |
|---|---|---|
| O | J-48 | n-Pr |
| O | J-49 | n-Pr |
| O | J-50 | n-Pr |
| O | J-51 | n-Pr |
| O | J-52 | n-Pr |
| O | J-53 | n-Pr |
| O | J-54 | n-Pr |
| O | J-55 | n-Pr |
| O | J-56 | n-Pr |
| O | J-57 | n-Pr |
| O | J-58 | n-Pr |
| O | J-59 | n-Pr |
| O | J-60 | n-Pr |
| O | J-61 | n-Pr |
| O | J-62 | n-Pr |
| O | J-63 | n-Pr |
| O | J-64 | n-Pr |
| O | J-65 | n-Pr |
| O | J-66 | n-Pr |
| O | J-67 | n-Pr |
| O | J-68 | n-Pr |
| O | J-69 | n-Pr |
| O | J-70 | n-Pr |
| O | J-71 | n-Pr |
| O | J-72 | n-Pr |
| O | J-73 | n-Pr |
| O | J-74 | n-Pr |
| O | J-75 | n-Pr |
| O | J-76 | n-Pr |
| O | J-77 | n-Pr |
| O | J-78 | n-Pr |
| O | J-79 | n-Pr |
| O | J-80 | n-Pr |
| O | J-81 | n-Pr |
| O | J-82 | n-Pr |
| O | J-83 | n-Pr |
| O | J-84 | n-Pr |
| O | J-85 | n-Pr |
| O | J-86 | n-Pr |
| O | J-87 | n-Pr |
| O | J-88 | n-Pr |
| O | J-89 | n-Pr |
| O | J-90 | n-Pr |
| O | J-91 | n-Pr |
| O | J-92 | n-Pr |
| O | J-93 | n-Pr |
| O | J-94 | n-Pr |
| O | J-95 | n-Pr |
| O | J-96 | n-Pr |
| O | J-97 | n-Pr |
| O | J-98 | n-Pr |
| O | J-99 | n-Pr |
| O | J-100 | n-Pr |
| O | J-101 | n-Pr |
| O | J-102 | n-Pr |
| O | J-103 | n-Pr |
| O | J-104 | n-Pr |
| O | J-105 | n-Pr |
| O | J-106 | n-Pr |
| O | J-107 | n-Pr |
| O | J-108 | n-Pr |
| O | J-109 | n-Pr |
| O | J-110 | n-Pr |
| O | J-111 | n-Pr |
| O | J-112 | n-Pr |
| O | J-113 | n-Pr |
| O | J-114 | n-Pr |
| O | J-115 | n-Pr |
| O | J-116 | n-Pr |
| O | J-117 | n-Pr |
| O | J-118 | n-Pr |
| O | J-119 | n-Pr |

TABLE 5

| W¹ | Z² | R³ |
|---|---|---|
| S | J-1 | H |
| S | J-2 | H |
| S | J-3 | H |
| S | J-4 | H |
| S | J-5 | H |
| S | J-6 | H |
| S | J-7 | H |
| S | J-8 | H |
| S | J-9 | H |
| S | J-10 | H |
| S | J-11 | H |
| S | J-12 | H |
| S | J-13 | H |
| S | J-14 | H |
| S | J-15 | H |
| S | J-16 | H |
| S | J-17 | H |
| S | J-18 | H |
| S | J-19 | H |
| S | J-20 | H |
| S | J-21 | H |
| S | J-22 | H |
| S | J-23 | H |
| S | J-24 | H |
| S | J-25 | H |
| S | J-26 | H |
| S | J-27 | H |
| S | J-28 | H |
| S | J-29 | H |
| S | J-30 | H |
| S | J-31 | H |
| S | J-32 | H |
| S | J-33 | H |
| S | J-34 | H |
| S | J-35 | H |
| S | J-36 | H |
| S | J-37 | H |
| S | J-38 | H |
| S | J-39 | H |
| S | J-40 | H |
| S | J-41 | H |
| S | J-42 | H |
| S | J-43 | H |
| S | J-44 | H |
| S | J-45 | H |
| S | J-46 | H |
| S | J-47 | H |
| S | J-48 | H |
| S | J-49 | H |
| S | J-50 | H |
| S | J-51 | H |
| S | J-52 | H |
| S | J-53 | H |
| S | J-54 | H |
| S | J-55 | H |
| S | J-56 | H |
| S | J-57 | H |
| S | J-58 | H |
| S | J-59 | H |
| S | J-60 | H |
| S | J-61 | H |
| S | J-62 | H |
| S | J-63 | H |
| S | J-64 | H |
| S | J-65 | H |
| S | J-66 | H |
| S | J-67 | H |
| S | J-68 | H |
| S | J-69 | H |
| S | J-70 | H |
| S | J-71 | H |
| S | J-72 | H |
| S | J-73 | H |
| S | J-74 | H |
| S | J-75 | H |
| S | J-76 | H |
| S | J-77 | H |
| S | J-78 | H |

TABLE 5-continued

| W¹ | Z² | R³ |
|---|---|---|
| S | J-79 | H |
| S | J-80 | H |
| S | J-81 | H |
| S | J-82 | H |
| S | J-83 | H |
| S | J-84 | H |
| S | J-85 | H |
| S | J-86 | H |
| S | J-87 | H |
| S | J-88 | H |
| S | J-89 | H |
| S | J-90 | H |
| S | J-91 | H |
| S | J-92 | H |
| S | J-93 | H |
| S | J-94 | H |
| S | J-95 | H |
| S | J-96 | H |
| S | J-97 | H |
| S | J-98 | H |
| S | J-99 | H |
| S | J-100 | H |
| S | J-101 | H |
| S | J-102 | H |
| S | J-103 | H |
| S | J-101 | H |
| S | J-105 | H |
| S | J-106 | H |
| S | J-107 | H |
| S | J-108 | H |
| S | J-109 | H |
| S | J-110 | H |
| S | J-111 | H |
| S | J-112 | H |
| S | J-113 | H |
| S | J-114 | H |
| S | J-115 | H |
| S | J-116 | H |
| S | J-117 | H |
| S | J-118 | H |
| S | J-119 | H |

TABLE 6

| W¹ | Z² | R³ |
|---|---|---|
| S | J-1 | Me |
| S | J-2 | Me |
| S | J-3 | Me |
| S | J-4 | Me |
| S | J-5 | Me |
| S | J-6 | Me |
| S | J-7 | Me |
| S | J-8 | Me |
| S | J-9 | Me |
| S | J-10 | Me |
| S | J-11 | Me |
| S | J-12 | Me |
| S | J-13 | Me |
| S | J-14 | Me |
| S | J-15 | Me |
| S | J-16 | Me |
| S | J-17 | Me |
| S | J-18 | Me |
| S | J-19 | Me |
| S | J-20 | Me |
| S | J-21 | Me |
| S | J-22 | Me |
| S | J-23 | Me |
| S | J-24 | Me |
| S | J-25 | Me |
| S | J-26 | Me |
| S | J-27 | Me |
| S | J-28 | Me |
| S | J-29 | Me |
| S | J-30 | Me |
| S | J-31 | Me |
| S | J-32 | Me |
| S | J-33 | Me |
| S | J-34 | Me |
| S | J-35 | Me |
| S | J-36 | Me |
| S | J-37 | Me |
| S | J-38 | Me |
| S | J-39 | Me |
| S | J-40 | Me |
| S | J-41 | Me |
| S | J-42 | Me |
| S | J-43 | Me |
| S | J-44 | Me |
| S | J-45 | Me |
| S | J-46 | Me |
| S | J-47 | Me |
| S | J-48 | Me |
| S | J-49 | Me |
| S | J-50 | Me |
| S | J-51 | Me |
| S | J-52 | Me |
| S | J-53 | Me |
| S | J-54 | Me |
| S | J-55 | Me |
| S | J-56 | Me |
| S | J-57 | Me |
| S | J-58 | Me |
| S | J-59 | Me |
| S | J-60 | Me |
| S | J-61 | Me |
| S | J-62 | Me |
| S | J-63 | Me |
| S | J-64 | Me |
| S | J-65 | Me |
| S | J-66 | Me |
| S | J-67 | Me |
| S | J-68 | Me |
| S | J-69 | Me |
| S | J-70 | Me |
| S | J-71 | Me |
| S | J-72 | Me |
| S | J-73 | Me |
| S | J-74 | Me |
| S | J-75 | Me |
| S | J-76 | Me |
| S | J-77 | Me |
| S | J-78 | Me |
| S | J-79 | Me |
| S | J-80 | Me |
| S | J-81 | Me |
| S | J-82 | Me |
| S | J-83 | Me |
| S | J-84 | Me |
| S | J-85 | Me |
| S | J-86 | Me |
| S | J-87 | Me |
| S | J-88 | Me |
| S | J-89 | Me |
| S | J-90 | Me |
| S | J-91 | Me |
| S | J-92 | Me |
| S | J-93 | Me |
| S | J-94 | Me |
| S | J-95 | Me |
| S | J-96 | Me |
| S | J-97 | Me |
| S | J-98 | Me |
| S | J-99 | Me |
| S | J-100 | Me |
| S | J-101 | Me |
| S | J-102 | Me |
| S | J-103 | Me |
| S | J-104 | Me |
| S | J-105 | Me |
| S | J-106 | Me |
| S | J-107 | Me |

TABLE 6-continued
| W¹ | Z² | R³ |
|---|---|---|
| S | J-108 | Me |
| S | J-109 | Me |
| S | J-110 | Me |
| S | J-111 | Me |
| S | J-112 | Me |
| S | J-113 | Me |
| S | J-114 | Me |
| S | J-115 | Me |
| S | J-116 | Me |
| S | J-117 | Me |
| S | J-118 | Me |
| S | J-119 | Me |
TABLE NO. 2
[Chem. 38]
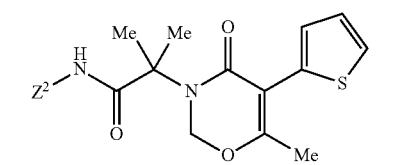
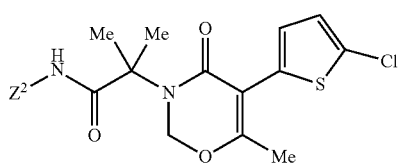
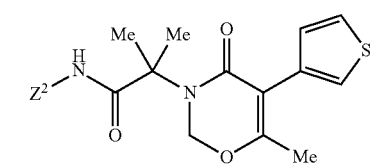
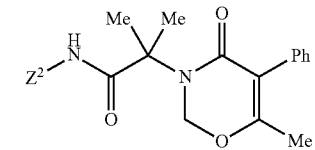
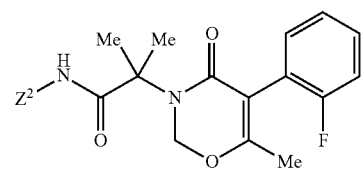
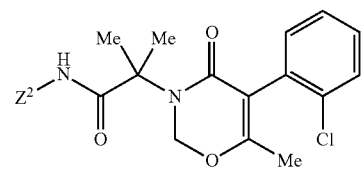
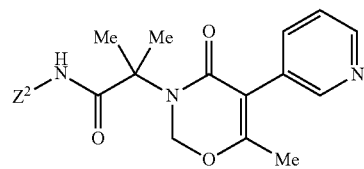
TABLE NO. 2-continued
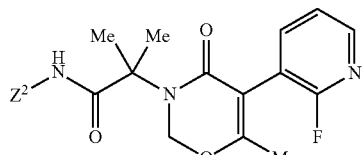
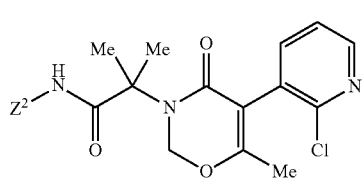
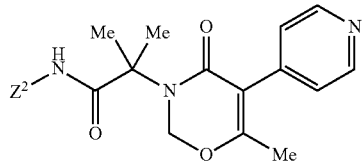
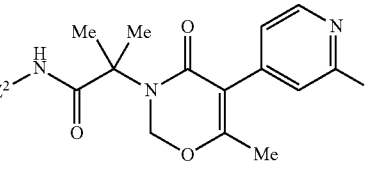
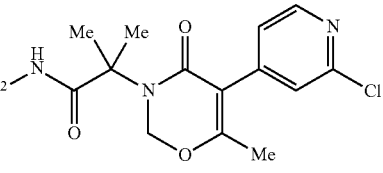
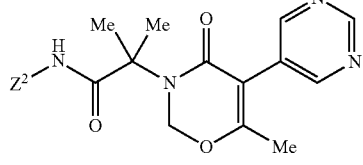
TABLE 7
| Z² |
|---|
| Ja-1 |
| Ja-2 |
| Ja-3 |
| Ja-4 |
| Ja-5 |
| Ja-6 |
| Ja-7 |
| Ja-8 |

TABLE 7-continued

| $Z^2$ |
|---|
| Ja-9 |
| Ja-10 |
| Ja-11 |
| Ja-12 |
| Ja-13 |
| Ja-14 |
| Ja-15 |
| Ja-16 |
| Ja-17 |
| Ja-18 |
| Ja-19 |
| Ja-20 |
| Ja-21 |
| Ja-22 |
| Ja-23 |
| Ja-24 |
| Ja-25 |
| Ja-26 |
| Ja-27 |
| Ja-28 |
| Ja-29 |
| Ja-30 |
| Ja-31 |
| Ja-32 |
| Ja-33 |
| Ja-34 |
| Ja-35 |
| Ja-36 |
| Ja-37 |
| Ja-38 |
| Ja-39 |
| Ja-40 |
| Ja-41 |
| Ja-42 |
| Ja-43 |
| Ja-44 |
| Ja-45 |
| Ja-46 |
| Ja-47 |
| Ja-48 |
| Ja-49 |
| Ja-50 |
| Ja-51 |
| Ja-52 |
| Ja-53 |
| Ja-54 |
| Ja-55 |
| Ja-56 |
| Ja-57 |
| Ja-58 |
| Ja-59 |
| Ja-60 |
| Ja-61 |
| Ja-62 |
| Ja-63 |
| Ja-64 |
| Ja-65 |
| Ja-66 |
| Ja-67 |
| Ja-68 |
| Ja-69 |
| Ja-70 |
| Ja-71 |
| Ja-72 |
| Ja-73 |
| Ja-74 |
| Ja-75 |
| Ja-76 |
| Ja-77 |
| Ja-78 |
| Ja-79 |
| Ja-80 |
| Ja-81 |
| Ja-82 |
| Ja-83 |
| Ja-84 |

The compounds of the present invention, as paddy field herbicides, can be used both in submerged soil treatment and foliar treatment. As paddy field weeds, for example, Potamogetonaceae weeds, represented by *Potamogeton distinctus* and the like, Alismataceae weeds represented by *Alisma canaliculatum*, *Sagittaria pygmaea* and *Sagittaria trifolia* and the like, Gramineae weeds represented by *Leptochloa chinensis*, *Echinochloa crus-galli*, *Echinochloa oryzicola*, *Homalocenchrus japonicus* and *Paspalum distichum* and the like, Cyperaceae weeds represented by *Eleocharis kuroguwai*, *Scirpus juncoides*, *Scirpus nipponicus*, *Cyperus serotinus*, *Cyperus difformis* and *Cyperus hakonensis* and the like, Lemnaceae weeds represented by *Spirodela polyrhiza* and *Lemna paucicostata* and the like, Commelinaceae weeds represented by *Murdannia keisak* and the like, Pontederiaceae weeds represented by *Monochoria korsakowii* and *Monochoria vaginalis* and the like, Elatinaceae weeds represented by *Elatine triandra* and the like, Lythraceae weeds represented by *Ammannia multiflora* and *Rotala indica* and the like, Oenotheraceae weeds represented by *Ludwigia epilobioides* and the like, Scrophulariaceae weeds represented by *Dopatrium junceum*, *Gratiola japonica*, *Limnophila sessilifolia*, *Lindernia pyxidaria* and *Lindernia dubia* and the like, Leguminosae weeds represented by *Aeschynomene indica* and the like, and Compositae weeds represented by *Bidens frondosa* and *Bidens tripartita* and the like, and the like are mentioned.

Further, the compounds of the present invention, as herbicides for farmland and orchard use, can be used for soil treatment, soil incorporation treatment and foliar treatment. As farmland weeds, for example, broad-leaved weeds such as Solanaceae weeds represented by *Solanum nigrum* and *Datura stramonium* and the like, Geraniaceae weeds represented by *Granium carolinianum* and the like, Malvaceae weeds represented by *Abutilon theophrasti* and *Sida spinosa* and the like, Convolvulaceae weeds represented by *Ipomoea* spps. such as *Ipomoea purpurea* and *Calystegia* spps. and the like, Amaranthaceae weeds represented by *Amaranthus lividus* and *Amaranthus retroflexus* and the like, Compositae weeds represented by *Xanthium pennsylvanicum*, *Ambrosia artemisiaefolia*, *Helianthus annuus*, *Galinsoga ciliata*, *Cirsium arvense*, *Senecio vulgaris* and *Erigeron annuus* and the like, Cruciferae weeds represented by *Rorippa indica*, *Sinapis arvensis* and *Capsella Bursapastoris* and the like, Polygonaceae weeds represented by *Polygonum Blumei* and *Polygonum convolvulus* and the like, Portulacaceae weeds represented by *Portulaca oleracea* and the like, Chenopodiaceae weeds represented by *Chenopodium album*, *Chenopodium ficifolium* and *Kochia scoparia* and the like, Caryophyllaceae weeds represented by *Stellaria media* and the like, Scrophulariaceae weeds represented by *Veronica persica* and the like, Commelinaceae weeds represented by *Commelina communis* and the like, Labiatae weeds represented by *Lamium amplexicaule* and *Lamium purpureum* and the like, Euphorbiaceae weeds represented by *Euphorbia supina* and *Euphorbia maculata* and the like, Rubiaceae weeds represented by *Galium spurium* and *Rubia akane* and the like, Violaceae weeds represented by *Viola mandshurica* and the like and Leguminosae weeds represented by *Sesbania exaltata* and *Cassia obtusifolia* and the like, and Oxalidaceae and the like represented by *Oxalis corniculata*. Graminaceous weeds represented by *Sorgham bicolor*, *Panicum dichotomiflorum*, *Sorghum halepense*, *Echinochloa crus-galli* var. *crus-galli*, *Echinochloa crus-galli* var. *praticola*, *Echinochloa utilis*, *Digitaria ciliaris*, *Avena fatua*, *Alopecurus myosuroides*, *Eleusine indica*, *Setaria viridis*, *Setaria faberi* and *Alopecurus aegualis* and the like and Cyperaceous weeds represented by *Cyperus rotundus, Cyperus esculentus* and the like, and the like are mentioned.

Further, the compounds of the present invention, other than in agricultural and horticultural fields such as paddy fields, farmland and orchards, can also be used in any of the treatment methods of soil treatment, soil incorporation treatment and foliar treatment, on non-agricultural and horticultural land, such as in lawns, sports fields, vacant land, roadsides and railtrack sides. As such weeds, in addition to those mentioned as farmland and orchard weeds, *Poa annua, Taraxacum officinale, Conyza sumatrensis, Cardamine flexuosa, Trifolium repens, Hydrocotyle sibthorpioides, Plantago asiatica, Cyperus brevifolius, Kyllinga brevifolia, Equisetum arvense* and the like are mentioned.

The compounds of the present invention can as necessary be applied as formulations or mixed at the time of spreading with other types of herbicide, various insecticides, fungicides, plant growth regulators or synergists.

In particular, through mixing and applying with other herbicides, cost reductions due to reduction of the dosage applied, broadening of the herbicidal spectrum due to the synergistic action of the mixed agents, and higher herbicidal efficacy can be expected. At this time, simultaneous combination with a plurality of known herbicides is also possible.

As preferred herbicides which can be mixed and used with the compounds of the present invention, for example, acetochlor (generic name), acifluorfen (generic name), aclonifen (generic name), alachlor (generic name), alloxydim (generic name), alloxydim-sodium (generic name), ametryn (generic name), amicarbazone (generic name), amidosulfuron (generic name), aminocyclopirachlor (generic name), aminocyclopirachlor salts and esters, aminopyralid (generic name), aminopyralid salts and esters, amiprophos-methyl (generic name), amitrol (generic name), anilofos (generic name), asulam (generic name), atrazine (generic name), azafenidin (generic name), azimsulfuron (generic name), beflubutamid (generic name), benazolin-ethyl (generic name), bencarbazone (generic name), benfluralin, benefin (generic name), benfuresate (generic name), bensulfuron-methyl (generic name), bensulide (generic name), bentazone (generic name), bentazone-sodium (generic name), bentazone salts, benthiocarb (generic name), benzfendizone (generic name), benzobicyclon (generic name), benzofenap (generic name), bialaphos (generic name), bialaphos-sodium (generic name), bicyclopyrone (generic name), bifenox (generic name), bispyribac (generic name), bispyribac-sodium (generic name), bromacil (generic name), bromobutide (generic name), bromofenoxim (generic name), bromoxynil (generic name), bromoxynil salts and esters, butachlor (generic name), butafenacil (generic name), butamifos (generic name), butenachlor (generic name), butralin (generic name), butroxydim (generic name), butylate (generic name), cafenstrole (generic name), carbetamide (generic name), carfentrazone-ethyl, chlomethoxyfen (generic name), chlomethoxynil (generic name), chloramben (generic name), chloramben salts and esters, chloransulam-methyl (generic name), chlorflurenol-methyl (generic name), chloridazon (generic name), chlorimuron-ethyl (generic name), chlorobromuron (generic name), chlorotoluron (generic name), chloroxuron (generic name), chlorphtalim (generic name), chlorpropham (generic name), chloro IPC (chlorpropham (generic name)), chlorsulfuron (generic name), chlorthal-dimethyl (generic name), chlorthiamid (generic name), cinidon-ethyl (generic name), cinmethylin (generic name), cinosulfuron (generic name), clethodim (generic name), clodinafop (generic name), clodinafop-propargyl (generic name), clomazone (generic name), clomeprop (generic name), clopyralid (generic name), clopyralid salts and esters, CNP (generic name), cumyluron (generic name), cyanazin (generic name), cycloate (generic name), cyclopyrimorate (generic name, SW-065/study name), cyclosulfamuron (generic name), cycloxydim (generic name), cyhalofop-butyl (generic name), DAH-500 (study name), dalapon (generic name), dazomet (generic name), desmedipham (generic name), desmetryn (generic name), dicamba (generic name), dicamba salts and esters, dichlobenil (generic name), diclofop (generic name), diclofop-methyl (generic name), dichlorprop (generic name), dichlorprop salts and esters, dichlorprop-P (generic name), dichlorprop-P salts and esters, diclosulam (generic name), difenzoquat (generic name), diflufenican (generic name), diflufenzopyr (generic name), diflufenzopyr-sodium (generic name), dimepiperate (generic name), dimethametryn (generic name), dimethachlor (generic name), dimethenamid (generic name), dimethenamid-P (generic name), dimethipin (generic name), dinitramine (generic name), dinoseb (generic name), dinoterb (generic name), DNOC (generic name) diphenamid (generic name), diquat (generic name), dithiopyl (generic name), diuron (generic name), DSMA (generic name), dymron (generic name), endothal (generic name), EPTC (generic name), esprocarb (generic name), ethalfluralin (generic name), ethametsulfuron-methyl (generic name), ethofumesate (generic name), etobenzanid (generic name), ethoxysulfuron (generic name), flazasulfuron (generic name), fenoxaprop (generic name), fenoxaprop-ethyl (generic name), fenoxasulfone (generic name), fenquinotrione (generic name), fentrazamide (generic name), flamprop (generic name), flazasulfuron (generic name), florasulam (generic name), fluazifop (generic name), fluazifop-butyl (generic name), fluazolate (generic name), flucarbazone-sodium (generic name), flucetosulfuron (generic name), flucloralin (generic name), flufenacet (generic name), flufenpyl-ethyl (generic name), flumetsulam (generic name), flumiclorac-pentyl (generic name), flumioxazin (generic name), fluometuron (generic name), fluoroglycofen-ethyl (generic name), flupyrsulfuron (generic name), flupoxam (generic name), flurenol (generic name), fluridone (generic name), flurochloridone (generic name), fluroxypyr (generic name), fluroxypyr-esters, flurprimidol (generic name), flurtamone (generic name), fluthiacet-methyl (generic name), fomesafen (generic name), foramsulfuron (generic name), fosamine (generic name), glufosinate (generic name), glufosinate-ammonium (generic name), glyphosate (generic name), glyphosate-ammonium (generic name), glyphosate-isopropylamine (glyphosate-isopropylammonium (generic name)), glyphosate-potassium (generic name), glyphosate-sodium (generic name), glyphosate-trimesium (generic name), halauxifen (generic name), halauxifen salts and esters, halosafen (generic name), halosulfuron (generic name), halosulfuron-methyl (generic name), haloxyfop (generic name), haloxyfop-methyl (generic name), hexazinone (generic name), imazamethabenz-methyl (generic name), imazamox (generic name), imazapic (generic name), imazapyr (generic name), imazethapyr (generic name), imazaquin (generic name), imazosulfuron (generic name), indanofan (generic name), indaziflam (generic name), iodosulfuron-methyl-sodium (generic name), ioxynil octanoate (generic name), ioxynil salts and esters, ipfencarbazone (generic name), isoproturon (generic name), isouron (generic name), isoxaben (generic name), isoxaflutole (generic name), karbutilate (generic name), lactofen (generic name), lenacil (generic name), linuron (generic name), maleic hydrazide (generic name), MCPA (generic name), MCPA salts and esters, MCPB (generic name), MCPB salts and esters, mecoprop, MCPP (generic name), mecoprop salts and esters, mecoprop-P, MCPP-P (generic name), mecoprop-P salts and esters, mefenacet (generic name), mefluidide (generic name), mesosulfuron-methyl (generic name), mesotrione (generic name), metam (generic name), metamifop (generic name), metamitron (generic name), metazachlor (generic name), methabenzthiazuron (generic name), metazosulfuron (generic name), methiozolin (generic name), methyl azide (generic name), methyl bromide (generic name), methyl dymron (generic name), methyl iodide (generic name), metobenzuron (generic name), metolachlor (generic name), metolachlor-S (generic name), metosulam (generic name), metribuzin (generic name), metsulfuron-methyl (generic name), metoxuron (generic name), molinate (generic name), monolinuron (generic name), monosulfuron (generic name), monosulfuron-methyl (generic name), MSMA (generic name), naproanilide (generic name), napropamide (generic name), naptalam (generic name), naptalam-sodium (generic name), neburon (generic name), nicosulfuron (generic name), norflurazon (generic name), OK-701 (study name), oleic acid (generic name), orbencarb (generic name), orthosulfamuron (generic name), oryzalin (generic name), oxadiargyl (generic name), oxadiazon (generic name), oxasulfuron (generic name), oxaziclomefone (generic name), oxyfluorfen (generic name), paraquat (generic name), pelargonic acid (generic name), pendimethalin (generic name), penoxsulam (generic name), pentanochlor (generic name), pentoxazone (generic name), pethoxamid (generic name), phenmedipham-ethyl (generic name), picloram (generic name), picloram salts and esters, picolinafen (generic name), pinoxaden (generic name), piperophos (generic name), pretilachlor (generic name), primisulfuron-methyl (generic name), prodiamine (generic name), profluazol (generic name), profoxydim (generic name), prometon (generic name), prometryn (generic name), propachlor (generic name), propanil (generic name), propaquizafop (generic name), propazin (generic name), propham (generic name), propisochlor (generic name), propoxycarbazone-sodium (generic name), propyrisulfuron (generic name), propyzamide (generic name), prosulfocarb (generic name), prosulfuron (generic name), pyraclonil (generic name), pyraflufen-ethyl (generic name), pyrasulfotole (generic name), pyrazolynate (generic name), pyrazosulfuron (generic name), pyrazosulfuron-ethyl (generic name), pyrazoxyfen (generic name), pyribenzoxim (generic name), pyributicarb (generic name), pyridafol (generic name), pyridate (generic name), pyriftalid (generic name), pyriminobac-methyl (generic name), pyrimisulfan (generic name), pyrithiobac-sodium (generic name), pyroxasulfone (generic name), pyroxsulam (generic name), quinclorac (generic name), quinmerac (generic name), quinoclamine (generic name), quizalofop (generic name), quizalofop-ethyl (generic name), quizalofop-tefuryl (generic name), quizalofop-P (generic name), quizalofop-P-ethyl (generic name), quizalofop-P-tefuryl (generic name), rimsulfuron (generic name), saflufenacil (generic name), sethoxydim (generic name), siduron (generic name), simazine (generic name), simetryn (generic name), SL-261 (study name), sulcotrione (generic name), sulfentrazone (generic name), sulfometuron-methyl (generic name), sulfosulfuron (generic name), TCBA (2,3,6-TBA (generic name)), 2,3,6-TBA salts and esters, TCTP (chlorthal-dimethyl, tetrachlorothiophene (generic name)), tebutam (generic name), tebuthiuron (generic name), tefuryltrione (generic name), tembotrione (generic name), tepraloxydim (generic name), terbacil (generic name), terbumeton (generic name), terbuthylazine (generic name), terbutryn (generic name), tetrapion/flupropanate (generic name), thenylchlor (generic name), thiazafluron (generic name), thiazopyr (generic name), thidiazimin (generic name), thidiazuron (generic name), thiencarbazone-methyl (generic name), thifensulfuron-methyl (generic name), tolpyralate (generic name), topramezon (generic name), tralkoxydim (generic name), triafamone (generic name), triallate (generic name), triasulfuron (generic name), triaziflam (generic name), tribenuron-methyl (generic name), triclopyr (generic name), triclopyr salts and esters, tridiphane (generic name), trietazine (generic name), trifludimoxadin (generic name), trifloxysulfuron (generic name), trifluralin (generic name), triflusulfuron-methyl (generic name), tritosulfuron (generic name), 2,4-PA (generic name), 2,4-PA salts and esters, 2,4-DB (generic name), 2,4-DB salts and esters and the like are mentioned. These components can be used singly or as mixtures of 2 or more types, and the ratios if they are mixed can be freely selected.

As safeners, for example, AD-67, benoxacor (generic name), cloquintocet-mexyl (generic name), cyomerinil (generic name), dichlormid (generic name), dicyclonone (generic name), cyprosulfamide (generic name), diethorate (generic name), DKA-24, dymron (generic name), fenclorazole-ethyl (generic name), fenclorim (generic name), HEXIM (generic name), flurazole (generic name), fluxofenim (generic name), furilazole (generic name), isoxadifen (generic name), isoxadifen-ethyl (generic name), MCPA, mecoprop (generic name), mefenpyr (generic name), mefenpyr-ethyl (generic name), mefenpyr-diethyl (generic name), mephenate (generic name), MG-191, NA (naphthalic anhydride), OM (octamethylenediamine), oxabetrinil (generic name), PPG-1292, R-29148 and the like are mentioned. These components can be used singly or as mixtures of 2 or more types, and the ratios if they are mixed can be freely selected.

When the compounds of the present invention are applied as herbicides, they are usually mixed with suitable solid carriers or liquid carriers, and with further addition, as desired, of surfactants, penetrants, spreading agents, thickeners, antifreeze agents, binders, anticaking agents, disintegrants, stabilizers and the like, and can be supplied for use in formulations of any dosage form, such as wettable powder, emulsion, flowable, dry flowable, liquid, powder, granules or gels. Further, for labor-saving, and increased safety, the aforesaid formulations of any dosage form can be supplied after sealing into water-soluble packages.

As solid carriers for example natural mineral substances such as quartz, kaolinite, pyrophyllite, sericite, talc, bentonite, acidic clay, attapulgite, zeolite and diatomaceous earth. inorganic salts such as calcium carbonate, ammonium sulfate, sodium sulfate and potassium chloride, synthetic silicic acid and synthetic silicate salts are mentioned.

As liquid carriers, for example alcohols such as ethylene glycol, propylene glycol and isopropanol, aromatic hydrocarbons such as xylene, alkylbenzenes and alkylnaphthalenes, ethers such as butyl cellosolve, ketones such as cyclohexanone, esters such as γ-butyrolactone, amides such as N-methylpyrrolidone and N-octylpyrrolidone, plant oils such as soya bean oil, rapeseed oil, cottonseed oil and sunflower oil, and water are mentioned.

These solid and liquid carriers can be used singly, or 2 or more types can be used together.

As surfactants, for example nonionic surfactants such as polyoxyethylene alkyl ethers, polyoxyethylene alkyl aryl ethers, polyoxyethylene styryl phenyl ethers, polyoxyethylene polyoxypropylene block copolymers, polyoxyethylene fatty acid esters, sorbitan fatty acid esters and polyoxyethylene sorbitan fatty acid esters, anionic surfactants such as alkylsulfate salts, alkylbenzenesulfonate salts, ligninsulfonate salts, alkylsulfosuccinate salts, naphthalenesulfonate salts, alkylnaphthalenesulfonate salts, naphthalenesulfonic acid formalin condensation product salts, alkylnaphthalenesulfonic acid formalin condensation product salts, polyoxyethylene alkyl aryl ether sulfate and phosphate salts, polyoxyethylenestyryl phenyl ether sulfate and phosphate salts, polycarboxylic acid salts and polystyrene sulfonate salts, cationic surfactants such as alkylamine salts and quaternary alkylammonium salts, and amphoteric surfactants such as amino acid type and betaine type are mentioned.

There is no particular restriction as to the content of these surfactants but normally the range from 0.05 to 20 parts by weight per 100 parts by weight of formulation of the present invention is desirable. Further, these surfactants can be used singly, or 2 or more types can be used together.

The compounds of the present invention can as necessary be applied as formulations or mixed at the time of spreading with other types of herbicide, various insecticides, fungicides, plant growth regulators or synergists.

In particular, through mixing and applying with other herbicides, cost reductions due to reduction of the dosage applied, broadening of the herbicidal spectrum due to the synergistic action of the mixed agents, and higher herbicidal efficacy can be expected. At this time, simultaneous combination with a plurality of known herbicides is also possible.

The application dosages of the compounds of the present invention will differ depending on the use location, application timing, application method, crop cultivated and the like, but in general an active component dosage from 0.005 to about 50 kg per hectare (ha) is suitable.

Next, compounding examples of formulations where the compounds of the present invention are used are shown. However, the present invention is not limited only to these compounding examples. Also, in the following compounding examples "parts" means parts by weight.

Wettable Powder

| | |
|---|---|
| Compound of the present invention | 0.1-80 parts |
| Solid carrier | 5-98.9 parts |
| Surfactant | 1-10 parts |
| Others | 0-5 parts |

As others, for example anticaking agents, stabilizers and the like are mentioned.

Emulsion

| | |
|---|---|
| Compound of the present invention | 0.1-30 parts |
| Liquid carrier | 45-95 parts |
| Surfactant | 4.9-15 parts |
| Others | 0-10 parts |

As others, for example spreading agents, stabilizers and the like are mentioned.

Flowable

| | |
|---|---|
| Compound of the present invention | 0.1-70 parts |
| Liquid carrier | 15-98.89 parts |
| Surfactant | 1-12 parts |
| Others | 0.01-30 parts |

As others, for example antifreeze agents, thickeners and the like are mentioned.

Dry Flowable

| | |
|---|---|
| Compound of the present invention | 0.1-90 parts |
| Solid carrier | 0-98.9 parts |
| Surfactant | 1-20 parts |
| Others | 0-10 parts |

As others, for example binders, stabilizers and the like are mentioned.

Liquid

| | |
|---|---|
| Compound of the present invention | 0.01-70 parts |
| Liquid carrier | 20-99.99 parts |
| Others | 0-10 parts |

As others, for example antifreeze agents, spreading agents and the like are mentioned.

Granules

| | |
|---|---|
| Compound of the present invention | 0.01-80 parts |
| Solid carrier | 10-99.99 parts |
| Others | 0-10 parts |

As others, for example binders, stabilizers and the like are mentioned.

Powder

| | |
|---|---|
| Compound of the present invention | 0.01-30 parts |
| Solid carrier | 65-99.99 parts |
| Others | 0-10 parts |

As others, for example anti-drift agents, stabilizers and the like are mentioned.

At the time of use, the aforesaid formulations can be dispersed as such or after dilution 1 to 10,000-fold with water Formulation Examples Next, pesticide formulations with compounds of the present invention as active component, are shown but they are not limited only to these. Also, in the following compounding examples "parts" means parts by weight.

Compounding Example 1

Wettable Powder

| | |
|---|---|
| Compound of the present invention No. A-1-01 | 20 parts |
| Pyrophyllite | 76 parts |
| Sorpol 5039 (anionic surfactant: Toho Chemical Industries (Corp.) brand name) | 2 parts |
| Carplex #80 (synthetic water-containing silicic acid: Shionogi (Corp.) brand name) | 2 parts |

The above are made into a wettable powder by homogeneous mixing and milling.

Compounding Example 2

Emulsion

| | |
|---|---|
| Compound of the present invention No. A-1-01 | 5 parts |
| Xylene | 75 parts |
| N-methylpyrrolidone | 15 parts |
| Sorpol 2680 (anionic surfactant: Toho Chemical Industries (Corp.) brand name) | 5 parts |

The above are made into an emulsion by homogeneous mixing.

Compounding Example 3

Flowable

| | |
|---|---|
| Compound of the present invention No. A-1-01 | 25 parts |
| Agrisol S-710 (nonionic surfactant: Kao (Corp.) brand name) | 10 parts |
| Lunox 1000C (anionic surfactant: Toho Chemical Industries (Corp.) brand name) | 0.5 parts |
| Xanthan gum | 0.02 parts |
| Water | 64.48 parts |

The above are made into a flowable by homogeneous mixing, then wet milling.

Compounding Example 4

Dry Flowable

| | |
|---|---|
| Compound of the present invention No. A-1-01 | 75 parts |
| Hitenol NE-15 (anionic surfactant: Dai-Ichi Kogyo Seiyaku (Co.) brand name) | 5 parts |
| Vanillex N (anionic surfactant: Nippon Paper (Corp.) brand name) | 10 parts |
| Carplex #80 (synthetic water-containing silicic acid: Shionogi (Corp.) brand name) | 10 parts |

The above are made into a dry flowable by homogeneous mixing and milling, addition of a small quantity of water, then stirring, mixing and kneading, granulating with an extrusion granulator and drying.

Compounding Example 5

Granules

| | |
|---|---|
| Compound of the present invention No. A-1-01 | 1 part |
| Bentonite | 55 parts |
| Talc | 44 parts |

The above are made into granules by homogeneous mixing and milling, addition of a small quantity of water, then stirring, mixing and kneading, granulating with an extrusion granulator and drying.

Practical Examples

The present invention is explained in more detail below by specifically stating as practical examples examples of the synthesis of heterocyclic amide compounds represented by the formula (1) used as active components in the herbicides of the present invention, and test examples, but the present invention is not limited by these.

Further, the proton nuclear magnetic resonance chemical shift values in the practical examples were measured at 300 MHz using $Me_4Si$ (tetramethyl silane) as the reference substance. Further, the solvents used in the measurements are stated in the following synthesis examples. Further, the symbols in the proton nuclear magnetic resonance chemical shift values of the practical examples have the following meanings.

s: singlet, brs: broad singlet, d: doublet, t: triplet, m: multiplet

Synthesis Examples

Synthesis Example 1

N-(4,6-dichloropyridin-2-yl)-2-methyl-2-(4-oxo-5-phenyl-1,3,5-oxadiazinan-3-yl) propionamide (Compound No. A-2-17)

Step 1: Synthesis of 2-methyl-2-(4-oxo-5-phenyl-1,3,5-oxadiazinan-3-yl)propionyl chloride 650 mg (5.12 mmol) of oxalyl chloride were added with ice cooling to a mixed solution of 900 mg (3.41 mmol) of 2-methyl-2-(4-oxo-5-phenyl-1,3,5-oxadiazinan-3-yl)propionic acid, 0.5 ml N,N-dimethylformamide and 20 ml methylene chloride. After completion of the addition, said reaction mixture liquid was stirred for 1 hour with ice cooling. After completion of the stirring, by distilling off the solvent from said reaction liquid under reduced pressure, 960 mg of the desired compound were obtained as a white solid.

Step 2: Synthesis of N-(4,6-dichloropyridin-2-yl)-2-methyl-2-(4-oxo-5-phenyl-1,3,5-oxa-diazinan-3-yl) propionamide A mixed solution of 960 mg (3.40 mmol) of 2-methyl-2-(4-oxo-5-phenyl-1,3,5-oxadiazinan-3-yl)propionyl chloride, 660 mg (4.05 mmol) of 2-amino-4,6-dichloropyridine and 10 ml tetrahydrofuran was added over 30 minutes with ice cooling to a mixed solution of 162 mg (4.25 mmol) of 63 wt. % sodium hydride (dispersion in mineral oil) and 30 ml tetrahydrofuran. After completion of the addition, said reaction mixture liquid was stirred for 3 hours with ice cooling. After completion of the stirring, the reaction was stopped by addition of 40 ml of water, and said reaction liquid was extracted with ethyl acetate (2×50 ml). The organic layer obtained was dried with anhydrous sodium sulfate, and the solvent distilled off under reduced pressure. The residue obtained was purified by silica gel chromatography

[n-hexane:ethyl acetate=9:1 to 1:9 (volume ratio, likewise below)] and 560 mg of the desired compound were obtained as a white solid.

Melting point: 183-186° C.

Synthesis Example 2

N-(4,6-dichloropyridin-2-yl)-2-methyl-2-(5-phenyl-4-thioxo-1,3,5-oxadiazinan-3-yl) propionamide (Compound No. A-2-18)

260 mg (0.643 mmol) of 2,4-bis(4-methoxyphenyl)-1,3-dithia-2,4-diphosphetan-2,4-disulfide were added at room temperature to a mixed solution of 130 mg (0.318 mmol) of N-(4,6-dichloropyridin-2-yl)-2-methyl-2-(4-oxo-5-phenyl-1,3,5-oxadiazinan-3-yl)propionamide and 5 ml toluene. After completion of the addition, said reaction mixture liquid was stirred for 1 hour with heating under reflux. After completion of the stirring, said reaction liquid was purified by silica gel chromatography (n-hexane:ethyl acetate=9:1 to 3:7, and 45 mg of the desired compound were obtained as a white solid.

Melting point: 187-189° C.

Synthesis Example 3

2-methyl-2-(4-oxo-5-phenyl-1,3,5-oxadiazinan-3-yl)-N-propyl-N-[4-(trifluoromethyl)-pyridin-2-yl] propionamide (Compound No. A-5-05)

180 mg (1.51 mmol) of thionyl chloride were added with ice cooling to a mixed solution of 200 mg (0.757 mmol) of 2-methyl-2-(4-oxo-5-phenyl-1,3,5-oxadiazinan-3-yl)propionic acid, 310 mg of (1.52 mmol) of N-propyl-4-(trifluoromethyl)pyridin-2-amine, 10 mg (0.0819 mmol) of 4-(dimethylamino)pyridine and 5 ml pyridine. After completion of the addition, said reaction mixture liquid was stirred for 3 hours with ice cooling. After completion of the stirring, the solvent was distilled off from said reaction liquid under reduced pressure. The residue obtained was purified by silica gel chromatography (n-hexane:ethyl acetate=9:1 to 3:7, and 115 mg of the desired compound were obtained as a white solid.

Melting point: 163-164° C.

Synthesis Example 4

N-(3-ethyl-1,2,4-thiadiazol-2-yl)-2-methyl-2-[6-methyl-4-oxo-5-(thiophen-3-yl)-2H-1,3-oxazin-3(4H)-yl]propionamide (Compound No. B-1-02)

270 mg (1.42 mmol) of 1-(3-dimethylaminopropyl)-3-ethyl carbodiimide hydrochloride were added at room temperature to a mixed solution of 200 mg (0.711 mmol) of 2-methyl-2-[6-methyl-4-oxo-5-(thiophen-3-yl)-2H-1,3-oxazin-3(4H)-yl)propionic acid, 180 mg (1.39 mmol) of 3-ethyl-1,2,4-thiadiazol-5-amine, 140 mg (1.38 mmol) of triethylamine, 10 mg (0.0819 mmol) of 4-(dimethylamino) pyridine and 3 ml methylene chloride. After completion of the addition, said reaction mixture liquid was stirred overnight at room temperature. After completion of the stirring, the reaction was stopped by addition of 20 ml of water, and said reaction liquid was extracted with chloroform (2×20 ml). The organic layer obtained was dried with anhydrous sodium sulfate, and the solvent distilled off under reduced pressure. The residue obtained was purified by silica gel chromatography (n-hexane:ethyl acetate=9:1 to 3:7), and 81 mg of the desired compound were obtained as a yellow solid.

Melting point: 171-172° C.

Synthesis Example 5

2-[5-(2-fluoropyridin-3-yl)-6-methyl-4-oxo-2H-1,3-oxazin-3(4H)-yl]-2-methyl-N-[4-(trifluoromethyl) pyridin-2-yl] propionamide (Compound No. B-2-17)

100 mg (0.522 mmol) of 1-(3-dimethylaminopropyl)-3-ethylcarbodiimide hydrochloride were added at room temperature to a mixed solution of 100 mg (0.340 mmol) of 2-[5-(2-fluoropyridin-3-yl)-6-methyl-4-oxo-2H-1,3-oxazin-3(4H)-yl]-2-methylpropionic acid, 80 mg (0.494 mmol) of 4-(trifluoromethyl)pyridin-2-amine, 70 mg (0.514 mmol) of 3H-[1,2,3]triazolo[4,5-b]pyridin-3-ol and 5 ml N,N-dimethylformamide. After completion of the addition, said reaction mixture liquid was stirred overnight at room temperature. After completion of the stirring, the reaction was stopped by addition of 20 ml of water, and said reaction liquid was extracted with chloroform (2×20 ml). The organic layer obtained was dried with anhydrous sodium sulfate, and the solvent distilled off under reduced pressure. The residue obtained was purified by silica gel chromatography (n-hexane:ethyl acetate=9:1 to 1:9) and 20 mg of the desired compound were obtained as a white solid.

Melting point: 130-131° C.

Synthesis Example 6

N-(6-chloropyridin-2-yl)-2-methyl-2-[6-methyl-4-oxo-5-(pyrimidin-5-yl)-2H-1,3-oxazin-3(4H)-yl] propionamide (Compound No. B-2-22)

Step 1: Synthesis of 2-methyl-2-[6-methyl-4-oxo-5-(pyrimidin-5-yl)-2H-1,3-oxazin-(4H)-yl) propionyl chloride 210 mg (1.65 mmol) of oxalyl chloride were added with ice cooling to a mixed solution of 360 mg (1.30 mmol) of 2-methyl-2-[6-methyl-4-oxo-5-(pyrimidin-5-yl)-2H-1,3-oxazin-3(4H)-yl)propionic acid, 0.1 ml N,N-dimethylformamide and 15 ml methylene chloride. After completion of the addition, said reaction mixture liquid was stirred for 1 hour at room temperature. After completion of the stirring, by distilling off the solvent from said reaction liquid under reduced pressure, 360 mg of the desired compound were obtained as a white solid.

Step 2: Synthesis of N-(6-chloropyridin-2-yl)-2-methyl-2-[6-methyl-4-oxo-5-(pyrimidin-5-yl)-2H-1,3-oxazin-3(4H)-yl]propionamide 400 mg (3.95 mmol) of triethylamine were added with ice cooling to a mixed solution of 360 mg (1.22 mmol) of 2-methyl-2-[6-methyl-4-oxo-5-(pyrimidin-5-yl)-2H-1,3-oxazin-3(4H)-yl)propionyl chloride, 170 mg (1.32 mmol) of 6-chloropyridin-2-amine and 10 ml methylene chloride. After completion of the addition, said reaction mixture liquid was stirred for 1 hour at room temperature. After completion of the stirring, the reaction was stopped by addition of 20 ml of water, and said reaction liquid was extracted with chloroform (2×20 ml). The organic layer obtained was dried with anhydrous sodium sulfate, and the solvent distilled off under reduced pressure. The residue obtained was purified by silica gel chromatography (n-hexane:ethyl acetate=9:1 to 1:9), and 114 mg of the desired compound were obtained as a resinous substance.

$^1$H-NMR (CDCl$_3$, Me$_4$Si, 300 MHz): δ 9.11 (s, 1H), 8.66 (s, 2H), 8.23 (brs, 1H), 8.19 (d, 1H, J=8.4 Hz), 7.65 (dd, 1H, J=8.4 Hz, 4.5 Hz), 7.05 (d, 1H, J=4.5 Hz), 5.36 (s, 2H), 2.04 (s, 3H), 1.64 (s, 6H).

Reference Example 1

2-methyl-2-(4-oxo-5-phenyl-1,3,5-oxadiazinan-3-yl) propionic acid

Step 1: Synthesis of methyl 2-methyl-2-(3-phenylureido)propionate 1.68 g (13.0 mmol) of N,N-diisopropylethylamine were added with ice cooling to a mixed solution of 1.55 g (13.0 mmol) of isocyanatobenzene, 2.00 g (13.0 mmol) of methyl 2-amino-2-methylpropionate hydrochloride and 50 ml methylene chloride. After completion of the addition, said reaction mixture liquid was stirred overnight at room temperature. After completion of the stirring, the reaction was stopped by addition of 50 ml of water, and said reaction liquid was extracted with methylene chloride (2×50 ml). The organic layer obtained was dried with anhydrous sodium sulfate, the solvent distilled off under reduced pressure, and 2.80 g of the desired compound were obtained as a white solid.

Melting point: 72-74° C.

Step 2: Synthesis of methyl 2-methyl-2-(4-oxo-1,3, 5-oxadiazinan-3-yl)propionate 3 ml of trifluoroacetic acid were added at room temperature to a mixed solution of 2.30 g (9.74 mmol) of methyl 2-methyl-2-(3-phenylureido)propionate, 950 mg (29.1 mmol) of paraformaldehyde and 30 ml of 1,2-dichloroethane. After completion of the addition, said reaction mixture liquid was stirred overnight at room temperature. After completion of the stirring, the reaction was stopped by addition of 50 ml of water, and said reaction liquid was extracted with chloroform (2×50 ml). The organic layer obtained was dried with anhydrous sodium sulfate, and the solvent distilled off under reduced pressure. The residue obtained was purified by silica gel chromatography (n-hexane:ethyl acetate=9:1 to 3:7), and 1.24 g of the desired compound were obtained as a white solid.

Melting point: 67-69° C.

Step 3: Synthesis of 2-methyl-2-(4-oxo-5-phenyl-1, 3,5-oxadiazinan-3-yl)propionic acid 15 ml of 1 mol/L aqueous sodium hydroxide solution were added at room temperature to a mixed solution of 1.24 g (4.46 mmol) of methyl 2-methyl-2-(4-oxo-5-phenyl-1,3, 5-oxa-diazinan-3-yl)propionate and 15 ml methanol. After completion of the addition, said reaction mixture liquid was stirred with heating under reflux for hours. After completion of the stirring, the solvent was distilled off from said reaction mixture under reduced pressure. 20 ml of 1 mol/L aqueous hydrochloric acid solution were added to the residue obtained, and by filtering off the solid precipitated, 470 mg of the desired compound were obtained as a white solid.

Melting point: 174-177° C.

Reference Example 2

N-propyl-4-(trifluoromethyl)pyridin-2-amine 1.95 g (33.0 mmol) of propan-1-amine were added at room temperature to a mixed solution of 2.00 g (11.0 mmol) of 2-chloro-4-(trifluoromethyl)pyridine and 15 ml of N-methyl-pyrrolidin-2-one. After completion of the addition, said reaction mixture liquid was stirred for 3 hours at 140° C. After completion of the stirring, the reaction was stopped by addition of 30 ml of water, and said reaction liquid was extracted with ethyl acetate (2×50 ml). The organic layer obtained was dried with anhydrous sodium sulfate, and the solvent distilled off under reduced pressure. The residue obtained was purified by silica gel chromatography (n-hexane:ethyl acetate=99:1 to 80:20), and 1.80 g of the desired compound were obtained as a white solid.

Melting point: 46-47° C.

Reference Example 3

Ethyl 2-[3-(2-chloropyridin-3-yl)ureido]-2-methyl-propionate 1.57 g (7.79 mmol) of (4-nitrophenyl) chloroformate were added in portions over 30 minutes with ice cooling to a mixed solution of 1.00 g (7.78 mmol) of 3-amino-2-chloropyridine, 620 mg (7.84 mmol) of pyridine and 20 ml methylene chloride. After completion of the addition, said reaction mixture was stirred for 2 hours with ice cooling. After this, 1.30 g (7.76 mmol) of ethyl 2-amino-2-methylpropionate hydrochloride and 2.00 g (15.84 mmol) of N,N-diisopropylethylamine were added with ice cooling to said reaction mixture. After completion of the addition, said reaction mixture liquid was stirred overnight with ice cooling. After completion of the addition, the reaction was stopped by addition of 30 ml of water, and said reaction liquid was extracted with methylene chloride (2×300 ml). The organic layer obtained was dried with anhydrous sodium sulfate, and the solvent distilled off under reduced pressure. The residue obtained was purified by silica gel chromatography (n-hexane:ethyl acetate=9:1 to 3:7), and 1.60 g of the desired compound were obtained as a white solid.

$^1$H-NMR (CDCl$_3$, Me$_4$Si, 300 MHz): δ 8.56-8.51 (m, 1H), 8.02-7.99 (m, 1H), 7.27-7.16 (m, 1H), 6.84 (brs, 1H), 5.58 (brs, 1H), 4.19 (q, 2H, J=7.2 Hz), 1.63 (s, 6H), 1.28 (t, 3H, J=7.2 Hz).

Reference Example 4

6-chloro-4-fluoropyridin-2-amine 7.46 g (49.11 mmol) of cesium fluoride were added at room temperature to a mixed solution of 2.00 g (12.27 mmol) of 4,6-dichloropyridin-2-amine and 30 ml dimethyl sulfoxide. After completion of the addition, said reaction mixture liquid was stirred for 12 hours at 170° C. After completion of the stirring, the reaction was stopped by addition of 100 ml of water, and said reaction liquid was extracted with ethyl acetate (2×300 ml). The organic layer obtained was dried with anhydrous sodium sulfate, and the solvent distilled off under reduced pressure. The residue obtained was purified by silica gel chromatography (n-hexane:ethyl acetate=9:1 to 5:5), and 95 mg of the desired compound were obtained as a white solid.

Reference Example 5

4-chloro-6-fluoropyridin-2-amine 7.46 g (49.11 mmol) of cesium fluoride were added at room temperature to a mixed solution of 2.00 g (12.27 mmol) of 4,6-dichloropyridin-2-amine and 30 ml dimethyl sulfoxide. After completion of the addition, said reaction mixture liquid was stirred for 12 hours at 170° C. After completion of the stirring, the reaction was stopped by addition of 100 ml of water, and said reaction liquid was extracted with ethyl acetate (2×300 ml). The organic layer obtained was dried with anhydrous sodium sulfate, and the solvent distilled off under reduced pressure. The residue obtained was purified by silica gel chromatography (n-hexane:ethyl acetate=9:1 to 5:5), and 55 mg of the desired compound were obtained as a white solid.

Reference Example 6

4-chloro-6-methoxypyridin-2-amine 1.19 g (6.17 mmol) of a 28 wt. % sodium methoxide methanolic solution were added at room temperature to a mixed solution of 1.00 g (6.13 mmol) of 4,6-dichloropyridin-2-amine and 8 ml dimethyl sulfoxide. After completion of the addition, said reaction mixture liquid was stirred for 10 hours at 50° C. After completion of the stirring, the reaction was stopped by addition of 20 ml of water, and said reaction liquid was extracted with diethyl ether (2×30 ml). The organic layer obtained was dried with anhydrous sodium sulfate, and the solvent distilled off under reduced pressure. The residue obtained was purified by silica gel chromatography (n-hexane:ethyl acetate=9:1 to 1:9), and 280 mg of the desired compound were obtained as a colorless liquid.

$^1$H-NMR (CDCl$_3$, Me$_4$Si, 300 MHz): δ 6.39 (s, 1H), 6.07 (s, 1H), 4.37 (brs, 2H), 3.83 (s, 3H).

Reference Example 7

4-chloro-6-phenoxypyridin-2-amine 630 mg (6.69 mmol) of phenol and 1.00 g (6.13 mmol) of 4,6-dichloropyridin-2-amine were added at room temperature to a mixed solution of 250 mg (6.56 mmol) of 63 wt. % sodium hydride (dispersion in mineral oil) and 15 ml dimethyl sulfoxide. After completion of the addition, said reaction mixture liquid was stirred for 14 hours at 100° C. After completion of the stirring, the reaction was stopped by addition of 30 ml of water, and said reaction liquid was extracted with diethyl ether (2×30 ml). The organic layer obtained was dried with anhydrous sodium sulfate, and the solvent distilled off under reduced pressure. The residue obtained was purified by silica gel chromatography (n-hexane:ethyl acetate=9:1 to 1:9), and 70 mg of the desired compound were obtained as a brown solid.

$^1$H-NMR (CDCl$_3$, Me$_4$Si, 300 MHz): δ 7.44-7.35 (m, 2H), 7.21-7.18 (m, 1H), 7.13-7.09 (m, 2H), 6.19 (s, 1H), 6.08 (s, 1H), 4.52 (brs, 2H).

Reference Example 8

6-chloro-4-phenoxypyridin-2-amine 630 mg (6.69 mmol) of phenol and 1.00 g (6.13 mmol) of 4,6-dichloropyridin-2-amine were added at room temperature to a mixed solution of 250 mg (6.56 mmol) of 63 wt. % sodium hydride (dispersion in mineral oil) and 15 ml dimethyl sulfoxide. After completion of the addition, said reaction mixture liquid was stirred for 14 hours at 100° C. After completion of the stirring, the reaction was stopped by addition of 30 ml of water, and said reaction liquid was extracted with diethyl ether (2×30 ml). The organic layer obtained was dried with anhydrous sodium sulfate, and the solvent distilled off under reduced pressure. The residue obtained was purified by silica gel chromatography (n-hexane:ethyl acetate=9:1 to 1:9), and 210 mg of the desired compound were obtained as a brown solid.

$^1$H-NMR (CDCl$_3$, Me$_4$Si, 300 MHz): δ 7.45-7.36 (m, 2H), 7.24-7.21 (m, 1H), 7.11-7.05 (m, 2H), 6.27 (s, 1H), 5.84 (s, 1H), 4.48 (brs, 2H).

Reference Example 9

4-chloro-6-cyclopropylpyridin-2-amine 500 mg (3.07 mmol) of 4,6-dichloropyridin-2-amine, 270 mg (3.14 mmol) of cyclopropyl-boronic acid and 1.08 g (10.19 mmol) of sodium carbonate were added at room temperature to a mixed solution of 360 mg (0.312 mmol) of tetrakis(triphenylphosphine)palladium(0), 10 ml toluene and 5 ml water. After completion of the addition, the air in the reaction vessel was replaced with nitrogen gas. After completion of the replacement, said reaction mixture liquid was stirred for 6 hours with heating under reflux under a nitrogen gas atmosphere. After completion of the stirring, the reaction was stopped by addition of 20 ml of water, and said reaction liquid was extracted with ethyl acetate (2×30 ml). The organic layer obtained was dried with anhydrous sodium sulfate, and the solvent distilled off under reduced pressure. The residue obtained was purified by silica gel chromatography (n-hexane:ethyl acetate=9:1 to 6:4), and 10 mg of the desired compound were obtained as a white solid.

$^1$H-NMR (CDCl$_3$, Me$_4$Si, 300 MHz): δ 6.50 (s, 1H), 6.28 (s, 1H), 4.40 (brs, 2H), 1.88-1.79 (m, 1H), 1.06-1.00 (m, 2H), 0.99-0.95 (m, 2H).

Reference Example 10

6-chloro-4-(difluoromethoxy)pyridin-2-amine

Step 1: Synthesis of 2,6-dichloro-4-(difluoromethoxy)pyridine 720 mg (5.21 mmol) of potassium carbonate were added at room temperature to a mixed solution of 600 mg (3.66 mmol) of 2,6-dichloropyridin-4-ol, 1.08 g (5.32 mmol) of 2-bromo-2,2-difluoroethyl acetate and 15 ml N,N-dimethylformamide. After completion of the addition, said reaction mixture liquid was stirred for 4 hours at 50° C. After completion of the stirring, the reaction was stopped by addition of 30 ml of water, and said reaction liquid was extracted with ethyl acetate (2×30 ml). The organic layer obtained was dried with anhydrous sodium sulfate, and the solvent distilled off under reduced pressure. The residue obtained was purified by silica gel chromatography (n-hexane:ethyl acetate=99:1 to 90:10), and 740 mg of the desired compound were obtained as a colorless liquid.

Step 2: Synthesis of 2-bromo-6-chloro-4-(difluoromethoxy)pyridine 4.40 g (28.7 mmol) of bromotrimethylsilane were added at room temperature to a mixed solution of 410 mg (1.92 mmol) of 2,6-dichloro-4-(difluoromethoxy)pyridine and 10 ml acetonitrile. After completion of the addition, said reaction mixture liquid was stirred for 2 days with heating under reflux. After completion of the stirring, the solvent was distilled off from said reaction liquid under reduced pressure. The residue obtained was purified by silica gel chromatography (n-hexane:ethyl acetate=99:1 to 90:10), and 410 mg of the desired compound were obtained as a colorless liquid.

Step 3: Synthesis of
6-chloro-4-(difluoromethoxy)pyridin-2-amine 2.90 g (47.7 mmol) of aqueous ammonia (28 wt. %) and 110 mg (0.796 mmol) of potassium carbonate were added at room temperature to a mixed solution of 410 mg (1.59 mmol) of 2-bromo-6-chloro-4-(difluoromethoxy)pyridine, 25 mg (0.175 mmol) of copper(1) oxide, 30 mg (0.340 mmol) of N,N'-dimethylethylenediamine and 10 ml ethylene glycol. After completion of the addition, said reaction mixture liquid was stirred for 3 hours with heating under reflux. After completion of the stirring, the reaction was stopped by addition of 30 ml of water, and said reaction liquid was extracted with ethyl acetate (2×30 ml). The organic layer obtained was dried with anhydrous sodium sulfate, and the solvent distilled off under reduced pressure. The residue obtained was purified by silica gel chromatography (n-hexane:ethyl acetate=9:1 to 5:5), and 65 mg of the desired compound were obtained as a white solid.

$^1$H-NMR (CDCl$_3$, Me$_4$Si, 300 MHz): δ 6.56 (t, 1H, J=72 Hz), 6.45-6.42 (m, 1H), 6.09-6.06 (m, 1H), 4.68 (brs, 2H).

Reference Example 11

6-methoxy-4-(trifluoromethyl)pyridin-2-amine 640 mg (3.32 mmol) of 28 wt. % methanolic sodium methoxide solution were added to a mixed solution of 200 mg (1.11 mmol) of 6-fluoro-4-(trifluoromethyl)pyridin-2-amine and 5 ml methanol. After completion of the addition, said reaction mixture liquid was stirred for 3 hours with heating under reflux. After completion of the stirring, the reaction was stopped by addition of 10 ml of water, and said reaction liquid was extracted with ethyl acetate (2×20 ml). The organic layer obtained was washed with water, then dried with anhydrous sodium sulfate, and the solvent distilled off under reduced pressure. The residue obtained was purified by silica gel chromatography (n-hexane:ethyl acetate=9:1 to 7:3), and 190 mg of the desired compound were obtained as a yellow solid.

Reference Example 12

6-fluoro-4-methylpyridin-2-amine 8 ml of aqueous ammonia (28 wt. %) and 150 mg (1.09 mmol) of potassium carbonate were added at room temperature to a mixed solution of 1.00 g (5.26 mmol) of 2-bromo-6-fluoro-4-methylpyridine, 38 mg (0.266 mmol) of copper (1) oxide, 46 mg (0.522 mmol) of N,N'-dimethylethylenediamine and 10 ml ethylene glycol. After completion of the addition, said reaction mixture liquid was stirred for 10 hours with heating under reflux. After completion of the stirring, the reaction was stopped by addition of 30 ml of water, and said reaction liquid was extracted with ethyl acetate (2×20 ml). The organic layer obtained was washed with water, then dried with anhydrous sodium sulfate, and the solvent distilled off under reduced pressure. The residue obtained was purified by silica gel chromatography (n-hexane:ethyl acetate=9:1 to 6:4), and 400 mg of the desired compound were obtained as a white solid.

$^1$H-NMR (CDCl$_3$, Me$_4$Si, 300 MHz): δ 6.13 (s, 1H), 6.06 (s, 1H), 4.37 (brs, 2H), 2.24 (s, 3H).

Reference Example 13

4-ethyl-6-fluoropyridin-2-amine 100 mg (0.524 mmol) of 4-bromo-6-fluoropyridin-2-amine, 58 mg (0.785 mmol) of ethylboronic acid and 250 mg (1.81 mmol) of potassium carbonate were added at room temperature to a mixed solution of 16 mg (0.0138 mmol) of tetrakis(triphenylphosphine)-palladium(0), 2 ml 1,4-dioxane and 2 ml water. After completion of the addition, the air in the reaction vessel was replaced with nitrogen gas. After completion of the replacement, said reaction mixture liquid was stirred for 10 hours under a nitrogen atmosphere with heating under reflux. After completion of the stirring, the reaction was stopped by addition of 10 ml of water, and said reaction liquid was extracted with ethyl acetate (3×15 ml). The organic layer obtained was washed with water, then dried with anhydrous sodium sulfate, and the solvent distilled off under reduced pressure. The residue obtained was purified by silica gel chromatography (n-hexane:ethyl acetate=10:0 to 9:1), and 50 mg of the desired compound were obtained as a colorless liquid.

Reference Example 14

6-(fluoromethyl)pyridin-2-amine

Step 1: Synthesis of
2-bromo-6-(fluoromethyl)pyridine 2.10 g (13.0 mmol) of (diethylamino)sulfur trifluoride were added with ice cooling to a mixed solution of 2.24 g (11.9 mmol) of (6-bromopyridin-2-yl)methanol and 40 ml methylene chloride. After completion of the addition, said reaction mixture liquid was stirred for 1 hour with ice cooling. After completion of the stirring, the reaction was stopped by addition of 30 ml of saturated aqueous sodium hydrogen carbonate solution, and said reaction liquid was extracted with methylene chloride (2×30 ml). The organic layer obtained was washed with water, then dried with anhydrous sodium sulfate, and the solvent distilled off under reduced pressure. The residue obtained was purified by silica gel chromatography (n-hexane:ethyl acetate=10:0 to 9:1), and 860 mg of the desired compound were obtained as a white solid.

Step 2: Synthesis of
(6-fluoromethyl)pyridin-2-amine 7 ml of aqueous ammonia (28 wt. %) and 120 mg (0.868 mmol) of potassium carbonate were added at room temperature to a mixed solution of 850 mg (4.47 mmol) of 2-bromo-6-(fluoro-methyl)pyridine, 31 mg (0.217 mmol) of copper (1) oxide, 40 mg (0.454 mmol) of N,N'-dimethylethylenediamine and 10 ml ethylene glycol. After completion of the addition, said reaction mixture liquid was stirred for 8 hours with heating under reflux. After completion of the stirring, the reaction was stopped by addition of 30 ml of water, and said reaction liquid was extracted with ethyl acetate (2×20 ml). The organic layer obtained was washed with water, then dried with anhydrous sodium sulfate, and the solvent distilled off under reduced pressure. The residue obtained was purified by silica gel chromatography (n-hexane:ethyl acetate=9:1 to 6:4), and 150 mg of the desired compound were obtained as a white solid.

$^1$H-NMR (CDCl$_3$, Me$_4$Si, 300 MHz): δ 7.47 (dd, 1H, J=7.2 Hz, 8.4 Hz), 6.78 (d, 1H, J=7.2 Hz), 6.45 (d, 1H, J=8.4 Hz), 5.28 (d, 2H, J=47 Hz), 4.47 (brs, 2H).

Reference Example 15

6-(difluoromethyl)pyridin-2-amine

Step 1: Synthesis of 2-bromo-6-(difluoromethyl)pyridine 3.81 g (23.6 mmol) of (diethylamino)sulfur trifluoride were added with ice cooling to a mixed solution of 2.00 g (10.8 mmol) of 6-bromopicolinaldehyde and 40 ml methylene chloride. After completion of the addition, said reaction mixture liquid was stirred for 2 hours with ice cooling. After completion of the stirring, the reaction was stopped by addition of 30 ml of saturated aqueous sodium hydrogen carbonate solution, and said reaction liquid was extracted with methylene chloride (2×30 ml). The organic layer obtained was washed with water, then dried with anhydrous sodium sulfate, and the solvent distilled off under reduced pressure. The residue obtained was purified by silica gel chromatography (n-hexane:ethyl acetate=10:0 to 8:2), and 1.87 g of the desired compound were obtained as a white solid.

$^1$H-NMR (CDCl$_3$, Me$_4$Si, 300 MHz): δ 7.73-7.58 (m, 3H), 6.58 (t, 1H, J=56 Hz).

Step 2: Synthesis of (6-difluoromethyl)pyridin-2-amine 13 ml of aqueous ammonia (28 wt. %) and 250 mg (1.81 mmol) of potassium carbonate were added at room temperature to a mixed solution of 1.86 g (8.94 mmol) of 2-bromo-6-(fluoromethyl)pyridine, 64 mg (0.447 mmol) of copper(1) oxide, 80 mg (0.908 mmol) of N,N'-dimethylethylenediamine and 18 ml ethylene glycol. After completion of the addition, said reaction mixture liquid was stirred for 22 hours with heating under reflux. After completion of the stirring, the reaction was stopped by addition of 30 ml of water, and said reaction liquid was extracted with ethyl acetate (2×20 ml). The organic layer obtained was washed with water, then dried with anhydrous sodium sulfate, and the solvent distilled off under reduced pressure. The residue obtained was purified by silica gel chromatography (n-hexane:ethyl acetate=9:1 to 6:4), and 770 mg of the desired compound were obtained as a colorless liquid.

$^1$H-NMR (CDCl$_3$, Me$_4$Si, 300 MHz): δ 7.53 (dd, 1H, J=7.2 Hz, 8.1 Hz), 6.94 (d, 1H, J=7.2 Hz), 6.57 (d, 1H, J=8.1 Hz), 6.42 (t, 1H, J=56 Hz), 4.58 (brs, 2H).

Reference Example 16

4-(difluoromethoxy)pyridin-2-amine

Step 1: Synthesis of 2-bromo-4-(difluoromethoxy)pyridine 1.40 g (6.90 mmol) of ethyl 2-bromo-2,2-difluoroacetate were added at room temperature to a mixed solution of 1.00 g (5.75 mmol) of 2-bromopyridin-4-ol, 1.59 g (11.5 mmol) of potassium carbonate and 20 ml N,N-dimethylformamide. After completion of the addition, said reaction mixture liquid was stirred for 30 minutes at 50° C. After completion of the stirring, the reaction was stopped by addition of 30 ml of water, and said reaction liquid was extracted with ethyl acetate (2×20 ml). The organic layer obtained was washed with water, then dried with anhydrous sodium sulfate, and the solvent distilled off under reduced pressure. The residue obtained was purified by silica gel chromatography (n-hexane:ethyl acetate=10:0 to 8:2), and 1.12 g of the desired compound were obtained as a colorless liquid.

$^1$H-NMR (CDCl$_3$, Me$_4$Si, 300 MHz): δ 8.33 (d, 1H, J=5.4 Hz), 7.25 (s, 1H), 7.03-6.99 (m, 1H), 6.62 (t, 1H, J=72 Hz).

Step 2: Synthesis of (4-difluoromethoxy)pyridin-2-amine 8 ml of aqueous ammonia (28 wt. %) and 140 mg (1.01 mmol) of potassium carbonate were added at room temperature to a mixed solution of 1.12 g (5.00 mmol) of 2-bromo-4-(difluoro-methoxy)pyridine, 35 mg (0.245 mmol) of copper(1) oxide, 40 mg (0.454 mmol) of N,N'-dimethylethylenediamine and 10 ml ethylene glycol. After completion of the addition, said reaction mixture liquid was stirred for 8 hours with heating under reflux. After completion of the stirring, the reaction was stopped by addition of 20 ml of water, and said reaction liquid was extracted with ethyl acetate (2×20 ml). The organic layer obtained was washed with water, then dried with anhydrous sodium sulfate, and the solvent distilled off under reduced pressure. The residue obtained was purified by silica gel chromatography (n-hexane:ethyl acetate=9:1 to 1:1), and 120 mg of the desired compound were obtained as a pale yellow liquid.

$^1$H-NMR (CDCl$_3$, Me$_4$Si, 300 MHz): δ 8.02 (d, 1H, J=5.7 Hz), 6.56 (t, 1H, J=73 Hz), 6.39 (dd, 1H, J=5.7 Hz, 2.1 Hz), 6.17 (d, 1H, J=2.1 Hz), 4.51 (brs, 2H).

Reference Example 17

6-fluoro-4-methoxypyridin-2-amine 89 mg (0.461 mmol) of 28 wt. % methanolic sodium methoxide solution were added at room temperature to a mixed solution of 50 mg (0.384 mmol) of 4,6-difluoropyridin-2-amine and 2 ml methanol. After completion of the addition, said reaction mixture liquid was stirred for 24 hours at 60° C. After completion of the stirring, the reaction was stopped by addition of 10 ml of water, and said reaction liquid was extracted with ethyl acetate (2×10 ml). The organic layer obtained was dried with anhydrous sodium sulfate, and the solvent distilled off under reduced pressure. The residue obtained was purified by silica gel chromatography (n-hexane:ethyl acetate=9:1 to 7:3), and 29 mg of the desired compound were obtained as a white solid.

Reference Example 18

6-fluoro-[3,4'-bipyridin]-2'-amine 490 mg (3.48 mmol) of (6-fluoropyridin-3-yl)boronic acid and 1.70 g (16.1 mmol) of sodium carbonate were added at room temperature to a mixed solution of 400 mg (2.31 mmol) of 4-bromopyridin-2-amine, 90 mg (0.123 mmol) of [1,1'-bis(diphenylphosphino)ferrocene] palladium(2) dichloride, 4 ml toluene and 6 ml water. After completion of the addition, the air in the reaction vessel was replaced with nitrogen gas. After completion of the replacement, said reaction mixture liquid was stirred for 2 hours under a nitrogen gas atmosphere with heating under reflux. After completion of the stirring, the reaction was stopped by addition of 15 ml of water, and said reaction liquid was extracted with ethyl acetate (3×30 ml). The organic layer obtained was dried with anhydrous sodium sulfate, and the solvent distilled off under reduced pressure. The residue obtained was purified by silica gel chromatography (methanol:ethyl acetate=1:9), and 430 mg of the desired compound were obtained as a white solid.

$^1$H-NMR (CDCl$_3$, Me$_4$Si, 300 MHz): δ 8.43 (d, 1H, J=2.4 Hz), 8.15 (d, 1H, J=5.4 Hz), 7.99-7.93 (m, 1H), 7.06-7.00 (m, 1H), 6.86-6.78 (m, 1H), 6.64 (s, 1H), 4.61 (brs, 2H).

Reference Example 19

4-(1-methyl-1H-pyrazol-5-yl)pyridin-2-amine 440 mg (3.49 mmol) of (1-methyl-1H-pyrazol-5-yl)boronic acid and 1.70 g (16.1 mmol) of sodium carbonate were added at room temperature to a mixed solution of 400 mg (2.31 mmol) of 4-bromopyridin-2-amine, 90 mg (0.123 mmol) of [1,1'-bis(diphenylphosphino)ferrocene]palladium(2) dichloride, 20 ml toluene and 5 ml water. After completion of the addition, the air in the reaction vessel was replaced with nitrogen gas. After completion of the replacement, said reaction mixture liquid was stirred for 2 hours under a nitrogen gas atmosphere with heating under reflux. After completion of the stirring, the reaction was stopped by addition of 30 ml of water, and said reaction liquid was extracted with ethyl acetate (3×30 ml). The organic layer obtained was dried with anhydrous sodium sulfate, and the solvent distilled off under reduced pressure. The residue obtained was purified by silica gel chromatography (methanol:ethyl acetate=1:9), and 100 mg of the desired compound were obtained as a brown solid.

Reference Example 20

4-(thiophen-3-yl)pyridin-2-amine 720 mg (5.63 mmol) of thiophen-3-ylboronic acid and 1.70 g (16.1 mmol) of sodium carbonate were added at room temperature to a mixed solution of 400 mg (2.31 mmol) of 4-bromopyridin-2-amine, 90 mg (0.123 mmol) of [1,1'-bis(diphenylphosphino)ferrocene] palladium(2) dichloride, 20 ml toluene and 5 ml water. After completion of the addition, the air in the reaction vessel was replaced with nitrogen gas. After completion of the replacement, said reaction mixture liquid was stirred for 2 hours under a nitrogen atmosphere with heating under reflux. After completion of the stirring, the reaction was stopped by addition of 30 ml of water, and said reaction liquid was extracted with ethyl acetate (3×30 ml). The organic layer obtained was dried with anhydrous sodium sulfate, and the solvent distilled off under reduced pressure. The residue obtained was purified by silica gel chromatography (methanol:ethyl acetate=1:9), and 100 mg of the desired compound were obtained as a white solid.

Reference Example 21

2-[5-(2-fluoropyridin-3-yl)-6-methyl-4-oxo-2H-1,3-oxazin-3(4H)-yl]-2-methylpropionic acid Step 1: Synthesis of 5-(2-fluoropyridin-3-yl)-2,2,6-trimethyl-4H-1,3-dioxin-4-one 1.81 g (2.66 mmol) of [1,3-bis(2,6-diisopropylphenyl) imidazol-2-ylide ne] (3-chloro-pyridyl)palladium(2) dichloride were added at room temperature to a mixed solution of 14.3 g (53.4 mmol) of 5-iodo-2,2,6-trimethyl-4H-1,3-dioxin-4-one, 11.3 g (80.1 mmol) of (2-fluoropyridin-3-yl) boronic acid, 33.93 g (320 mmol) of sodium carbonate, 150 ml tetrahydrofuran and 150 ml water. After completion of the addition, the air in the reaction vessel was replaced with nitrogen gas. After completion of the replacement, said reaction mixture liquid was stirred for 4 hours with heating under reflux under a nitrogen gas atmosphere. After completion of the stirring, the reaction was stopped by addition of 200 ml of water, and said reaction liquid was extracted with ethyl acetate (2×300 ml). The organic layer obtained was washed with water, then dried with anhydrous sodium sulfate, and the solvent distilled off under reduced pressure. The residue obtained was purified by silica gel chromatography (n-hexane:ethyl acetate=9:1 to 6:4), and 8.86 g of the desired compound were obtained as a brown solid.

Step 2: Synthesis of benzyl 2-[5-(2-fluoropyridin-3-yl)-6-methyl-4-oxo-2H-1,3-oxazin-3(4H)-yl)-2-methyl propionate 8.85 g (37.3 mmol) of 5-(2-fluoropyridin-3-yl)-2,2,6-trimethyl-4H-1,3-dioxin-4-one were added at room temperature to a mixed solution of 7.66 g (37.3 mmol) of benzyl 2-methyl-2-(methylenamino)propionate and 100 ml xylene. After completion of the addition, said reaction mixture liquid was stirred with heating under reflux for 5 hours. After completion of the stirring, the solvent was distilled off from said reaction mixture under reduced pressure. The residue obtained was purified by silica gel chromatography (n-hexane:ethyl acetate=9:1 to 3:7), and 13.0 g of the desired compound were obtained as a colorless liquid.

Step 3: Synthesis of 2-[5-(2-fluoropyridin-3-yl)-6-methyl-4-oxo-2H-1,3-oxazin-3-(4H)-yl)-2-methyl propionic acid 1.30 g of 5 wt. % Pd/C (N. E. Chemcat Corp. STD type) were added to a mixed solution of 12.9 g (33.6 mmol) of benzyl 2-[5-(2-fluoropyridin-3-yl)-6-methyl-4-oxo-2H-1,3-oxazin-3(4H)-yl)-2-methyl propionate and 150 ml tetrahydrofuran. After completion of the addition, the air in the reaction vessel was replaced with hydrogen gas. After completion of the replacement, said reaction mixture liquid was stirred overnight at room temperature under a hydrogen atmosphere. After completion of the stirring, the gas within the reaction vessel was replaced with nitrogen gas, and said reaction liquid was filtered through celite. The solvent was distilled off from the filtrate obtained under reduced pressure, and 7.46 g of the desired compound were obtained as a white solid.

Melting point: 179-182° C.

Reference Example 22

Synthesis of 2-methyl-2-[6-methyl-4-oxo-5-(pyrimidin-5-yl)-2H-1,3-oxazin-3(4H)-yl) propionic acid Step 1: Synthesis of 2,2,6-trimethyl-5-(pyrimidin-5-yl)-4H-1,3-dioxin-4-one 1.30 g (1.91 mmol) of [1,3-bis(2,6-diisopropylphenyl) imidazol-2-ylidene] (3-chloro-pyridyl)palladium(2) dichloride were added at room temperature to a mixed solution of 6.00 g (32.7 mmol) of (2,2,6-trimethyl-4-oxo-4H-1,3-dioxin-5-yl)boronic acid, 7.70 g (48.7 mmol) of 5-bromopyrimidine, 16.6 g (157 mmol) of sodium carbonate, 100 ml tetrahydrofuran and 100 ml water. After completion of the addition, the air in the reaction vessel was replaced with nitrogen gas. After completion of the replacement, said reaction mixture liquid was stirred overnight with heating under reflux under a nitrogen gas atmosphere. After completion of the stirring, the reaction was stopped by addition of 200 ml of water, and said reaction liquid was extracted with ethyl acetate (2×300 ml). The organic layer obtained was washed with water, then dried with anhydrous sodium sulfate, and the solvent distilled off under reduced pressure. The residue obtained was purified by silica gel chromatography (n-hexane:ethyl acetate=9:1 to 1:9), and 2.00 g of the desired compound were obtained as a yellow solid.

Step 2: Synthesis of 4-nitrobenzyl 2-methyl-2-[6-methyl-4-oxo-5-(pyrimidin-5-yl)-2H-1,3-oxazin-3 (4H)-yl)propionate 2.50 g (11.4 mmol) of 2,2,6-trimethyl-5-(pyrimidin-5-yl)-4H-1,3-dioxin-4-one were added at room temperature to a mixed solution of 2.85 g (11.4) of 4-nitrobenzyl 2-methyl-2-(methylenamino)propionate and 100 ml xylene. After completion of the addition, said reaction mixture liquid was stirred with heating under reflux for 5 hours. After completion of the stirring, the solvent was distilled off from said reaction liquid under reduced pressure. The residue obtained was purified by silica gel chromatography (n-hexane:ethyl acetate=9:1 to 3:7), and 1.80 g of the desired compound were obtained as a colorless liquid.

Step 3: Synthesis of 2-methyl-2-[6-methyl-4-oxo-5-(pyrimidin-5-yl)-2H-1,3-oxazin-3(4H)-yl)propionic acid 500 mg of 5 wt. % Pd/C (N. E. Chemcat Corp. STD type) were added to a mixed solution of 1.80 g (4.36 mmol) of 4-nitrobenzyl 2-methyl-2-[6-methyl-4-oxo-5-(pyrimidin-5-yl)-2H-1,3-oxazin-3(4H)-yl) propionate, 40 ml methanol and 80 ml ethyl acetate. After completion of the addition, the air in the reaction vessel was replaced with hydrogen gas. After completion of the replacement, said reaction mixture liquid was stirred for 4 hours at 50° C. under a hydrogen atmosphere. After completion of the stirring, the gas in the reaction vessel was replaced with nitrogen gas, and said reaction liquid was filtered through celite. The solvent was distilled off from the filtrate obtained under reduced pressure. The residue obtained was purified by silica gel chromatography (n-hexane:ethyl acetate=9:1 to 1:9), and 800 mg of the desired compound were obtained as a colorless liquid.

The compounds of the present invention can be synthesized in accordance with the aforesaid Synthesis Examples. Examples of compounds of the present invention produced similarly to Synthesis Example 1 to Synthesis Example 6 are shown in table 3 to table 14, but the present invention is not limited only to these. Also, in the tables the term Me represents a methyl group, and similarly below Et represents an ethyl group, Pr a propyl group, OMe methoxy group, OEt ethoxy group, OPh phenoxy group, SMe methylthio group, Ph phenyl group, $CO_2Me$ methoxycarbonyl group, n-normal, i-iso and c-cyclo.

Further, in the tables, the term "m.p." represents "melting point" and the term "*1" resinous state respectively.

The respective structures of the aromatic heterocycles shown in the tables are shown below.

[Chem. 39]

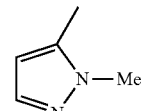 T-1a

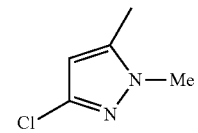 T-1b

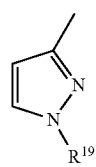 T-3a

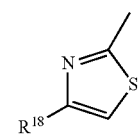 T-4a

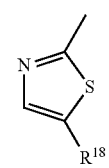 T-4b

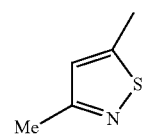 T-7a

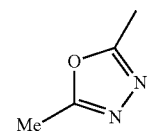 T-10a

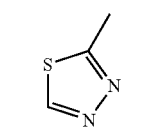 T-13a

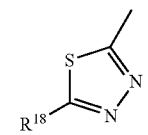 T-13b

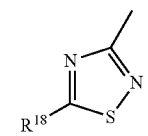 T-14a

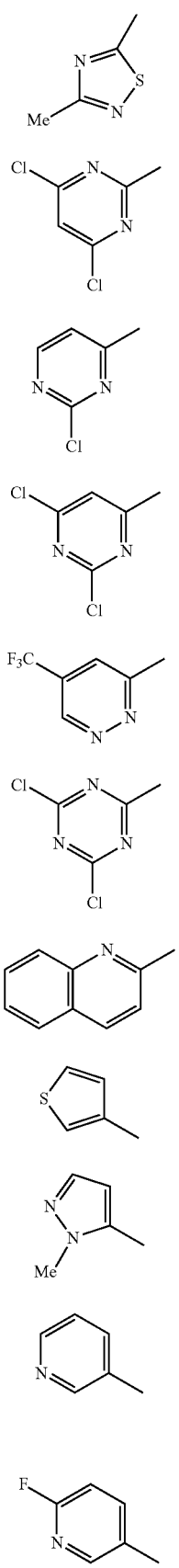
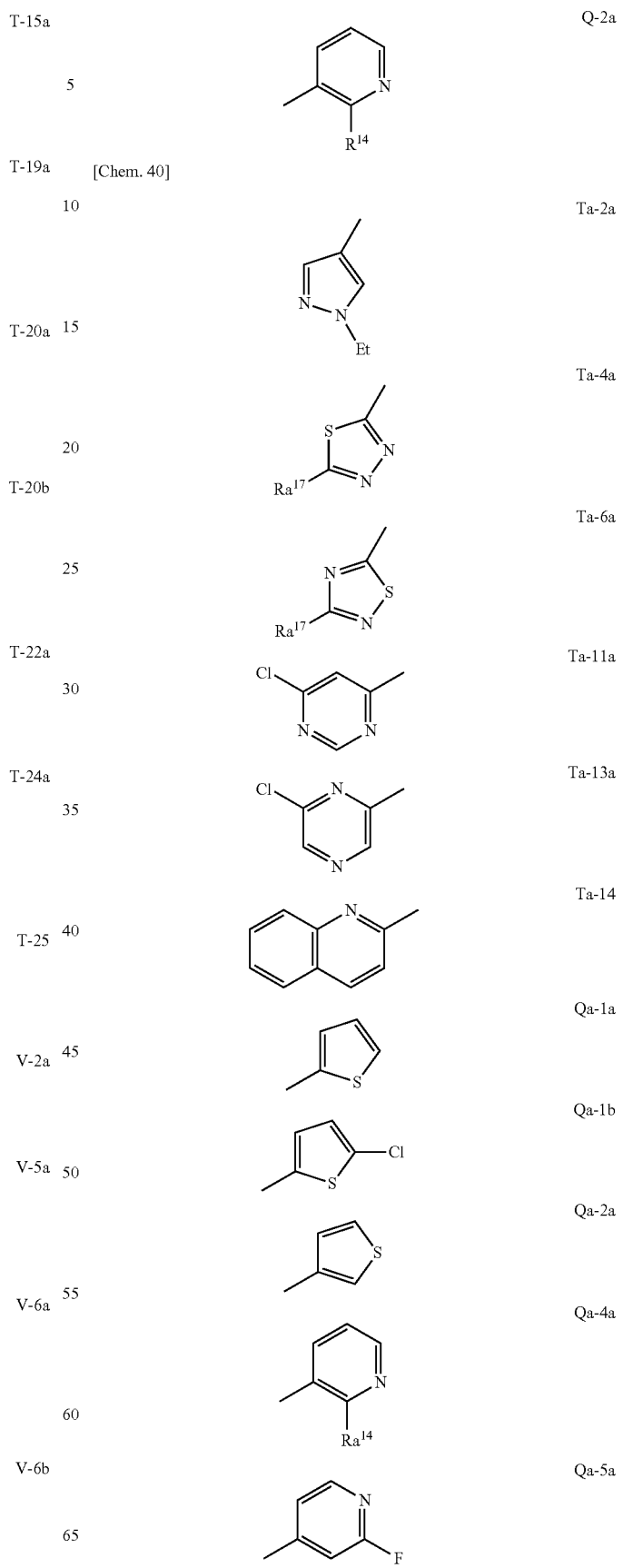

Qa-8a

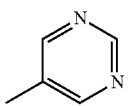

Qa-9

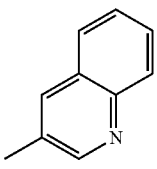

TABLE NO. 3

[Chem. 41]

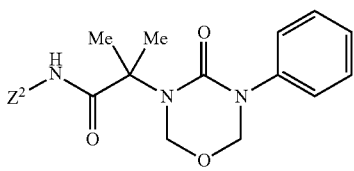

TABLE 8

| No. | Z² | R¹⁸ | R¹⁹ | m.p. (° C.) |
|---|---|---|---|---|
| A-1-01 | T-1a | | | 211-212 |
| A-1-02 | T-1b | | | 214-215 |
| A-1-03 | T-3a | | Me | 180-181 |
| A-1-04 | T-3a | | CF₂H | 200-201 |
| A-1-05 | T-4a | Me | | 147-158 |
| A-1-06 | T-4a | CF₃ | | 192-201 |
| A-1-07 | 1-4b | Cl | | 185-206 |
| A-1-08 | T-4b | Me | | 215-222 |
| A-1-09 | T-4b | NO₂ | | 174-179 |
| A-1-10 | T-7a | | | 198-211 |
| A-1-11 | T-10a | | | 116-120 |
| A-1-12 | T-13a | | | 92-95 |
| A-1-13 | T-13b | Me | | 215-220 |
| A-1-14 | T-13b | CF₃ | | 47-52 |
| A-1-15 | T-13b | SMe | | 237-240 |
| A-1-16 | T-14a | OMe | | 162-168 |
| A-1-17 | T-14a | SMe | | 210-213 |
| A-1-18 | T-15a | | | 247-249 |
| A-1-19 | T-19a | | | 222-225 |
| A-1-20 | T-20a | | | 224-225 |
| A-1-21 | T-20b | | | 263-265 |
| A-1-22 | T-22a | | | 165-168 |
| A-1-23 | T-24a | | | 219-221 |
| A-1-24 | T-25 | | | 175-180 |

TABLE NO. 4

[Chem. 42]

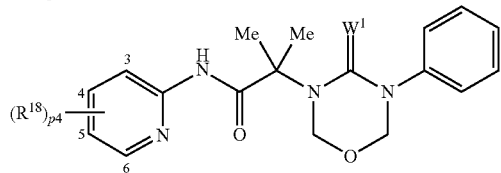

TABLE 9

| No. | (R¹⁸)ₚ₄ | W¹ | m.p. (° C.) |
|---|---|---|---|
| A-2-01 | H | O | 185-187 |
| A-2-02 | 3-F | O | 180-184 |
| A-2-03 | 4-F | O | 168-171 |
| A-2-04 | 5-F | O | 156-158 |
| A-2-05 | 6-F | O | 164-168 |
| A-2-06 | 4-Cl | O | 182-184 |
| A-2-07 | 6-Cl | O | 157-158 |
| A-2-08 | 4-Br | O | 188-190 |
| A-2-09 | 6-Br | O | 140-141 |
| A-2-10 | 4-I | O | 189-194 |
| A-2-11 | 6-I | O | 147-149 |
| A-2-12 | 3,5-diF | O | 165-166 |
| A-2-13 | 4,6-diF | O | 164-166 |
| A-2-14 | 4-F-6-Cl | O | 186-187 |
| A-2-15 | 4-Cl-6-F | O | 127-128 |
| A-2-16 | 3,6-diCl | O | *1 |
| A-2-17 | 4,6-diCl | O | 183-186 |
| A-2-18 | 4,6-diCl | S | 187-189 |
| A-2-19 | 4-Br-6-F | O | 213-214 |
| A-2-20 | 4-Me-6-F | O | 145-146 |
| A-2-21 | 4-Et-6-F | O | 145-155 |
| A-2-22 | 4-CF₃-6-F | O | 214-216 |
| A-2-23 | 4-OMe-6-F | O | 150-155 |
| A-2-24 | 4-Cl-6-Br | O | 165-170 |
| A-2-25 | 4-Cl-6-Me | O | 206-207 |
| A-2-26 | 4-Me-6-Cl | O | 133-134 |
| A-2-27 | 4-CF₂H-6-Cl | O | *1 |
| A-2-28 | 4-CF₃-6-Cl | O | 195-199 |
| A-2-29 | 4-Cl-6-c-Pr | O | *1 |
| A-2-30 | 4-c-Pr-6-Cl | O | 137-138 |
| A-2-31 | 4-Cl-6-Ph | O | 136-137 |
| A-2-32 | 4-Cl-6-OMe | O | 110-111 |
| A-2-33 | 4-OMe-6-Cl | O | 116-117 |
| A-2-34 | 4-OCF₂H-6-Cl | O | 132-133 |
| A-2-35 | 4-Cl-6-OPh | O | 142-144 |
| A-2-36 | 4-OPh-6-Cl | O | 160-161 |
| A-2-37 | 4-Me | O | 103-105 |
| A-2-38 | 6-Me | O | 152-153 |
| A-2-39 | 6-CH₂F | O | 133-135 |
| A-2-40 | 4-CF₂H | O | 213-216 |
| A-2-41 | 6-CF₂H | O | 118-120 |
| A-2-42 | 4-CF₃ | O | 174-177 |
| A-2-43 | 5-CF₃ | O | 167-170 |
| A-2-44 | 6-CF₃ | O | 143-147 |
| A-2-45 | 4-c-Pr | O | 153-154 |
| A-2-46 | 6-c-Pr | O | 145-146 |

TABLE 10

| No. | (R¹⁸)ₚ₄ | W¹ | m.p. (° C.) |
|---|---|---|---|
| A-2-47 | 4-CO₂Me | O | 164-166 |
| A-2-48 | 4-CN | O | *1 |
| A-2-49 | 4-Ph | O | 187-188 |
| A-2-50 | 6-Ph | O | 120-122 |
| A-2-51 | 4-OMe | O | 178-184 |
| A-2-52 | 6-OMe | O | 134-135 |
| A-2-53 | 4-OCF₂H | O | 177-178 |
| A-2-54 | 6-OCF₂H | O | 61-63 |
| A-2-55 | 4-OPh | O | 178-179 |
| A-2-56 | 4,6-diMe | O | 178-182 |
| A-2-57 | 4-Me-6-CF₃ | O | 109-110 |
| A-2-58 | 4-CF₃-6-Me | O | 220-221 |
| A-2-59 | 4-CF₃-6-OMe | O | 118-120 |
| A-2-60 | 4-CF₃-6-OEt | O | 132-137 |

TABLE NO. 5

[Chem. 43]

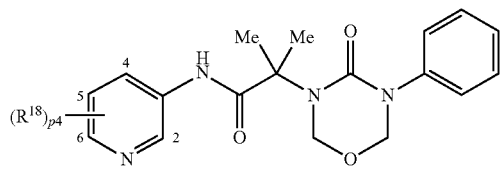

TABLE 11

| No. | $(R^{18})_{p4}$ | m.p. (° C.) |
|---|---|---|
| A-3-01 | 5-F | 168-169 |
| A-3-02 | 5-Cl | 167-168 |
| A-3-03 | 5-Br | 174-175 |
| A-3-04 | 2-F-5-Br | 148-150 |
| A-3-05 | 5,6-diCl | *1 |
| A-3-06 | 2,5-diCl | *1 |
| A-3-07 | 2-Cl-5-Br | *1 |
| A-3-08 | 2-Br-5-Cl | *1 |
| A-3-09 | 2-Cl-5-Me | 50-56 |
| A-3-10 | 5-CF$_3$ | 179-180 |

TABLE NO. 6

[Chem. 44]

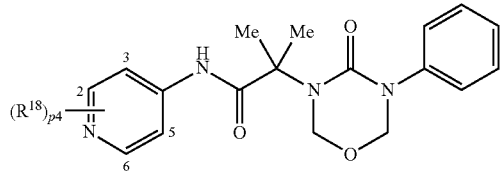

TABLE 12

| No. | $(R^{18})_{p4}$ | m.p. (° C.) |
|---|---|---|
| A-4-01 | 2-F | 241-243 |
| A-4-02 | 2-Cl | 247-248 |
| A-4-03 | 2-Br | 219-220 |
| A-4-04 | 2,6-diF | 259-261 |
| A-4-05 | 2,6-diCl | 262-264 |
| A-4-06 | 2-CF$_3$ | 218-222 |

TABLE NO. 7

[Chem. 45]

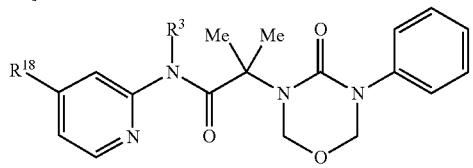

TABLE 13

| No. | $R^{18}$ | $R^3$ | m.p. (° C.) |
|---|---|---|---|
| A-5-01 | V-2a | H | 175-182 |
| A-5-02 | V-5a | H | *1 |
| A-5-03 | V-6a | H | *1 |

TABLE 13-continued

| No. | $R^{18}$ | $R^3$ | m.p. (° C.) |
|---|---|---|---|
| A-5-04 | V-6b | H | *1 |
| A-5-05 | CF$_3$ | n-Pr | 163-164 |

TABLE NO. 8

[Chem. 46]

TABLE 14

| No. | $Z^1$ | $R^{14}$ | $(R^{18})_{p4}$ | m.p. (° C.) |
|---|---|---|---|---|
| A-6-01 | 2,6-diF—Ph | | 4,6-diCl | 202-204 |
| A-6-02 | 2,6-diF—Ph | | 4-Cl-6-Br | 205-208 |
| A-6-03 | 3,4-diCl—Ph | | 4-CF$_3$ | 185-186 |
| A-6-04 | 3-Cl-4-Me—Ph | | 4-CF$_3$ | 152-153 |
| A-6-05 | 3-Cl-4-OMe—Ph | | 4-CF$_3$ | 168-169 |
| A-6-06 | 2-Cl—Ph | | 4,6-diCl | *1 |
| A-6-07 | 3-Me—Ph | | 4-CF$_3$ | 146-147 |
| A-6-08 | 3-Me—Ph | | 4,6-diCl | 160-161 |
| A-6-09 | 4-Me—Ph | | 4-CF$_3$ | 201-203 |
| A-6-10 | 4-Me—Ph | | 4,6-diF | 139-140 |
| A-6-11 | 4-Me—Ph | | 4-Cl-6-F | 134-135 |
| A-6-12 | 4-Me—Ph | | 4,6-diCl | 175-178 |
| A-6-13 | Q-2a | Cl | 4-CF$_3$ | 156-157 |

TABLE NO. 9

[Chem. 47]

TABLE 15

| No. | $(R^{18})_{p4}$ | $R^1$ | $R^2$ | m.p. (° C.) |
|---|---|---|---|---|
| A-7-01 | 4,6-diCl | Me | H | *1 |
| A-7-02 | 4-CF$_3$ | Me | H | *1 |
| A-7-03 | 4-CF$_3$ | i-Pr | H | 79-84 |
| A-7-04 | 4,6-diCl | —(CH$_2$)—(CH$_2$)— | | 114-115 |
| A-7-05 | 4-CF$_3$ | —(CH$_2$)—(CH$_2$)— | | *1 |

TABLE NO. 10

[Chem. 48]

TABLE 16

| No. | Za¹ | Z² | Ra¹⁴ | Ra¹⁷ | m. p. (° C.) |
|---|---|---|---|---|---|
| B-1-01 | Qa-2a | Ta-6a | | Me | 203-205 |
| B-1-02 | Qa-2a | Ta-6a | | Et | 171-172 |
| B-1-03 | Qa-2a | Ta-6a | | i-Pr | 143-146 |
| B-1-04 | Qa-2a | Ta-6a | | OMe | 196-198 |
| B-1-05 | Qa-2a | Ta-6a | | SMe | 198-201 |
| B-1-06 | Qa-4a | Ta-6a | F | Cl | 225-228 |
| B-1-07 | Qa-4a | Ta-11a | F | | 121-127 |
| B-1-08 | Qa-4a | Ta-13a | F | | 162-166 |
| B-1-09 | Ph | Ta-2a | | | 138-141 |
| B-1-10 | Ph | Ta-4a | | CF₃ | 183-186 |
| B-1-11 | Ph | Ta-4a | | Ph | 206-207 |
| B-1-12 | Ph | Ta-6a | | Cl | 210-215 |
| B-1-13 | Ph | Ta-6a | | Me | 193-195 |
| B-1-14 | Ph | Ta-6a | | Et | 189-192 |
| B-1-15 | Ph | Ta-6a | | OMe | 209-211 |
| B-1-16 | Ph | Ta-6a | | SMe | 205-208 |
| B-1-17 | Ph | Ta-6a | | Ph | 195-198 |
| B-1-18 | Ph | Ta-14 | | | 134-139 |

TABLE NO. 11

[Chem. 49]

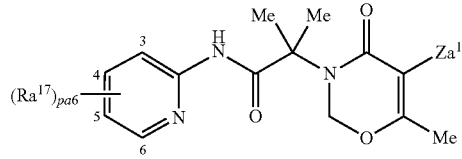

TABLE 17

| No. | Za¹ | Ra¹⁴ | (Ra¹⁷)ₚₐ₆ | m. p. (° C.) |
|---|---|---|---|---|
| B-2-01 | Qa-1a | | 6-Cl | 84-86 |
| B-2-02 | Qa-1b | | 6-Cl | 124-125 |
| B-2-03 | Qa-1b | | 6-Br | 118-120 |
| B-2-04 | Qa-2a | | 6-F | 169-171 |
| B-2-05 | Qa-2a | | 6-Cl | 143-144 |
| B-2-06 | Qa-2a | | 6-Br | *1 |
| B-2-07 | Qa-4a | F | 4-Cl | *1 |
| B-2-08 | Qa-4a | F | 6-Cl | 110-112 |
| B-2-09 | Qa-4a | F | 4-Br | *1 |
| B-2-10 | Qa-4a | F | 6-Br | 100-105 |
| B-2-11 | Qa-4a | F | 4,6-diCl | 186-187 |
| B-2-12 | Qa-4a | F | 4-Cl-6-Br | 155-156 |
| B-2-13 | Qa-4a | F | 4-CF₃-6-F | 168-171 |
| B-2-14 | Qa-4a | F | 4-CF₃-6-OMe | *1 |
| B-2-15 | Qa-4a | F | 4-Me-6-Cl | 149-152 |
| B-2-16 | Qa-4a | F | 4-CF₃-6-Cl | 154-155 |
| B-2-17 | Qa-4a | F | 4-CF₃ | 130-131 |
| B-2-19 | Qa-4a | Cl | 6-F | *1 |
| B-2-20 | Qa-4a | Cl | 6-Cl | *1 |
| B-2-21 | Qa-5a | | 6-Cl | *1 |
| B-2-22 | Qa-8a | | 6-Cl | *1 |
| B-2-23 | Qa-9 | | 6-Cl | *1 |
| B-2-24 | Ph | | 3-F | 130-135 |
| B-2-25 | Ph | | 4-F | 146-152 |
| B-2-26 | Ph | | 5-F | 135-140 |
| B-2-27 | Ph | | 6-F | 190-192 |
| B-2-28 | Ph | | 4-Cl | 138-145 |
| B-2-29 | Ph | | 6-Cl | 120-122 |
| B-2-30 | Ph | | 4-Br | 140-150 |
| B-2-31 | Ph | | 6-Br | 88-91 |
| B-2-32 | Ph | | 6-I | *1 |
| B-2-33 | Ph | | 4,6-diF | 200-201 |
| B-2-34 | Ph | | 4,6-diCl | 185-187 |
| B-2-35 | Ph | | 4-Br-6-F | 184-186 |
| B-2-36 | Ph | | 4-Cl-6-Br | 108-120 |
| B-2-37 | Ph | | 4-CF₃-6-Cl | 159-162 |
| B-2-38 | Ph | | 4-Me-6-F | 40-46 |
| B-2-39 | Ph | | 4-Et-6-F | 120-130 |
| B-2-40 | Ph | | 4-CF₃-6-F | 128-130 |
| B-2-41 | Ph | | 4-OMe-6-F | 152-157 |
| B-2-42 | Ph | | 4-Cl-6-Me | 186-188 |
| B-2-43 | Ph | | 4-Me-6-Cl | *1 |
| B-2-44 | Ph | | 4-CF₂H-6-Cl | 100-102 |
| B-2-45 | Ph | | 4-Cl-6-Ph | *1 |

TABLE 18

| No. | Za¹ | Ra¹⁴ | (Ra¹⁷)ₚₐ₆ | m. p. (° C.) |
|---|---|---|---|---|
| B-2-46 | Ph | | 4-Cl-6-OMe | 95-103 |
| B-2-47 | Ph | | 4-OMe-6-Cl | 146-150 |
| B-2-48 | Ph | | 4-OPh-6-Cl | 176-179 |
| B-2-49 | Ph | | 4-CF₃-6-OMe | 155-158 |
| B-2-50 | Ph | | 4-CF₃-6-OEt | 156-159 |
| B-2-51 | Ph | | 4-CF₃-6-Me | 125-130 |
| B-2-52 | Ph | | 4-Me | 100-130 |
| B-2-53 | Ph | | 6-Me | 154-156 |
| B-2-54 | Ph | | 4-CF₂H | 157-161 |
| B-2-55 | Ph | | 6-CF₂H | 126-129 |
| B-2-56 | Ph | | 6-CH₂F | *1 |
| B-2-57 | Ph | | 4-CF₃ | 170-172 |
| B-2-58 | Ph | | 6-CF₃ | *1 |
| B-2-59 | Ph | | 4-Ph | 222-223 |
| B-2-60 | Ph | | 6-Ph | *1 |
| B-2-61 | Ph | | 4-CO₂Me | 180-183 |
| B-2-62 | Ph | | 4-CN | 176-180 |
| B-2-63 | Ph | | 4-OMe | 120-129 |
| B-2-64 | Ph | | 4-OCF₂H | 130-137 |

TABLE NO. 12

[Chem. 50]

TABLE 19

| No. | Za¹ | Ra¹⁴ | (Ra¹⁷)ₚₐ₆ | m. p. (° C.) |
|---|---|---|---|---|
| B-3-01 | Ph | | 5-F | 175-178 |
| B-3-02 | Ph | | 5-Cl | 175-178 |
| B-3-03 | Ph | | 5-CF₃ | *1 |
| B-3-04 | Ph | | 2-Cl-5-Me | 122-126 |
| B-3-05 | Qa-4a | F | 5-CF₃ | *1 |

TABLE NO. 13

[Chem. 51]

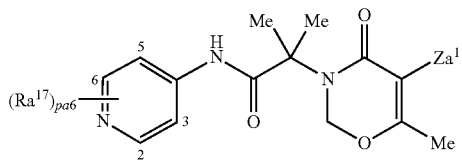

TABLE 20

| No. | Za¹ | Ra¹⁴ | (Ra¹⁷)_pa6 | m. p. (° C.) |
|---|---|---|---|---|
| B-4-01 | Qa-4a | F | 2-CF₃ | *1 |
| B-4-02 | Ph | | 2-F | *1 |
| B-4-03 | Ph | | 2-Cl | *1 |
| B-4-04 | Ph | | 2,6-diF | 190-196 |
| B-4-05 | Ph | | 2,6-diCl | 204-206 |
| B-4-06 | Ph | | 2-CF₃ | *1 |

TABLE NO. 16

[Chem. 52]

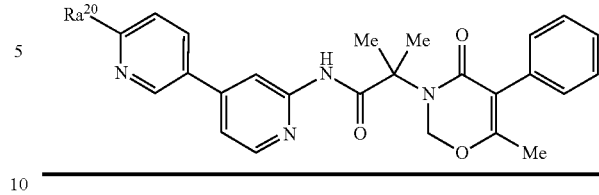

TABLE 21

| No. | Ra²⁰ | m. p. (° C.) |
|---|---|---|
| B-5-01 | F | 155-160 |

The $^1$H-NMR data of compounds of the present invention for which no melting point is stated are shown in Table No. 15.

Also, the proton nuclear magnetic resonance chemical shift values were measured at 300 MHz in deuterochloroform solvent, using Me₄Si (tetramethylsilane) as the reference substance. Further, the meanings of the symbols in Table No. 15 are shown below. s: singlet, brs: broad singlet, d: doublet, t: triplet, m: multiplet.

TABLE NO. 15

| No. | $^1$H-NMR (CDCl₃, Me₄Si, 300 MHz) |
|---|---|
| A-2-16 | δ 8.88 (brs, 1H), 7.61 (d, 1H, J = 9.0 Hz), 7.37-7.18 (m, 5H), 7.04 (d, 1H, J = 9.0 Hz), 5.16 (s, 2H), 5.11 (s, 2H), 1.68 (s, 6H). |
| A-2-27 | δ 8.49 (s, 1H), 8.35 (s, 1H), 7.37-7.15 (m, 6H), 6.52 (t, 1H, J = 5.4 Hz), 5.18 (s, 2H), 5.10 (s, 2H), 1.59 (s, 6H). |
| A-2-29 | δ 8.25 (brs, 1H), 8.06 (s, 1H), 7.35-7.16 (m, 5H), 6.82 (s, 1H), 5.17 (s, 2H), 5.11 (s, 2H), 1.91-1.85 (m, 1H), 1.63 (s, 6H), 1.13 (d, J = 6.3 Hz, 2H), 0.94 (d, J = 6.3 Hz, 2H). |
| A-2-48 | δ 8.62 (brs, 1H), 8.56 (t, 1H, J = 1.0 Hz), 8.36 (dd, 1H, J = 5.1 Hz, 1.0 Hz), 7.35-7.16 (m, 6H), 5.16 (s, 2H), 5.11 (s, 2H), 1.63 (s, 6H). |
| A-3-05 | δ 8.73 (brs, 1H), 8.37 (s, 1H), 8.24 (s, 1H), 7.39-7.20 (m, 5H), 5.17 (s, 2H), 5.08 (s, 2H), 1.65 (s, 6H). |
| A-3-06 | δ 8.45 (d, 1H, J = 2.7 Hz), 8.49 (brs, 1H), 8.02 (d, 1H, J = 2.7 Hz), 7.37-7.20 (m, 5H), 5.19 (s, 2H), 5.14 (s, 2H), 1.66 (s, 6H). |
| A-3-07 | δ 8.97 (d, 1H, J = 1.8 Hz), 8.47 (brs, 1H), 8.11 (d, 1H, J = 1.8 Hz), 7.37-7.20 (m, 5H), 5.18 (s, 2H), 5.13 (s, 2H), 1.65 (s, 6H). |
| A-3-08 | δ 8.79 (s, 1H), 8.49 (brs, 1H), 8.0 (s, 1H), 7.37-7.19 (m, 5H), 5.19 (s, 2H), 5.13 (s, 2H), 1.65 (s, 6H). |
| A-5-02 | δ 8.80 (brs, 1H), 8.45 (s, 1H), 8.29 (d, 1H, J = 1.8 Hz), 7.57 (d, 1H, J = 1.8 Hz), 7.34-7.15 (m, 5H), 7.07 (dd, 1H, J = 5.4 Hz, 1.5 Hz), 6.44 (d, 1H, J = 1.8 Hz), 5.19 (s, 2H), 5.14 (s, 2H), 4.00 (s, 3H), 1.65 (s, 6H). |
| A-5-03 | δ 9.26 (brs, 1H), 8.89 (d, 1H, J = 1.5 Hz), 8.66 (d, 1H, J = 1.8 Hz), 8.64 (d, 1H, J = 1.8 Hz), 8.26 (d, 1H, J = 5.1 Hz), 7.97 (dt, 1H, J = 8.1 Hz, 1.8 Hz), 7.39-7.13 (m, 7H), 5.18 (s, 2H), 5.16 (s, 2H), 1.63 (s, 6H). |
| A-5-04 | δ 9.62 (brs, 1H), 8.64 (s, 1H), 8.45 (d, 1H, J = 2.7 Hz), 8.25 (d, 1H, J = 5.4 Hz), 8.07 (dt, 1H, J = 7.5 Hz, 2.7 Hz), 7.35-7.10 (m, 6H), 7.01 (dd, 1H, J = 8.5 Hz, 3.1 Hz), 5.19 (s, 2H), 5.17 (s, 2H), 1.63 (s, 6H). |
| A-6-06 | δ 8.45 (brs, 1H), 8.27 (s, 1H), 7.46-7.40 (m, 1H), 7.34-7.21 (m, 3H), 7.02 (s, 1H), 5.11 (s, 2H), 5.04 (brs, 2H), 1.60 (s, 6H). |
| A-7-01 | δ 9.07 (brs, 1H), 8.19 (s, 1H), 7.45-7.26 (m, 5H), 7.08 (s, 1H), 5.16 (s, 2H), 5.13-4.99 (m, 3H), 1.50 (d, 3H, J = 7.5 Hz). |
| A-7-02 | δ 9.33 (brs, 1H), 8.49-8.40 (m, 2H), 7.40-7.32 (m, 2H), 7.31-7.21 (m, 4H), 5.20-5.11 (m, 3H), 5.05 (s, 2H), 1.52 (d, 3H, J = 7.2 Hz). |
| A-7-05 | δ 9.41 (brs, 1H), 8.49-8.40 (m, 2H), 7.43-7.36 (m, 2H), 7.32-7.22 (m, 4H), 5.17 (s, 2H), 5.03 (s, 2H), 1.81-1.69 (m, 2H), 1.43-1.28 (m, 2H). |
| B-2-06 | δ 8.27 (brs, 1H), 8.24 (d, 1H, J = 8.1 Hz), 7.51 (t, 1H, J = 8.1 Hz), 7.28-7.23 (m, 2H), 7.16 (d, 1H, J = 6.6 Hz), 7.05 (dd, 1H, J = 4.8 Hz, 1.5 Hz), 5.26 (s, 2H), 2.05 (s, 3H), 1.60 (s, 6H). |
| B-2-07 | δ 8.39-8.34 (m, 2H), 8.19-8.12 (m, 2H), 7.88-7.82 (m, 1H), 7.20-7.15 (m, 1H), 7.07-7.00 (m, 1H), 5.35 (s, 2H), 1.96 (s, 3H), 1.64 (s, 6H). |

TABLE NO. 15-continued

| No. | ¹H-NMR (CDCl₃, Me₄Si, 300 MHz) |
|---|---|
| B-2-09 | δ 8.52 (s, 1H), 8.36 (brs, 1H), 8.17-8.12 (m, 1H), 8.08-8.06 (m, 1H), 7.90-7.86 (m, 1H), 7.20-7.12 (m, 2H), 5.34 (s, 2H), 1.96 (s, 3H), 1.64 (s, 6H). |
| B-2-14 | δ 8.23 (brs, 1H), 8.16-8.13 (m, 1H), 8.04 (s, 1H), 7.87-7.81 (m, 1H), 7.20-7.15 (m, 1H), 6.66 (s, 1H), 5.38 (s, 2H), 3.88 (s, 3H), 1.97 (s, 3H), 1.68 (s, 6H). |

TABLE 23

| No. | ¹H-NMR (CDCl₃, Me₄Si, 300 MHz) |
|---|---|
| B-2-19 | δ 8.32 (d, 1H, J = 3.6 Hz), 8.28 (brs, 1H), 8.08 (d, 1H, J = 8.1 Hz), 7.75-7.71 (m, 1H), 7.64 (d, 1H, J = 8.1 Hz), 7.24-7.20 (m, 1H), 6.60 (dd, 1H, J = 8.4 Hz, 2.4 Hz), 5.40-5.30 (m, 2H), 1.92 (s, 3H), 1.61 (s, 6H). |
| B-2-20 | δ 8.32 (dd, 1H, J = 4.8 Hz, 2.1 Hz), 8.27 (brs, 1H), 8.17 (d, 1H, J = 8.1 Hz), 7.66-7.59 (m, 2H), 7.24-7.20 (m, 1H), 7.02 (d, 1H, J = 7.5 Hz, 5.38-5.31 (m, 2H), 1.93 (s, 3H), 1.61 (s, 6H). |
| B-2-21 | δ 8.20-8.15 (m, 3H), 7.64 (t, 1H, J = 8.1 Hz), 7.12-6.99 (m, 2H), 6.90 (s, 1H), 5.32 (s, 2H), 2.29 (s, 3H), 1.63 (s, 6H). |
| B-2-22 | δ 9.11 (s, 1H), 8.66 (s, 2H), 8.23 (brs, 1H), 8.19 (d, 1H), J = 8.4 Hz), 7.65 (dd, 1H, J = 8.4 Hz, 4.5 Hz), 7.05 (d, 1H, J = 4.5 Hz), 5.36 (s, 2H), 2.04 (s, 3H), 1.64 (s, 6H). |
| B-2-23 | δ 8.71 (s, 1H), 8.29-8.20 (m, 3H), 8.05 (d, 1H, J = 8.4 Hz), 7.80 (d, 1H, J = 8.1 Hz), 7.72-7.63 (m, 2H), 7.51 (t, 1H, J = 7.7 Hz), 7.04 (d, 1H, J = 7.7 Hz) 5.38 (s, 2H), 2.04 (s, 3H), 1.65 (s, 6H). |
| B-2-32 | δ 8.27 (brs, 1H), 8.22 (d, 1H, J = 10.7 Hz), 7.44-7.28 (m, 7H), 5.29 (s, 2H), 1.96 (s, 3H), 1.61 (s, 6H). |
| B-2-43 | δ 8.22 (brs, 1H), 8.06 (s, 1H), 7.47-7.25 (m, 5H), 6.86 (s, 1H), 5.28 (s, 2H), 2.31 (s, 3H), 1.96 (s, 3H), 1.60 (s, 6H). |
| B-2-45 | δ 8.42 (brs, 1H), 8.29 (s, 1H), 7.91-7.87 (m, 2H), 7.49-7.40 (m, 4H), 7.27-7.36 (m, 5H), 5.34 (s, 2H), 1.97 (s, 3H), 1.62 (s, 6H). |
| B-2-56 | δ 8.28 (brs, 1H), 8.19 (d, 1H, J = 8.4 Hz), 7.71 (t, 1H, J = 7.8 Hz), 7.50-7.43 (m, 1H), 7.33-7.21 (m, 2H), 7.12 (d, 1H, J = 7.5 Hz), 6.90-6.76 (m, 2H), 5.40-5.20 (m, 4H), 1.96 (s, 3H), 1.65 (s, 6H). |
| B-2-58 | δ 8.46 (d, 1H, J = 8.2 Hz), 8.38 (brs, 1H), 7.81 (m, 1H), 7.40-7.20 (m, 6H), 5.32 (s, 2H), 1.96 (s, 3H), 1.64 (s, 6H). |
| B-2-60 | δ 8.38 (brs, 1H), 8.17 (d, 1H, J = 7.7 Hz), 7.90 (d, 2H, J = 7.7 Hz), 7.72 (t, 1H, J = 7.7 Hz), 7.50-7.40 (m, 7H), 7.30-7.26 (m, 2H), 5.35 (s, 2H), 1.97 (s, 3H), 1.68 (s, 6H). |
| B-3-03 | δ 8.91 (brs, 1H), 8.69 (s, 1H), 8.56 (s, 1H), 8.48 (s, 1H), 7.38-7.26 (m, 5H), 5.32 (s, 2H), 1.97 (s, 3H), 1.72 (s, 6H). |
| B-3-05 | δ 8.71 (s, 2H), 8.59 (s, 1H), 8.49 (s, 1H), 8.21-8.18 (m, 1H), 7.88-7.81 (m, 1H), 7.23-7.19 (m, 1H), 5.37 (s, 2H), 1.97 (s, 3H), 1.71 (s, 6H). |
| B-4-01 | δ 8.92 (brs, 1H), 8.54-8.51 (m, 1H), 8.20-8.17 (m, 1H), 7.89 (s, 1H), 7.87-7.79 (m, 1H), 7.65-7.60 (m, 1H), 7.24-7.20 (m, 1H), 5.36 (s, 2H), 1.97 (s, 3H), 1.69 (s, 6H). |
| B-4-02 | δ 9.06 (brs, 1H), 8.03 (d, 1H, J = 6.0 Hz), 7.39-7.15 (m, 7H), 5.30 (s, 2H), 1.97 (s, 3H), 1.67 (s, 6H). |
| B-4-03 | δ 8.97 (brs, 1H), 8.17 (s, 1H, J = 5.7 Hz), 7.57 (d, 1H, J = 1.8 Hz), 7.38-7.21 (m, 6H), 5.29 (s, 2H), 1.95 (s, 3H), 1.67 (s, 6H). |
| B-4-06 | δ 9.18 (brs, 1H), 8.54 (d, 1H, J = 5.3 Hz), 7.88 (s, 1H), 7.64-7.60 (m, 1H), 7.40-7.20 (m, 5H), 5.31 (s, 2H), 1.97 (s, 3H), 1.71 (s, 6H). |

Test Examples

Next, the usefulness of the compounds of the present invention as herbicides is illustrated specifically below in the following test examples, but the present invention is not limited only to these.

Test Example 1

Weedkilling efficacy test on preemergent weed treatment in the submerged state

Alluvial soil was introduced into 1/10,000 Are Wagner pots, and 4 cm depth submerged conditions were created by addition of water and mixing. Seeds of barnyard grass, bulrush and oval-leafed pondweed were mixed and sown into the aforesaid cups, then 2.5 leaf stage rice seedlings were transplanted. On the sowing day, emulsions of compounds of the present invention prepared according to compounding example 2 were diluted with water to give the specified dosages and applied onto the water surface. The plants were grown after placing the cups in a greenhouse at 25 to 30° C. 3 weeks after the pesticide treatment the effect on each type of plant was investigated on the basis of the following assessment criteria. The results are shown in table No. 16.

Assessment Criteria

5 . . . weed kill ratio 90% or more, (practically complete withering)

4 . . . weed kill ratio 70% or more, less than 90%

3 . . . weed kill ratio 40% or more, less than 70%

2 . . . weed kill ratio 20% or more, less than 40%

1 . . . weed kill ratio 5% or more, less than 20%

0 . . . weed kill ratio 5% or less (practically no effect)

Test Example 2

Weedkilling efficacy test on growth period weed treatment in the submerged state Alluvial soil was introduced into 1/10,000 Are Wagner pots, and 4 cm depth submerged conditions were created by addition of water and mixing. Seeds of barnyard grass, bulrush and oval-leafed pondweed were mixed and sown into the aforesaid cups, and the plants were grown by placing in a greenhouse at 25 to 30° C. When the barnyard grass, bulrush and oval-leafed pondweed had reached the 1-2 leaf stage, emulsions of compounds of the present invention prepared according to compounding example 2 were diluted with water to give the specified dosages and applied onto the water surface. 3 weeks after the pesticide treatment the effect on each type of plant was investigated on the basis of the assessment criteria of test example 1. The results are shown in table No. 17.

Test Example 3

Weedkilling Efficacy Test Through Soil Treatment

Sterilized diluvial soil was introduced into 21 cm long, 13 cm wide, 7 cm deep plastic boxes, and seeds of crabgrass, green foxtail, barnyard grass, wild oat, black-grass, Italian ryegrass, common wind-grass, Indian mallow, redroot pigweed, fig-leafed goosefoot, chickweed, catchweed, birds-eye speedwell, corn, soybean, rice, wheat, beet and rapeseed were each spot-sown, and covered with about 1.5 cm of soil. Next, emulsions of compounds of the present invention prepared according to compounding example 2 were diluted with water to give the specified dosages, and applied uniformly onto the soil surface with a small sprayer. The plants were grown by placing the plastic boxes in a greenhouse at 25 to 30° C., and 3 weeks after the pesticide treatment the effect on each type of plant was investigated on the basis of the assessment criteria of test example 1. The results are shown in table No. 18.

Test Example 4

Testing of Weedkilling Efficacy by Foliar Treatment

Sterilized diluvial soil was introduced into 21 cm long, 13 cm wide, 7 cm deep plastic boxes, and seeds of crabgrass, green foxtail, barnyard grass, wild oat, black-grass, Italian ryegrass, common wind-grass, Indian mallow, redroot pigweed, fig-leafed goosefoot, chickweed, catchweed, birds-eye speedwell, corn, soybean, rice, wheat, beet and rapeseed were each spot-sown, and covered with about 1.5 cm of soil, then the plants were grown in a greenhouse at 25 to 30° C. After they had grown for 14 days, emulsions of compounds of the present invention prepared according to compounding example 2 were diluted with water to give the specified dosages, and applied uniformly onto the stem and leaf parts with a small sprayer. 3 weeks after the pesticide treatment the effect on each type of plant was investigated on the basis of the assessment criteria of test example 1. The results are shown in table No. 19.

Also, the meanings of the symbols in table Nos. 16 to 19 are shown below.

A: barnyard grass, B: bulrush, C: oval-leafed pondweed, D: crabgrass, E: green foxtail, F: barnyard grass, G: wild oat, H: black-grass, I: Italian ryegrass, J: common wind-grass, K: Indian mallow, L: redroot pigweed, M: fig-leafed goosefoot, N: chickweed, O: catchweed, p: birds-eye speedwell, a: transplanted rice, b: directly sown rice, c: corn, d: soybean, e: wheat, f: beet, g: rapeseed Further, pesticide dosage (g/ha) indicates the concentration regulated such that treatment was with only the stated number of grams (g), when calculated per hectare (ha).

TABLE NO. 16

[Table 24]

| NO. | Treatment dosage (g/ha) | A | B | C | a |
|---|---|---|---|---|---|
| A- 1-03 | 320 | 0 | 5 | 2 | 0 |
| A- 1-04 | 320 | 5 | 5 | 4 | 0 |
| A- 1-05 | 252 | 5 | 5 | 5 | 0 |
| A- 1-07 | 252 | 5 | 5 | 5 | 0 |
| A- 1-08 | 252 | 5 | 5 | 5 | 0 |
| A- 1-09 | 320 | 5 | 5 | 4 | 0 |
| A- 1-10 | 252 | 3 | 5 | 3 | 0 |
| A- 1-12 | 320 | 5 | 5 | 4 | 0 |
| A- 1-13 | 320 | 5 | 5 | 5 | 3 |
| A- 1-14 | 320 | 4 | 5 | 3 | 1 |
| A- 1-15 | 320 | 4 | 5 | 5 | 0 |
| A- 1-17 | 320 | 2 | 5 | 3 | 0 |
| A- 1-18 | 320 | 5 | 5 | 5 | 2 |
| A- 1-19 | 252 | 2 | 3 | 2 | 0 |
| A- 1-24 | 320 | 5 | 5 | 5 | 0 |
| A- 2-01 | 252 | 5 | 5 | 4 | 0 |
| A- 2-03 | 252 | 5 | 5 | 5 | 1 |
| A- 2-04 | 320 | 4 | 5 | 4 | 0 |
| A- 2-05 | 252 | 5 | 5 | 5 | 3 |
| A- 2-06 | 252 | 5 | 5 | 5 | 4 |
| A- 2-07 | 252 | 5 | 5 | 5 | 4 |
| A- 2-09 | 252 | 5 | 5 | 5 | 0 |
| A- 2-10 | 320 | 5 | 5 | 5 | 1 |
| A- 2-11 | 252 | 5 | 5 | 5 | 0 |
| A- 2-13 | 252 | 5 | 5 | 5 | 3 |
| A- 2-14 | 320 | 5 | 5 | 5 | 3 |
| A- 2-15 | 280 | 5 | 5 | 5 | 4 |
| A- 2-16 | 252 | 0 | 5 | 2 | 0 |
| A- 2-17 | 252 | 5 | 5 | 5 | 3 |
| A- 2-18 | 320 | 5 | 5 | 5 | 0 |
| A- 2-19 | 320 | 5 | 5 | 5 | 3 |
| A- 2-20 | 320 | 5 | 5 | 5 | 3 |
| A- 2-21 | 320 | 5 | 5 | 5 | 5 |
| A- 2-22 | 320 | 5 | 5 | 5 | 5 |
| A- 2-23 | 320 | 5 | 5 | 5 | 3 |
| A- 2-24 | 252 | 5 | 5 | 5 | 0 |
| A- 2-25 | 320 | 5 | 5 | 5 | 3 |
| A- 2-26 | 320 | 5 | 5 | 5 | 4 |
| A- 2-28 | 252 | 5 | 5 | 5 | 2 |
| A- 2-30 | 320 | 5 | 5 | 5 | 1 |
| A- 2-31 | 320 | 5 | 5 | 5 | 0 |
| A- 2-32 | 320 | 5 | 5 | 5 | 4 |
| A- 2-33 | 315 | 5 | 5 | 5 | 4 |
| A- 2-34 | 320 | 5 | 5 | 5 | 3 |
| A- 2-35 | 320 | 5 | 5 | 5 | 1 |
| A- 2-36 | 320 | 5 | 5 | 5 | 2 |
| A- 2-37 | 252 | 5 | 5 | 5 | 0 |
| A- 2-38 | 252 | 5 | 5 | 4 | 0 |
| A- 2-39 | 315 | 5 | 5 | 5 | 1 |
| A- 2-40 | 320 | 5 | 5 | 5 | 1 |

TABLE 25

| A- 2-41 | 315 | 5 | 5 | 5 | 0 |
|---|---|---|---|---|---|
| A- 2-42 | 252 | 5 | 5 | 5 | 4 |
| A- 2-43 | 320 | 3 | 5 | 5 | 0 |
| A- 2-44 | 252 | 5 | 5 | 4 | 0 |
| A- 2-45 | 252 | 5 | 5 | 5 | 0 |
| A- 2-46 | 252 | 5 | 4 | 3 | 1 |
| A- 2-47 | 320 | 2 | 4 | 0 | 0 |
| A- 2-48 | 252 | 5 | 5 | 5 | 0 |
| A- 2-49 | 252 | 5 | 5 | 5 | 1 |
| A- 2-50 | 252 | 5 | 5 | 5 | 0 |
| A- 2-51 | 252 | 4 | 5 | 2 | 0 |

TABLE 25-continued

| | | | | | |
|---|---|---|---|---|---|
| A-2-52 | 252 | 5 | 5 | 5 | 1 |
| A-2-53 | 320 | 5 | 5 | 5 | 1 |
| A-2-54 | 320 | 5 | 5 | 4 | 1 |
| A-2-55 | 234 | 5 | 5 | 5 | 0 |
| A-2-56 | 252 | 5 | 5 | 5 | 0 |
| A-2-57 | 320 | 5 | 5 | 5 | 0 |
| A-2-58 | 320 | 5 | 5 | 5 | 1 |
| A-2-59 | 320 | 5 | 5 | 5 | 1 |
| A-2-60 | 320 | 5 | 5 | 5 | 2 |
| A-3-01 | 252 | 5 | 5 | 4 | 1 |
| A-3-02 | 252 | 5 | 5 | 5 | 2 |
| A-3-03 | 252 | 5 | 5 | 5 | 0 |
| A-3-04 | 252 | 5 | 5 | 5 | 3 |
| A-3-05 | 320 | 3 | 5 | 5 | 0 |
| A-3-06 | 252 | 5 | 5 | 4 | 1 |
| A-3-07 | 252 | 5 | 5 | 4 | 0 |
| A-3-08 | 252 | 5 | 5 | 4 | 0 |
| A-3-09 | 252 | 2 | 4 | 0 | 1 |
| A-3-10 | 252 | 5 | 5 | 5 | 1 |
| A-4-02 | 252 | 5 | 5 | 5 | 1 |
| A-4-03 | 252 | 5 | 5 | 5 | 1 |
| A-4-04 | 320 | 5 | 5 | 5 | 0 |
| A-4-06 | 252 | 5 | 5 | 5 | 0 |
| A-5-01 | 320 | 4 | 5 | 5 | 0 |
| A-5-04 | 320 | 3 | 5 | 0 | 0 |
| A-6-01 | 252 | 5 | 5 | 5 | 3 |
| A-6-02 | 252 | 5 | 5 | 5 | 0 |
| A-6-03 | 320 | 3 | 5 | 0 | 0 |
| A-6-04 | 320 | 4 | 4 | 2 | 0 |
| A-6-05 | 320 | 2 | 2 | 2 | 0 |
| A-6-06 | 252 | 5 | 5 | 5 | 2 |
| A-6-07 | 320 | 5 | 5 | 5 | 1 |
| A-6-08 | 320 | 5 | 5 | 5 | 0 |
| A-6-09 | 320 | 4 | 5 | 4 | 0 |
| A-6-10 | 320 | 5 | 5 | 5 | 1 |
| A-6-11 | 320 | 5 | 5 | 5 | 0 |
| A-6-12 | 320 | 5 | 5 | 5 | 2 |
| A-6-13 | 320 | 5 | 5 | 5 | 0 |
| A-7-01 | 1000 | 5 | 5 | 4 | 0 |
| A-7-04 | 1000 | 0 | 5 | 0 | 0 |

TABLE 26

| NO. | Treatment dosage (g/ha) | A | B | C | a |
|---|---|---|---|---|---|
| B-1-01 | 252 | 5 | 5 | 5 | 4 |
| B-1-02 | 252 | 5 | 5 | 5 | 0 |
| B-1-03 | 252 | 5 | 5 | 5 | 3 |
| B-1-04 | 252 | 5 | 5 | 5 | 0 |
| B-1-05 | 252 | 5 | 5 | 5 | 4 |
| B-1-06 | 252 | 5 | 5 | 5 | 0 |
| B-1-07 | 252 | 4 | 5 | 4 | 1 |
| B-1-08 | 252 | 5 | 5 | 5 | 0 |
| B-1-09 | 252 | 2 | 5 | 4 | 0 |
| B-1-10 | 252 | 5 | 5 | 5 | 3 |
| B-1-11 | 252 | 4 | 5 | 5 | 0 |
| B-1-12 | 252 | 5 | 5 | 5 | 0 |
| B-1-13 | 252 | 5 | 5 | 5 | 0 |
| B-1-14 | 252 | 5 | 5 | 5 | 1 |
| B-1-15 | 252 | 5 | 5 | 5 | 0 |
| B-1-16 | 252 | 5 | 5 | 5 | 2 |
| B-1-17 | 252 | 5 | 5 | 5 | 0 |
| B-1-18 | 320 | 5 | 5 | 5 | 0 |
| B-2-01 | 252 | 5 | 5 | 5 | 2 |
| B-2-02 | 252 | 5 | 5 | 5 | 0 |
| B-2-03 | 252 | 5 | 5 | 5 | 0 |
| B-2-04 | 252 | 5 | 5 | 5 | 3 |
| B-2-05 | 252 | 5 | 5 | 5 | 0 |
| B-2-06 | 252 | 5 | 5 | 5 | 4 |
| B-2-07 | 252 | 5 | 5 | 5 | 0 |
| B-2-08 | 252 | 5 | 5 | 5 | 0 |
| B-2-09 | 252 | 5 | 5 | 5 | 1 |
| B-2-10 | 320 | 5 | 5 | 5 | 1 |
| B-2-12 | 320 | 5 | 5 | 5 | 5 |
| B-2-13 | 320 | 5 | 5 | 5 | 1 |
| B-2-14 | 320 | 5 | 5 | 4 | 3 |

TABLE 26-continued

| NO. | Treatment dosage (g/ha) | A | B | C | a |
|---|---|---|---|---|---|
| B-2-15 | 320 | 5 | 5 | 5 | 3 |
| B-2-16 | 320 | 5 | 5 | 5 | 4 |
| B-2-17 | 252 | 5 | 5 | 5 | 3 |
| B-2-19 | 1000 | 5 | 5 | 4 | 0 |
| B-2-20 | 1000 | 5 | 5 | 4 | 0 |
| B-2-21 | 252 | 0 | 5 | 3 | 0 |
| B-2-22 | 1000 | 3 | 3 | 1 | 0 |
| B-2-24 | 320 | 2 | 5 | 3 | 0 |
| B-2-25 | 252 | 5 | 5 | 5 | 2 |
| B-2-26 | 320 | 5 | 5 | 5 | 0 |
| B-2-27 | 252 | 5 | 5 | 5 | 0 |
| B-2-29 | 252 | 5 | 5 | 5 | 0 |
| B-2-30 | 252 | 5 | 5 | 5 | 1 |
| B-2-31 | 252 | 5 | 5 | 5 | 0 |
| B-2-32 | 252 | 5 | 5 | 5 | 0 |
| B-2-33 | 252 | 5 | 5 | 5 | 3 |
| B-2-34 | 252 | 5 | 5 | 5 | 0 |
| B-2-35 | 320 | 5 | 5 | 5 | 0 |
| B-2-36 | 252 | 5 | 5 | 5 | 0 |

TABLE 27

| | | | | | |
|---|---|---|---|---|---|
| B-2-37 | 252 | 5 | 5 | 5 | 2 |
| B-2-38 | 320 | 5 | 5 | 5 | 3 |
| B-2-39 | 320 | 5 | 5 | 5 | 1 |
| B-2-40 | 320 | 5 | 5 | 5 | 3 |
| B-2-41 | 320 | 5 | 5 | 5 | 3 |
| B-2-42 | 320 | 5 | 5 | 5 | 4 |
| B-2-43 | 320 | 5 | 5 | 5 | 3 |
| B-2-44 | 320 | 5 | 5 | 5 | 5 |
| B-2-45 | 320 | 5 | 5 | 4 | 2 |
| B-2-46 | 320 | 5 | 5 | 5 | 0 |
| B-2-47 | 320 | 5 | 5 | 5 | 1 |
| B-2-48 | 266 | 5 | 5 | 4 | 0 |
| B-2-49 | 320 | 5 | 5 | 5 | 3 |
| B-2-50 | 320 | 5 | 5 | 5 | 0 |
| B-2-51 | 320 | 5 | 5 | 5 | 0 |
| B-2-53 | 108.36 | 5 | 5 | 5 | 0 |
| B-2-54 | 320 | 5 | 5 | 5 | 5 |
| B-2-55 | 315 | 5 | 5 | 5 | 3 |
| B-2-56 | 320 | 5 | 5 | 5 | 1 |
| B-2-57 | 252 | 5 | 5 | 5 | 4 |
| B-2-58 | 252 | 5 | 5 | 5 | 0 |
| B-2-59 | 252 | 2 | 4 | 2 | 0 |
| B-2-60 | 252 | 5 | 5 | 5 | 0 |
| B-2-61 | 320 | 0 | 0 | 4 | 0 |
| B-2-62 | 320 | 5 | 5 | 5 | 1 |
| B-2-63 | 252 | 5 | 5 | 4 | 0 |
| B-2-64 | 320 | 5 | 5 | 5 | 4 |
| B-3-01 | 252 | 5 | 5 | 5 | 0 |
| B-3-02 | 252 | 5 | 5 | 5 | 3 |
| B-3-03 | 252 | 5 | 5 | 5 | 0 |
| B-3-04 | 252 | 5 | 5 | 4 | 0 |
| B-3-05 | 252 | 5 | 5 | 4 | 0 |
| B-4-01 | 252 | 5 | 5 | 5 | 0 |
| B-4-02 | 252 | 5 | 5 | 5 | 3 |
| B-4-03 | 252 | 5 | 5 | 5 | 4 |
| B-4-04 | 320 | 5 | 5 | 5 | 0 |
| B-4-05 | 252 | 5 | 5 | 5 | 0 |
| B-4-06 | 252 | 5 | 5 | 5 | 0 |
| B-5-01 | 320 | 4 | 5 | 4 | 0 |

TABLE NO. 17

[Table 28]

| NO. | Treatment dosage (g/ha) | A | B | C |
|---|---|---|---|---|
| A-1-03 | 320 | 0 | 2 | 0 |
| A-1-04 | 320 | 3 | 4 | 4 |
| A-1-05 | 252 | 3 | 5 | 3 |

TABLE NO. 17-continued

[Table 28]

| NO. | Treatment dosage (g/ha) | A | B | C |
|---|---|---|---|---|
| A-1-07 | 252 | 5 | 5 | 5 |
| A-1-08 | 252 | 4 | 5 | 3 |
| A-1-09 | 320 | 4 | 5 | 5 |
| A-1-10 | 252 | 0 | 5 | 0 |
| A-1-12 | 320 | 1 | 5 | 3 |
| A-1-13 | 320 | 3 | 5 | 3 |
| A-1-14 | 320 | 2 | 5 | 2 |
| A-1-15 | 320 | 3 | 5 | 5 |
| A-1-17 | 320 | 0 | 4 | 2 |
| A-1-18 | 320 | 3 | 5 | 5 |
| A-1-19 | 252 | 3 | 2 | 2 |
| A-1-24 | 320 | 4 | 5 | 5 |
| A-2-01 | 252 | 3 | 5 | 2 |
| A-2-03 | 252 | 5 | 5 | 3 |
| A-2-04 | 320 | 5 | 5 | 4 |
| A-2-05 | 252 | 4 | 5 | 4 |
| A-2-06 | 252 | 5 | 5 | 5 |
| A-2-07 | 252 | 4 | 5 | 5 |
| A-2-09 | 252 | 5 | 5 | 5 |
| A-2-10 | 320 | 5 | 5 | 5 |
| A-2-11 | 252 | 4 | 5 | 3 |
| A-2-13 | 252 | 5 | 5 | 5 |
| A-2-14 | 320 | 5 | 5 | 5 |
| A-2-15 | 280 | 5 | 5 | 5 |
| A-2-17 | 252 | 5 | 5 | 5 |
| A-2-18 | 320 | 5 | 5 | 5 |
| A-2-19 | 320 | 5 | 5 | 5 |
| A-2-20 | 320 | 5 | 5 | 5 |
| A-2-21 | 320 | 5 | 5 | 5 |
| A-2-22 | 320 | 5 | 5 | 5 |
| A-2-23 | 320 | 5 | 5 | 5 |
| A-2-24 | 252 | 5 | 5 | 5 |
| A-2-25 | 320 | 5 | 5 | 5 |
| A-2-26 | 320 | 5 | 5 | 5 |
| A-2-28 | 252 | 5 | 5 | 5 |
| A-2-30 | 320 | 5 | 5 | 5 |
| A-2-31 | 320 | 5 | 5 | 4 |
| A-2-32 | 320 | 5 | 5 | 5 |
| A-2-33 | 315 | 5 | 5 | 5 |
| A-2-34 | 320 | 5 | 5 | 5 |
| A-2-35 | 320 | 4 | 4 | 4 |
| A-2-36 | 320 | 5 | 3 | 5 |
| A-2-37 | 252 | 5 | 5 | 3 |
| A-2-38 | 252 | 3 | 5 | 3 |
| A-2-39 | 315 | 4 | 5 | 4 |
| A-2-40 | 320 | 5 | 5 | 5 |
| A-2-41 | 315 | 5 | 5 | 5 |

TABLE 29

| NO. | Treatment dosage (g/ha) | A | B | C |
|---|---|---|---|---|
| A-2-42 | 252 | 5 | 5 | 5 |
| A-2-43 | 320 | 2 | 4 | 2 |
| A-2-44 | 252 | 3 | 5 | 1 |
| A-2-45 | 252 | 4 | 4 | 3 |
| A-2-46 | 252 | 4 | 2 | 0 |
| A-2-48 | 252 | 4 | 5 | 5 |
| A-2-49 | 252 | 4 | 4 | 4 |
| A-2-50 | 252 | 4 | 4 | 3 |
| A-2-52 | 252 | 4 | 5 | 2 |
| A-2-53 | 320 | 5 | 5 | 5 |
| A-2-54 | 320 | 3 | 4 | 3 |
| A-2-55 | 234 | 0 | 2 | 5 |
| A-2-56 | 252 | 4 | 5 | 3 |
| A-2-57 | 320 | 5 | 5 | 5 |
| A-2-58 | 320 | 5 | 5 | 5 |
| A-2-60 | 320 | 5 | 5 | 5 |
| A-3-01 | 252 | 1 | 5 | 2 |
| A-3-02 | 252 | 2 | 5 | 3 |
| A-3-03 | 252 | 3 | 5 | 4 |
| A-3-04 | 252 | 5 | 5 | 3 |
| A-3-05 | 320 | 4 | 5 | 5 |
| A-3-06 | 252 | 3 | 4 | 2 |
| A-3-07 | 252 | 4 | 5 | 1 |
| A-3-08 | 252 | 2 | 3 | 2 |
| A-3-10 | 252 | 3 | 5 | 4 |
| A-4-02 | 252 | 2 | 5 | 4 |
| A-4-03 | 252 | 2 | 5 | 4 |
| A-4-04 | 320 | 3 | 5 | 4 |
| A-4-06 | 252 | 4 | 5 | 4 |
| A-5-01 | 320 | 4 | 4 | 4 |
| A-5-04 | 320 | 0 | 2 | 0 |
| A-6-01 | 252 | 5 | 5 | 5 |
| A-6-02 | 252 | 5 | 5 | 5 |
| A-6-03 | 320 | 0 | 2 | 0 |
| A-6-04 | 320 | 1 | 2 | 0 |
| A-6-06 | 252 | 5 | 5 | 5 |
| A-6-07 | 320 | 4 | 5 | 3 |
| A-6-08 | 320 | 5 | 5 | 4 |
| A-6-09 | 320 | 3 | 3 |   |
| A-6-10 | 320 | 4 | 5 | 5 |
| A-6-11 | 320 | 4 | 5 | 5 |
| A-6-12 | 320 | 4 | 5 | 5 |
| A-6-13 | 320 | 2 | 4 | 4 |
| A-7-01 | 1000 | 3 | 5 | 1 |
| A-7-04 | 1000 | 0 | 1 | 0 |

TABLE 30

| NO. | Treatment dosage (g/ha) | A | B | C |
|---|---|---|---|---|
| B-1-01 | 252 | 5 | 5 | 5 |
| B-1-02 | 252 | 4 | 5 | 5 |
| B-1-03 | 252 | 5 | 5 | 5 |
| B-1-04 | 252 | 5 | 5 | 5 |
| B-1-05 | 252 | 5 | 5 | 5 |
| B-1-06 | 252 | 4 | 5 | 2 |
| B-1-07 | 252 | 0 | 3 | 0 |
| B-1-08 | 252 | 4 | 5 | 4 |
| B-1-09 | 252 | 1 | 4 | 2 |
| B-1-10 | 252 | 4 | 5 | 5 |
| B-1-11 | 252 | 1 | 4 | 3 |
| B-1-12 | 252 | 5 | 5 | 5 |
| B-1-13 | 252 | 5 | 5 | 5 |
| B-1-14 | 252 | 5 | 5 | 5 |
| B-1-15 | 252 | 4 | 5 | 5 |
| B-1-16 | 252 | 5 | 5 | 5 |
| B-1-17 | 252 | 5 | 5 | 4 |
| B-1-18 | 320 | 4 |   | 5 |
| B-2-01 | 252 | 5 | 5 | 5 |
| B-2-02 | 252 | 5 | 5 | 5 |
| B-2-03 | 252 | 5 | 5 | 4 |
| B-2-04 | 252 | 5 | 5 | 5 |
| B-2-05 | 252 | 5 | 5 | 5 |
| B-2-06 | 252 | 5 | 5 | 5 |
| B-2-07 | 252 | 3 | 5 | 2 |
| B-2-08 | 252 | 5 | 5 | 5 |
| B-2-09 | 252 | 4 | 5 | 3 |
| B-2-10 | 320 | 5 | 5 | 5 |
| B-2-12 | 320 | 5 | 5 | 5 |
| B-2-13 | 320 | 5 | 5 | 5 |
| B-2-14 | 320 | 4 | 4 | 4 |
| B-2-15 | 320 | 4 | 5 | 5 |
| B-2-16 | 320 | 5 | 5 | 5 |
| B-2-17 | 252 | 4 | 5 | 3 |
| B-2-19 | 1000 | 2 | 5 | 3 |
| B-2-20 | 1000 | 1 | 5 | 3 |
| B-2-24 | 320 | 1 | 4 | 3 |
| B-2-25 | 252 | 5 | 5 | 5 |
| B-2-26 | 320 | 5 | 5 | 5 |
| B-2-27 | 252 | 4 | 5 | 5 |
| B-2-29 | 252 | 5 | 5 | 5 |
| B-2-30 | 252 | 5 | 5 | 3 |
| B-2-31 | 252 | 5 | 5 | 0 |
| B-2-32 | 252 | 4 | 5 | 4 |
| B-2-33 | 252 | 5 | 5 | 5 |
| B-2-34 | 252 | 5 | 5 | 5 |
| B-2-35 | 320 | 5 | 5 | 5 |
| B-2-36 | 252 | 5 | 5 | 5 |

TABLE 30-continued

| NO. | Treatment dosage (g/ha) | A | B | C |
|---|---|---|---|---|
| B-2-37 | 252 | 5 | 5 | 5 |
| B-2-38 | 320 | 5 | 5 | 5 |

TABLE 31

| NO. | Treatment dosage (g/ha) | A | B | C |
|---|---|---|---|---|
| B-2-39 | 320 | 5 | 5 | 5 |
| B-2-40 | 320 | 5 | 5 | 5 |
| B-2-41 | 320 | 5 | 5 | 5 |
| B-2-42 | 320 | 5 | 5 | 5 |
| B-2-43 | 320 | 5 | 5 | 5 |
| B-2-44 | 320 | 5 | 5 | 5 |
| B-2-45 | 320 | 4 | 2 | 4 |
| B-2-46 | 320 | 5 | 5 | 5 |
| B-2-47 | 320 | 5 | 5 | 5 |
| B-2-48 | 266 | 0 | 2 | 0 |
| B-2-49 | 320 | 5 | 5 | 5 |
| B-2-50 | 320 | 5 | 4 | 4 |
| B-2-51 | 320 | 5 | 5 | 5 |
| B-2-53 | 108.36 | 3 | 5 | 4 |

TABLE 31-continued

| NO. | Treatment dosage (g/ha) | A | B | C |
|---|---|---|---|---|
| B-2-54 | 320 | 5 | 5 | 5 |
| B-2-55 | 315 | 5 | 5 | 5 |
| B-2-56 | 320 | 5 | 5 | 5 |
| B-2-57 | 252 | 5 | 5 | 5 |
| B-2-58 | 252 | 3 | 5 | 4 |
| B-2-59 | 252 | 0 | 1 | 0 |
| B-2-60 | 252 | 4 | 3 | 3 |
| B-2-61 | 320 | 0 | 2 | 2 |
| B-2-62 | 320 | 4 | 3 | 5 |
| B-2-63 | 252 | 3 | 4 | 3 |
| B-2-64 | 320 | 5 | 5 | 5 |
| B-3-01 | 252 | 3 | 5 | 4 |
| B-3-02 | 252 | 4 | 5 | 5 |
| B-3-03 | 252 | 5 | 5 | 5 |
| B-3-04 | 252 | 4 | 4 | 3 |
| B-3-05 | 252 | 3 | 5 | 2 |
| B-4-01 | 252 | 2 | 3 | 2 |
| B-4-02 | 252 | 3 | 5 | 4 |
| B-4-03 | 252 | 4 | 5 | 4 |
| B-4-04 | 320 | 5 | 5 | 5 |
| B-4-05 | 252 | 4 | 5 | |
| B-4-06 | 252 | 4 | 5 | 5 |
| B-5-01 | 320 | 3 | 3 | 4 |

TABLE 32

[Table No. 18]

| NO. | Treatment dosage (g/ha) | D | E | F | G | H | I | J | K | L | M | N | O | P | b | c | d | e | f | g |
|---|---|---|---|---|---|---|---|---|---|---|---|---|---|---|---|---|---|---|---|---|
| A-1-04 | 320 | 3 | 3 | 2 | 2 | 4 | 5 | 5 | 0 | 0 | 3 | 4 | 2 | 3 | 0 | 0 | 2 | 0 | 3 | 4 |
| A-1-05 | 315 | 5 | 5 | | 4 | 5 | 5 | | 4 | 5 | 3 | 4 | | 5 | 5 | 1 | 0 | 0 | 3 | |
| A-1-06 | 80 | | | | | 5 | 5 | 5 | | | | | | | | | | | | 4 |
| A-1-07 | 315 | 5 | 5 | | 5 | 5 | 5 | | 4 | 5 | 4 | 4 | | 5 | 5 | 3 | 1 | 2 | 5 | |
| A-1-08 | 315 | 5 | 5 | | 3 | 5 | 4 | | 1 | 4 | 2 | 2 | | 4 | 1 | 0 | 0 | 0 | | |
| A-1-10 | 315 | 4 | 4 | | 0 | 2 | 4 | | 3 | 4 | 4 | 0 | | 0 | 0 | 0 | 0 | 0 | 4 | |
| A-1-12 | 320 | | 5 | 3 | 3 | 5 | 5 | 5 | 0 | 0 | 4 | 3 | 0 | 3 | 5 | 0 | 4 | 0 | 2 | 0 |
| A-1-13 | 320 | 3 | 3 | 3 | 3 | 5 | 5 | 5 | 0 | 0 | 3 | 3 | 0 | 4 | 3 | 0 | 0 | 1 | 1 | 4 |
| A-1-15 | 320 | 0 | 0 | 0 | 0 | 1 | 4 | 5 | 0 | 0 | 0 | 0 | 0 | 3 | 0 | 0 | 0 | 0 | 0 | 1 |
| A-1-18 | 320 | 5 | 5 | 4 | 4 | 5 | 5 | 5 | 0 | 4 | 4 | 2 | 0 | 4 | 5 | 0 | 4 | 0 | 1 | 4 |
| A-1-20 | 80 | | | | | 5 | 5 | 5 | | | | | | | | | | 1 | | 1 |
| A-1-21 | 80 | | | | | 4 | 4 | 5 | | | | | | | | | | 0 | | 0 |
| A-1-24 | 320 | 3 | 3 | 2 | 0 | 1 | 3 | 4 | 0 | 0 | | 0 | | 4 | 0 | 0 | 0 | 0 | 0 | 0 |
| A-2-01 | 315 | 4 | 4 | | 2 | 5 | 5 | | 0 | 3 | 4 | 3 | | 5 | 3 | 0 | 2 | 0 | 0 | |
| A-2-03 | 315 | 5 | 5 | | 5 | 5 | 5 | | 0 | 4 | 4 | 4 | 5 | 5 | 5 | 3 | 0 | 2 | 0 | |
| A-2-04 | 320 | 3 | 3 | 3 | 0 | 2 | 3 | 4 | 0 | 0 | 0 | 2 | 0 | 0 | 0 | 0 | 0 | 0 | 0 | 0 |
| A-2-05 | 315 | 5 | 5 | | 5 | 5 | 5 | | 3 | 5 | 4 | 4 | | 5 | 5 | 4 | 4 | 4 | 5 | |
| A-2-06 | 315 | 5 | 5 | | 5 | 5 | 5 | | 4 | 5 | 4 | 4 | | 5 | 5 | 3 | 3 | 1 | 4 | |
| A-2-07 | 315 | 5 | 5 | | 5 | 5 | 5 | | 0 | 5 | 4 | 4 | | | 4 | 4 | 3 | 5 | | |
| A-2-08 | 80 | | | | | 5 | 5 | 5 | | | | | | | | | | 0 | | 0 |
| A-2-09 | 315 | 5 | 5 | | 5 | 5 | 5 | | 3 | 5 | 4 | 4 | | 5 | 5 | 3 | 3 | 1 | 4 | |
| A-2-10 | 320 | 5 | 5 | 5 | 2 | 5 | 5 | 5 | 0 | 1 | 4 | 3 | | 4 | 4 | 0 | 0 | 0 | 3 | 3 |
| A-2-11 | 315 | 5 | 5 | | 2 | 5 | 5 | | 0 | 0 | 3 | 4 | 2 | 4 | 3 | 0 | 0 | 1 | 2 | |
| A-2-13 | 315 | 5 | 5 | 5 | 5 | 5 | 5 | 5 | 5 | 5 | | 5 | 5 | 5 | 5 | 4 | 3 | 5 | 4 | 5 |
| A-2-14 | 320 | 5 | 5 | 5 | 5 | 5 | 5 | 5 | 5 | 5 | 5 | 5 | 5 | 5 | 5 | 4 | 4 | 4 | 4 | 4 |
| A-2-15 | 320 | 5 | 5 | 5 | 5 | 5 | 5 | 5 | 4 | 4 | 4 | 5 | 5 | 5 | 5 | 4 | 3 | 4 | 3 | 4 |
| A-2-17 | 315 | 5 | 5 | | 5 | 5 | 5 | | 5 | 5 | 5 | 5 | | 5 | 5 | 4 | 5 | 4 | 5 | |
| A-2-18 | 320 | 5 | 5 | 5 | 3 | 5 | 5 | 5 | 2 | 3 | 3 | 3 | | 5 | 5 | 1 | 0 | 0 | 3 | 3 |
| A-2-19 | 320 | 5 | 5 | 5 | 5 | 5 | 5 | 5 | 0 | 0 | 4 | 5 | 4 | 4 | 0 | 2 | | 2 | 4 | 5 |
| A-2-20 | 320 | 5 | 5 | 5 | 5 | 5 | 5 | 5 | 4 | 4 | 4 | 4 | 5 | 5 | 5 | 1 | 3 | 3 | 4 | 4 |
| A-2-21 | 320 | 5 | 5 | 5 | 5 | 5 | 5 | 5 | 2 | 4 | 5 | 4 | 4 | 5 | 5 | 0 | 3 | 1 | 0 | 4 |
| A-2-22 | 320 | 5 | 5 | 5 | 5 | 5 | 5 | 5 | 4 | 4 | 4 | 4 | | 5 | 5 | 0 | 4 | 0 | 4 | 4 |
| A-2-23 | 320 | 5 | 5 | 5 | 4 | 5 | 5 | 5 | 0 | 0 | 4 | 4 | 5 | 5 | 5 | 0 | 0 | 0 | 3 | 4 |
| A-2-24 | 315 | 5 | 5 | | 5 | 5 | 5 | | 4 | 4 | 4 | 4 | | | 4 | 0 | 1 | 4 | | |
| A-2-25 | 320 | 5 | 5 | 5 | 4 | 5 | 5 | 5 | 5 | 4 | 4 | 4 | | 5 | 5 | 0 | 0 | 0 | 4 | 3 |
| A-2-26 | 320 | 5 | 5 | 5 | 5 | 5 | 5 | 5 | 0 | 2 | 4 | 3 | | 5 | 5 | 0 | 2 | 3 | 3 | 4 |
| A-2-27 | 80 | | | | | 5 | 5 | 5 | | | | | | | | | | 1 | | 2 |
| A-2-28 | 315 | 5 | 5 | | 5 | 5 | 5 | | 4 | 4 | 5 | 5 | | | 5 | 1 | 3 | 1 | 5 | |
| A-2-29 | 230 | 5 | 5 | 5 | 3 | 5 | 5 | 5 | 3 | 2 | 3 | 4 | 3 | 5 | 1 | 1 | 0 | 0 | 3 | 4 |
| A-2-30 | 320 | 5 | 5 | 5 | 4 | 5 | 5 | 5 | 0 | 0 | 3 | 3 | 0 | 4 | 3 | 0 | 0 | 1 | 3 | 4 |
| A-2-31 | 320 | 2 | 2 | 2 | 2 | 3 | 1 | 4 | 0 | 0 | 2 | 3 | 3 | 0 | 0 | 0 | 0 | 0 | 0 | 0 |
| A-2-32 | 320 | 5 | 5 | 5 | 5 | 5 | 5 | 5 | 0 | 3 | 5 | 4 | 5 | 5 | 2 | 1 | 0 | 0 | 4 | 4 |
| A-2-33 | 315 | 5 | 5 | 4 | 4 | 5 | 5 | 5 | 0 | 2 | | 4 | 5 | 5 | 3 | 0 | 0 | 1 | 3 | |
| A-2-34 | 320 | 5 | 5 | 5 | 5 | 5 | 5 | 5 | 0 | 0 | 4 | 4 | | 4 | 4 | 0 | 0 | 0 | 4 | 1 |
| A-2-35 | 320 | 4 | 3 | 3 | 0 | 3 | 3 | 4 | 0 | 0 | 0 | 0 | 0 | | 0 | 0 | 0 | 0 | 0 | 1 |
| A-2-36 | 320 | 5 | 5 | 4 | 0 | 5 | 5 | 5 | 0 | 3 | 3 | 3 | 0 | 4 | 0 | 0 | 0 | 0 | 2 | 1 |

TABLE 32-continued

[Table No. 18]

| NO. | Treatment dosage (g/ha) | D | E | F | G | H | I | J | K | L | M | N | O | P | b | c | d | e | f | g |
|---|---|---|---|---|---|---|---|---|---|---|---|---|---|---|---|---|---|---|---|---|
| A-2-37 | 315 | 5 | 4 | | 3 | 3 | 5 | | 0 | 1 | 3 | 1 | 0 | 5 | 2 | 1 | 0 | 0 | 0 | |
| A-2-38 | 315 | 5 | 5 | | 5 | 5 | 5 | | 2 | 5 | 4 | 4 | | | 5 | 2 | 2 | 0 | 4 | |
| A-2-39 | 315 | 5 | 5 | 5 | 4 | 5 | 5 | 5 | 0 | 0 | | 2 | 5 | 5 | 4 | 0 | 0 | 1 | 3 | 2 |
| A-2-40 | 320 | 5 | 5 | 5 | 5 | 5 | 5 | 5 | 4 | 4 | 4 | 4 | 5 | 5 | 5 | 2 | 3 | 1 | 4 | 4 |

TABLE 33

| NO. | Treatment dosage (g/ha) | D | E | F | G | H | I | J | K | L | M | N | O | P | b | c | d | e | f | g |
|---|---|---|---|---|---|---|---|---|---|---|---|---|---|---|---|---|---|---|---|---|
| A-2-41 | 315 | 5 | 5 | 5 | 3 | 5 | 5 | 5 | 0 | 2 | | 4 | | 5 | 3 | 0 | 0 | 2 | 1 | 2 |
| A-2-42 | 315 | 5 | 5 | | 5 | 5 | 5 | | 5 | 5 | 4 | 4 | 4 | 5 | 5 | 4 | 3 | 4 | 5 | |
| A-2-44 | 315 | 5 | 5 | | 1 | 5 | 5 | | 0 | 0 | 3 | 4 | | 4 | 2 | 0 | 0 | 0 | 0 | |
| A-2-45 | 315 | 5 | 4 | | 0 | 2 | 3 | | 0 | 0 | 4 | 4 | 3 | 4 | 2 | 0 | 0 | 0 | 0 | |
| A-2-48 | 315 | 5 | 5 | 5 | 5 | 5 | 5 | 5 | 0 | 0 | | 4 | 5 | 5 | 5 | 0 | 0 | 0 | 2 | 4 |
| A-2-49 | 315 | 4 | 4 | 4 | 0 | 4 | 5 | 5 | 0 | | 3 | 0 | 4 | 0 | 0 | 0 | 0 | 1 | 0 | |
| A-2-50 | 315 | 3 | 4 | | 0 | 2 | 2 | | 0 | 0 | 0 | 0 | | 3 | 0 | 0 | 0 | 0 | 0 | |
| A-2-51 | 315 | 3 | 3 | | 0 | 3 | 2 | | 1 | 2 | 2 | 0 | | 4 | 0 | 0 | 0 | 0 | 0 | |
| A-2-52 | 315 | 5 | 5 | | 3 | 5 | 5 | | 0 | 0 | 4 | 4 | | 4 | 2 | 1 | 0 | 0 | 0 | |
| A-2-53 | 320 | 4 | 4 | 4 | 4 | 5 | 5 | 5 | 0 | 0 | 3 | 4 | 5 | 5 | 3 | 0 | 0 | 0 | 4 | 4 |
| A-2-54 | 320 | 3 | 3 | 1 | 3 | 4 | 5 | 5 | 0 | 0 | 0 | 3 | 0 | 4 | 1 | 0 | 0 | 0 | 3 | 1 |
| A-2-55 | 234 | 4 | 3 | 1 | 0 | 4 | 0 | 4 | 0 | 0 | 0 | 0 | 0 | 0 | 0 | 0 | 0 | 0 | 0 | 0 |
| A-2-56 | 315 | 5 | 5 | | 5 | 5 | 5 | | 3 | 3 | 4 | 3 | | | 5 | 0 | 0 | 0 | 2 | |
| A-2-57 | 320 | 5 | 5 | 4 | 4 | 5 | 5 | 5 | 4 | 4 | 3 | 3 | 0 | 4 | 5 | 0 | 0 | 1 | 0 | 4 |
| A-2-58 | 320 | 5 | 5 | 5 | 5 | 5 | 5 | 5 | 4 | 4 | 4 | 3 | 4 | 5 | 5 | 3 | 3 | 1 | 4 | 4 |
| A-2-59 | 320 | 5 | 5 | 5 | 4 | 5 | 5 | 5 | 3 | 4 | 5 | 4 | 4 | 5 | 5 | 0 | 0 | 0 | | 5 |
| A-2-60 | 320 | 5 | 5 | 5 | 5 | 5 | 5 | 5 | 0 | 4 | | 4 | 3 | 4 | 4 | 1 | 0 | 0 | 0 | 0 |
| A-3-01 | 315 | 5 | 5 | | 4 | 5 | 5 | | 0 | 3 | 5 | 2 | | 5 | | 3 | 0 | 2 | 5 | |
| A-3-02 | 315 | 5 | 5 | | 5 | 5 | 5 | | 0 | 3 | 4 | 0 | | | | 2 | 0 | 4 | 4 | |
| A-3-03 | 315 | 5 | 5 | | 4 | 5 | 5 | | 0 | 4 | 4 | 0 | | | 5 | 2 | 0 | 0 | 4 | |
| A-3-04 | 315 | 5 | 5 | | 5 | 5 | 5 | | 0 | 4 | 4 | 4 | 4 | 4 | 5 | 4 | 0 | 1 | 4 | |
| A-3-05 | 320 | 0 | 0 | 0 | 0 | 4 | 4 | 4 | 0 | 0 | | 0 | | 0 | | 0 | 0 | 0 | 0 | 0 |
| A-3-06 | 315 | 5 | 5 | | 2 | 3 | 5 | | 1 | 3 | 4 | 4 | 0 | 4 | 4 | 2 | 0 | 0 | 3 | |
| A-3-07 | 315 | 4 | 4 | | 3 | 4 | 5 | | 0 | 0 | 4 | 3 | 0 | | 0 | 0 | 0 | 0 | 2 | |
| A-3-08 | 315 | 5 | 5 | | 2 | 3 | 4 | | 0 | 3 | 4 | 3 | 0 | 4 | 2 | 0 | 2 | 0 | 3 | |
| A-3-10 | 315 | 5 | 5 | | 5 | 5 | 5 | | 0 | 3 | 4 | 3 | | 4 | 2 | 1 | 0 | 0 | 3 | |
| A-4-02 | 315 | 5 | 5 | | 4 | 5 | 5 | | 0 | 4 | 2 | 2 | | 5 | 5 | 1 | 3 | 0 | 4 | |
| A-4-03 | 315 | 5 | 3 | | 5 | 5 | 5 | | 4 | 1 | 4 | 3 | | | 0 | 0 | 3 | 1 | | |
| A-4-04 | 320 | 5 | 5 | 4 | 4 | 5 | 5 | 5 | 0 | 0 | | | 3 | | 0 | 0 | 0 | 0 | | 3 |
| A-4-05 | 80 | | | | 5 | 5 | | | | | | | | | | | | 3 | | 3 |
| A-4-06 | 315 | 4 | 5 | | 3 | 3 | 5 | | 2 | 3 | 4 | 1 | 3 | 0 | | 0 | 0 | 0 | 4 | |
| A-5-01 | 320 | 0 | 0 | 0 | 0 | 1 | 3 | 3 | 0 | 0 | 3 | 2 | 0 | 3 | 0 | 0 | 0 | 0 | 0 | 2 |
| A-6-01 | 315 | 5 | 5 | | 5 | 5 | 5 | | 5 | 3 | 4 | 4 | | 5 | 5 | 1 | 3 | 0 | 4 | |
| A-6-02 | 315 | 5 | 5 | | 4 | 5 | 5 | | 3 | 4 | 4 | 4 | | | 5 | 0 | 0 | 0 | | |
| A-6-04 | 320 | 0 | 0 | 0 | 0 | 3 | 2 | 3 | 0 | 0 | 0 | 0 | 0 | 0 | 0 | 0 | 0 | 0 | 0 | |
| A-6-06 | 315 | 5 | 5 | | 2 | 5 | 5 | | 0 | 0 | | 3 | 5 | 5 | 1 | 0 | 0 | 0 | 0 | |
| A-6-07 | 320 | 4 | 5 | 3 | 0 | 4 | 5 | 5 | 0 | 2 | 0 | 0 | 0 | 0 | 3 | 2 | 0 | 0 | 0 | 0 |
| A-6-08 | 320 | 5 | 5 | 3 | 0 | 5 | 5 | 5 | 0 | 3 | 0 | 0 | 0 | 0 | 3 | 2 | 0 | 0 | 0 | 0 |
| A-6-09 | 320 | 3 | 3 | 2 | 0 | 5 | 5 | 5 | 0 | 0 | 3 | | 0 | 4 | 2 | 0 | 0 | 0 | 2 | 0 |
| A-6-10 | 320 | 4 | 4 | 3 | 2 | 5 | 5 | 5 | 0 | 3 | 5 | 4 | 0 | 5 | 1 | 0 | 1 | 0 | 0 | 4 |
| A-6-11 | 320 | 5 | 4 | 3 | 0 | 4 | 4 | 5 | 1 | 2 | 3 | | 0 | 4 | 2 | 0 | 0 | 0 | 1 | 2 |
| A-6-12 | 320 | 3 | 3 | 2 | 0 | 4 | 5 | 5 | 0 | 0 | 3 | 2 | 0 | 4 | 1 | 0 | 0 | 0 | 0 | 4 |
| A-6-13 | 320 | 1 | 3 | 1 | 0 | 1 | 2 | 4 | 0 | 2 | 0 | 0 | 0 | 0 | 0 | 0 | 0 | 0 | 0 | 0 |

TABLE 34

| NO. | Treatment dosage (g/ha) | D | E | F | G | H | I | J | K | L | M | N | O | P | b | c | d | e | f | g |
|---|---|---|---|---|---|---|---|---|---|---|---|---|---|---|---|---|---|---|---|---|
| B-1-01 | 315 | 5 | 5 |  | 5 | 5 | 5 |  | 3 | 4 | 5 | 3 |  | 5 | 5 | 0 | 2 | 4 | 3 |  |
| B-1-02 | 315 | 5 | 5 |  |  | 5 | 5 |  | 0 | 4 | 5 | 5 | 5 |  | 0 | 0 | 0 | 0 | 4 |  |
| B-1-03 | 315 | 5 | 5 |  | 5 | 5 | 5 |  | 4 | 4 | 5 | 3 |  | 5 | 5 | 0 | 0 | 3 | 3 |  |
| B-1-04 | 315 | 5 | 5 |  | 4 | 5 | 5 |  | 3 | 4 | 5 | 4 |  | 5 | 4 | 0 | 0 | 0 | 4 |  |
| B-1-05 | 315 | 5 | 5 |  | 5 | 5 | 0 |  | 4 | 4 | 5 | 4 |  | 5 | 5 | 1 | 0 | 0 | 5 |  |
| B-1-06 | 315 | 4 | 5 |  | 0 | 4 | 2 |  | 0 | 3 | 3 | 4 |  | 5 | 2 | 3 | 1 | 0 | 4 |  |
| B-1-07 | 315 | 4 | 4 |  | 0 | 0 | 3 |  | 0 | 0 | 0 | 0 | 0 | 4 | 3 | 1 | 0 | 0 | 0 |  |
| B-1-08 | 315 | 5 | 5 |  | 5 | 5 | 5 |  | 0 | 4 | 3 | 3 |  | 4 | 5 | 1 | 0 | 0 | 2 |  |
| B-1-10 | 315 | 5 | 5 |  | 4 | 5 | 3 |  | 3 | 3 | 3 | 2 | 0 | 4 | 5 | 3 | 0 | 0 | 3 |  |
| B-1-12 | 315 | 5 | 5 |  | 3 | 4 | 2 |  | 4 | 4 | 4 | 4 |  | 4 | 5 | 5 | 0 | 0 | 5 |  |
| B-1-13 | 315 | 5 | 5 |  |  | 5 | 5 |  | 2 | 4 | 4 | 4 | 5 | 5 | 5 | 3 | 4 | 5 | 5 |  |
| B-1-14 | 315 | 5 | 5 |  |  | 5 | 5 |  | 3 | 5 | 5 | 4 | 5 | 5 | 5 | 0 | 3 | 5 | 5 |  |
| B-1-15 | 315 | 5 | 5 |  |  | 5 | 5 |  | 4 | 5 |  | 5 |  | 5 | 5 | 0 | 0 | 4 | 4 |  |
| B-1-16 | 315 | 5 | 5 |  |  | 5 | 4 |  | 0 | 4 | 4 | 3 | 5 | 4 | 3 | 0 | 0 | 5 | 0 |  |
| B-1-17 | 315 | 5 | 5 |  |  | 5 | 5 |  | 0 | 4 | 5 | 3 | 5 | 5 | 0 | 0 | 0 | 3 | 0 |  |
| B-1-18 | 320 | 3 | 4 | 1 | 0 | 2 | 2 | 5 | 0 | 0 | 0 | 0 | 0 | 0 | 0 | 0 | 0 | 0 | 0 | 0 |
| B-2-01 | 315 | 5 | 5 |  |  | 5 | 5 |  | 3 | 4 | 4 | 3 |  | 5 | 5 | 0 | 0 |  | 4 |  |
| B-2-02 | 315 | 5 | 3 |  |  | 5 | 5 |  | 3 | 3 | 0 | 3 |  | 2 | 2 | 0 | 0 | 3 | 0 |  |
| B-2-03 | 315 | 3 | 3 |  |  | 5 | 3 |  | 0 | 3 | 0 | 4 | 0 | 4 | 1 | 0 | 0 | 1 | 0 |  |
| B-2-04 | 315 | 5 | 5 |  | 5 | 5 | 5 |  | 4 | 4 | 5 | 5 |  | 5 | 5 | 1 | 0 | 5 | 5 |  |
| B-2-05 | 315 | 5 | 5 |  |  | 5 | 5 |  | 1 | 4 | 5 | 5 |  | 5 | 3 | 0 | 0 | 0 | 5 |  |
| B-2-06 | 315 | 5 | 5 |  | 5 | 5 | 5 |  | 4 | 5 | 5 | 4 |  | 5 | 5 | 0 | 2 | 5 | 5 |  |
| B-2-07 | 315 | 5 | 5 |  | 3 | 5 | 5 |  | 2 | 3 | 3 | 3 | 3 | 5 | 4 | 3 | 1 | 0 | 1 |  |
| B-2-08 | 315 | 5 | 5 |  |  | 5 | 5 |  | 4 | 4 | 4 | 3 |  | 4 | 5 | 0 | 0 | 3 | 1 |  |
| B-2-09 | 315 | 5 | 5 |  | 3 | 4 | 5 |  | 0 | 0 | 3 | 2 | 3 | 4 | 3 | 0 | 0 | 0 | 1 |  |
| B-2-11 | 320 | 5 | 5 | 5 | 3 | 5 | 5 | 5 | 0 | 0 | 4 | 4 | 3 | 5 | 3 | 1 | 0 | 0 |  | 1 |
| B-2-12 | 320 | 5 | 5 | 5 | 1 | 5 | 5 | 5 | 0 | 0 | 3 | 4 | 2 | 4 | 3 | 0 | 0 | 0 | 0 | 0 |
| B-2-13 | 320 | 5 | 5 | 5 | 5 | 5 | 5 | 5 | 0 | 4 | 3 | 3 |  |  | 5 | 1 | 0 | 0 | 4 | 4 |
| B-2-14 | 320 | 5 | 5 | 5 | 5 | 5 | 5 | 5 | 0 | 3 | 3 | 3 | 4 | 4 | 4 | 0 | 0 | 0 | 3 | 1 |
| B-2-15 | 320 | 5 | 5 | 5 | 3 | 5 | 5 | 5 | 0 | 0 | 3 | 2 |  | 4 | 5 | 0 | 0 | 0 | 2 | 2 |
| B-2-16 | 320 | 5 | 5 | 5 | 5 | 5 | 5 | 5 | 2 | 0 | 4 | 4 |  |  | 5 | 1 | 1 | 1 |  | 3 |
| B-2-17 | 315 | 5 | 5 |  | 5 | 5 | 5 |  | 2 | 2 | 3 | 3 | 1 | 5 | 4 | 2 | 2 | 1 | 0 |  |
| B-2-19 | 1250 | 5 | 5 |  | 5 | 5 | 5 |  | 0 | 4 | 5 | 4 | 0 | 4 | 4 | 0 | 0 | 0 | 4 |  |
| B-2-20 | 1250 | 3 | 5 |  | 0 | 5 | 5 |  | 2 | 4 | 4 | 3 | 0 | 4 | 4 | 0 | 0 | 0 | 4 |  |
| B-2-24 | 320 | 3 | 3 | 3 | 0 | 0 | 0 | 3 | 0 | 0 | 0 | 3 | 0 | 0 | 0 | 0 | 0 | 0 | 0 | 0 |
| B-2-25 | 315 | 5 | 5 |  |  | 5 | 5 |  | 4 | 3 | 4 | 4 | 5 | 5 | 5 | 3 | 0 | 1 | 2 |  |
| B-2-26 | 320 | 5 | 5 | 5 | 1 | 5 | 5 | 5 | 0 | 4 | 4 | 3 | 2 | 0 | 2 | 0 | 0 | 0 | 0 | 0 |
| B-2-27 | 315 | 5 | 5 |  | 5 | 5 | 5 |  | 5 | 5 | 5 | 5 |  | 5 | 5 | 4 | 5 | 5 | 4 |  |
| B-2-28 | 80 |  |  |  |  | 5 | 5 | 5 |  |  |  |  |  |  |  |  |  |  | 0 | 0 |
| B-2-29 | 315 | 5 | 5 |  |  | 5 | 5 |  | 4 | 4 | 5 | 5 |  | 5 | 5 | 0 | 3 | 5 | 5 |  |
| B-2-30 | 315 | 5 | 5 |  | 5 | 5 | 5 |  | 3 | 3 | 5 | 4 | 5 |  | 4 | 1 | 1 | 0 | 4 |  |
| B-2-31 | 315 | 5 | 5 |  |  | 5 | 5 |  | 0 | 5 | 4 | 5 |  | 5 | 5 | 0 | 0 | 5 | 5 |  |
| B-2-32 | 315 | 5 | 5 |  | 3 | 4 | 5 |  | 2 | 4 | 3 | 4 |  |  | 3 | 0 | 1 | 0 | 3 |  |
| B-2-33 | 315 | 5 | 5 | 5 | 5 | 5 | 5 | 5 | 5 | 4 |  | 4 | 5 | 5 | 5 | 3 | 4 | 5 | 1 | 5 |
| B-2-34 | 315 | 5 | 5 |  |  | 5 | 5 | 5 |  | 5 | 5 | 4 | 5 |  | 5 | 2 | 1 | 1 | 5 |  |
| B-2-35 | 320 | 5 | 5 | 4 | 4 | 5 | 5 | 5 | 4 | 3 |  |  | 0 | 4 | 2 | 1 | 0 | 1 | 4 | 4 |
| B-2-36 | 315 | 5 | 5 |  | 1 | 5 | 4 |  | 4 | 4 | 3 | 4 | 5 | 4 | 4 | 1 | 1 | 0 | 3 |  |
| B-2-37 | 315 | 5 | 5 |  |  | 5 | 5 |  | 4 | 5 | 4 | 4 | 4 |  | 3 | 1 | 0 | 0 | 4 |  |
| B-2-38 | 320 | 5 | 5 | 5 | 5 | 5 | 5 | 5 | 1 | 3 | 4 | 4 | 5 | 5 | 5 | 1 | 4 | 0 | 4 | 4 |
| B-2-39 | 320 | 5 | 5 | 5 | 5 | 5 | 5 | 5 | 2 | 3 | 4 | 4 | 4 | 5 | 4 | 0 | 0 | 0 | 3 | 4 |

TABLE 35

| NO. | Treatment dosage (g/ha) | D | E | F | G | H | I | J | K | L | M | N | O | P | b | c | d | e | f | g |
|---|---|---|---|---|---|---|---|---|---|---|---|---|---|---|---|---|---|---|---|---|
| B-2-40 | 320 | 5 | 5 | 5 | 5 | 5 | 5 | 5 | 5 | 4 | 5 | 4 |  | 5 | 5 | 0 | 2 | 0 | 3 | 4 |
| B-2-41 | 320 | 5 | 5 | 5 | 3 | 5 | 5 | 5 | 2 | 3 | 4 | 4 |  | 5 | 4 | 0 | 0 | 0 | 3 | 4 |
| B-2-42 | 320 | 5 | 5 | 5 | 5 | 5 | 5 | 4 | 3 | 4 | 4 | 4 |  | 5 | 4 | 1 | 0 | 0 | 4 | 4 |
| B-2-43 | 320 | 5 | 4 | 5 | 5 | 5 | 5 | 5 | 0 | 3 | 3 | 4 | 4 | 5 | 3 | 0 | 2 | 1 | 4 | 4 |
| B-2-44 | 320 | 5 | 5 | 5 | 2 | 5 | 5 | 5 | 0 | 0 | 3 | 3 | 0 | 4 | 3 | 0 | 0 | 1 | 3 | 4 |
| B-2-46 | 320 | 5 | 5 | 5 | 3 | 5 | 5 | 5 | 3 | 4 | 4 | 4 | 4 | 5 | 4 | 1 | 0 | 0 | 4 | 4 |
| B-2-47 | 320 | 4 | 5 | 4 | 2 | 5 | 5 | 5 | 0 | 0 | 2 | 3 | 4 | 5 | 3 | 0 | 0 | 0 | 2 | 3 |
| B-2-49 | 320 | 5 | 5 | 5 | 3 | 5 | 5 | 5 | 1 | 4 | 3 | 4 |  | 5 | 3 | 0 | 0 | 0 | 3 | 3 |
| B-2-50 | 320 | 5 | 5 | 4 | 0 | 2 | 3 | 5 | 0 | 2 |  | 0 | 0 | 0 | 1 | 1 | 0 | 0 | 0 | 0 |
| B-2-51 | 320 | 5 | 5 | 5 | 5 | 5 | 5 | 5 | 2 | 4 | 4 | 4 | 3 |  | 3 | 1 | 0 | 0 | 4 | 2 |
| B-2-52 | 80 |  |  |  | 4 | 5 | 5 |  |  |  |  |  |  |  |  |  |  | 0 |  | 1 |
| B-2-53 | 135.45 | 5 | 5 |  |  | 5 | 5 |  | 0 | 3 | 4 | 0 |  | 5 | 3 | 0 | 0 | 2 |  |  |
| B-2-54 | 320 | 5 | 5 | 5 | 5 | 5 | 5 | 5 | 3 | 4 | 3 | 4 | 4 | 5 | 5 | 2 | 0 | 0 | 4 | 4 |
| B-2-55 | 315 | 5 | 5 | 5 | 4 | 5 | 5 | 5 | 1 | 4 |  | 4 |  | 5 | 4 | 0 | 3 | 0 | 3 | 2 |
| B-2-56 | 320 | 5 | 5 | 5 | 3 | 5 | 5 | 5 | 0 | 2 | 4 | 4 | 5 | 5 | 2 | 1 | 0 | 1 | 2 | 1 |
| B-2-57 | 315 | 5 | 5 |  | 5 | 5 | 5 |  | 5 | 5 | 4 | 4 | 5 | 5 | 5 | 4 | 4 | 0 | 3 |  |
| B-2-58 | 315 | 5 | 5 |  |  | 3 | 4 | 5 |  | 1 | 3 | 4 | 4 | 0 | 5 | 3 | 1 | 0 | 0 |  |
| B-2-61 | 320 |  |  |  | 0 | 4 | 2 | 5 | 0 | 0 | 0 | 0 | 0 |  | 0 | 0 | 0 | 0 |  |  |
| B-2-62 | 320 | 4 | 4 | 3 | 3 | 3 | 4 | 5 | 0 | 2 | 3 | 3 | 0 | 4 | 0 | 0 | 0 | 0 | 0 | 0 |
| B-2-63 | 315 | 4 | 4 |  | 2 | 1 | 3 |  | 0 | 1 | 3 | 3 | 3 | 4 | 0 | 0 | 0 | 0 | 0 |  |

TABLE 35-continued

| NO. | | | | | | | | | | | | | | | | | | | |
|---|---|---|---|---|---|---|---|---|---|---|---|---|---|---|---|---|---|---|---|
| B-2-64 | 320 | 5 | 5 | 5 | 3 | 5 | 5 | 5 | 3 | 4 | | 4 | 0 | 5 | 4 | 1 | 0 | 0 | 4 | 3 |
| B-3-01 | 315 | 5 | 5 | | 5 | 5 | 5 | | 2 | 4 | 5 | 4 | | | | 3 | 0 | 5 | 4 | |
| B-3-02 | 315 | 5 | 5 | | 5 | 5 | 5 | | 3 | 5 | 4 | 4 | | | | 3 | 0 | 5 | 4 | |
| B-3-03 | 315 | 5 | 5 | | 4 | 5 | 5 | | 0 | 0 | 1 | 0 | 0 | 3 | 4 | 4 | 0 | 0 | 2 | |
| B-3-04 | 315 | 5 | 5 | 5 | 3 | 4 | 5 | 5 | 0 | 0 | | 3 | 2 | 4 | 1 | 0 | 0 | 0 | 1 | 0 |
| B-3-05 | 315 | 5 | 5 | | 5 | 4 | 5 | | 0 | 0 | 5 | 3 | 0 | 4 | 1 | 2 | 0 | 1 | 1 | |
| B-4-01 | 315 | 4 | 4 | | 3 | 0 | 5 | | 0 | 0 | 3 | 0 | 0 | 4 | 2 | 2 | 3 | 0 | 3 | |
| B-4-02 | 315 | 5 | 5 | | 5 | 5 | 5 | | 4 | 5 | 5 | 4 | | 5 | | 4 | 1 | 1 | 3 | |
| B-4-03 | 315 | 5 | 5 | | 4 | 5 | 5 | | 3 | 5 | 5 | 3 | | | | 2 | 3 | 1 | 4 | |
| B-4-04 | 320 | 5 | 5 | 5 | 0 | 5 | 5 | 5 | 0 | 3 | 3 | 4 | | | 3 | 0 | 0 | 0 | 2 | 4 |
| B-4-05 | 315 | 5 | 5 | | 5 | 5 | 5 | | 3 | 4 | 4 | 3 | | 5 | 5 | 0 | 0 | 0 | | |
| B-4-06 | 315 | 5 | 5 | | 5 | 5 | 5 | | 1 | 3 | 4 | | 4 | | | 2 | 0 | 3 | 4 | |
| B-5-01 | 320 | 0 | 2 | 0 | 0 | 0 | 0 | 4 | 0 | 0 | 0 | 0 | 0 | | 0 | 0 | 0 | 0 | 0 | 0 |

TABLE 36

[Table No. 19]

| NO. | Treatment dosage (g/ha) | D | E | F | G | H | I | J | K | L | M | N | O | P | b | c | d | e | f | g |
|---|---|---|---|---|---|---|---|---|---|---|---|---|---|---|---|---|---|---|---|---|
| A-1-04 | 320 | 1 | 1 | 1 | 2 | 4 | 4 | 4 | 3 | 2 | 4 | 4 | 2 | 4 | 0 | 0 | 4 | 0 | 4 | 4 |
| A-1-05 | 315 | 4 | 4 | | 4 | 5 | 4 | | 3 | 2 | 4 | 3 | 2 | | 4 | 3 | 3 | 0 | 4 | |
| A-1-06 | 80 | | | | | 5 | 5 | 5 | | | | | | | | | | 2 | | 3 |
| A-1-07 | 315 | 5 | 5 | | 5 | 5 | 5 | | 4 | 4 | 4 | 4 | 4 | | 5 | 4 | 4 | 3 | 1 | |
| A-1-08 | 315 | 4 | 4 | | 3 | 5 | 4 | | 3 | 4 | 3 | 1 | 0 | | 3 | 1 | 0 | 2 | 0 | |
| A-1-10 | 315 | 1 | 0 | | 0 | 1 | 2 | | 0 | 0 | 3 | 0 | 0 | 0 | 0 | 0 | 0 | 0 | 2 | |
| A-1-12 | 320 | 4 | 1 | 4 | | 5 | 5 | 5 | 0 | 1 | 4 | 3 | 3 | 4 | 4 | 2 | 3 | 4 | 1 | 4 |
| A-1-13 | 320 | 4 | 4 | 0 | 4 | 4 | 4 | 3 | 1 | 2 | 4 | 2 | 3 | 3 | 4 | 3 | 3 | 4 | 0 | 3 |
| A-1-15 | 320 | 1 | 2 | 0 | 0 | 1 | 1 | 3 | 0 | 0 | 3 | 0 | 0 | 3 | 0 | 0 | 0 | 1 | 0 | 1 |
| A-1-18 | 320 | 4 | 4 | 4 | 4 | 4 | 4 | 4 | 3 | 2 | 4 | 4 | 4 | 4 | 4 | 0 | 4 | 1 | 4 | 4 |
| A-1-20 | 80 | | | | | 4 | 5 | 4 | | | | | | | | | | 0 | | 2 |
| A-1-21 | 80 | | | | | 4 | 4 | 4 | | | | | | | | | | 0 | | 0 |
| A-1-21 | 320 | 3 | 3 | 1 | 0 | 1 | 1 | 4 | 2 | 0 | 4 | 0 | 3 | 4 | 0 | 0 | 1 | 0 | 3 | 3 |
| A-2-01 | 315 | 4 | 3 | | 1 | 1 | 4 | | 0 | 1 | 3 | 3 | 1 | 4 | 2 | 0 | 3 | 0 | 0 | |
| A-2-03 | 315 | 5 | 5 | | 5 | 5 | 5 | | 2 | 2 | 4 | 3 | 5 | 5 | 5 | 4 | 2 | 2 | 0 | |
| A-2-04 | 320 | 3 | 3 | 2 | 1 | 1 | 1 | 3 | 1 | 2 | 4 | 3 | 0 | | 0 | 0 | 4 | 0 | 0 | 0 |
| A-2-05 | 315 | 5 | 5 | | 5 | 5 | 5 | | 4 | 4 | 4 | 4 | 5 | 5 | 5 | 5 | 5 | 3 | 4 | |
| A-2-06 | 315 | 5 | 5 | | 5 | 5 | 5 | | 4 | 4 | 4 | 4 | 4 | | 5 | 4 | 3 | 1 | 3 | |
| A-2-07 | 315 | 5 | 5 | | 5 | 5 | 5 | | 3 | 3 | 4 | 5 | 5 | | 5 | 5 | 4 | 4 | | |
| A-2-08 | 80 | | | | | 5 | 5 | 5 | | | | | | | | | | 3 | | 5 |
| A-2-09 | 315 | 5 | 5 | | 5 | 5 | 5 | | 4 | 4 | 3 | 4 | 5 | | 5 | 5 | 5 | 2 | 3 | |
| A-2-10 | 320 | 5 | 4 | 4 | 3 | 5 | 5 | 5 | 4 | 3 | 3 | 3 | 4 | 4 | 3 | 0 | 3 | 0 | 3 | 4 |
| A-2-11 | 315 | 5 | 5 | | 3 | 3 | 5 | | 1 | 1 | 3 | 3 | 1 | 4 | 5 | 3 | 3 | 0 | 0 | |
| A-2-13 | 315 | 5 | 5 | 5 | 5 | 5 | 5 | 5 | 5 | 4 | | 4 | 5 | 5 | 5 | 5 | 4 | 4 | 4 | 4 |
| A-2-14 | 320 | 5 | 5 | 5 | 5 | 5 | 5 | 5 | 5 | 4 | 4 | 5 | 5 | 5 | 4 | 4 | 3 | 3 | 4 |
| A-2-15 | 320 | 5 | 5 | 5 | 5 | 5 | 5 | 5 | 4 | 4 | 3 | 4 | 5 | 5 | 5 | 5 | 5 | 4 | 3 | 4 |
| A-2-17 | 315 | 5 | 5 | | 5 | 5 | 5 | | 4 | 4 | 5 | 4 | 4 | | 5 | 5 | 5 | 4 | 4 | |
| A-2-18 | 320 | 4 | 4 | 5 | 3 | 4 | 5 | 5 | 3 | 3 | 1 | 2 | 4 | 4 | 4 | 1 | 0 | 0 | 2 | 4 |
| A-2-19 | 320 | 5 | 5 | 4 | 4 | 5 | 5 | 5 | 4 | 4 | 5 | 4 | 4 | 2 | 3 | | | 0 | 4 | 5 |
| A-2-20 | 320 | 5 | 5 | 5 | 5 | 5 | 5 | 5 | 4 | 5 | | 4 | 4 | 5 | 5 | 4 | 4 | 3 | 4 | 4 |
| A-2-21 | 320 | 5 | 5 | 5 | 4 | 5 | 5 | 5 | 3 | 3 | 4 | 4 | 4 | 5 | 5 | 3 | 4 | 4 | 3 | 4 |
| A-2-22 | 320 | 5 | 5 | 5 | 4 | 5 | 5 | 5 | 5 | 4 | 4 | 4 | 5 | 5 | 5 | 4 | 4 | 2 | 3 | 4 |
| A-2-23 | 320 | 5 | 5 | 5 | 5 | 5 | 5 | 5 | 4 | 4 | 4 | 4 | 4 | | 5 | 5 | 4 | 4 | 4 | 4 |
| A-2-24 | 315 | 5 | 5 | | 3 | 5 | 5 | | 5 | 4 | 4 | 4 | 5 | | 5 | 3 | 4 | 0 | 4 | |
| A-2-25 | 320 | 5 | 5 | 5 | 4 | 5 | 5 | 5 | 5 | 4 | 4 | 4 | 4 | 5 | 4 | 4 | 1 | 4 | 4 |
| A-2-26 | 320 | 5 | 5 | 5 | 5 | 5 | 5 | 5 | 4 | 4 | 5 | 4 | 4 | 5 | 5 | 3 | 4 | 3 | 4 | 4 |
| A-2-27 | 80 | | | | | 3 | 4 | 5 | | | | | | | | | | 0 | | 2 |
| A-2-28 | 315 | 5 | 5 | | 4 | 5 | 5 | | 5 | 4 | 4 | 4 | 5 | | 5 | 5 | 4 | 3 | 4 | |
| A-2-29 | 280 | 5 | 5 | 5 | 4 | 5 | 5 | 5 | 4 | 4 | 4 | 4 | 4 | 4 | 4 | 1 | 4 | 0 | 4 | 4 |
| A-2-30 | 320 | 5 | 5 | 5 | 5 | 3 | 5 | 5 | 4 | 3 | 4 | 4 | 4 | 4 | 0 | 3 | 4 | 0 | 3 | 4 |
| A-2-31 | 320 | 2 | 3 | 2 | 3 | 1 | 0 | 3 | 2 | 3 | | 3 | 4 | 5 | 0 | 0 | 3 | 0 | 4 | 2 |
| A-2-32 | 320 | 5 | 5 | 5 | 4 | 5 | 5 | 5 | 4 | | 4 | 5 | 5 | 5 | 4 | 4 | 0 | 3 | 4 |
| A-2-33 | 315 | 5 | 5 | 5 | 5 | 4 | 5 | | 5 | 2 | | 4 | 4 | | 5 | 4 | 3 | 1 | 4 | 4 |
| A-2-34 | 320 | 5 | 5 | 4 | 4 | 4 | 5 | 5 | 2 | 2 | 3 | 4 | 4 | | 4 | 2 | 4 | 0 | 3 | 4 |
| A-2-35 | 320 | 2 | 1 | 1 | 0 | 0 | 0 | 1 | 4 | 3 | 3 | 2 | 0 | 4 | 0 | 0 | 0 | 0 | 0 | 3 |
| A-2-36 | 320 | 3 | 2 | 1 | 2 | 1 | 0 | 2 | 5 | 4 | 3 | 3 | 4 | 3 | 0 | 0 | 5 | 0 | 4 | 4 |
| A-2-37 | 315 | 4 | 5 | | 0 | 1 | 4 | | | 1 | 2 | 3 | 3 | 0 | 4 | 2 | 2 | 0 | 0 | |
| A-2-38 | 315 | 5 | 5 | | 5 | 5 | 5 | | 4 | 3 | 4 | 2 | 3 | 4 | 5 | 3 | 4 | 1 | 4 | |
| A-2-39 | 315 | 4 | 4 | 3 | 4 | 5 | 5 | 5 | 2 | 1 | | 3 | 4 | 4 | 2 | 4 | 1 | 3 | 3 |
| A-2-40 | 320 | 5 | 5 | 5 | 4 | 5 | 5 | 5 | 4 | 3 | | 3 | 4 | 4 | 4 | 3 | 2 | 3 | 3 | 3 |

TABLE 37

| NO. | Treatment dosage (g/ha) | D | E | F | G | H | I | J | K | L | M | N | O | P | b | c | d | e | f | g |
|---|---|---|---|---|---|---|---|---|---|---|---|---|---|---|---|---|---|---|---|---|
| A-2-41 | 315 | 4 | 4 | 3 | 3 | 5 | 5 | 5 | 3 | 2 |   | 4 | 1 | 4 | 4 | 0 | 4 | 0 | 3 | 3 |
| A-2-42 | 315 | 5 | 5 |   | 5 | 5 | 5 |   | 4 | 4 | 5 | 4 | 5 | 5 | 5 | 5 | 3 | 3 | 4 |   |
| A-2-44 | 315 | 4 | 4 |   | 2 | 5 | 5 |   | 2 | 0 | 2 | 0 | 1 | 4 | 3 | 1 | 0 | 0 | 0 |   |
| A-2-45 | 315 | 5 | 4 |   | 0 | 1 | 1 |   | 3 | 3 | 4 | 4 | 2 | 4 | 4 | 0 | 3 | 0 | 1 |   |
| A-2-48 | 315 | 5 | 5 | 4 | 4 | 4 | 4 | 5 | 4 | 3 |   | 3 | 3 | 5 | 4 | 1 | 4 | 0 | 3 | 4 |
| A-2-49 | 315 | 3 | 3 | 2 | 0 | 0 | 0 | 3 | 0 | 0 |   | 3 | 1 | 3 | 0 | 0 | 0 | 0 | 1 | 0 |
| A-2-50 | 315 | 2 | 3 |   | 0 | 0 | 0 |   | 0 | 0 | 0 | 0 | 0 | 3 | 0 | 0 | 0 | 0 | 2 |   |
| A-2-51 | 315 | 1 | 1 |   | 0 | 0 | 0 |   | 0 | 0 | 3 | 0 | 3 |   | 0 | 0 | 0 | 0 | 0 |   |
| A-2-52 | 315 | 5 | 5 |   | 3 | 4 | 5 |   | 3 | 2 | 3 | 2 | 3 | 4 | 5 | 3 | 4 | 0 | 0 |   |
| A-2-53 | 320 | 4 | 3 | 4 | 3 | 4 | 4 | 5 | 2 | 0 |   | 3 | 3 | 4 | 3 | 2 | 1 | 0 | 3 | 3 |
| A-2-54 | 320 | 2 | 2 | 1 | 3 | 4 | 4 | 5 | 0 | 0 | 3 | 1 | 0 | 5 | 0 | 0 | 0 | 0 | 1 | 0 |
| A-2-55 | 234 | 3 | 2 | 0 | 0 | 0 | 0 | 0 | 5 | 5 | 4 | 1 | 4 | 4 | 0 | 1 | 4 | 0 | 2 | 4 |
| A-2-56 | 315 | 5 | 5 |   | 4 | 5 | 5 |   | 3 | 3 | 4 | 3 | 3 | 4 | 5 | 3 | 4 | 2 | 0 |   |
| A-2-57 | 320 | 4 | 5 | 5 | 3 | 5 | 5 | 5 | 1 | 3 | 4 | 1 | 2 |   | 5 | 3 | 1 | 0 | 3 | 4 |
| A-2-58 | 320 | 5 | 5 | 5 | 4 | 5 | 5 | 5 | 3 | 3 |   | 3 | 3 | 4 | 3 | 3 | 1 | 0 | 4 | 3 |
| A-2-59 | 320 | 5 | 5 | 5 | 4 | 5 | 5 | 5 | 5 | 4 | 4 | 4 | 4 | 4 | 5 | 3 | 5 | 0 | 4 | 4 |
| A-2-60 | 320 | 3 | 3 | 3 | 3 | 5 | 5 | 5 | 4 | 2 | 4 | 3 | 2 | 4 | 0 | 0 | 3 | 0 | 0 | 0 |
| A-3-01 | 315 | 4 | 5 |   | 3 | 5 | 5 |   | 0 | 2 |   | 0 | 1 |   | 3 | 0 | 0 | 2 | 4 |   |
| A-3-02 | 315 | 5 | 5 |   | 4 | 5 | 5 |   | 2 | 3 |   | 3 | 5 |   | 5 |   | 2 | 0 | 0 |   |
| A-3-03 | 315 | 5 | 5 |   | 4 | 5 | 5 |   | 4 | 3 | 4 | 0 | 3 | 1 | 5 | 4 | 4 | 0 | 0 |   |
| A-3-04 | 315 | 5 | 5 |   | 5 | 5 | 5 |   | 4 | 3 | 4 | 3 | 4 | 4 | 5 | 3 | 2 | 3 | 3 |   |
| A-3-05 | 320 | 3 | 1 | 0 | 0 | 1 | 1 | 3 | 3 | 0 | 4 | 1 | 0 |   | 0 | 0 | 3 | 0 | 0 | 4 |
| A-3-06 | 315 | 5 | 5 |   | 3 | 2 | 4 |   | 3 | 3 | 3 | 3 | 0 | 4 | 4 | 3 | 4 | 0 | 4 |   |
| A-3-07 | 315 | 5 | 5 |   | 0 | 1 | 4 |   | 2 | 1 | 2 | 3 | 0 |   | 1 | 0 | 1 | 0 | 0 |   |
| A-3-09 | 315 | 3 | 3 |   | 1 | 0 | 4 |   | 2 | 2 | 3 | 2 | 0 | 4 | 0 | 0 | 3 | 0 | 2 |   |
| A-3-10 | 315 | 5 | 5 |   | 4 | 5 | 4 |   | 2 | 3 | 4 | 3 | 3 |   | 4 | 2 | 3 | 0 | 2 |   |
| A-4-02 | 315 | 5 | 4 |   | 3 | 5 | 4 |   | 3 | 4 | 3 | 3 | 4 | 4 | 4 | 2 | 5 | 0 | 3 |   |
| A-4-03 | 315 | 5 | 5 |   | 4 | 5 | 4 |   | 2 | 3 | 4 | 2 | 3 | 4 | 5 | 0 | 3 | 1 | 0 |   |
| A-4-04 | 320 | 4 | 3 | 1 | 3 | 3 | 3 | 3 | 4 | 3 | 4 | 3 | 4 |   | 0 | 0 | 0 | 0 | 3 | 3 |
| A-4-05 | 80 |   |   |   | 4 | 4 | 3 |   |   |   |   |   |   |   |   |   |   | 0 |   | 2 |
| A-4-06 | 315 | 4 | 4 |   | 3 | 5 | 4 |   | 2 | 2 | 3 | 0 | 3 | 4 | 4 | 3 | 1 | 1 | 0 |   |
| A-5-01 | 320 | 0 | 0 | 0 | 0 | 0 | 0 | 3 | 0 | 0 | 4 | 3 | 1 |   | 0 | 0 | 0 | 0 | 3 | 3 |
| A-6-01 | 315 | 5 | 5 |   | 4 | 5 | 5 |   | 5 | 4 | 4 | 4 | 4 |   | 5 | 3 | 4 | 0 | 2 |   |
| A-6-02 | 315 | 5 | 5 |   | 3 | 5 | 4 |   | 5 | 4 | 4 | 4 | 4 |   | 5 | 4 | 3 | 0 | 0 |   |
| A-6-06 | 315 | 5 | 5 |   | 3 | 4 | 3 |   | 5 | 4 | 3 | 4 | 4 | 5 | 4 | 4 | 4 | 0 | 2 |   |
| A-6-07 | 320 | 3 | 4 | 3 | 1 | 3 | 4 | 4 | 0 | 2 | 0 | 0 | 0 | 0 | 3 | 0 | 0 | 0 | 0 | 0 |
| A-6-08 | 320 | 4 | 4 | 3 | 0 | 2 | 4 | 0 | 2 | 4 | 1 | 0 | 0 | 3 | 2 | 1 | 0 | 0 | 0 | 1 |
| A-6-09 | 320 | 2 | 2 | 1 | 0 | 2 | 4 | 4 | 0 | 0 | 3 | 0 | 2 | 4 | 0 | 0 | 0 | 0 | 3 | 2 |
| A-6-10 | 320 | 4 | 4 | 2 | 3 | 5 | 5 | 5 | 1 | 2 | 4 | 1 | 0 | 3 | 1 | 1 | 3 | 0 | 1 | 4 |
| A-6-11 | 320 | 3 | 4 | 2 | 1 | 4 | 4 | 5 | 2 | 2 | 2 | 2 | 0 | 3 | 1 | 0 | 2 | 0 | 1 | 4 |
| A-6-12 | 320 | 2 | 3 | 1 | 0 | 1 | 5 | 5 | 0 | 0 | 4 | 3 | 2 | 4 | 0 | 0 | 0 | 0 | 4 | 4 |
| A-6-13 | 320 | 0 | 1 | 0 | 0 | 0 | 0 | 0 | 1 | 1 | 2 | 0 | 0 | 2 | 0 | 0 | 0 | 0 | 0 | 0 |

TABLE 38

| NO. | Treatment dosage (g/ha) | D | E | F | G | H | I | J | K | L | M | N | O | P | b | c | d | e | f | g |
|---|---|---|---|---|---|---|---|---|---|---|---|---|---|---|---|---|---|---|---|---|
| B-1-01 | 315 | 5 | 5 |   |   | 5 | 5 |   | 4 | 5 | 5 | 4 | 4 | 4 | 5 | 4 | 4 | 1 | 4 |   |
| B-1-02 | 315 | 5 | 5 |   |   | 5 | 5 |   | 0 | 3 | 4 | 3 | 4 | 4 | 0 | 0 | 0 | 0 | 5 |   |
| B-1-03 | 315 | 4 | 4 |   |   | 5 | 5 |   | 4 | 4 | 5 | 3 | 3 | 4 | 4 | 2 | 4 | 0 | 3 |   |
| B-1-04 | 315 | 4 | 4 |   |   | 5 | 5 |   | 4 | 4 | 5 | 3 | 4 | 3 | 4 | 3 | 0 | 0 | 5 |   |
| B-1-05 | 315 | 5 | 5 |   |   | 5 | 4 |   | 5 | 5 | 5 | 4 | 4 | 5 | 4 | 2 | 0 | 0 | 4 |   |
| B-1-06 | 315 | 4 | 4 |   | 0 | 1 | 1 |   | 1 | 2 | 4 | 3 | 3 | 4 | 1 | 0 | 1 | 0 | 2 |   |
| B-1-07 | 315 | 3 | 2 |   | 0 | 0 | 0 |   | 0 | 3 | 0 | 0 | 0 | 3 | 0 | 0 | 0 | 0 | 0 |   |
| B-1-08 | 315 | 5 | 4 |   | 2 | 5 | 4 |   | 0 | 0 | 3 | 4 | 3 | 4 | 4 | 0 | 0 | 0 | 3 |   |
| B-1-10 | 315 | 5 | 5 |   | 2 | 4 | 0 |   | 4 | 2 | 3 | 2 | 2 | 4 | 5 | 4 | 2 | 0 | 2 |   |
| B-1-12 | 315 | 5 | 5 |   | 3 | 4 | 1 |   | 3 | 0 | 4 | 4 | 3 | 3 | 3 | 5 | 0 | 0 | 4 |   |
| B-1-13 | 315 | 5 | 5 |   |   | 5 | 5 |   | 5 | 5 | 4 | 4 | 5 | 4 | 5 | 2 | 5 | 4 | 3 |   |
| B-1-14 | 315 | 5 | 5 |   |   | 5 | 5 |   | 5 | 5 | 4 | 4 | 4 | 4 | 4 | 3 | 4 | 4 | 5 |   |
| B-1-15 | 315 | 5 | 5 |   |   | 5 | 4 |   | 5 | 5 | 3 | 4 | 4 | 4 | 4 | 4 | 4 | 3 | 4 |   |
| B-1-16 | 315 | 5 | 5 |   |   | 5 | 3 |   | 5 | 4 | 3 | 0 | 4 | 0 | 4 | 2 | 3 | 1 | 1 |   |
| B-1-17 | 315 | 5 | 5 |   |   | 5 | 1 |   | 5 | 5 | 4 | 3 | 4 | 3 | 4 | 5 | 0 | 0 | 0 |   |
| B-1-18 | 320 | 2 | 3 | 2 | 0 | 1 | 1 | 3 | 3 | 2 | 3 | 3 | 4 | 4 | 0 | 1 | 0 | 0 | 0 | 3 |
| B-2-01 | 315 | 5 | 5 |   |   | 5 | 5 |   | 3 | 5 | 4 | 4 | 4 | 0 | 5 | 0 | 5 | 1 | 4 |   |
| B-2-02 | 315 | 4 | 3 |   |   | 4 | 3 |   | 0 | 4 | 3 | 0 | 0 | 1 | 4 | 0 | 0 | 0 | 3 |   |
| B-2-03 | 315 | 3 | 1 |   |   | 3 | 3 |   | 0 | 1 | 3 | 0 | 0 | 2 | 1 | 0 | 1 | 0 | 1 |   |
| B-2-04 | 315 | 5 | 5 |   |   | 5 | 5 |   | 5 | 5 | 5 | 4 | 4 | 5 | 5 | 3 | 4 | 5 | 5 |   |
| B-2-05 | 315 | 5 | 5 |   |   | 5 | 5 |   | 3 | 3 | 4 | 4 | 4 | 5 | 4 | 3 | 3 | 3 | 4 |   |
| B-2-06 | 315 | 5 | 5 |   |   | 5 | 5 |   | 3 | 5 | 4 | 4 | 4 | 5 | 5 | 1 | 4 | 4 | 4 |   |

TABLE 38-continued

| NO. | Treatment dosage (g/ha) | D | E | F | G | H | I | J | K | L | M | N | O | P | b | c | d | e | f | g |
|---|---|---|---|---|---|---|---|---|---|---|---|---|---|---|---|---|---|---|---|---|
| B-2-07 | 315 | 5 | 4 |  | 3 | 4 | 5 |  | 1 | 2 | 3 | 2 | 2 | 3 | 4 | 1 | 3 | 0 | 3 |  |
| B-2-08 | 315 | 5 | 5 |  |  | 5 | 5 |  | 4 | 4 | 4 | 4 | 3 | 4 | 4 | 0 | 4 | 2 | 5 |  |
| B-2-09 | 315 | 5 | 5 |  | 0 | 4 | 4 |  | 0 | 0 | 4 | 3 | 1 | 4 | 5 | 0 | 0 | 0 | 1 |  |
| B-2-11 | 320 | 5 | 5 | 5 | 4 | 5 | 5 | 5 | 5 | 4 | 5 | 4 | 4 |  | 3 | 5 | 4 | 0 | 4 | 4 |
| B-2-12 | 320 | 5 | 5 | 5 | 4 | 5 | 5 | 5 | 5 | 4 | 4 | 4 | 4 |  | 5 | 4 | 4 | 0 | 4 | 4 |
| B-2-13 | 320 | 5 | 5 | 5 | 3 | 5 | 5 | 5 | 5 | 4 | 4 | 4 | 5 | 5 | 3 | 4 | 4 | 0 | 4 | 4 |
| B-2-14 | 320 | 4 | 5 | 4 | 4 | 5 | 5 | 5 | 5 | 4 | 4 | 4 | 4 | 3 | 3 | 3 | 3 | 0 | 3 | 4 |
| B-2-15 | 320 | 4 | 5 | 4 | 3 | 4 | 5 | 5 | 1 | 2 | 4 | 4 | 3 |  | 5 | 4 | 1 | 2 | 3 | 4 |
| B-2-16 | 320 | 5 | 5 | 5 | 5 | 5 | 5 | 5 | 5 | 4 | 5 | 4 | 4 |  | 5 | 4 | 3 | 3 | 4 | 4 |
| B-2-17 | 315 | 5 | 5 |  | 4 | 4 | 5 |  | 1 | 3 | 2 | 2 | 0 | 2 | 5 | 3 | 0 | 0 | 2 |  |
| B-2-19 | 1250 | 5 | 5 |  | 3 | 5 | 4 |  | 0 | 3 | 3 | 3 | 3 | 5 | 4 | 1 | 1 | 0 | 3 |  |
| B-2-20 | 1250 | 5 | 5 |  | 0 | 4 | 4 |  | 0 | 3 | 3 | 2 | 0 | 4 | 0 | 1 | 3 | 0 | 4 |  |
| B-2-24 | 320 | 0 | 1 | 0 | 0 | 0 | 0 | 1 | 0 | 0 | 4 | 2 | 3 |  | 0 | 0 | 0 | 0 | 0 | 0 |
| B-2-25 | 315 | 5 | 5 |  | 5 | 5 | 5 |  | 4 | 2 | 4 | 4 | 5 | 5 | 5 | 3 | 3 | 0 | 3 |  |
| B-2-26 | 320 | 3 | 4 | 3 | 3 | 4 | 3 | 5 | 3 | 4 | 4 | 3 | 3 |  | 1 | 3 | 4 | 0 | 4 | 1 |
| B-2-27 | 315 | 5 | 5 |  | 5 | 5 | 5 |  | 4 | 4 | 3 | 4 | 4 |  | 5 | 4 | 4 | 4 | 4 |  |
| B-2-28 | 80 |  |  |  |  | 5 | 5 | 5 |  |  |  |  |  |  |  |  |  | 0 |  | 3 |
| B-2-29 | 315 | 5 | 5 |  |  | 5 | 5 |  | 5 | 5 | 4 | 5 | 4 | 4 | 5 | 4 | 5 | 5 | 4 |  |
| B-2-30 | 315 | 5 | 5 |  | 3 | 3 | 4 |  | 4 | 4 | 4 | 3 | 4 | 4 | 5 | 1 | 4 | 0 | 4 |  |
| B-2-31 | 315 | 5 | 5 |  |  | 5 | 5 |  | 5 | 5 | 4 | 5 | 3 | 4 | 5 | 4 | 5 | 5 | 4 |  |
| B-2-32 | 315 | 5 | 5 |  | 4 | 3 | 5 |  | 4 | 3 | 3 | 3 |  |  | 3 | 1 | 4 | 0 | 1 |  |
| B-2-33 | 315 | 5 | 5 | 5 | 5 | 5 | 5 | 5 | 4 | 4 |  | 4 | 5 | 5 | 5 | 3 | 4 | 4 | 4 | 4 |
| B-2-34 | 315 | 5 | 5 |  | 5 | 5 | 5 |  | 5 | 4 | 3 | 3 | 0 | 3 | 5 | 3 | 5 | 1 | 4 |  |
| B-2-35 | 320 | 5 | 5 | 5 | 2 | 4 | 4 | 4 | 3 | 3 | 4 | 3 | 5 |  | 4 | 1 | 4 | 0 | 3 | 4 |
| B-2-36 | 315 | 5 | 5 |  | 1 | 3 | 0 |  | 4 | 3 | 4 | 4 | 4 |  | 4 | 3 | 3 | 0 | 3 |  |
| B-2-37 | 315 | 5 | 5 |  | 3 | 4 | 4 |  | 4 | 4 | 3 | 4 | 3 | 4 | 4 | 3 | 3 | 1 | 4 |  |
| B-2-38 | 320 | 5 | 5 | 5 | 5 | 5 | 5 | 5 | 4 | 4 | 4 | 4 | 4 | 4 | 5 | 5 | 4 | 1 | 4 | 4 |
| B-2-39 | 320 | 5 | 5 | 5 | 4 | 5 | 5 | 5 | 4 | 3 | 5 | 4 | 4 | 5 | 4 | 4 | 4 | 0 | 4 | 4 |

TABLE 39

| NO. | Treatment dosage (g/ha) | D | E | F | G | H | I | J | K | L | M | N | O | P | b | c | d | e | f | g |
|---|---|---|---|---|---|---|---|---|---|---|---|---|---|---|---|---|---|---|---|---|
| B-2-40 | 320 | 5 | 5 | 5 | 5 | 5 | 5 | 5 | 5 | 5 | 5 | 4 | 5 | 4 | 5 | 5 | 5 | 1 | 4 | 4 |
| B-2-41 | 320 | 5 | 5 | 3 | 5 | 5 | 5 | 5 | 4 | 3 | 4 | 5 | 5 | 4 | 4 | 4 | 0 | 4 | 5 |  |
| B-2-42 | 320 | 5 | 5 | 5 | 3 | 5 | 5 | 5 | 5 | 4 | 4 | 5 | 4 | 3 | 4 | 0 | 4 | 4 |  |  |
| B-2-43 | 320 | 5 | 5 | 5 | 3 | 5 | 5 | 5 | 3 | 3 | 4 | 3 | 1 |  | 5 | 3 | 4 | 0 | 3 | 4 |
| B-2-44 | 320 | 4 | 5 | 4 | 3 | 5 | 5 | 5 | 4 | 3 | 3 | 4 | 5 | 5 | 3 | 1 | 4 | 4 | 3 | 5 |
| B-2-46 | 320 | 4 | 5 | 4 | 3 | 4 | 4 | 5 | 3 | 0 |  | 2 | 4 | 4 | 3 | 1 | 0 | 0 | 4 | 4 |
| B-2-47 | 320 | 3 | 4 | 1 | 2 | 2 | 2 | 4 | 0 | 0 |  | 2 | 3 | 4 | 0 | 0 | 0 | 0 | 3 | 3 |
| B-2-49 | 320 | 5 | 5 | 4 | 3 | 3 | 1 | 4 | 4 | 3 | 3 | 3 | 3 | 4 | 0 | 3 | 3 | 0 | 3 | 3 |
| B-2-50 | 320 | 2 | 2 | 0 | 0 | 1 | 1 | 1 | 1 | 0 | 3 | 0 | 0 | 0 | 0 | 0 | 0 | 0 | 0 | 0 |
| B-2-51 | 320 | 5 | 5 | 5 | 5 | 5 | 5 | 5 | 4 | 4 | 4 | 4 | 4 | 4 | 0 | 3 | 1 | 4 | 3 |  |
| B-2-52 | 80 |  |  |  | 2 | 3 | 5 |  |  |  |  |  |  |  |  |  |  | 0 |  | 0 |
| B-2-53 | 135.45 | 5 | 5 |  |  | 5 | 5 |  | 4 | 4 | 3 | 1 | 3 | 4 | 4 | 1 | 4 | 1 | 0 |  |
| B-2-54 | 320 | 5 | 5 | 5 | 5 | 5 | 5 | 5 | 4 | 4 | 4 | 4 | 4 | 5 | 3 | 4 | 0 | 4 | 4 |  |
| B-2-55 | 315 | 5 | 5 | 5 | 3 | 5 | 4 | 5 | 4 | 4 |  | 4 | 5 | 5 | 5 | 4 | 4 | 2 | 4 | 4 |
| B-2-56 | 320 | 5 | 5 | 4 | 5 | 4 | 5 | 5 | 0 | 3 |  | 4 | 4 | 4 | 4 | 5 | 4 | 3 | 3 | 3 |
| B-2-57 | 315 | 5 | 5 |  | 5 | 5 | 5 |  | 5 | 5 | 3 | 3 | 5 |  | 5 | 5 | 4 | 1 | 3 |  |
| B-2-58 | 315 | 5 | 5 |  | 3 | 5 | 5 |  | 3 | 3 | 3 | 3 | 1 |  | 4 | 3 | 3 | 1 | 4 |  |
| B-2-61 | 320 |  |  |  | 0 | 0 | 0 | 1 | 0 | 0 | 0 | 0 | 0 | 2 |  | 0 | 0 | 0 | 2 |  |
| B-2-62 | 320 | 3 | 3 | 3 | 1 | 3 | 2 | 4 | 4 | 4 | 3 | 2 | 1 | 4 | 0 | 0 | 0 | 0 | 0 | 4 |
| B-2-63 | 315 | 3 | 3 |  | 0 | 0 | 1 |  | 0 | 0 | 3 | 2 | 2 | 1 | 0 | 0 | 2 | 0 | 0 |  |
| B-2-64 | 320 | 5 | 5 | 5 | 4 | 5 | 5 | 5 | 4 | 4 | 4 | 4 | 4 | 4 | 0 | 4 | 0 | 4 | 4 |  |
| B-3-01 | 315 | 5 | 5 |  | 5 | 5 | 5 |  | 3 | 3 |  | 2 | 4 | 3 | 5 | 4 | 4 | 1 |  |  |
| B-3-02 | 315 | 5 | 5 |  | 5 | 5 | 5 |  | 4 | 3 | 2 |  | 4 | 3 | 5 | 4 | 4 | 3 | 3 |  |
| B-3-03 | 315 | 5 | 5 |  | 4 | 5 | 5 |  | 2 | 2 | 2 | 2 | 0 | 1 | 5 | 4 | 3 | 0 | 0 |  |
| B-3-04 | 315 | 3 | 4 | 3 | 3 | 3 | 3 | 4 | 2 | 0 |  | 3 | 2 | 3 | 0 | 0 | 0 | 0 | 2 | 1 |
| B-3-05 | 315 | 4 | 4 |  | 4 | 3 | 4 |  | 3 | 3 | 3 | 3 | 1 | 5 | 4 | 0 | 2 | 1 | 2 |  |
| B-4-01 | 315 | 2 | 1 |  | 0 | 0 | 2 |  | 0 | 0 | 1 | 2 | 0 | 4 | 0 | 0 | 0 | 0 | 1 |  |
| B-4-02 | 315 | 5 | 5 |  | 5 | 5 | 5 |  | 3 | 4 | 4 | 3 | 5 | 5 | 5 | 4 | 4 | 0 |  |  |
| B-4-03 | 315 | 5 | 5 |  | 5 | 5 | 5 |  | 4 | 3 | 3 | 1 | 5 | 4 | 5 | 4 | 4 | 0 | 4 |  |
| B-4-04 | 320 | 4 | 4 | 4 | 2 | 4 | 4 | 4 | 5 | 3 | 4 | 3 | 4 | 4 | 4 | 1 | 1 | 4 | 4 | 3 |
| B-4-05 | 315 | 5 | 5 |  | 4 | 4 | 5 |  | 3 | 3 | 2 | 2 | 1 | 4 | 5 | 3 | 3 | 0 | 0 |  |
| B-4-06 | 315 | 5 | 5 |  | 5 | 5 | 5 |  | 3 | 4 | 3 | 4 |  | 5 | 5 | 4 | 1 | 3 |  |  |
| B-5-01 | 320 | 0 | 0 | 0 | 0 | 0 | 0 | 0 | 0 | 0 | 3 | 0 | 1 | 3 | 0 | 0 | 0 | 0 | 0 | 0 |

POSSIBLE INDUSTRIAL APPLICATIONS

The heterocyclic amide compounds of the present invention are novel compounds and are useful as selective herbicides for use on rice, corn, soybean, wheat, beet and rapeseed.

The invention claimed is:
1. A heterocyclic amide compound represented by the formula (1):

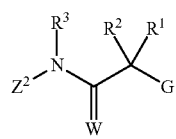

(1)

wherein, W is an oxygen atom or sulfur atom,
$R^1$ and $R^2$ are each independently a hydrogen atom, $C_1$-$C_6$ alkyl or ($C_1$-$C_6$) alkyl optionally substituted with $R^8$, or $R^1$ and $R^2$ together forming a $C_2$-$C_6$ alkylene chain, or $R^1$ and $R^2$ together with the linking carbon atom may form a 3-7 membered ring,
$R^3$ is a hydrogen atom, $C_1$-$C_6$ alkyl or ($C_1$-$C_6$) alkyl optionally substituted with $R^9$,
$R^8$ is a halogen atom or —$OR^{10}$,
$R^9$ is a halogen atom or —$OR^{11}$,
$R^{10}$ and $R^{11}$ are each independently a hydrogen atom or $C_1$-$C_6$ alkyl,
G is a ring represented by G-1 or G-2, and wherein if G represents a ring represented by G-1,

G-1

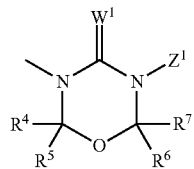

$W^1$ is an oxygen atom or sulfur atom,
$Z^1$ is $C_1$-$C_6$ alkyl, ($C_1$-$C_6$) alkyl optionally substituted with $R^{12}$, $C_3$-$C_6$ cycloalkyl, ($C_3$-$C_6$) cycloalkyl optionally substituted with $R^{12}$, $C_2$-$C_6$ alkenyl, ($C_2$-$C_6$) alkenyl optionally substituted with $R^{12}$, $C_2$-$C_6$ alkynyl, ($C_2$-$C_6$) alkynyl optionally substituted with $R^{12}$, phenyl, phenyl substituted with $(R^{13})_{p1}$ or Q-1 to Q-3, and
$Z^2$ is any of T-1 to T-24,

T-1

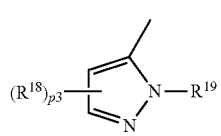

T-2

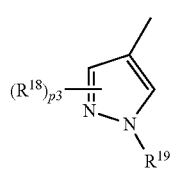

T-3

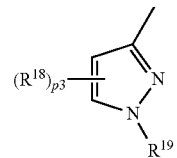

T-4

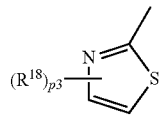

T-5

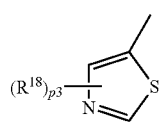

T-6

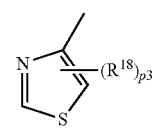

T-7

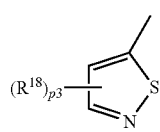

T-8

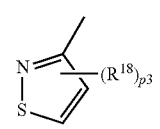

T-9

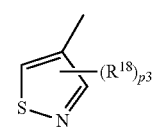

T-10

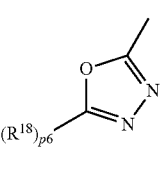

T-11

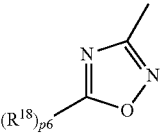

T-12

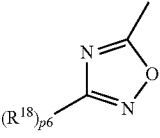

T-13

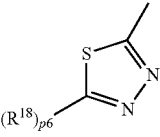

T-14

(R¹⁸)p6 — [1,3,4-thiadiazole with methyl]

T-15

(R¹⁸)p6 — [1,3,4-thiadiazole isomer with methyl]

T-16

(R¹⁸)p4 — [2-methylpyridine]

T-17

(R¹⁸)p4 — [3-methylpyridine]

T-18

(R¹⁸)p4 — [4-methylpyridine]

T-19

(R¹⁸)p5 — [methylpyrimidine]

T-20

(R¹⁸)p5 — [methylpyrimidine isomer]

T-21

(R¹⁸)p5 — [methylpyrimidine isomer]

T-22

(R¹⁸)p5 — [methylpyridazine]

T-23

(R¹⁸)p5 — [methylpyridazine isomer]

T-24

(R¹⁸)p3 — [methylpyrazine]

$R^4$, $R^5$, $R^6$ and $R^7$ are each independently a hydrogen atom or $C_1$-$C_6$ alkyl, Q-1 to Q-3 are the following structural formulae,

Q-1

(R¹⁴)p2 — [2-methylpyridine]

Q-2

(R¹⁴)p2 — [3-methylpyridine]

Q-3

(R¹⁴)p2 — [4-methylpyridine]

$R^{12}$ is a halogen atom, phenyl or —$OR^{15}$, $R^{13}$ is a halogen atom, $C_1$-$C_6$ alkyl, $C_1$-$C_6$ haloalkyl or —$OR^{16}$, and when p1 represents a whole number 2 or more, each $R^{13}$ may be the same or different, furthermore, if 2 $R^{13}$ are adjacent, the 2 adjacent $R^{13}$, by forming —$CH_2CH_2CH_2$—, —$CH_2CH_2O$—, —$CH_2OCH_2$—, —$OCH_2O$—, —$CH_2CH_2S$—, —$CH_2SCH_2$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$CH_2CH_2CH_2S$—, —$OCH_2CH_2S$— or —CH=CH—CH=CH—, may form a 5-membered ring or 6-membered ring together with the carbon atom to which the 2 $R^{13}$ are each bound, and in that case the hydrogen atoms bound to each carbon atom forming the ring may optionally be substituted with halogen atom(s), $C_1$-$C_6$ alkyl group(s) or $C_1$-$C_6$ haloalkyl group(s), $R^{14}$ is a halogen atom, $C_1$-$C_6$ alkyl, $C_1$-$C_6$ haloalkyl or —$OR^{17}$, and when p2 represents a whole number 2 or more, each $R^{14}$ may be the same or different, furthermore, if 2 $R^{14}$ are adjacent, the 2 adjacent $R^{14}$, by forming —$CH_2CH_2CH_2$—, —$CH_2CH_2O$—, —$CH_2OCH_2$—, —$OCH_2O$—, —$CH_2CH_2S$—, —$CH_2SCH_2$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$CH_2CH_2CH_2S$—, —$OCH_2CH_2S$— or —CH=CH—CH=CH—, may form a 5-membered ring or 6-membered ring together with the carbon atom to which the 2 $R^{14}$ are each bound, and in that case the hydrogen atoms bound to each carbon atom forming the ring may optionally be substituted with halogen atom(s), $C_1$-$C_6$ alkyl group(s) or $C_1$-$C_6$ haloalkyl group(s), $R^{15}$ is a hydrogen atom or $C_1$-$C_6$ alkyl, $R^{16}$ is a hydrogen atom, $C_1$-$C_6$ alkyl, $C_1$-$C_6$ haloalkyl or phenyl, $R^{17}$ is $C_1$-$C_6$ alkyl, $C_1$-$C_6$ haloalkyl or phenyl, $R^{18}$ is a halogen atom, $C_1$-$C_6$ alkyl, $C_1$-$C_6$ haloalkyl, $C_3$-$C_6$ cycloalkyl, cyano, —$C(O)OR^{20}$, phenyl, —$OR^{23}$, nitro, —$N(R^{24})R^{25}$, —$S(O)_qR^{26}$ or V-1 to V-8, and when p3, p4 or p5 represents a whole number 2 or more, each $R^{18}$ may be the same or different, furthermore, if 2 $R^{18}$ are adjacent, the 2 adjacent $R^{18}$, by forming —$CH_2CH_2CH_2$—, —$CH_2CH_2O$—, —$CH_2OCH_2$—, —$OCH_2O$—, —$CH_2CH_2S$—, —$CH_2SCH_2$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$CH_2CH_2CH_2S$—, —$OCH_2CH_2S$— or —CH=CH—CH=CH—, may form a 5-membered ring or 6-membered ring together with the carbon atom to which the 2 $R^{18}$ are each bound, and in that case the hydrogen atoms bound to each carbon atom forming the ring may optionally be substituted with halogen atom(s), $C_1$-$C_6$ alkyl group(s) or $C_1$-$C_6$ haloalkyl group(s), V-1 to V 8 are the following structural formulae,

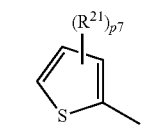
V-1

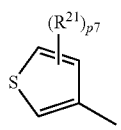
V-2

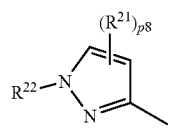
V-3

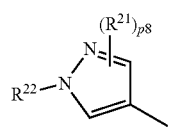
V-4

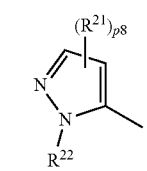
V-5

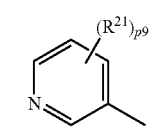
V-6

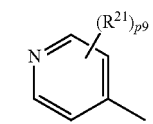
V-7

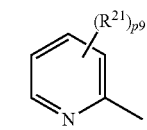
V-8

$R^{19}$ and $R^{20}$ are each independently $C_1$-$C_6$ alkyl or $C_1$-$C_6$ haloalkyl, $R^{21}$ is a halogen atom, $C_1$-$C_6$ alkyl or $C_1$-$C_6$ haloalkyl, and when p7, p8 or p9 represents a whole number 2 or more, each $R^{21}$ may be the same or different, furthermore, if 2 $R^{21}$ are adjacent, the 2 adjacent $R^{21}$, by forming —$CH_2CH_2CH_2$—, —$CH_2CH_2O$—, —$CH_2OCH_2$—, —$OCH_2O$—, —$CH_2CH_2S$—, —$CH_2SCH_2$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$CH_2CH_2CH_2S$—, —$OCH_2CH_2S$— or —CH=CH—CH=CH—, may form a 5-membered ring or 6-membered ring together with the carbon atom to which the 2 $R^{21}$ are each bound, and in that case the hydrogen atoms bound to each carbon atom forming the ring may optionally be substituted with halogen atom(s), $C_1$-$C_6$ alkyl group(s) or $C_1$-$C_6$ haloalkyl group(s), $R^{22}$ is $C_1$-$C_6$ alkyl or $C_1$-$C_6$ haloalkyl, $R^{23}$ is a hydrogen atom, $C_1$-$C_6$ alkyl, $C_1$-$C_6$ haloalkyl or phenyl, $R^{24}$ and $R^{25}$ are each independently a hydrogen atom or $C_1$-$C_6$ alkyl, or else $R^{24}$, by forming a $C_2$-$C_6$ alkylene chain together with $R^{25}$, can form a 3-7 membered ring together with the linking nitrogen atom, and in this case this alkylene chain can contain 1 oxygen atom, sulfur atom or nitrogen atom, and may optionally be substituted with halogen atom(s), $C_1$-$C_6$ alkyl group(s), $C_1$-$C_6$ haloalkyl group(s), $C_1$-$C_6$ alkoxy group(s), formyl group(s), $C_1$-$C_6$ alkylcarbonyl group(s), $C_1$-$C_6$ alkoxycarbonyl group(s) or oxo group(s), $R^{26}$ is $C_1$-$C_6$ alkyl or $C_1$-$C_6$ haloalkyl, p1 is a whole number 1, 2, 3, 4 or 5,
p2 is a whole number 0, 1, 2, 3 or 4,
p3 is a whole number 0, 1 or 2,
p4 is a whole number 0, 1, 2, 3 or 4,
p5 is a whole number 0, 1, 2 or 3,
p6 is a whole number 0 or 1,
p7 is a whole number 0, 1, 2 or 3,
p8 is a whole number 0, 1 or 2,
p9 is a whole number 0, 1, 2, 3 or 4, and
q is a whole number 0, 1 or 2, or
G is a ring represented by G-2,

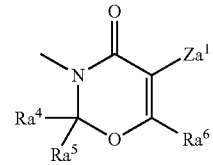
G-2

$Za^1$ is phenyl, phenyl substituted with $(Ra^{13})_{pa1}$ or Qa-1 to Qa-8, $Z^2$ is an any of Ta-1 to Ta-13

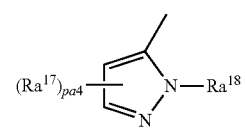
Ta-1

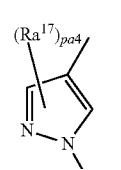
Ta-2

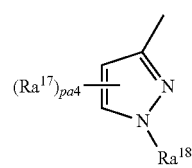
Ta-3

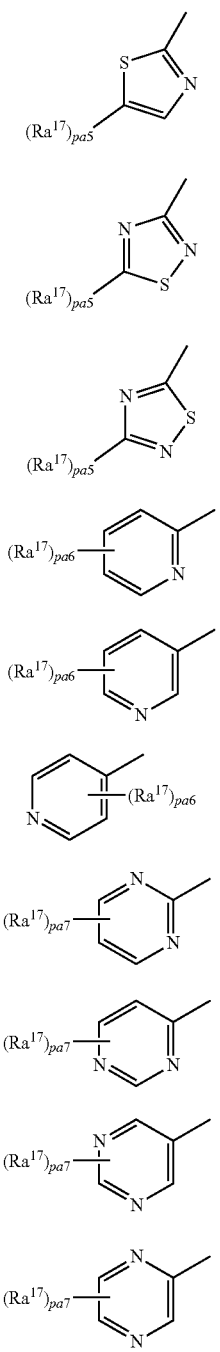

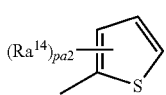

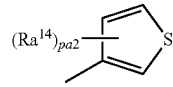

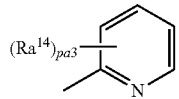

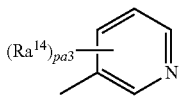

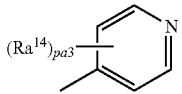

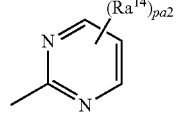

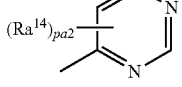

$Ra^4$ and $Ra^5$ are each independently a hydrogen atom or $C_1$-$C_6$ alkyl, $Ra^6$ is a hydrogen atom, $C_1$-$C_6$ alkyl or ($C_1$-$C_6$) alkyl optionally substituted with $Ra^9$, Qa-1 to Qa 8 are the following structural formulae, $Ra^9$ is a halogen atom or —$ORa^{12}$, $Ra^{12}$ is a hydrogen atom or $C_1$-$C_6$ alkyl, $Ra^{13}$ is a halogen atom, $C_1$-$C_6$ alkyl, $C_1$-$C_6$ haloalkyl or —$ORa^{15}$, and when pa1 represents a whole number 2 or more, each $Ra^{13}$ may be the same or different, furthermore, if 2 $Ra^{13}$ are adjacent, the 2 adjacent $Ra^{13}$, by forming —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —CH$_2$CH$_2$CH$_2$S—, —OCH$_2$CH$_2$S— or —CH═CH—CH═CH—, may form a 5-membered ring or 6-membered ring together with the carbon atom to which the 2 $Ra^{13}$ are each bound, and in that case the hydrogen atoms bound to each carbon atom forming the ring may optionally be substituted with halogen atom(s), $C_1$-$C_6$ alkyl group(s) or $C_1$-$C_6$ haloalkyl group(s), $Ra^{14}$ is a halogen atom, $C_1$-$C_6$ alkyl, $C_1$-$C_6$ haloalkyl or —$ORa^{16}$, and when pa2 or pa3 represents a whole number 2 or more, each $Ra^{14}$ may be the same or different, furthermore, if 2 $Ra^{14}$ are adjacent, the 2 adjacent $Ra^{14}$, by forming —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —CH$_2$CH$_2$CH$_2$S—, —OCH$_2$CH$_2$S— or —CH═CH—CH═CH—, may form a 5-membered ring or 6-membered ring together with the carbon atom to which the 2 $Ra^{14}$ are each bound, and in that case the hydrogen atoms bound to each carbon atom forming the ring may optionally be substituted with halogen atom(s), $C_1$-$C_6$ alkyl group(s) or $C_1$-$C_6$ haloalkyl group(s), $Ra^{15}$ is a hydrogen atom, $C_1$-$C_6$ alkyl, $C_1$-$C_6$ haloalkyl or phenyl, $Ra^{16}$ is $C_1$-$C_6$ alkyl, $C_1$-$C_6$ haloalkyl or phenyl, $Ra^{17}$ is a halogen atom, $C_1$-$C_6$ alkyl, $C_1$-$C_6$ haloalkyl, $C_3$-$C_6$ cycloalkyl, cyano, —C(O)O$Ra^{19}$, phenyl, —O$Ra^{21}$, nitro, —N($Ra^{22}$)$Ra^{23}$, —S(O)$_{qa}$$Ra^{24}$ or Va-1 to Va-3, and when pa4, pa6 or pa7 represents a whole number 2 or more, each $Ra^{17}$ may be the same or different, furthermore, if 2 $Ra^{17}$ are adjacent, the 2 adjacent $Ra^{17}$, by forming —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —CH$_2$CH$_2$CH$_2$S—, —OCH$_2$CH$_2$S— or —CH=CH—CH=CH—, may form a 5-membered ring or 6-membered ring together with the carbon atom to which the 2 $Ra^{17}$ are each bound, and in that case the hydrogen atoms bound to each carbon atom forming the ring may optionally be substituted with halogen atom(s), $C_1$-$C_6$ alkyl group(s) or $C_1$-$C_6$ haloalkyl group(s), Va-1 to Va 3 are the following structural formulae,

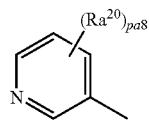

Va-1

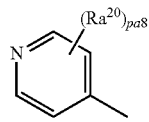

Va-2

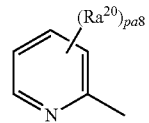

Va-3

$Ra^{18}$ and $Ra^{19}$ are each independently $C_1$-$C_6$ alkyl or $C_1$-$C_6$ haloalkyl, $Ra^{20}$ is a halogen atom, $C_1$-$C_6$ alkyl or $C_1$-$C_6$ haloalkyl, and when pa8 represents a whole number 2 or more, each $Ra^{20}$ may be the same or different, furthermore, if 2 $Ra^{20}$ are adjacent, the 2 adjacent $Ra^{20}$, by forming —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —CH$_2$CH$_2$CH$_2$S—, —OCH$_2$CH$_2$S— or —CH=CH—CH=CH—, may form a 5-membered ring or 6-membered ring together with the carbon atom to which the 2 $Ra^{20}$ are each bound, and in that case the hydrogen atoms bound to each carbon atom forming the ring may optionally be substituted with halogen atom(s), $C_1$-$C_6$ alkyl group(s) or $C_1$-$C_6$ haloalkyl group(s), $Ra^{21}$ is $C_1$-$C_6$ alkyl, $C_1$-$C_6$ haloalkyl or phenyl, $Ra^{22}$ and $Ra^{23}$ are each independently a hydrogen atom or $C_1$-$C_6$ alkyl, or else $Ra^{22}$, by forming a $C_2$-$C_6$ alkylene chain together with $Ra^{23}$, can form a 3-7 membered ring together with the linking nitrogen atom, and in this case this alkylene chain can contain 1 oxygen atom, sulfur atom or nitrogen atom, and may optionally be substituted with halogen atom(s), $C_1$-$C_6$ alkyl group(s), $C_1$-$C_6$ haloalkyl group(s), $C_1$-$C_6$ alkoxy group(s), formyl group(s), $C_1$-$C_6$ alkylcarbonyl group(s) or $C_1$-$C_6$ alkoxycarbonyl group(s), $Ra^{24}$ is $C_1$-$C_6$ alkyl or $C_1$-$C_6$ haloalkyl, pa1 is a whole number 1, 2, 3, 4 or 5, pa2 is a whole number 0, 1, 2 or 3, pa3 is a whole number 0, 1, 2, 3 or 4, pa4 is a whole number 0, 1 or 2, pa5 is a whole number 0 or 1, pa6 is a whole number 0, 1, 2, 3 or 4, pa1 is a whole number 0, 1, 2 or 3, and pa8 is a whole number 0, 1, 2, 3 or 4, qa is a whole number 0, 1 or 2, or a salt thereof.

2. The heterocyclic amide compound or salt thereof as claimed in claim 1, wherein G is G 1.

3. The heterocyclic amide compound or salt thereof as claimed in claim 2, wherein $R^4$, $R^5$, $R^6$ and $R^7$ are hydrogen atoms, $R^8$, $R^9$, $R^{12}$ and $R^{14}$ are each independently halogen atoms, $R^{16}$ is a hydrogen atom, $C_1$-$C_6$ alkyl or $C_1$-$C_6$ haloalkyl, $R^{18}$ is a halogen atom, $C_1$-$C_6$ alkyl, $C_1$-$C_6$ haloalkyl, $C_3$-$C_6$ cycloalkyl, cyano, —C(O)O$R^{20}$, phenyl, —O$R^{23}$, nitro, —S(O)$_q$$R^{26}$, V-2, V-5 or V-6, and when p3, p4 or p5 represents a whole number 2 or more, each $R^{18}$ may be the same or different, furthermore, if 2 $R^{18}$ are adjacent, the 2 adjacent $R^{18}$, by forming —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —CH$_2$CH$_2$CH$_2$S—, —OCH$_2$CH$_2$S— or —CH=CH—CH=CH—, may form a 5-membered ring or 6-membered ring together with the carbon atom to which the 2 $R^{18}$ are each bound, and in that case the hydrogen atoms bound to each carbon atom forming the ring may optionally be substituted with halogen atom(s), $C_1$-$C_6$ alkyl group(s) or $C_1$-$C_6$ haloalkyl group(s), and $R^{21}$ is a halogen atom.

4. The heterocyclic amide compound or salt thereof as claimed in claim 3, wherein W is a oxygen atom, $R^1$ and $R^2$ are each independently a hydrogen atom or $C_1$-$C_6$ alkyl, or else by $R^1$ forming a $C_2$ alkylene chain together with $R^2$, or $R^1$ and $R^2$ may form a 3-membered ring together with the linking carbon atom, $R^3$ is a hydrogen atom or $C_1$-$C_6$ alkyl, $R^{13}$ is a halogen atom, $C_1$-$C_6$ alkyl, $C_1$-$C_6$ haloalkyl or —O$R^{16}$, $R^{16}$ is $C_1$-$C_6$ alkyl or $C_1$-$C_6$ haloalkyl, $R^{18}$ is a halogen atom, $C_1$-$C_6$ alkyl, $C_1$-$C_6$ haloalkyl, $C_3$-$C_6$ cycloalkyl, cyano, —C(O)O$R^{20}$, phenyl, —O$R^{23}$, nitro, —S(O)$_q$$R^{26}$, V-2, V-5 or V-6, and if 2 $R^{18}$ are adjacent, the 2 adjacent $R^{18}$, by forming —CH=CH—CH=CH—, may form a 6-membered ring together with the carbon atom to which the 2 $R^{18}$ are each bound, $R^{20}$ and $R^{22}$ are each independently $C_1$-$C_6$ alkyl,
$R^{23}$ is $C_1$-$C_6$ alkyl, $C_1$-$C_6$ haloalkyl or phenyl, and
$R^{26}$ is $C_1$-$C_6$ alkyl.

5. The heterocyclic amide compound or salt thereof as claimed in claim 4, wherein
$Z^1$ is $C_3$-$C_6$ cycloalkyl, ($C_3$-$C_6$) cycloalkyl optionally substituted with $R^{12}$, phenyl, phenyl substituted with $(R^{13})_{p1}$ or Q-1 to Q-3,
$Z^2$ is T-1, T-2, T-3, T-4, T-5, T-6, T-7, T-8, T-9, T-10, T-13, T-14, T-15, T-16, T-17, T-18, T-19, T-20, T-21, T-22, T-23 or T-24,
$R^{13}$ is a halogen atom, $C_1$-$C_6$ alkyl or —$OR^{16}$, and
$R^{16}$ is $C_1$-$C_6$ alkyl.

6. The heterocyclic amide compound or salt thereof as claimed in claim 5, wherein
$Z^2$ is T-1, T-2, T-3, T-4, T-7, T-10, T-13, T-14, T-15, T-16, T-17, T-18, T-19, T-20, T-21, T-22, T-23 or T-24.

7. The heterocyclic amide compound or salt thereof as claimed in claim 6, wherein
$Z^1$ is phenyl, phenyl substituted with $(R^{13})_{p1}$ or Q-2, and
$Z^2$ is T-1, T-3, T-4, T-7, T-10, T-13, T-14, T-15, T-16, T-17, T-18, T-19, T-20, T-22 or T-24.

8. The heterocyclic amide compound or salt thereof as claimed in claim 1, wherein
G is G 2.

9. The heterocyclic amide compound or salt thereof as claimed in claim 8, wherein
$R^1$ and $R^2$ are each independently $C_1$-$C_6$ alkyl or ($C_1$-$C_6$) alkyl optionally substituted with $R^8$, or else by $R^1$ and $R^2$ together forming a $C_2$-$C_6$ alkylene chain, $R^1$ and $R^2$ together with the linking carbon atom may form a 3-7 membered ring,
$R^3$ is a hydrogen atom,
$R^8$ is a halogen atom,
$Ra^4$ and $Ra^5$ are hydrogen atoms,
$Ra^6$ is $C_1$-$C_6$ alkyl or ($C_1$-$C_6$) alkyl optionally substituted with $Ra^9$,
$Ra^9$ is a halogen atom,
$Ra^{13}$ is a halogen atom, $C_1$-$C_6$ alkyl or $C_1$-$C_6$ haloalkyl, and when pa1 represents a whole number 2 or more, each $Ra^n$ may be the same or different,
furthermore, if 2 $Ra^n$ are adjacent, the 2 adjacent $Ra^{13}$, by forming —$CH_2CH_2CH_2$—, —$CH_2CH_2O$—, —$CH_2OCH_2$—, —$OCH_2O$—, —$CH_2CH_2S$—, —$CH_2SCH_2$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$CH_2CH_2CH_2S$—, —$OCH_2CH_2S$— or —CH=CH—CH=CH—, may form a 5-membered ring or 6-membered ring together with the carbon atom to which the 2 $Ra^{13}$ are each bound, and in that case the hydrogen atoms bound to each carbon atom forming the ring may optionally be substituted with halogen atom(s), $C_1$-$C_6$ alkyl group(s) or $C_1$-$C_6$ haloalkyl group(s),
$Ra^{14}$ is a halogen atom, $C_1$-$C_6$ alkyl or $C_1$-$C_6$ haloalkyl, and when pa2 or pa3 represents a whole number 2 or more, each $Ra^{14}$ may be the same or different,
furthermore, if 2 $Ra^{14}$ are adjacent, the 2 adjacent $Ra^{14}$, by forming —$CH_2CH_2CH_2$—, —$CH_2CH_2O$—, —$CH_2OCH_2$—, —$OCH_2O$—, —$CH_2CH_2S$—, —$CH_2SCH_2$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$CH_2CH_2CH_2S$—, —$OCH_2CH_2S$— or —CH=CH—CH=CH—, may form a 5-membered ring or 6-membered ring together with the carbon atom to which the 2 $Ra^{14}$ are each bound, and in that case the hydrogen atoms bound to each carbon atom forming the ring may optionally be substituted with halogen atom(s), $C_1$-$C_6$ alkyl group(s) or $C_1$-$C_6$ haloalkyl group(s),
$Ra^{17}$ is a halogen atom, $C_1$-$C_6$ alkyl, $C_1$-$C_6$ haloalkyl, $C_3$-$C_6$ cycloalkyl, cyano, —$C(O)ORa^{19}$, phenyl, —$ORa^{21}$, nitro, —$S(O)_{qa}Ra^{24}$ or Va-1 to Va-3, and when pa4, pa6 or pa7 represents a whole number 2 or more, each $Ra^{17}$ may be the same or different,
furthermore, if 2 $Ra^{17}$ are adjacent, the 2 adjacent $Ra^{17}$, by forming —$CH_2CH_2CH_2$—, —$CH_2CH_2O$—, —$CH_2OCH_2$—, —$OCH_2O$—, —$CH_2CH_2S$—, —$CH_2SCH_2$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$CH_2CH_2CH_2S$—, —$OCH_2CH_2S$— or —CH=CH—CH=CH—, may form a 5-membered ring or 6-membered ring together with the carbon atom to which the 2 $Ra^{17}$ are each bound, and in that case the hydrogen atoms bound to each carbon atom forming the ring may optionally be substituted with halogen atom(s), $C_1$-$C_6$ alkyl group(s) or $C_1$-$C_6$ haloalkyl group(s), and
$Ra^{20}$ is a halogen atom.

10. The heterocyclic amide compound or salt thereof as claimed in claim 9, wherein
W is a oxygen atom,
$R^1$, $R^2$ and $Ra^b$ are each independently $C_1$-$C_6$ alkyl,
$Ra^{13}$ is a halogen atom,
$Ra^{14}$ is a halogen atom, and if 2 $Ra^{14}$ are adjacent, the 2 adjacent $Ra^{14}$, by forming —CH=CH—CH=CH—, may form a 6-membered ring together with the carbon atom to which the 2 $Ra^{14}$ are each bound,
$Ra^{17}$ is a halogen atom, $C_1$-$C_6$ alkyl, $C_1$-$C_6$ haloalkyl, cyano, —$C(O)ORa^{19}$, phenyl, —$ORa^{21}$, —$S(O)_{qa}Ra^{24}$ or Va-1, and if 2 $Ra^{17}$ are adjacent, the 2 adjacent $Ra^{17}$, by forming —CH=CH—CH=CH—, may form a 6-membered ring together with the carbon atom to which the 2 $Ra^{17}$ are each bound, and
$Ra^{18}$, $Ra^{19}$ and $Ra^{24}$ are each independently $C_1$-$C_6$ alkyl.

11. The heterocyclic amide compound or salt thereof as claimed in claim 10, wherein
$Za^1$ is phenyl, phenyl substituted with $(Ra^{13})_{pa1}$, Qa-1, Qa-2, Qa-3, Qa-4, Qa-5 or Qa-8, and
$Z^2$ is Ta-2, Ta-4, Ta-5, Ta-6, Ta-7, Ta-8, Ta-9, Ta-11 or Ta-13.

12. The heterocyclic amide compound or salt thereof as claimed in claim 11, characterized in that
$Za^1$ is phenyl, Qa-1, Qa-2, Qa-4, Qa-5 or Qa-8, and
$Z^2$ is Ta-2, Ta-4, Ta-6, Ta-7, Ta-8, Ta-9, Ta-11 or Ta-13.

13. A pesticide composition comprising 1 or more compounds selected from the heterocyclic amide compounds or salts thereof as claimed in claim 1.

14. A herbicide composition comprising 1 or more compounds selected from the heterocyclic amide compounds or salts thereof as claimed in claim 1.

* * * * *